(12) United States Patent
Popov et al.

(10) Patent No.: US 12,115,246 B2
(45) Date of Patent: *Oct. 15, 2024

(54) COMPOSITIONS AND METHODS FOR OPHTHALMIC AND/OR OTHER APPLICATIONS

(71) Applicant: The Johns Hopkins University, Baltimore, MD (US)

(72) Inventors: Alexey Popov, Waltham, MA (US); Elizabeth M. Enlow, Waltham, MA (US); Hongming Chen, Belmont, MA (US); James Bourassa, Somerville, MA (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/110,273

(22) Filed: Feb. 15, 2023

(65) Prior Publication Data

US 2023/0201111 A1 Jun. 29, 2023

Related U.S. Application Data

(60) Continuation of application No. 17/170,701, filed on Feb. 8, 2021, now Pat. No. 11,596,599, which is a continuation of application No. 16/988,470, filed on Aug. 7, 2020, now Pat. No. 10,993,908, which is a continuation of application No. 16/888,371, filed on May 29, 2020, now Pat. No. 10,940,108, which is a division of application No. 15/808,746, filed on Nov. 9, 2017, now Pat. No. 10,688,045, which is a continuation of application No. 14/070,506, filed on Nov. 2, 2013, now Pat. No. 9,827,191, which is a continuation-in-part of application No. 13/886,658, filed on May 3, 2013, now abandoned.

(60) Provisional application No. 61/784,701, filed on Mar. 14, 2013, provisional application No. 61/738,949, filed on Dec. 18, 2012, provisional application No. 61/642,313, filed on May 3, 2012, provisional application No. 61/642,261, filed on May 3, 2012.

(51) Int. Cl.
| | | |
|---|---|---|
| *A61K 9/00* | (2006.01) | |
| *A61K 9/10* | (2006.01) | |
| *A61K 9/50* | (2006.01) | |
| *A61K 9/51* | (2006.01) | |
| *A61K 31/56* | (2006.01) | |
| *A61K 47/02* | (2006.01) | |
| *A61P 27/02* | (2006.01) | |

(52) U.S. Cl.
CPC .......... *A61K 9/0048* (2013.01); *A61K 9/5031* (2013.01); *A61K 9/5123* (2013.01); *A61K 9/5138* (2013.01); *A61K 9/5146* (2013.01); *A61K 31/56* (2013.01)

(58) Field of Classification Search
CPC .. A61K 9/0048; A61K 9/5031; A61K 9/5123; A61K 9/5138; A61K 9/5146; A61K 31/56; A61K 47/10; A61P 27/02
See application file for complete search history.

(56) References Cited

U.S. PATENT DOCUMENTS

| | | |
|---|---|---|
| 4,757,128 A | 7/1988 | Domb et al. |
| 4,789,724 A | 12/1988 | Domb et al. |
| 4,792,598 A | 12/1988 | Ziegast |
| 4,839,343 A | 6/1989 | Waeber et al. |
| 4,868,274 A | 6/1989 | Gupta et al. |
| 4,904,479 A | 2/1990 | Illum |
| 4,906,474 A | 3/1990 | Langer et al. |
| 4,910,225 A | 3/1990 | Ogawa et al. |
| 4,996,335 A | 2/1991 | Bodor |
| 4,999,417 A | 3/1991 | Domb |
| 5,145,684 A | 9/1992 | Liversidge et al. |
| 5,298,262 A | 3/1994 | Na et al. |
| 5,364,884 A | 11/1994 | Varma et al. |
| 5,429,824 A | 7/1995 | June |

(Continued)

FOREIGN PATENT DOCUMENTS

| | | |
|---|---|---|
| AU | 2006220411 A1 | 10/2006 |
| CA | 2 564 982 A1 | 11/2005 |

(Continued)

OTHER PUBLICATIONS

US 5,685,309 A, 11/1997, Edwards et al. (withdrawn)
U.S. Appl. No. 13/886,493, filed May 3, 2013, Nanocrystals, Compositons, and MethodsThat Aid Particle Transport in Mucus.
U.S. Appl. No. 14/731,921, filed Jun. 5, 2015, Nanocrystals, Compositions, and MethodsThat Aid Particle Transport in Mucus. .
U.S. Appl. No. 14/731,972, filed Jun. 5, 2016, Nanocrystals, Compostions, and Methods That Aid Particle Transport in Mucus.
U.S. Appl. No. 15/187,552, filed Jun. 20, 2016, Nanocrystals, Compositions, and Methods That Aid Particle Transport in Mucus.

(Continued)

*Primary Examiner* — Mina Haghighatian
(74) *Attorney, Agent, or Firm* — K&L Gates LLP; Louis C. Cullman; Benjamin D. Heuberger

(57) ABSTRACT

Particles, compositions, and methods that aid particle transport in mucus are provided. The particles, compositions, and methods may be used, in some instances, for ophthalmic and/or other applications. In some embodiments, the compositions and methods may involve modifying the surface coatings of particles, such as particles of pharmaceutical agents that have a low aqueous solubility. Such compositions and methods can be used to achieve efficient transport of particles of pharmaceutical agents though mucus barriers in the body for a wide spectrum of applications, including drug delivery, imaging, and diagnostic applications. In certain embodiments, a pharmaceutical composition including such particles is well-suited for ophthalmic applications, and may be used for delivering pharmaceutical agents to the front of the eye and/or the back of the eye.

13 Claims, 58 Drawing Sheets

(56) References Cited

U.S. PATENT DOCUMENTS

| | | |
|---|---|---|
| 5,518,187 A | 5/1996 | Bruno et al. |
| 5,534,259 A | 7/1996 | Zalipsky et al. |
| 5,540,930 A | 7/1996 | Guy |
| 5,543,158 A | 8/1996 | Gref et al. |
| 5,552,160 A | 9/1996 | Liversidge et al. |
| 5,567,435 A | 10/1996 | Hubbell |
| 5,576,311 A | 11/1996 | Guy |
| 5,578,325 A | 11/1996 | Domb et al. |
| 5,612,053 A | 3/1997 | Baichwal et al. |
| 5,665,331 A | 9/1997 | Bagchi et al. |
| 5,696,298 A | 12/1997 | Emanuele |
| 5,718,388 A | 2/1998 | Czekai et al. |
| 5,718,921 A | 2/1998 | Mathiowitz et al. |
| 5,747,061 A | 5/1998 | Aselem et al. |
| 5,800,807 A | 9/1998 | Hu et al. |
| 5,862,999 A | 1/1999 | Czekai et al. |
| 5,869,130 A | 2/1999 | Ferrier |
| 5,916,596 A | 6/1999 | Desai et al. |
| 5,922,357 A | 7/1999 | Coombes et al. |
| 5,989,591 A | 11/1999 | Nagi et al. |
| 6,106,819 A | 8/2000 | Sucher |
| 6,153,607 A | 11/2000 | Pflugfelder et al. |
| 6,165,509 A | 12/2000 | Hoffman et al. |
| 6,197,346 B1 | 3/2001 | Mathiowitz et al. |
| 6,217,908 B1 | 4/2001 | Mathiowitz et al. |
| 6,235,313 B1 | 5/2001 | Mathiowitz et al. |
| 6,264,981 B1 | 7/2001 | Zhang et al. |
| 6,270,806 B1 | 8/2001 | Liversidge |
| 6,287,588 B1 | 9/2001 | Shih |
| 6,365,187 B2 | 4/2002 | Mathiowitz et al. |
| 6,372,246 B1 | 4/2002 | Wei et al. |
| 6,413,539 B1 | 7/2002 | Shalaby |
| 6,432,381 B2 | 8/2002 | Liversidge |
| 6,495,164 B1 | 12/2002 | Ramstack |
| 6,589,549 B2 | 7/2003 | Shih |
| 6,610,318 B2 | 8/2003 | Bellmann et al. |
| 6,627,228 B1 | 9/2003 | Milstein et al. |
| 6,703,039 B2 | 3/2004 | Xia et al. |
| 6,706,289 B2 | 3/2004 | Lewis et al. |
| 7,060,299 B2 | 6/2006 | Alavattam et al. |
| 7,153,524 B2 | 12/2006 | Yoshihara et al. |
| 7,157,426 B2 | 1/2007 | Quay et al. |
| 7,163,697 B2 | 1/2007 | Hanes |
| 7,495,052 B2 | 2/2009 | Raiche et al. |
| 7,534,449 B2 | 5/2009 | Saltzman et al. |
| 7,550,441 B2 | 6/2009 | Farokhzad et al. |
| 7,544,371 B2 | 9/2009 | Kunzler et al. |
| 7,659,259 B2 | 2/2010 | Xia et al. |
| 7,763,278 B2 | 7/2010 | Cooper et al. |
| 7,795,237 B2 | 9/2010 | Ahmed et al. |
| 7,842,232 B2 | 11/2010 | Bosch et al. |
| 7,906,136 B2 | 3/2011 | Wong et al. |
| 8,133,512 B2 | 3/2012 | Kunzler et al. |
| 8,354,476 B2 | 1/2013 | Hanes |
| 8,409,607 B2 | 4/2013 | Hughes |
| 8,465,776 B2 | 6/2013 | Hughes |
| 8,481,069 B2 | 7/2013 | Hughes |
| 8,512,738 B2 | 8/2013 | Edelman |
| 8,628,801 B2 | 1/2014 | Garreta |
| 8,632,809 B2 | 1/2014 | Asgharian |
| 8,633,172 B2 | 1/2014 | Loftsson et al. |
| 8,663,674 B2 | 3/2014 | Wen |
| 8,758,816 B2 | 6/2014 | Fuge et al. |
| 8,859,525 B2 | 10/2014 | Marlow et al. |
| 8,889,193 B2 | 11/2014 | McDonnell |
| 8,911,768 B2 | 12/2014 | Whitcup |
| 8,957,034 B2 | 2/2015 | Hanes |
| 8,962,577 B2 | 2/2015 | Hanes |
| 9,056,057 B2 | 6/2015 | Popov |
| 9,458,169 B2 * | 10/2016 | Enlow .................. A61P 27/02 |
| 9,790,232 B2 * | 10/2017 | Enlow .................. A61K 9/10 |
| 9,827,191 B2 * | 11/2017 | Popov .................. A61P 27/02 |
| 10,646,436 B2 * | 5/2020 | Popov .................. A61K 9/5123 |
| 10,646,437 B2 * | 5/2020 | Popov .................. A61K 9/5123 |
| 10,688,041 B2 * | 6/2020 | Popov .................. A61K 9/10 |
| 10,688,045 B2 * | 6/2020 | Popov .................. A61K 9/5138 |
| 10,857,096 B2 * | 12/2020 | Popov .................. A61K 9/0048 |
| 10,864,219 B2 * | 12/2020 | Popov .................. A61P 29/00 |
| 10,940,108 B2 * | 3/2021 | Popov .................. A61K 9/5031 |
| 10,945,948 B2 * | 3/2021 | Popov .................. A61K 31/56 |
| 10,993,908 B2 * | 5/2021 | Popov .................. A61K 9/5031 |
| 11,219,196 B2 * | 1/2022 | Choi .................. A01K 85/18 |
| 11,219,597 B2 * | 1/2022 | Popov .................. A61K 47/10 |
| 11,318,088 B2 * | 5/2022 | Popov .................. A61K 31/56 |
| 11,596,599 B2 * | 3/2023 | Popov .................. A61K 9/5123 |
| 11,878,072 B2 * | 1/2024 | Popov .................. A61K 31/56 |
| 2002/0035264 A1 | 3/2002 | Karali et al. |
| 2002/0068090 A1 | 6/2002 | Bell et al. |
| 2003/0086895 A1 | 5/2003 | Hanes et al. |
| 2004/0071778 A1 | 4/2004 | Bellmann et al. |
| 2004/0076670 A1 | 4/2004 | Klinksick et al. |
| 2004/0175429 A1 | 9/2004 | Alavattam et al. |
| 2004/0209807 A1 | 10/2004 | Quay et al. |
| 2004/0234611 A1 | 11/2004 | Ahlheim |
| 2004/0258763 A1 | 12/2004 | Bell |
| 2005/0009910 A1 | 1/2005 | Hughes |
| 2005/0058603 A1 | 3/2005 | Gao et al. |
| 2005/0065091 A1 | 3/2005 | Peyman |
| 2005/0065901 A1 | 3/2005 | Peyman et al. |
| 2005/0095205 A1 | 5/2005 | Krishnamoorthy |
| 2005/0101676 A1 | 5/2005 | Fahl et al. |
| 2005/0182039 A1 | 8/2005 | Meyering |
| 2005/0191359 A1 | 9/2005 | Goldshtein et al. |
| 2005/0266067 A1 | 12/2005 | Sengupta et al. |
| 2005/0266090 A1 | 12/2005 | Prokop et al. |
| 2005/0288265 A1 | 12/2005 | Locher et al. |
| 2006/0018949 A1 | 1/2006 | Ammon et al. |
| 2006/0083781 A1 | 4/2006 | Shastri et al. |
| 2006/0210622 A1 | 9/2006 | Pace et al. |
| 2006/0257487 A1 | 11/2006 | Owen et al. |
| 2006/0292099 A1 * | 12/2006 | Milburn .................. A61K 9/0048 424/70.1 |
| 2007/0071756 A1 | 3/2007 | Peyman |
| 2007/0093461 A1 | 4/2007 | Shafiee |
| 2007/0110812 A1 | 5/2007 | Xia et al. |
| 2007/0141143 A1 * | 6/2007 | Smithey .................. A61K 9/1641 424/464 |
| 2007/0149480 A1 | 6/2007 | Ghosh et al. |
| 2007/0149593 A1 | 6/2007 | Ghosh |
| 2007/0178051 A1 | 8/2007 | Pruitt et al. |
| 2007/0212420 A1 | 9/2007 | Xia et al. |
| 2007/0218103 A1 | 9/2007 | Kunzler et al. |
| 2007/0218104 A1 | 9/2007 | Kunzler et al. |
| 2007/0231360 A1 | 10/2007 | Peyman |
| 2007/0249536 A1 | 10/2007 | Ma |
| 2007/0292524 A1 | 12/2007 | Ringe et al. |
| 2007/0299044 A1 | 12/2007 | Farng et al. |
| 2008/0086199 A1 | 4/2008 | Dave |
| 2008/0102128 A1 | 5/2008 | Constancis et al. |
| 2008/0145432 A1 | 6/2008 | Kakizawa |
| 2008/0159984 A1 | 7/2008 | Ben-Sasson |
| 2008/0166411 A1 | 7/2008 | Shah |
| 2008/0166414 A1 | 7/2008 | Hanes et al. |
| 2008/0175887 A1 | 7/2008 | Wang |
| 2008/0194468 A1 | 8/2008 | Bodor |
| 2008/0248125 A1 | 10/2008 | Irache Garreta et al. |
| 2008/0267876 A1 | 10/2008 | Benita et al. |
| 2008/0305172 A1 | 12/2008 | Ahlheim |
| 2008/0306039 A1 * | 12/2008 | Matsuhisa .................. A61K 47/26 514/179 |
| 2009/0074786 A1 | 3/2009 | Dor et al. |
| 2009/0087493 A1 | 4/2009 | Dai et al. |
| 2009/0087494 A1 | 4/2009 | Kompella et al. |
| 2009/0155182 A1 | 6/2009 | Mauro et al. |
| 2009/0203709 A1 | 8/2009 | Steinberg |
| 2009/0226531 A1 | 9/2009 | Lyons et al. |
| 2009/0247604 A1 | 10/2009 | Tang |
| 2010/0074957 A1 | 3/2010 | Robinson et al. |
| 2010/0076045 A1 | 3/2010 | Castillo et al. |
| 2010/0215580 A1 | 8/2010 | Hanes |
| 2010/0222308 A1 * | 9/2010 | Zhang .................. A61P 11/02 514/171 |
| 2010/0227905 A1 | 9/2010 | Kabra |
| 2010/0247668 A1 | 9/2010 | Eliasof et al. |

(56) References Cited

U.S. PATENT DOCUMENTS

| | | |
|---|---|---|
| 2010/0290983 A1 | 11/2010 | Rabinow et al. |
| 2010/0311808 A1* | 12/2010 | Lyons .............. A61K 9/1647 514/44 A |
| 2012/0028910 A1 | 2/2012 | Combal |
| 2012/0052041 A1 | 3/2012 | Basu |
| 2012/0053161 A1 | 3/2012 | Castillo et al. |
| 2012/0121718 A1 | 5/2012 | Lai et al. |
| 2012/0157499 A1 | 6/2012 | Hughes |
| 2012/0252756 A1 | 10/2012 | Coffey et al. |
| 2012/0269894 A1 | 10/2012 | Ahlheim |
| 2012/0289486 A1 | 11/2012 | Bodor |
| 2012/0321719 A1 | 12/2012 | McDonnell et al. |
| 2013/0071349 A1 | 3/2013 | Robinson |
| 2013/0236556 A1 | 3/2013 | Lai |
| 2013/0122064 A1 | 5/2013 | Ahlheim |
| 2013/0164343 A1 | 6/2013 | Hanes |
| 2013/0177609 A1 | 7/2013 | Proksch et al. |
| 2013/0183244 A1 | 7/2013 | Hanes |
| 2013/0210912 A1 | 8/2013 | Pavio et al. |
| 2013/0217657 A1 | 8/2013 | Lindstrom |
| 2013/0272994 A1 | 10/2013 | Hanes |
| 2013/0274217 A1 | 10/2013 | Hanes |
| 2013/0316001 A1 | 11/2013 | Popov |
| 2013/0316006 A1 | 11/2013 | Popov et al. |
| 2013/0316009 A1 | 11/2013 | Popov |
| 2013/0323313 A1 | 12/2013 | Suk |
| 2014/0031408 A1 | 1/2014 | Edelman |
| 2014/0107025 A1 | 4/2014 | Wirostko |
| 2014/0178475 A1 | 6/2014 | Figueiredo |
| 2014/0248358 A1 | 9/2014 | Figueiredo |
| 2014/0249158 A1 | 9/2014 | Figueiredo |
| 2014/0276482 A1 | 9/2014 | Astafieva |
| 2014/0294986 A1 | 10/2014 | Liu |
| 2014/0296191 A1 | 10/2014 | Patel et al. |
| 2014/0329913 A1 | 11/2014 | Hanes |
| 2014/0378401 A1 | 12/2014 | Horn |
| 2015/0038473 A1 | 2/2015 | Stein et al. |
| 2015/0044270 A1 | 2/2015 | McDonnell |
| 2015/0086484 A1 | 3/2015 | Hanes |
| 2015/0125539 A1 | 5/2015 | Popov |
| 2015/0187552 A1 | 7/2015 | Vandermey et al. |
| 2015/0265542 A1 | 9/2015 | Popov |
| 2015/0265543 A1 | 9/2015 | Popov |
| 2015/0297531 A1 | 10/2015 | Ensign |
| 2016/0287526 A1 | 10/2016 | Popov et al. |

FOREIGN PATENT DOCUMENTS

| | | |
|---|---|---|
| CN | 101129385 A | 2/2008 |
| CN | 101317847 | 10/2008 |
| EP | 0 692 510 B1 | 12/2004 |
| EP | 1 744 759 B1 | 9/2009 |
| EP | 2 127 655 A1 | 12/2009 |
| EP | 2335686 | 6/2011 |
| JP | 2011-140470 | 7/2011 |
| WO | 95/03356 A1 | 2/1995 |
| WO | 95/11669 A1 | 5/1995 |
| WO | 95/22318 A1 | 8/1995 |
| WO | 97/20578 A1 | 6/1997 |
| WO | 97/44013 A1 | 11/1997 |
| WO | 98/29097 A1 | 7/1998 |
| WO | 98/31346 A1 | 7/1998 |
| WO | 99/01498 A1 | 1/1999 |
| WO | 00/46147 A2 | 8/2000 |
| WO | 02/38127 A2 | 5/2002 |
| WO | 02/053189 A2 | 7/2002 |
| WO | 03/000237 A2 | 1/2003 |
| WO | 2004060977 | 7/2004 |
| WO | 2004/069225 | 8/2004 |
| WO | 2005/046671 A1 | 5/2005 |
| WO | 2005055985 A1 | 6/2005 |
| WO | 2005/072710 A2 | 8/2005 |
| WO | 2005/094836 A2 | 10/2005 |
| WO | 2006/044660 A2 | 4/2006 |
| WO | 2006/062875 A1 | 6/2006 |
| WO | 2006/063249 A2 | 6/2006 |
| WO | 2006063249 | 6/2006 |
| WO | 2006/091780 A2 | 8/2006 |
| WO | 2006094808 | 9/2006 |
| WO | 2007084418 | 7/2007 |
| WO | 2007/133808 A2 | 11/2007 |
| WO | 2008/030557 A2 | 3/2008 |
| WO | 2008/033924 A2 | 3/2008 |
| WO | 2008030557 | 3/2008 |
| WO | 2010040188 | 4/2008 |
| WO | 2008103673 | 8/2008 |
| WO | 2008/124632 A1 | 10/2008 |
| WO | 2009061607 | 5/2009 |
| WO | 2010132664 | 11/2010 |
| WO | 2011080148 A2 | 7/2011 |
| WO | 2011097347 | 8/2011 |
| WO | 2011/106168 A1 | 9/2011 |
| WO | 2011106702 | 9/2011 |
| WO | 2011/157428 A2 | 12/2011 |
| WO | 2011/159328 A1 | 12/2011 |
| WO | 2012/013884 A1 | 2/2012 |
| WO | 2012/014114 A1 | 2/2012 |
| WO | 2012/038942 A1 | 3/2012 |
| WO | 2012/038943 A1 | 3/2012 |
| WO | 2012/038944 A1 | 3/2012 |
| WO | 2012/039979 A2 | 3/2012 |
| WO | 2012054923 | 4/2012 |
| WO | 2012/059158 A1 | 5/2012 |
| WO | 2012/061703 A1 | 5/2012 |
| WO | 2012/071042 A1 | 5/2012 |
| WO | 2012/074980 A2 | 6/2012 |
| WO | 2012/088431 A1 | 6/2012 |
| WO | 2012/088469 A1 | 6/2012 |
| WO | 2012/093117 A1 | 7/2012 |
| WO | 2012/109363 A2 | 8/2012 |
| WO | 2012/127506 A1 | 9/2012 |
| WO | 2012/149228 A1 | 11/2012 |
| WO | 2012/155062 A1 | 11/2012 |
| WO | 2012/162698 A1 | 11/2012 |
| WO | 2013/040347 A1 | 3/2013 |
| WO | 2013/061269 A1 | 5/2013 |
| WO | 2013/065028 A1 | 5/2013 |
| WO | 2013/090804 A2 | 6/2013 |
| WO | 2013110028 | 7/2013 |
| WO | 2013138343 | 9/2013 |
| WO | 2013138346 | 9/2013 |
| WO | 2013166385 | 11/2013 |
| WO | 2013166408 | 11/2013 |
| WO | 2013166436 | 11/2013 |
| WO | 2013166498 | 11/2013 |
| WO | 2014047439 | 3/2014 |

OTHER PUBLICATIONS

U.S. Appl. No. 15/354,704, filed Nov. 17, 2016, Nanocrystals, Compositions, and Methods That Aid Particle Transport in Mucus.
U.S. Appl. No. 15/616,799, filed Jun. 7, 2017, Nanocrystals, Compositions, and Methods That Aid Particle Transport in Mucus.
U.S. Appl. No. 15/976,736, filed May 10, 2018, Nanocrystals, Compositions, and Methods That Aid Particle Transport in Mucus.
U.S. Appl. No. 16/923,980, filed Jul. 8, 2020, Nanocrystals, Compositions, and Methods That Aid Particle Transport in Mucus.
U.S. Appl. No. 18/100,363, filed Jan. 23, 2023, Nanocrystals, Compositions, and Methods That Aid Particle Transport in Mucus.
U.S. Appl. No. 13/886,602, filed May 3, 2013, Particles, Compositions, and Methods for Ophthalmic and/or Other Applications.
U.S. Appl. No. 13/886,658, filed May 3, 2013, Particles, Compositions, and Methods for Ophthalmic and/or Other Applications.
U.S. Appl. No. 15/992,494, filed May 30, 2018, Particles, Compositions, and Methods for Ophthalmic and/or Other Applications.
U.S. Appl. No. 16/945,398, filed Jul. 31, 2020, Particles, Compositions, and Methods for Ophthalmic and/or Other Applications.
U.S. Appl. No. 14/070,506, filed Nov. 2, 2013, Particles, Compositions, and Methods for Ophthalmic and/or Other Applications.
U.S. Appl. No. 15/808,746, filed Nov. 9, 2017, Compositions, and Methods for Ophthalmic and/or Other Applications.

(56) References Cited

OTHER PUBLICATIONS

U.S. Appl. No. 15/977,911, filed May 11, 2018, Compositions, and Methods for Ophthalmic and/or Other Applications.
U.S. Appl. No. 15/977,940, filed May 11, 2018, Compositions, and Methods for Ophthalmic and/or Other Applications.
U.S. Appl. No. 16/221,253, filed Dec. 14, 2018, Compositions, and Methods for Ophthalmic and/or Other Applications.
U.S. Appl. No. 16/888,371, filed May 29, 2020, Compositions, and Methods for Ophthalmic and/or Other Applications.
U.S. Appl. No. 16/896,007, filed Jun. 8, 2020, Compositions, and Methods for Ophthalmic and/or Other Applications.
U.S. Appl. No. 16/988,459, filed Aug. 7, 2020, Compositions, and Methods for Ophthalmic and/or Other Applications.
U.S. Appl. No. 16/988,470, filed Aug. 7, 2020, Compositions, and Methods for Ophthalmic and/or Other Applications.
U.S. Appl. No. 17/170,701, filed Feb. 8, 2021, Compositions, and Methods for Ophthalmic and/or Other Applications.
U.S. Appl. No. 17/207,442, filed Mar. 19, 2021, Compositions, and Methods for Ophthalmic and/or Other Applications.
U.S. Appl. No. 17/207,467, filed Mar. 19, 2021, Compositions, and Methods for Ophthalmic and/or Other Applications.
International Preliminary Report on Patentability of PCT/US2011/059321 (WO2012/061703).
International Preliminary Report on Patentability of PCT/US2011/051195 (WO2012/039979).
International Preliminary Report on Patentability of PCT/US2012/024344 (WO2012/0109363).
International Preliminary Report on Patentability of PCT/US2012/069882 (WO2013/090804).
International Preliminary Report on Patentability of PCT/US2013/022387 (WO2013/110028).
International Preliminary Report on Patentability of PCT/US2013/039731 (WO2013/166498).
International Preliminary Report on Patentability of PCT/US2011/026321 (WO2011/106702).
International Preliminary Report on Patentability of PCT/US2013/039499 (WO2013/166408).
International Preliminary Report on Patentability of PCT/US2013/039467 (WO2013/166385).
International Preliminary Report on Patentability of PCT/US2013/039540 (WO2013/166436).
International Preliminary Report on Patentability of PCT/US2014/063373 (WO2015/066444).
Sigurdsson et al. "Mucus as a barrier to lipophillic drugs" Int J Pharmaceutics 453:56-64, 2013.
International Preliminary Report on Patentability and Written Opinion for PCT/US2005/002556 mailed Jul. 31, 2006.
International Preliminary Report on Patentability and Written Opinion for PCT/US2007/019522 mailed Mar. 10, 2009.
Jones et al., Journal of Pharmaceutical Sciences, 95: 1060-1074, 2006.
Kassem et al., International Journal of Pharmaceutics, 340: 126-133, 2007.
Lieleg et al., Biophysical Journal, 98: 1782-1789, 2010.
Xia et al., European Journal of Pharmaceutical Sciences, 40: 325-334, 2010.
Bouazza, N.; et al. "Population Pharmacokinetics of Tenofovir in HIV-1-infected Pediatric Patients" J. Acquire Immune Defic Syndr. 2011, 58 (3), 283-288.
Declaration of Dr. Alexey Popov executed Feb. 21, 2013 with Curriculum vitae in EP2061433.
Hancock et al., "What is the True Solubility Advantage for Amorphous Pharmaceuticals?", Pharmaceutical Research, (Nov. 4, 2000), vol. 17, No. 4, pp. 397-404.
Lai et al., Journal of Virology, 83: 11196-11200 (Year: 2009).
Shuai et al., "Synthesis and characterization of several degradable aliphatic polyanhydrides", Journal of Beijing Institute of Technology (English Edition), (1996), vol. 5, No. 2, pp. 130-136 abstract only.
Vandervoort et al., European Journal of Pharmaceutics and Biopharmaceutic, 57: 251-261 (Year: 2004).
Yamagata et al., Improvement of the Oral Drug Absorption of Topotecan through the Inhibition of Intestinal Xenobiotic Efflux Transporter, Breast Cancer Resistance Protein, by Excipients, 35(7) Drug Metabolism and Disposition 1142-1148 (2007).
International Preliminary Report on Patentability from PCT/US2013/039467 (WO2013/166385 IPRP).
Cholkar K et al. "Novel strategies for anterior segment ocular drug delivery" J Ocul Pharmacol Ther, 29:106-123, 2013.
Gaudana R et al. "Ocular drug delivery" AAPS J, 12:348-360, 2010.
Molokhia SA et al. "Anterior eye segment drug delivery systems: current treatments and future challenges" J Ocul Pharmacol Ther, 29:92-104, 2013.
Patel PB et al. "Ophthalmic drug delivery systems: challenges and approaches" Syst Rev Pharm, 1:113-120, 2010.
Singh V et al. "The challenges of ophthalmic drug delivery: a review" Int J Drug Discovery, 3:56-62, 2011.
Mura S et al. "Biodegradable Nanoparticles Meet the Bronchial Airway Barrier: How Surface Properties Affect Their Interaction with Mucus and Epithelial Cells" Biomacromolecues 12:4136-4143, 2011.
Garg et al. "Mucoadhesive microspheres: a short review" Asian J Pharma Clin Res 5:24-27, 2012.
Danhier et al. "PLGA-based nanoparticles: An overview of biomedical applications" J Controlled Rel 161:505-522, 2012.
Corrigan et al. "Quantifying drug release from PLGA nanoparticles" Eur J Pharma Sci 37:477-485, 2009.
Kie et al. "PLGA Nanoparticles Improve the Oral Bioavailability of Curcumin in Rats: Characterizations and Mechanisms" J Agric Food Chem 59:9280-9289, 2011.
Lai et al., "Mucus-penetrating nanoparticles for drug and gene delivery to mucosal tissues", Adv. Drug Deliv. Rev., (Feb. 27, 2009), vol. 61, No. 2, 36 pages.
Lai et al., "Drug carrier nanoparticles that penetrate human chronic rhinosinusitis mucus", Biomaterials, (2011), vol. 32, pp. 6285-6290.
Lai et al., "Altering Mucus Rheology to "Solidify" Human Mucus at the Nanoscale", PLoS One, (Jan. 2009), vol. 4, Issue 1, pp. 1-6.
Lai et al., "Rapid transport of large polymeric nanoparticles in fresh undiluted human mucus", PNAS, (Jan. 30, 2007), vol. 104, No. 5, pp. 1482-1487.
Lai et al., "Nanoparticles reveal that human cervicovaginal mucus is riddled with pores larger than viruses", PNAS, (Jan. 12, 2010), vol. 107, No. 2, pp. 598-603.
Lipman et al., "Monoclonal Versus Polyclonal Antibodies: Distinguishing Characteristics, Applications, and Information Resources", ILAR Journal, (2005), vol. 46, No. 3, pp. 258-268.
Lo et al., "Formulation design and pharmaceutical development of a novel controlled release form of azithromycin for single-dose therapy", Drug Development and Industrial Pharmacy, (2009), vol. 35, No. 12, pp. 1522-1529.
Qiu et al., "Compatibility and degradation of new polyphosphazene/polyanhydride blend", CAPLUS, (2001), No. 5, Abstract Only.
Abelson et al., "Loteprednol Etabonate in the Management of Dry Eye Inflammation", Refractive eyecare for ophthalmologists, (Nov. 2000), vol. 4, No. 11, pp. 4-7.
Mert et al., "A poly(ethylene glycol)-based surfactant for formulation of drug-loaded mucus penetrating particles", Journal of Controlled Release, (2012), vol. 157, pp. 455-460.
Mu et al., "Vitamin E TPGS used as emulsifier in the solvent evaporation/extraction technique for fabrication of polymeric nanospheres for controlled release of paclitaxel (Taxol®)", Journal of Controlled Release, (2002), vol. 80, pp. 129-144.
Nance et al., "A Dense Poly(Ethylene Glycol) Coating Improves Penetration of Large Polymeric Nanoparticles Within Brain Tissue", Science Translational Medicine, (Aug. 29, 2012), vol. 4, Issue 149, pp. 1-8.
Newman et al., "Uptake of poly(D,L-lactic-co-glycolic acid) microspheres by antigen-presenting cells in vivo", Journal of Biomedical Materials Research, (Jun. 5, 2002), vol. 60, Issue 3, pp. 480-486.
Norris et al., "Effect of Size, Surface Charge, and Hydrophobicity on the Translocation of Polystyrene microspheres Through Gastro-

(56) References Cited

OTHER PUBLICATIONS intestinal Mucin", Journal of Applied Polymer Science, (Mar. 14, 1997), vol. 63, Issue 11, pp. 1481-1492.
Norris et al., "The Uptake and Translocation of Microparticles through GI Mucin", Pharma. Res., (1995), vol. 12, pp. S233 abstract only.
Peppas et al., "Ultrapure poly(vinyl alcohol) hydrogels with mucoadhesive drug delivery characteristics", European Journal of Pharmaceutics and Biopharmaceutics, (1997), vol. 43, pp. 51-58.
Peppas et al., "Poly(ethylene glycol)-containing hydrogels in drug delivery", Journal of Controlled Release, (1999), vol. 62, pp. 81-87.
Peracchia et al., "PEG-coated nanospheres from amphiphilic diblock and multiblock copolymers: Investigation of their drug encapsulation and release characteristics", Journal of Controlled Release, (1997), vol. 46, pp. 223-231.
Perry, "Sorbent Materials and Sorption-Process Analysis", Perry's Chemical Engineers' Handbook, (1984), vol. 6, pp. 16-5-16-6.
Pillai et al., "Polymers in drug delivery", Current Opinion in Chemical Biology, (2001), vol. 5, pp. 447-451.
Prasad et al., "Confocal microscopy of colloids", Journal of Physics Condensed Matter, (2007), vol. 19, pp. 1-25.
Prego et al., "The potential of chitosan for the oral administration of peptides", Expert Opinion Drug Deliver, (2005), vol. 2, No. 5, pp. 843-854.
Pui, "Rasburicase: a potent uricolytic agent", Expert Opin. Pharmacother., (2002), vol. 3, No. 4, pp. 433-452.
Qiu et al., "Design of a core-shelled polymer cylinder for potential programmable drug delivery", International Journal pf Pharmaceutics, (2001), vol. 219, pp. 151-160.
Rodeheaver et al., "Pluronic F-68: A Promising New Skin Wound Cleanser", Ann Emerg Med, (Nov. 1980), vol. 9, No. 11, pp. 572-576.
Rolland et al., "Direct Fabrication and Harvesting of Monodisperse, Shape-Specific Nanobiomaterials", J. Am. Chem. Soc., (2005), vol. 127, No. 28, pp. 10096-10100.
Schuster et al., "Nanoparticle diffusion in respiratory mucus from humans without lung disease", Biomaterials, (2013), vol. 34, pp. 3439-3446.
Serra et al., "Engineering Design and Molecular Dynamics of Mucoadhesive Drug Delivery Systems as Targeting Agents", Eur. J. Pharm. Biopharm., (Mar. 2009), vol. 71, No. 3, 24 pages.
Serra et al., "Design of poly(ethylene glycol)-tethered copolymers as novel mucoadhesive drug delivery systems", European Journal of Pharmaceutics and Biopharmaceutics, (2006), vol. 63, pp. 11-18.
Shakesheff et al., "The Adsorption of Poly(vinyl alcohol) to Biodegradable Microparticles Studied by X-Ray Photoelectron Spectroscopy (XPS)", Journal of Colloid and Interface Science, (1997), vol. 185, pp. 538-547.
Singh et al., "Cationic microparticles: A potent delivery system for DNA vaccines", PNAS, (Jan. 18, 2000), vol. 97, No. 2, pp. 811-816.
Singla et al., "Paclitaxel and its formulations", International Journal of Pharmaceutics, (2002), vol. 235, pp. 179-192.
Suh et al., "Real-time multiple-particle tracking: applications to drug and gene delivery", Advanced Drug Delivery Reviews, (2005), vol. 57, pp. 63-78.
Suh et al., "PEGylation of nanoparticles improves their cytoplasmic transport", International Journal of Nanomedicine, (2007), vol. 2, No. 4, pp. 735-741.
Suk et al., "The penetration of fresh undiluted sputum expectorated by cystic fibrosis patients by non-adhesive polymer nanoparticles", Biomaterials, (2009), vol. 30, pp. 2591-2597.
Suk et al., "N-acetylcysteine Enhances Cystic Fibrosis Sputum Penetration and Airway Gene Transfer by Highly Compacted DNA Nanoparticles", Molecular Therapy, (Nov. 2011), vol. 19, No. 11, pp. 1981-1989.
Suk et al., "Rabid transport of muco-inert nanoparticles in cystic fibrosis sputum treated with N-acetyl cysteine", Nanomedicine, (2011), vol. 6, No. 2, pp. 365-375.

Tang et al., "Biodegradable polymer nanoparticles that rapidly penetrate the human mucus barrier", PNAS, (Nov. 17, 2009), vol. 106, No. 46, pp. 19268-19273.
Vila et al., "Transport of PLA-PEG particles across the nasal mucosa: effect of particle size and PEG coating density", Journal of Controlled Release, (2004), vol. 98, pp. 231-244.
Whaley et al., "Novel Approaches to Vaginal Delivery and Safety of Microbicides: Biopharmaceuticals, Nanoparticles, and Vaccines", Antiviral Research, (2010), vol. 885, pp. S55-S66.
Wang et al., "Mucoadhesive Nanoparticles May Disrupt the Protective Human Mucus Barrier by Altering Its Microstructure", PLoS One, (Jun. 2011), vol. 6, Issue 6, pp. 1-7.
Wang et al., "Addressing the PEG Mucoadhesivity Paradox to Engineer Nanoparticles that "Slip" through the Human Mucus Barrier", Angew. Chem. Int. Ed., (2008), vol. 47, pp. 1-5.
Wu et al., "Novel Nanoparticles Formed via Self-Assembly of Poly(ethylene glycol-b-sebacic anhydride) and Their Degradation in Water", Macromolecules, (2000), vol. 33, pp. 9040-9043.
Xu et al., "Nanoparticle diffusion in, and microrheology of, the bovine vitreous ex vivo", Journal of Controlled Release, (2013), vol. 167, pp. 76-84.
Xu et al., "Scalable method to produce biodegradable nanoparticles that rapidly penetrate human mucus", Journal of Controlled Release, (2013), vol. 170, pp. 279-286.
Yang et al., "Biodegradable Nanoparticles Composed Entirely of Safe Materials that Rapible Penetrate Human Mucus", Angew. Chem. Int. Ed., (2011), vol. 50, pp. 2597-2600.
Yoncheva et al., "Bioadhesive properties of pegylated nanoparticles", Expert Opin. Drug Deliv., (2005), vol. 2, No. 2. pp. 205-218.
Yoncheva et al., "Evaluation of bioadhesive potential and intestinal transport of pegylated poly(anhydride) nanoparticles", International Journal of Pharmaceutics, (2007), vol. 334, pp. 156-165.
Yoo et al., "Biodegradable Nanoparticles Containing Doxorubicin-PLGA Conjugate for Sustained Release", Pharmaceutical Research, (1999), vol. 16, No. 7, pp. 1114-1118.
Yu et al., "Biodegradable mucus-penetrating nanoparticles composed of diblock copolymers of polyethylene glycol and poly(lactic-co-glycolic acid)", Drug Deliv. and Transl. Res., (2012), vol. 2, pp. 124-128.
Yang M. et al. "Production of virus-mimetic mucus-penetrating particles for drug and gene delivery in mucosal issues." 2008 Annual Meeting of AIChE Nanoscale Science and Engineering Forum, Nov. 16-21, 2008, Abstract 705b.
Ludwig A "The use of mucoadhesive polymers in ocular drug delivery." Adv Drug Deliv Rev 57:1595-1639, 2005.
Memon A. et al. "Optimization of formulation parameters on ocular loteprednol etabonate nanosuspension by media milling method." Int J Pharmaceut Biol Arch 4:46-51, 2012.
Sahib MN et al. "Solubilization of beclomethasone dipropionate in sterically stabilized phospholipid nanomicelles (SSMs): physicochemical and in vitro evaluations." Drug Des Devel Ther 6:29-42, 2012.
Alexandridis, "Poly(ethylene oxide)/poly(propylene oxide) block copolymer surfactants", Current Opinion in Colloid & Interface Science, (Oct. 1997), vol. 2, Issue 5, pp. 478-489.
International Preliminary Report on Patentability and Written Opinion for PCT/US2007/019522.
International Search Report issued Mar. 12, 2008 for PCT/US2007/019522.
International Search Report for PCT/US2005/002556 mailed Jun. 19, 2006.
International Search Report for PCT/US2011/059321 mailed Feb. 8, 2012.
International Search Report issued in PCT/US2014/063373, mailed on Feb. 24, 2015.
International Search Report mailed on Aug. 26, 2013, in PCT/US2013/039499.
International Search Report mailed on Oct. 17, 2013, in PCT/US2013/039540.
Kapin et al., Inflammation-Mediated Retinal Edema in the Rabbit Is Inhibited by Topical Nepafenac, Inflammation, (Oct. 2003), vol. 27, No. 5, pp. 281-291.

(56) References Cited

OTHER PUBLICATIONS

Lin et al., "Carbopol.pluronic phase change solutions for ophthalmic drug delivery", Journal of Controlled Release, (2000), vol. 69, pp. 379-388.
Schopf et al. "Long-acting Mucus-Penetrating Steroid Particles Exhibit Improved Duration of Action in a Lung Inflammation Model," 17th International Conference of the Inflammation Research Association, Bolton Landing, NY. (Aug. 29, 2012) Suppl 2 Vol 57 2012 ISSN . A154 p. S.
Schopf et al. "Long-acting Mucus-Penetrating Steroid Particles Exhibit Improved Duration of Action in a Lung Inflammation Model," Inflammation Research, 61(Suppl 1) Published online Aug. 14, 2012.
Schopf et al. "Enhanced Topical Delivery of a Small Molecule Receptor Tyrosine Kinase Inhibitor (RTKi) via Mucosal-Penetrating Particle Technology" Association for Research in Vision and Ophthamology, May 5-9, 2013.
Albertsson et al., "Synthesis, Characterization and Degradation of Aliphatic Polyanhydrides", British Polymer Journal, (1990), vol. 23, No. 3, pp. 205-212.
Apgar et al., "Multiple-Particle Tracking Measurements of the Heterogeneities in Solutions of Actin Filaments and Actin Bundles", Biophysical Journal, (Aug. 2000), vol. 79, No. 2, pp. 1095-1106.
Batrakove et al., "Pluronic Block Copolymers: Evolution of Drug Delivery Concept from Inert Nanocarriers to Biological Response Modifiers", J. Control Release, (Sep. 10, 2008), vol. 130, No. 2, 25 pages.
Bhalla, "Microtubule-targeted anticancer agents and apoptosis", Oncogene, (2003), vol. 22, pp. 9075-9086.
Boskey et al., "A Self-Sampling Method to Obtain Large Volumes of Undiluted Cervicovaginal Secretions", Sexually Transmitted Diseases, (Feb. 2003), vol. 30, No. 2, pp. 107-109.
Boylan et al., "Enhancement of airway gene transfer by DNA nanoparticles using a pH-responsive block copolymer glycol and poly-L-lysine", Biomaterials, (2012) vol. 33, pp. 2361-2371.
Boylan et al., "Highly compacted DNA nanoparticles with low MW Peg coatings: In vitro, ex vivo and in vivo evaluation", Journal of Controlled Release, (2012), vol. 157, pp. 72-79.
Brorson et al., "Mutational Analysis of Avidity and Fine Specificity of Anti-Levan Antibodies", The Journal of Immunology, (1999), pp. 6694-6701.
Brummell et al., "Probing the Combining Site of an Anti-Carbohydrate Antibody by Saturation-Mutagenesis: Role of the Heavy-Chain CDR3 Residues", Biochemistry, (1993), vol. 32, No. 4, pp. 1180-1187.
Bures et al., "Surface modifications and molecular imprinting of polymers in medical and pharmaceutical applications", Journal of Controlled Release, (2001), vol. 72, pp. 25-33.
Burks et al., "In vitro scanning saturation mutagenesis of an antibody binding pocket", Proc. Natl. Acad. Sci. USA, (Jan. 1997), vol. 94, pp. 412-417.
Chan et al., "Phase behavior and miscibility in blends of poly(sebacic anhydride)/poly(ethylene glycol)", Biomaterials, (2002), vol. 23, pp. 2353-2358.
Bin Choy et al., "Mucoadhesive Microparticles Engineered for Ophthalmic Drug Delivery", J. Phys. Chem Solids, (May 2008), vol. 69, No. 5-6, 8 pages.
Colman, "Effects of amino acid sequence changes on antibody-antigen interactions", Research in Immunology, (1994), vol. 145, pp. 33-36.
Cone, "Barrier properties of mucus", Advanced Drug Delivery Reviews, (2009), vol. 61, pp. 75-85.
Cone, "Mucus", Mucosal Immunology, (1999), Section Edition, Chapter 4, pp. 43-64.
Cu et al., "Controlled surface modification with poly(ethylene)glycol enhances diffusion of PLGA nanoparticles in human cervical mucus", Mol Pharm., (2009), vol. 6, No. 1, 18 pages.
Dawson et al., "Transport of Polymeric Nanoparticle Gene Carriers in Gastric Mucus", Biotechnol. Prog., (2004), vol. 20, No. 3, pp. 851-857.

Dawson et al., "Enhanced Viscoelasticity of Human Cystic Fibrotic Sputum Correlates with Increasing Microheterogeneity in Particle Transport", The Journal of Biological Chemistry, (2003), vol. 278, No. 50, pp. 50393-50401.
Dawson et al., "Primary parenteral transmission of bovine spongiform encephalopathy to the pig", The Veterinary Record, (Sep. 29, 1990), 1 page.
De Campos et al., "The effect of a PEG versus a chitosan coating on the interaction of drug colloidal carriers with the ocular mucosa", European Journal of Pharmaceutical Sciences, (2003), vol. 20, pp. 73-81.
Delgado et al., "Radiolabelled biodegradable microspheres for lung imaging", European Journal of Pharmaceutics and Biopharmaceutics, (2000), vol. 50, pp. 227-236.
Denis-Mize et al., "Plasmid DNA adsorbed onto cationic microparticles mediates target gene expression and antigen presentation by dendritic cells", Gene Therapy, (2000), vol. 7, pp. 2105-2112.
Donaldson et al., "A placebo-controlled multi-centred evaluation of an anaesthetic gel (Oraqix®) for periodontal therapy", Journal of Clinical Peridontology, (2003), vol. 30, pp. 171-175.
Dufner et al., "Harnessing phage and ribosome display for antibody optimisation", TRENDS in Biotechnology, (2006), vol. 24, No. 11, pp. 523-529.
Dumortier et al., "A Review of Poloxamer 407 Pharmaceutical and Pharmacological Characteristics", Pharmaceutical Research, (Dec. 2006), vol. 23, No. 12, pp. 2709-2728.
Ehrhardt et al., "Drug Absorption by the Respiratory Mucosa: Cell Culture Models and Particulate Drug Carriers", Journal of Aerosol Medicine, (2002), vol. 15, No. 2, pp. 131-139.
Emanuele, "FLOCOR™: a new anti-adhesive, rheologic agent", Expert Opinion on Investigational Drugs, (1998), vol. 7, No. 7, pp. 1193-1200.
Ensign et al., "Oral drug delivery with polymeric nanoparticles: The gastrointestinal mucus barriers", Advanced Drug Delivery Reviews, (2012), vol. 64, pp. 557-570.
Ensign et al., "Mucus Penetrating Nanoparticles: Biophysical Tool and Method of Drug and Gene Delivery", Advanced Materials, (2012), vol. 24, pp. 3887-3894.
Ensign et al., "Enhanced vaginal drug delivery through the use of hypotonic formulations that induce fluid uptake", Biomaterials, (2013), vol. 34, pp. 6922-6929.
Ensign et al., "Ex Vivo Characterization of Particle Transport in Mucus Secretions Coating Freshly Excised Mucosal Tissues", Molecular Pharmaceutics, (2013), vol. 10, pp. 2176-2182.
Ensign et al., "Mucus-Penetrating Nanoparticles for Vaginal Drug Deliver Protect Against Herpes Simplex Virus", Science Translational Medicine, (2012), vol. 4, Issue 138, pp. 1-10.
Escobar-Chavez et al., "Application of Thermo-Reversible Pluronic F-127 Gels in Pharmaceutical Formulations", J. Pharm. Pharmaceut. Sci., (2006), vol. 9, No. 3, pp. 339-358.
Farokhzad et al., "Targeted nanoparticle-aptamer bioconjugates for cancer chemotherapy in vivo", PNAS, (Apr. 18, 2006), vol. 103, No. 16, pp. 6315-6320.
Fresta et al., "Ocular Tolerability and In Vivo Bioavailability of Poly(ethylene glycol) (PEG)-Coated Polyethyl-2-Cyanoacrylate Nanosphere-Encapsulated Acyclovir", Journal of Pharmaceutical Science, (Mar. 2001), vol. 90, No. 3, pp. 288-297.
Fu et al., "New polymeric carriers for controlled drug delivery following inhalation or injection", Biomaterials, (2002), vol. 23, pp. 4425-4433.
Giannavola et al., "Influence of Preparation Conditions on Acyclovir-Loaded Poly-d, I-Lactic Acid Nanospheres and Effect of PEG Coating on Ocular Drug Bioavailability", Pharmaceutical Research, (Apr. 2003), vol. 20, No. 4, pp. 584-590.
Giunchedi et al., "Emulsion Spray-Drying for the Preparation of Albumin-Loaded PLGA Microspheres", Drug Development and Industrial Pharmacy, (2001), vol. 27, No. 7, pp. 745-750.
Hida et al., "Common Gene Therapy Viral Vectors Do Not Efficiently Penetrate Sputum from Cystic Fibrosis Patients", PLoS One, (May 2011), vol. 6, Issue 5, pp. 1-6.
Huang et al., "Molecular aspects of muco- and bioadhesion: Tethered structures and site-specific surfaces", Journal of Controlled Release, (2000), vol. 65, pp. 63-71.

(56) References Cited

OTHER PUBLICATIONS

Jachak et al., "Transport of metal oxide nanoparticles and single walled carbon nanotubes in human mucus", Nanotoxicology, (Sep. 2012), vol. 6, No. 6, pp. 614-622.

Jang et al., "The structural basis for DNA binding by an anti-DNA autoantibody", Molecular Immunology, (1998), vol. 35, pp. 1207-1217.

Jiang et al., "Pulsatile protein release from a laminated device comprising of polyanhydrides and pH-sensitive complexes", International Journal of Pharmaceutics, (2000), vol. 194, pp. 51-60.

Jiang et al., Preparation, characterization and degradation characteristics of polyanhydrides contained poly(ethylene glycol), Polymer International, (1999), vol. 48, pp. 47-52.

Kim et al., "Use of Single-Site-Functionalized PEG Dendrons to Prepare Gene Vectors that Penetrate Human Mucus Barriers", Angewandte Chemie International Edition, (2013), vol. 52, pp. 3985-3988.

Kim et al., "Comparison of the pharmacokinetic profiles of two locally administered doxycycline gels in crevicular fluid and saliva", Journal of Clinical Periodontology, (2004), vol. 31, pp. 286-292.

Knowles et al., "Mucus clearance as primary innate defense mechanism for mammalian airways", The Journal of Clinical Investigation, (Mar. 2002), vol. 109, No. 5, pp. 571-577.

Kobayashi et al., "Tryptophan H33 plays an important role in pyrimidine (6-4) pyrimidone photoproduct binding by a high-affinity antibody", Protein Engineering, (1999), vol. 12, No. 10, pp. 879-884.

Lai et al., "Micro- and macrorheology of mucus", Advanced Drug Delivery Reviews, (2009), vol. 61, pp. 86-100.

Wang et al. "Preparation, characterization of paclitaxel-loaded Pluronic P105 polymeric micelles and in vitro reversal of multidrug resistant tumor." Acta Pharmaceutica Sincia 43:640-646, 2008.

U.S. Appl. No. 15/977,940, filed May 11, 2018.

* cited by examiner

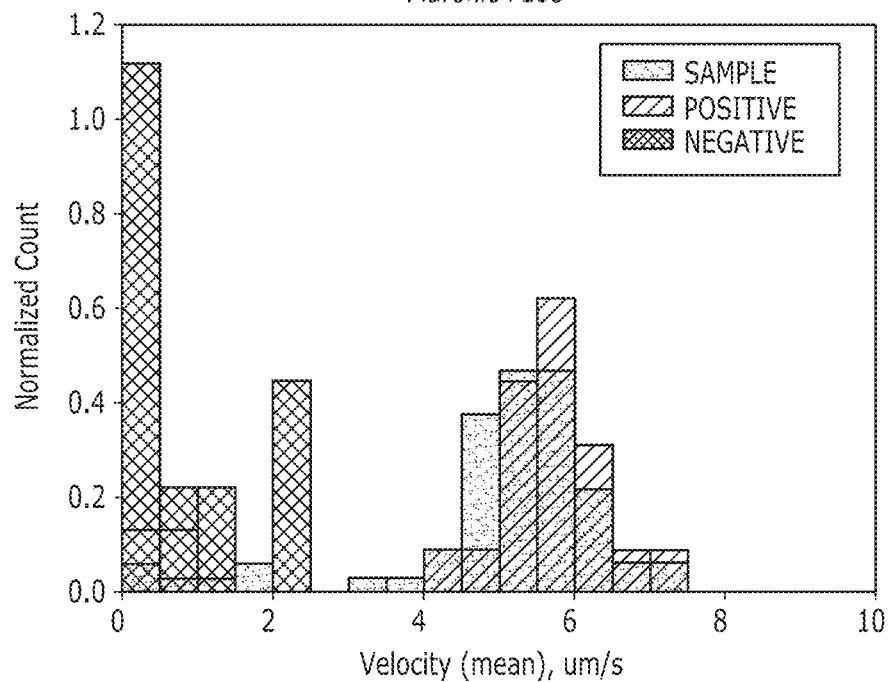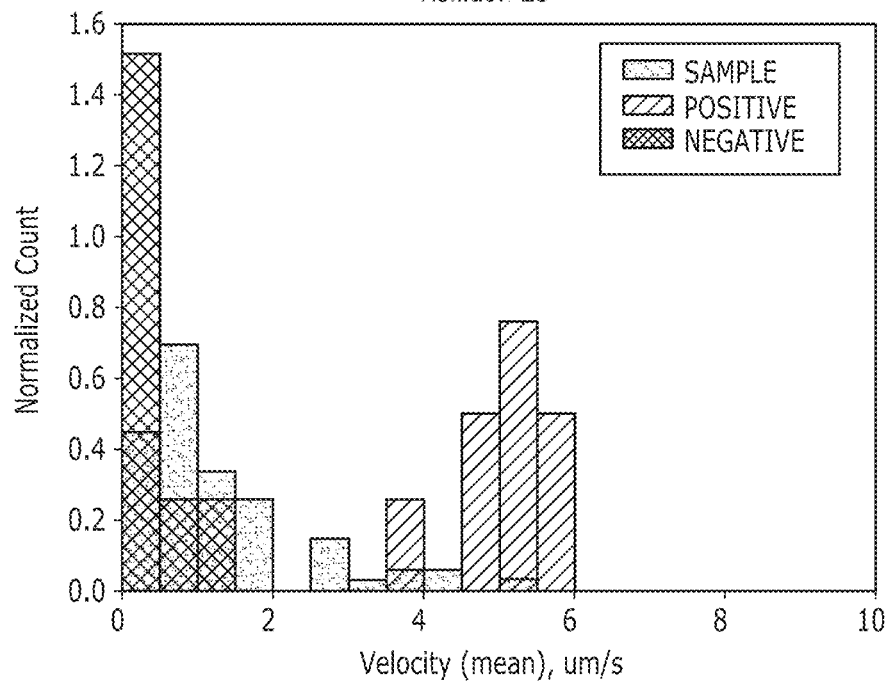

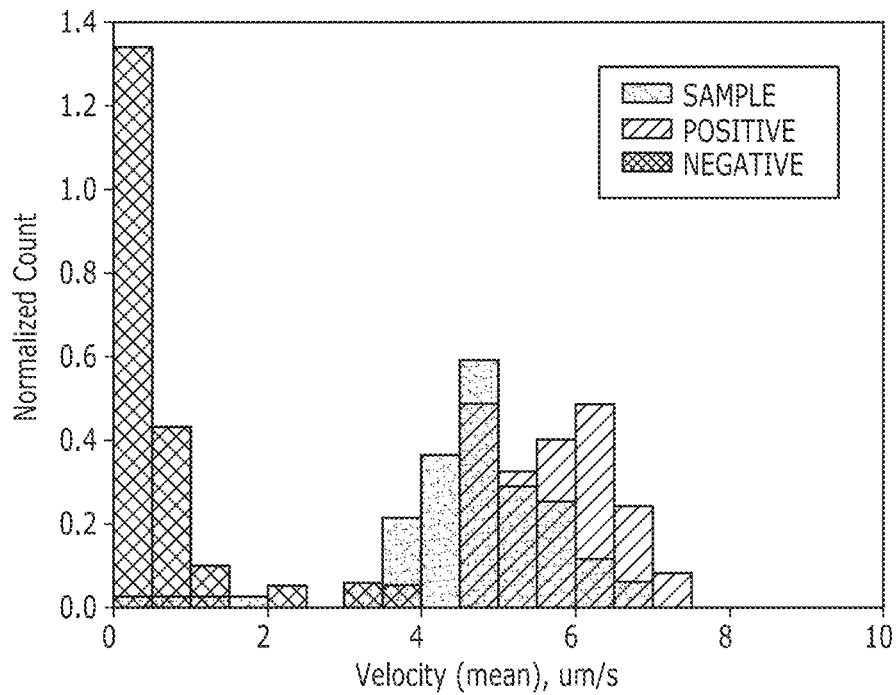
FIG. 13A PVA2K75
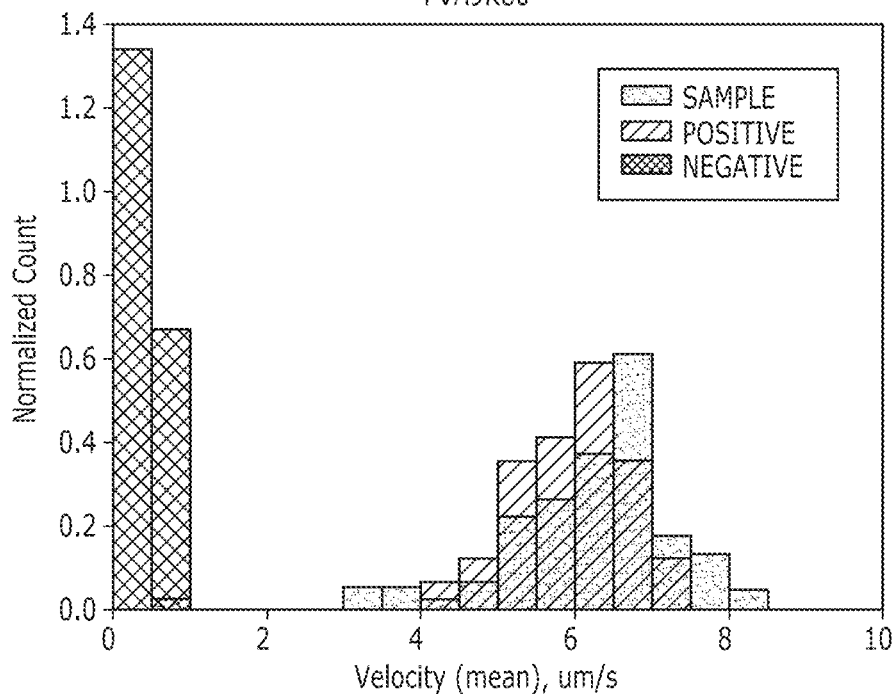
FIG. 13B PVA9K80

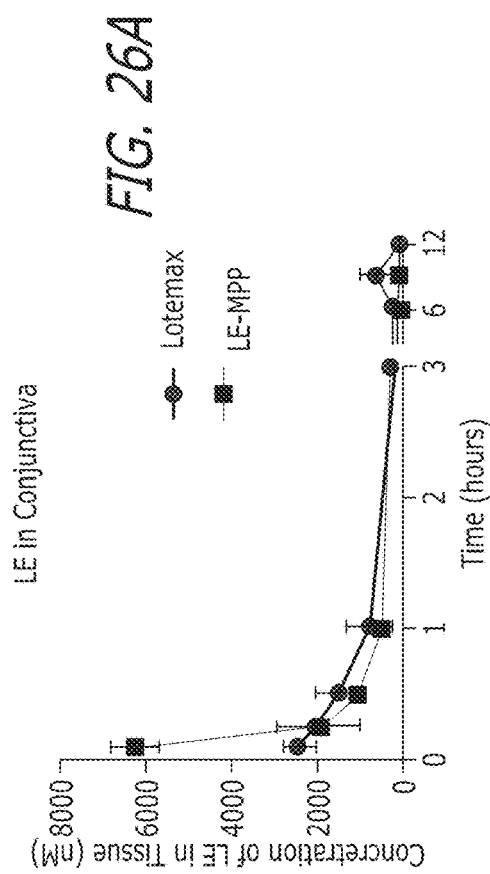
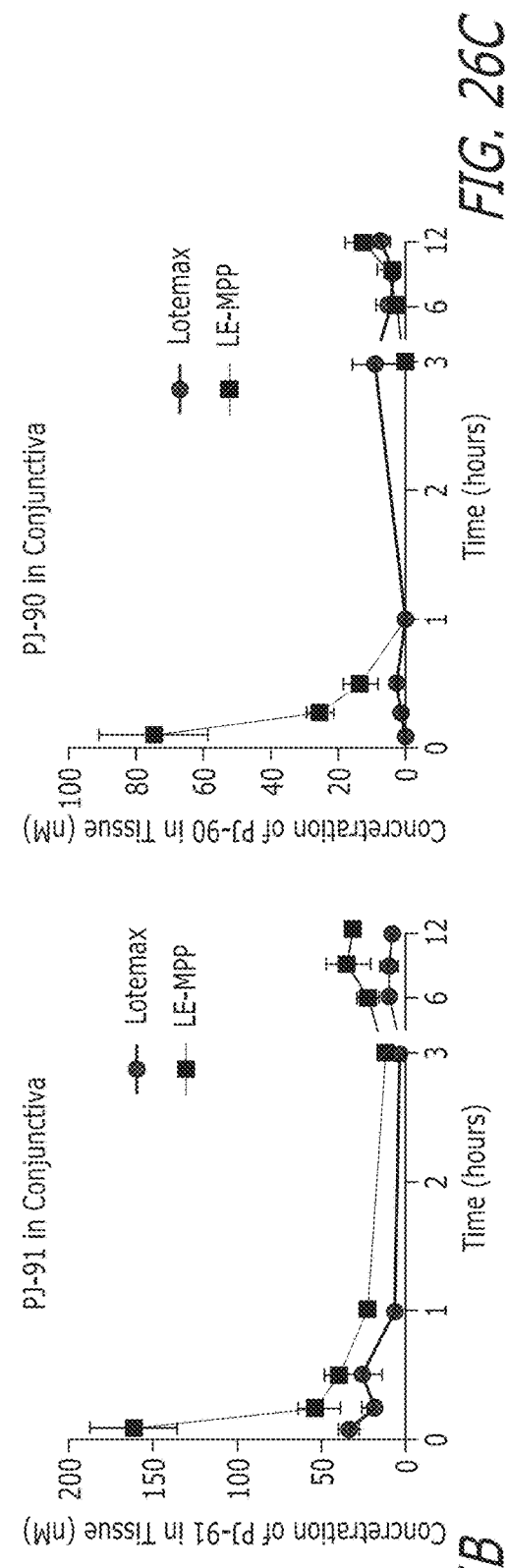
FIG. 26A
FIG. 26B
FIG. 26C

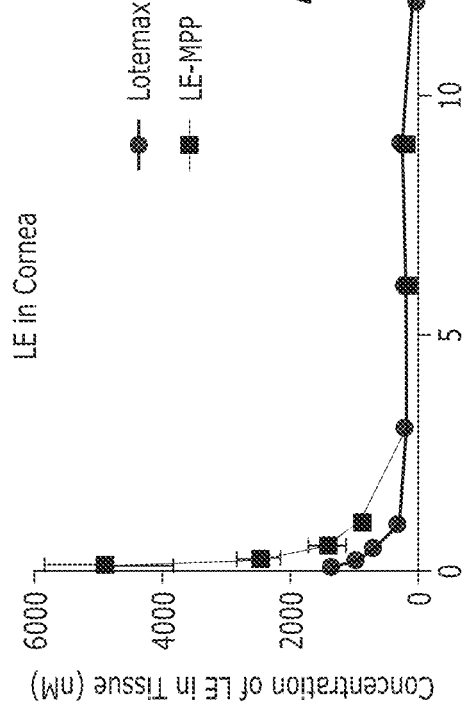
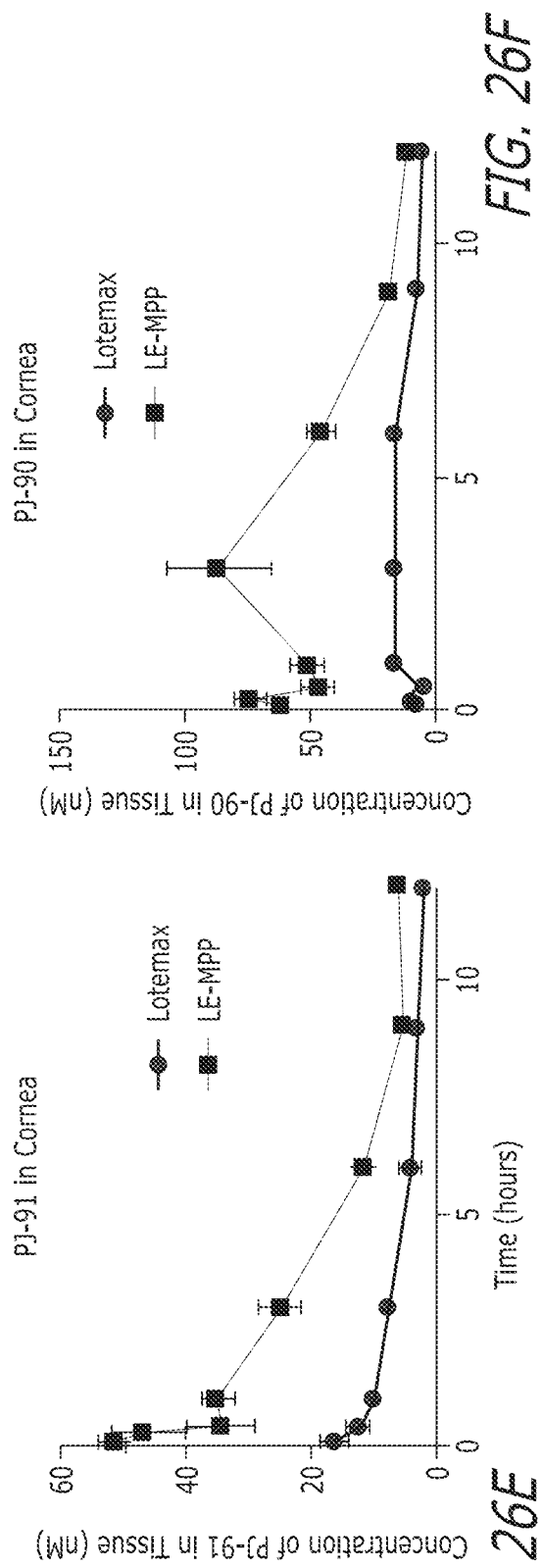
FIG. 26D
FIG. 26E
FIG. 26F

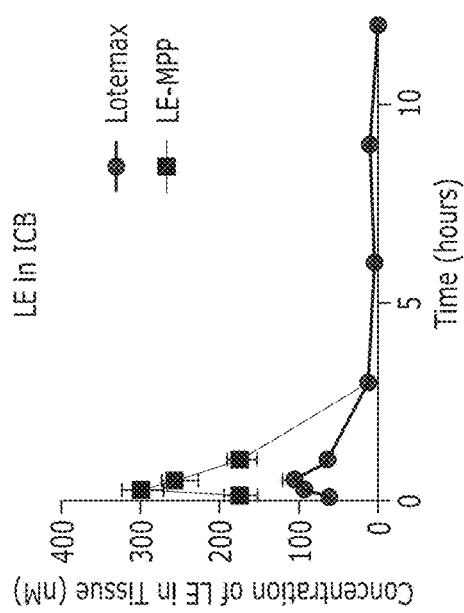
FIG. 26J
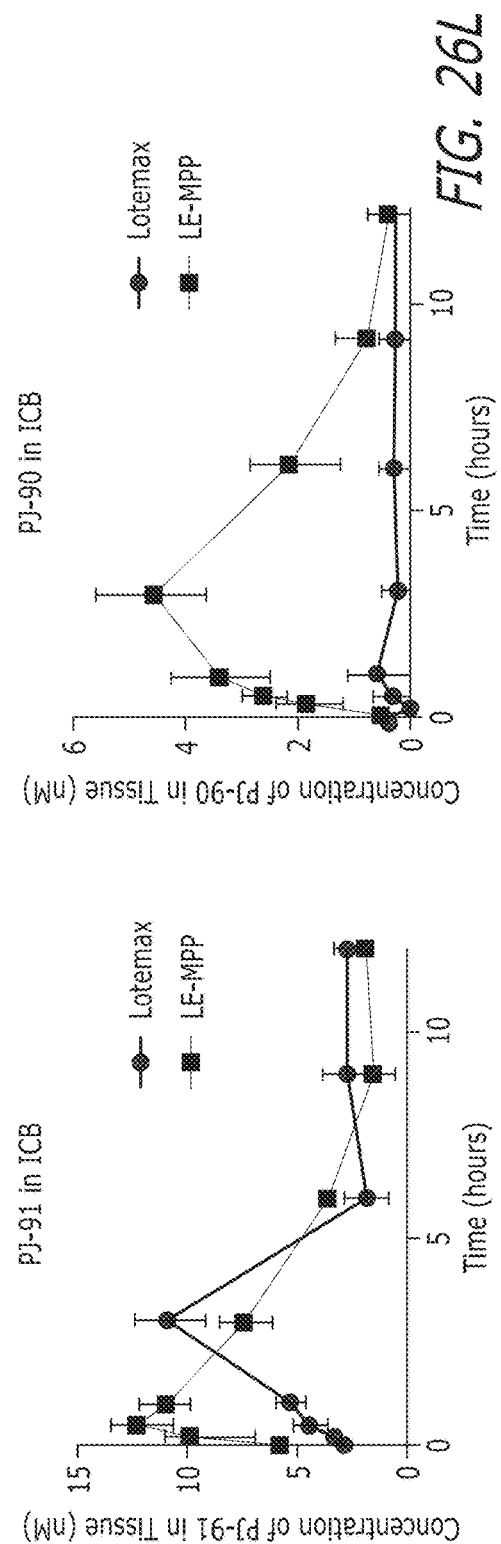
FIG. 26L
FIG. 26K

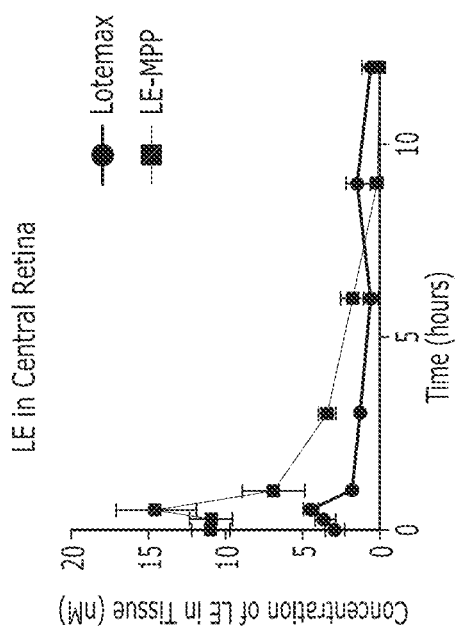
FIG. 26M
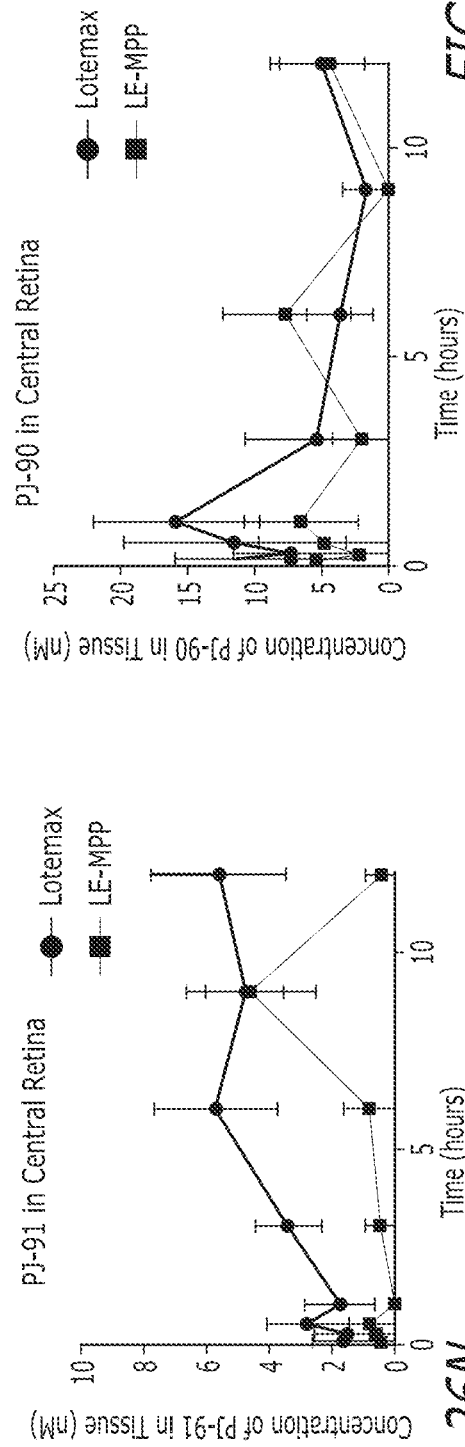
FIG. 26O
FIG. 26N

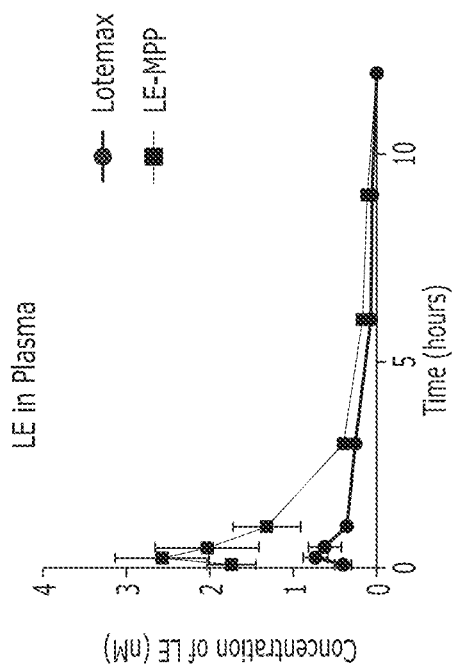
FIG. 26P
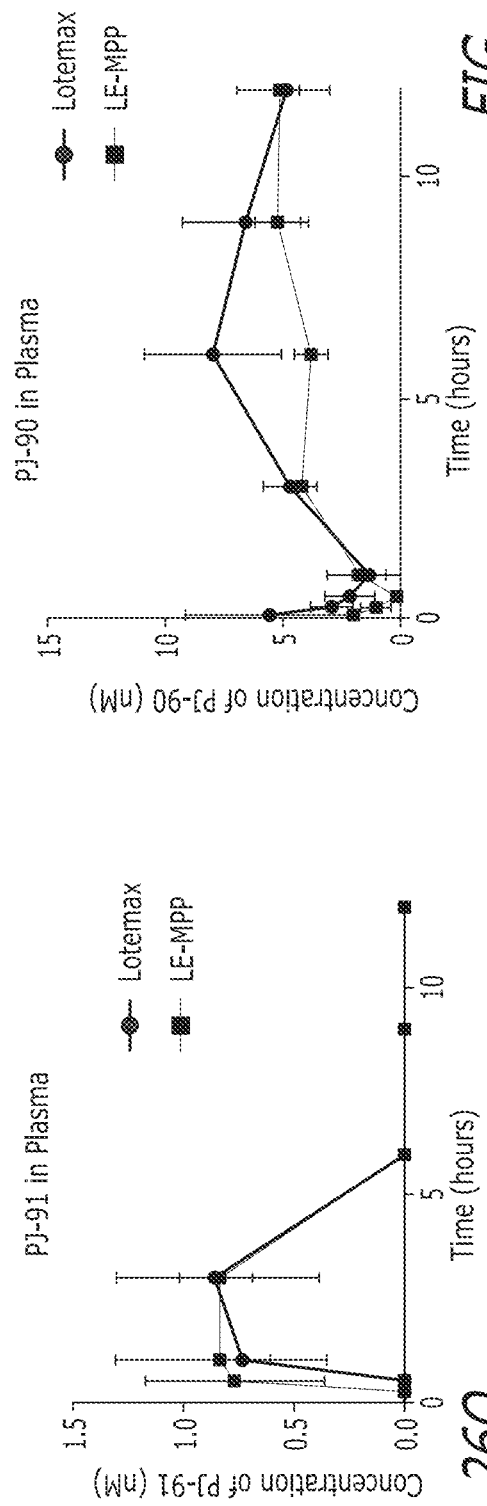
FIG. 26R
FIG. 26Q

COMPOSITIONS AND METHODS FOR OPHTHALMIC AND/OR OTHER APPLICATIONS

RELATED APPLICATIONS

The present application is a continuation of U.S. application Ser. No. 17/170,701 filed Feb. 8, 2021, which is a continuation of U.S. application Ser. No. 16/988,470 filed Aug. 7, 2020, now U.S. Pat. No. 10,993,908, which is a continuation of U.S. application Ser. No. 16/888,371 filed May 29, 2020, now U.S. Pat. No. 10,940,108, which is a division of U.S. application Ser. No. 15/808,746 filed Nov. 9, 2017, now U.S. Pat. No. 10,688,045, which is a continuation of U.S. application Ser. No. 14/070,506 filed Nov. 2, 2013, now U.S. Pat. No. 9,827,191, which is a continuation-in-part of U.S. application Ser. No. 13/886,658 filed May 3, 2013, which claims priority under 35 U.S.C. § 119(e) to U.S. Provisional Application 61/784,701 filed Mar. 14, 2013, 61/642,313 filed May 3, 2012, 61/642,261 filed May 3, 2012, and 61/738,949 filed Dec. 18, 2012. Each of these applications is incorporated herein by reference in their entirety.

STATEMENT REGARDING FEDERALLY-SPONSORED RESEARCH

This invention was made in part with government support under Grant No. 1R43EY021705-1 awarded by the National Eye Institute of the National Institutes of Health. The government has certain rights in the invention.

FIELD OF THE INVENTION

The present invention generally relates to particles, compositions, and methods that aid particle transport in mucus. The particles, compositions, and methods may be used in ophthalmic and/or other applications.

BACKGROUND OF THE INVENTION

A mucus layer present at various points of entry into the body, including the eyes, nose, lungs, gastrointestinal tract, and female reproductive tract, is naturally adhesive and serves to protect the body against pathogens, allergens, and debris by effectively trapping and quickly removing them via mucus turnover. For effective delivery of therapeutic, diagnostic, or imaging particles via mucus membranes, the particles must be able to readily penetrate the mucus layer to avoid mucus adhesion and rapid mucus clearance. Particles (including microparticles and nanoparticles) that incorporate pharmaceutical agents are particularly useful for ophthalmic applications. However, often it is difficult for administered particles to be delivered to an eye tissue in effective amounts due to rapid clearance and/or other reasons. Accordingly, new methods and compositions for administration (e.g., topical application or direct injection) of pharmaceutical agents to the eye would be beneficial.

SUMMARY OF THE INVENTION

The present description generally relates to particles, compositions, and methods that aid particle transport in mucus, especially particles, compositions, and methods for ophthalmic and/or other applications.

As described in more detail below, in some embodiments the compositions comprise a plurality of particles that include a corticosteroid such as loteprednol etabonate (LE) for treating an eye disease or condition. The particles include a surface-altering agent that reduces the adhesion of the particles to mucus and/or facilitates penetration of the particles through physiological mucus. Such compositions are advantageous over marketed formulations, such as Lotemax® or Alrex®, as the compositions described herein are able to more readily penetrate the mucus layer of an ocular tissue to avoid or minimize mucus adhesion and/or rapid mucus clearance. Therefore, the compositions may be more effectively delivered to and may be retained longer in the target issue. As a result, the compositions described herein may be administered at a lower dose and/or less frequently than marketed formulations to achieve similar or superior exposure. Moreover, the relatively low and/or infrequent dosage of the compositions described herein may result in fewer or less severe side effects, a more desirable toxicity profile, and/or improved patient compliance.

In some embodiments, the compositions described herein may comprise a plurality of particles that include a receptor tyrosine kinase (RTK) inhibitor, such as sorafenib, linifanib, MGCD-265, pazopanib, cediranib, and axitinib, for treating an eye disease or condition. Compositions including such particles are also provided, including compositions that can be administered topically to the eye. For reasons described herein, such compositions may have certain advantages over conventional formulations (e.g., an aqueous suspension of such pharmaceutical agents).

In certain embodiments, the compositions described herein may comprise a plurality of particles that include a non-steroidal anti-inflammatory drug (NSAID), such as a divalent or trivalent metal salt of bromfenac (e.g., bromfenac calcium), diclofenac (e.g., diclofenac free acid or a divalent or trivalent metal salt thereof), or ketorolac (e.g., ketorolac free acid or a divalent or trivalent metal salt thereof), for treating an eye disease or condition. Compositions including such particles are also provided, including compositions that can be administered topically to the eye. For reasons described herein, such compositions may have advantages over conventional formulations (e.g., an aqueous solution of the corresponding pharmaceutical agent).

In one set of embodiments, a pharmaceutical composition suitable for administration to an eye is provided. The pharmaceutical composition comprises a plurality of coated particles, comprising a core particle comprising loteprednol etabonate, wherein the loteprednol etabonate constitutes at least about 80 wt % of the core particle, and a coating comprising one or more surface-altering agents surrounding the core particle. The one or more surface-altering agents comprises at least one of: a) a triblock copolymer comprising a hydrophilic block-hydrophobic block-hydrophilic block configuration, wherein the hydrophobic block has a molecular weight of at least about 2 kDa, and the hydrophilic blocks constitute at least about 15 wt % of the triblock copolymer, b) a synthetic polymer having pendant hydroxyl groups on the backbone of the polymer, the polymer having a molecular weight of at least about 1 kDa and less than or equal to about 1000 kDa, wherein the polymer is at least about 30% hydrolyzed and less than about 95% hydrolyzed, or c) a polysorbate. The one or more surface altering agents is present on the outer surface of the core particle at a density of at least 0.01 molecules/nm$^2$. The one or more surface altering agents is present in the pharmaceutical composition in an amount of between about 0.001% to about 5% by weight. The plurality of coated particles have an average smallest cross-sectional dimension of less than about 1 micron. The pharmaceutical composition also includes one or more ophthalmically acceptable carriers, additives, and/or diluents.

In another set of embodiments, a pharmaceutical composition suitable for topical administration to an eye is provided. The pharmaceutical composition comprises a plurality of coated particles, comprising a core particle comprising loteprednol etabonate, wherein the loteprednol etabonate constitutes at least about 80 wt % of the core particle, and a coating comprising one or more surface-altering agents, wherein the one or more surface-altering agents comprise at least one of a poloxamer, a poly(vinyl alcohol), or a polysorbate. The one or more surface-altering agents is present on the outer surface of the core particle at a density of at least 0.01 molecules/nm$^2$. The one or more surface-altering agents is present in the pharmaceutical composition in an amount of between about 0.001% to about 5% by weight. The plurality of coated particles have an average smallest cross-sectional dimension of less than about 1 micron. The pharmaceutical composition also includes one or more ophthalmically acceptable carriers, additives, and/or diluents.

In another set of embodiments, a pharmaceutical composition suitable for administration to an eye is provided. The pharmaceutical composition comprises a plurality of coated particles, comprising a core particle comprising loteprednol etabonate; and a coating comprising a surface-altering agent surrounding the core particle, wherein the surface-altering agent comprises a (poly(ethylene oxide))-(poly(propylene oxide))-(poly(ethylene oxide)) triblock copolymer, wherein the hydrophobic block has a molecular weight of about 3600 Da, and the hydrophilic blocks constitute about 70 wt % of the triblock copolymer. The coated particles may have an average smallest cross-sectional dimension of about 200 nm to about 500 nm or about 200 nm to about 300 nm. The pharmaceutical composition may also comprise one or more ophthalmically acceptable carriers, additives, and/or diluents. The loteprednol etabonate is present in the pharmaceutical composition in an amount between about 0.1% to about 2% loteprednol etabonate by weight. The one or more surface altering agents is present in the pharmaceutical composition in an amount of between about 0.01% to about 2% by weight. In various embodiments, the ophthalmically acceptable carriers, additives, and/or diluents may comprise about 0.5-3% glycerin, about 0.1-1% sodium chloride, about 0.001-0.1% disodium ethylenediaminetetraacetic acid, and about 0.001-0.05% benzalkonium chloride. In addition, the composition may further comprise sodium citrate, citric acid, and water. In some embodiments, the ratio of the weight of the loteprednol etabonate to the weight of the surface-altering agent present in the pharmaceutical composition is greater than or equal to about 1:1, and less than or equal to about 3:1. The surface-altering agent may be Pluronic® F127, and may be non-covalently adsorbed to the core particles.

In another set of embodiments, a pharmaceutical composition suitable for administration to an eye is provided. The pharmaceutical composition comprises a plurality of coated particles, comprising a core particle comprising loteprednol etabonate; and a coating comprising a surface-altering agent surrounding the core particle, wherein the surface-altering agent comprises a (poly(ethylene oxide))-(poly(propylene oxide))-(poly(ethylene oxide)) triblock copolymer, wherein the hydrophobic block has a molecular weight of about 3600 Da, and the hydrophilic blocks constitute about 70 wt % of the triblock copolymer, about 0.5% to about 1% glycerin, about 0.1% to about 1% sodium chloride, about 0.01% to about 0.1% disodium ethylenediaminetetraacetic acid, and about 0.01% to about 0.03% benzalkonium chloride, wherein the loteprednol etabonate is present in the pharmaceutical composition in an amount between about 0.1% to about 1% loteprednol etabonate by weight; and wherein the ratio of the weight of the loteprednol etabonate to the weight of the surface-altering agent is about 2:1. The pharmaceutical composition may also include sodium citrate, citric acid, and water. In some embodiments, the loteprednol etabonate is present in the pharmaceutical composition in an amount of about 0.25% loteprednol etabonate by weight. In other embodiments, the loteprednol etabonate is present in the pharmaceutical composition in an amount of about 1% loteprednol etabonate by weight. In some embodiments, the glycerin is present in an amount of about 0.6%.

In another set of embodiments, a series of methods are provided. In one embodiment, a method for treating inflammation, macular degeneration, macular edema, uveitis, dry eye, blepharitis, and/or other disorder in an eye of a patient is provided. The method comprises administering to an eye of the patient, a pharmaceutical composition comprising a plurality of coated particles. The plurality of coated particles comprise a core particle comprising loteprednol etabonate, wherein the loteprednol etabonate constitutes at least about 80 wt % of the core particle, and a coating comprising one or more surface-altering agents surrounding the core particle. The one or more surface-altering agents comprises at least one of: a) a triblock copolymer comprising a hydrophilic block-hydrophobic block-hydrophilic block configuration, wherein the hydrophobic block has a molecular weight of at least about 2 kDa, and the hydrophilic blocks constitute at least about 15 wt % of the triblock copolymer, b) a synthetic polymer having pendant hydroxyl groups on the backbone of the polymer, the polymer having a molecular weight of at least about 1 kDa and less than or equal to about 1000 kDa, wherein the polymer is at least about 30% hydrolyzed and less than about 95% hydrolyzed, or c) a polysorbate. The one or more surface altering agents is present on the outer surface of the core particle at a density of at least 0.01 molecules/nm$^2$. The one or more surface altering agents is present in the pharmaceutical composition in an amount of between about 0.001% to about 5% by weight. The plurality of coated particles have an average smallest cross-sectional dimension of less than about 1 micron. The pharmaceutical composition also includes one or more ophthalmically acceptable carriers, additives, and/or diluents.

In another set of embodiments, a method for treating inflammation, macular degeneration, macular edema, uveitis, dry eye, blepharitis, and/or other disorder in an eye of a patient is provided. The method involves administering to an eye of the patient, a pharmaceutical composition comprising a plurality of coated particles, comprising a core particle comprising loteprednol etabonate, wherein the loteprednol etabonate constitutes at least about 80 wt % of the core particle, and a coating comprising one or more surface-altering agents, wherein the one or more surface-altering agents comprise at least one of a poloxamer, poly(vinyl alcohol), or a polysorbate. The one or more surface-altering agents is present on the outer surface of the core particle at a density of at least 0.01 molecules/nm$^2$. The one or more surface-altering agents is present in the pharmaceutical composition in an amount of between about 0.001% to about 5% by weight. The plurality of coated particles have an average smallest cross-sectional dimension of less than about 1 micron. The pharmaceutical composition also includes one or more ophthalmically acceptable carriers, additives, and/or diluents.

In another set of embodiments, a method for treating inflammation, macular degeneration, macular edema, uveitis, dry eye, blepharitis, and/or other disorder in an eye of a patient is provided. The method involves administering to an eye of the patient a pharmaceutical composition comprising a plurality of coated particles. The plurality of coated particles, comprises a core particle comprising loteprednol etabonate; and a coating comprising a surface-altering agent surrounding the core particle, wherein the surface-altering agent comprises a (poly(ethylene oxide))-(poly(propylene oxide))-(poly(ethylene oxide)) triblock copolymer, wherein the hydrophobic block has a molecular weight of about 3600 Da, and the hydrophilic blocks constitute about 70 wt % of the triblock copolymer. The coated particles may have an average smallest cross-sectional dimension of about 200 nm to about 500 nm or about 200 nm to about 300 nm. The pharmaceutical composition can also comprise one or more ophthalmically acceptable carriers, additives, and/or diluents. The loteprednol etabonate is present in the pharmaceutical composition in an amount between about 0.1% to about 2% loteprednol etabonate by weight. The one or more surface altering agents is present in the pharmaceutical composition in an amount of between about 0.01% to about 2% by weight. In various embodiments, the ophthalmically acceptable carriers, additives, and/or diluents may comprise about 0.5-3% glycerin, about 0.1-1% sodium chloride, about 0.001-0.1% disodium ethylenediaminetetraacetic acid, and about 0.001-0.05% benzalkonium chloride. In addition, the composition may also comprise sodium citrate, citric acid, and water. In some embodiments, the ratio of the weight of the loteprednol etabonate to the weight of the surface-altering agent present in the pharmaceutical composition is greater than or equal to about 1:1, and less than or equal to about 3:1. The surface-altering agent may be Pluronic® F127, and may be non-covalently adsorbed to the core particles.

In another set of embodiments, a method for treating inflammation, macular degeneration, macular edema, uveitis, dry eye, blepharitis, and/or other disorder in an eye of a patient is provided. The method involves administering to an eye of the patient a pharmaceutical composition that comprises a plurality of coated particles comprising a core particle comprising loteprednol etabonate; and a coating comprising a surface-altering agent surrounding the core particle, wherein the surface-altering agent comprises a (poly(ethylene oxide))-(poly(propylene oxide))-(poly(ethylene oxide)) triblock copolymer, wherein the hydrophobic block has a molecular weight of about 3600 Da, and the hydrophilic blocks constitute about 70 wt % of the triblock copolymer, about 0.5% to about 1% glycerin, about 0.1% to about 1% sodium chloride, about 0.01% to about 0.1% disodium ethylenediaminetetraacetic acid, and about 0.01% to about 0.03% benzalkonium chloride, wherein the loteprednol etabonate is present in the pharmaceutical composition in an amount between about 0.1% to about 1% loteprednol etabonate by weight; and wherein the ratio of the weight of the loteprednol etabonate to the weight of the surface-altering agent is about 2:1. The pharmaceutical composition can also include sodium citrate, citric acid, and water. In some embodiments, the loteprednol etabonate is present in the pharmaceutical composition in an amount of about 0.25% loteprednol etabonate by weight. In other embodiments, the loteprednol etabonate is present in the pharmaceutical composition in an amount of about 1% loteprednol etabonate by weight. In some embodiments, the glycerin is present in an amount of about 0.6%.

In another set of embodiments, a method of making a composition comprising a plurality of coated particles comprising a core particle comprising loteprednol etabonate; and a coating comprising a surface-altering agent surrounding the core particle, wherein the surface-altering agent comprises a (poly(ethylene oxide))-(poly(propylene oxide))-(poly(ethylene oxide)) triblock copolymer, wherein the hydrophobic block has a molecular weight of about 3600 Da, and the hydrophilic blocks constitute about 70 wt % of the triblock copolymer, and one or more ophthalmically acceptable carriers, additives, and/or diluents, wherein the loteprednol etabonate is present in the pharmaceutical composition in an amount between about 0.1% to about 2% loteprednol etabonate by weight; wherein the one or more surface altering agents is present in the pharmaceutical composition in an amount of between about 0.01% to about 2% by weight, wherein the plurality of coated particles have an average smallest cross-sectional dimension of about 0.2 microns to about 0.3 microns is provided. The method involves milling a coarse aqueous suspension containing about 2-20% loteprednol etabonate in the form of coarse or micronized crystals, about 0.2-20% of a (poly(ethylene oxide))-(poly(propylene oxide))-(poly(ethylene oxide)) triblock copolymer, wherein the hydrophobic block has a molecular weight of about 3600 Da, and the hydrophilic blocks constitute about 70 wt % of the triblock copolymer, about 0.5-3% glycerin, about 0.1-1% sodium chloride, and about 0.001-0.1% EDTA in the presence of milling media to produce a nanosuspension of loteprednol etabonate particles sized in the range of about 0.2 microns to about 0.3 microns, separating the nanosuspension of loteprednol etabonate particles from the milling media, and mixing the nanosuspension of loteprednol etabonate particles with diluent.

In another set of embodiments, a pharmaceutical composition suitable for administration to an eye is provided. The pharmaceutical composition includes a plurality of coated particles, comprising a core particle comprising a pharmaceutical agent or a salt thereof. The pharmaceutical agent or salt thereof constitutes at least about 80 wt % of the core particle, and the pharmaceutical agent or salt thereof comprises a receptor tyrosine kinase (RTK) inhibitor. The plurality of coated particles also includes a coating comprising one or more surface-altering agents surrounding the core particle, wherein the one or more surface-altering agents comprises at least one of: a) a triblock copolymer comprising a hydrophilic block-hydrophobic block-hydrophilic block configuration, wherein the hydrophobic block has a molecular weight of at least about 2 kDa, and the hydrophilic blocks constitute at least about 15 wt % of the triblock copolymer, b) a synthetic polymer having pendant hydroxyl groups on the backbone of the polymer, the polymer having a molecular weight of at least about 1 kDa and less than or equal to about 1000 kDa, wherein the polymer is at least about 30% hydrolyzed and less than about 95% hydrolyzed, or c) a polysorbate. The one or more surface altering agents is present on the outer surface of the core particle at a density of at least 0.01 molecules/$nm^2$. The one or more surface altering agents is present in the pharmaceutical composition in an amount of between about 0.001% to about 5% by weight. The plurality of coated particles have an average smallest cross-sectional dimension of less than about 1 micron. The pharmaceutical composition also includes one or more ophthalmically acceptable carriers, additives, and/or diluents.

In another set of embodiments, a method for treating macular degeneration, macular edema and/or another disorder in an eye of a patient is provided. The method involves administering to an eye of the patient, a pharmaceutical composition comprising a plurality of coated particles, comprising a core particle comprising a pharmaceutical agent or a salt thereof, wherein the pharmaceutical agent or salt thereof constitutes at least about 80 wt % of the core particle, and wherein the pharmaceutical agent or salt thereof comprises a receptor tyrosine kinase (RTK) inhibitor, and a coating comprising one or more surface-altering agents surrounding the core particle. The one or more surface-altering agents comprises at least one of: a) a triblock copolymer comprising a hydrophilic block-hydrophobic block-hydrophilic block configuration, wherein the hydrophobic block has a molecular weight of at least about 2 kDa, and the hydrophilic blocks constitute at least about 15 wt % of the triblock copolymer, b) a synthetic polymer having pendant hydroxyl groups on the backbone of the polymer, the polymer having a molecular weight of at least about 1 kDa and less than or equal to about 1000 kDa, wherein the polymer is at least about 30% hydrolyzed and less than about 95% hydrolyzed, or c) a polysorbate. The one or more surface altering agents is present on the outer surface of the core particle at a density of at least 0.01 molecules/nm$^2$. The one or more surface altering agents is present in the pharmaceutical composition in an amount of between about 0.001% to about 5% by weight. The plurality of coated particles have an average smallest cross-sectional dimension of less than about 1 micron. The pharmaceutical composition also includes one or more ophthalmically acceptable carriers, additives, and/or diluents.

In another set of embodiments, a pharmaceutical composition suitable for administration to an eye is provided. The pharmaceutical composition comprises a plurality of coated particles, comprising a core particle comprising a pharmaceutical agent or a salt thereof, wherein the pharmaceutical agent or salt thereof constitutes at least about 80 wt % of the core particle, and wherein the pharmaceutical agent or salt thereof comprises bromfenac calcium, diclofenac free acid, or ketorolac free acid, and a coating comprising one or more surface-altering agents surrounding the core particle. The one or more surface-altering agents comprises at least one of: a) a triblock copolymer comprising a hydrophilic block-hydrophobic block-hydrophilic block configuration, wherein the hydrophobic block has a molecular weight of at least about 2 kDa, and the hydrophilic blocks constitute at least about 15 wt % of the triblock copolymer, b) a synthetic polymer having pendant hydroxyl groups on the backbone of the polymer, the polymer having a molecular weight of at least about 1 kDa and less than or equal to about 1000 kDa, wherein the polymer is at least about 30% hydrolyzed and less than about 95% hydrolyzed, or c) a polysorbate. The one or more surface altering agents is present on the outer surface of the core particle at a density of at least 0.01 molecules/nm$^2$. The one or more surface altering agents is present in the pharmaceutical composition in an amount of between about 0.001% to about 5% by weight. The plurality of coated particles have an average smallest cross-sectional dimension of less than about 1 micron. The pharmaceutical composition also includes one or more ophthalmically acceptable carriers, additives, and/or diluents.

In another set of embodiments, a method for treating inflammation, macular degeneration, macular edema, uveitis, dry eye, blepharitis, glaucoma, and/or other disorder in an eye of a patient is provided. The method involves administering to an eye of the patient, a pharmaceutical composition comprising a plurality of coated particles, comprising a core particle comprising a pharmaceutical agent or a salt thereof, wherein the pharmaceutical agent or salt thereof constitutes at least about 80 wt % of the core particle, and wherein the pharmaceutical agent or salt thereof comprises bromfenac calcium, diclofenac free acid, or ketorolac free acid. The plurality of coated particles also includes a coating comprising one or more surface-altering agents surrounding the core particle, wherein the one or more surface-altering agents comprises at least one of: a) a triblock copolymer comprising a hydrophilic block-hydrophobic block-hydrophilic block configuration, wherein the hydrophobic block has a molecular weight of at least about 2 kDa, and the hydrophilic blocks constitute at least about 15 wt % of the triblock copolymer, b) a synthetic polymer having pendant hydroxyl groups on the backbone of the polymer, the polymer having a molecular weight of at least about 1 kDa and less than or equal to about 1000 kDa, wherein the polymer is at least about 30% hydrolyzed and less than about 95% hydrolyzed, or c) a polysorbate. The one or more surface altering agents is present on the outer surface of the core particle at a density of at least 0.01 molecules/nm$^2$. The one or more surface altering agents is present in the pharmaceutical composition in an amount of between about 0.001% to about 5% by weight. The plurality of coated particles have an average smallest cross-sectional dimension of less than about 1 micron. The pharmaceutical composition also includes one or more ophthalmically acceptable carriers, additives, and/or diluents.

In another set of embodiments, a pharmaceutical composition suitable for administration to an eye is provided. The pharmaceutical composition comprises a plurality of coated particles, comprising a core particle comprising a pharmaceutical agent or a salt thereof selected from the group consisting of a corticosteroid, a receptor tyrosine kinase (RTK) inhibitor, a cyclooxygenase (COX) inhibitor, an angiogenesis inhibitor, a prostaglandin analog, an NSAID, a beta blocker, and a carbonic anhydrase inhibitor. The plurality of coated particles also includes a coating comprising a surface-altering agent surrounding the core particle, wherein the one or more surface-altering agents comprises at least one of: a) a triblock copolymer comprising a hydrophilic block-hydrophobic block-hydrophilic block configuration, wherein the hydrophobic block has a molecular weight of at least about 2 kDa, and the hydrophilic blocks constitute at least about 15 wt % of the triblock copolymer, wherein the hydrophobic block associates with the surface of the core particle, and wherein the hydrophilic block is present at the surface of the coated particle and renders the coated particle hydrophilic, b) a synthetic polymer having pendant hydroxyl groups on the backbone of the polymer, the polymer having a molecular weight of at least about 1 kDa and less than or equal to about 1000 kDa, wherein the polymer is at least about 30% hydrolyzed and less than about 95% hydrolyzed, or c) a polysorbate. The one or more surface altering agents is present on the outer surface of the core particle at a density of at least 0.01 molecules/nm$^2$. The one or more surface altering agents is present in the pharmaceutical composition in an amount of between about 0.001% to about 5% by weight. The pharmaceutical composition also includes one or more ophthalmically acceptable carriers, additives, and/or diluents.

In another set of embodiments, a method of treating, diagnosing, preventing, or managing an ocular condition in a subject is provided. The method involves administering a composition to an eye of a subject, wherein the composition comprises a plurality of coated particles, the coated particles comprising a core particle comprising a pharmaceutical agent or a salt thereof selected from the group consisting of a corticosteroid, a receptor tyrosine kinase (RTK) inhibitor, a cyclooxygenase (COX) inhibitor, an angiogenesis inhibitor, a prostaglandin analog, an NSAID, a beta blocker, and a carbonic anhydrase inhibitor, and a coating comprising one or more surface-altering agents surrounding the core particle. The one or more surface-altering agents comprises at least one of: a) a triblock copolymer comprising a hydrophilic block-hydrophobic block-hydrophilic block configuration, wherein the hydrophobic block has a molecular weight of at least about 2 kDa, and the hydrophilic blocks constitute at least about 15 wt % of the triblock copolymer, wherein the hydrophobic block associates with the surface of the core particle, and wherein the hydrophilic block is present at the surface of the coated particle and renders the coated particle hydrophilic, or b) a synthetic polymer having pendant hydroxyl groups on the backbone of the polymer, the polymer having a molecular weight of at least about 1 kDa and less than or equal to about 1000 kDa, wherein the polymer is at least about 30% hydrolyzed and less than about 95% hydrolyzed, or c) a polysorbate. The method involves delivering the pharmaceutical agent to a tissue in the eye of the subject.

In another set of embodiments, a method of improving the ocular bioavailability of a pharmaceutical agent in a subject is provided. The method involves administering a composition to an eye of the subject, wherein the composition comprises a plurality of coated particles. The coated particles comprise a core particle comprising a pharmaceutical agent or a salt thereof selected from the group consisting of a corticosteroid, a receptor tyrosine kinase (RTK) inhibitor, a cyclooxygenase (COX) inhibitor, an angiogenesis inhibitor, a prostaglandin analog, an NSAID, a beta blocker, and a carbonic anhydrase inhibitor, and a coating comprising a surface-altering agent surrounding the core particle. The coating on the core particle is present in a sufficient amount to improve the ocular bioavailability of the pharmaceutical agent when administered in the composition, compared to the ocular bioavailability of the pharmaceutical agent when administered as a core particle without the coating.

In another set of embodiments, a method of improving the concentration of a pharmaceutical agent in a tissue of a subject is provided. The method involves administering a composition to an eye of the subject, wherein the composition comprises a plurality of coated particles. The coated particles comprise a core particle comprising the pharmaceutical agent or a salt thereof, wherein the pharmaceutical agent is loteprednol etabonate, and a coating comprising a surface-altering agent surrounding the core particle. The tissue is selected from the group consisting of a *retina*, a *macula*, a sclera, or a choroid. The coating on the core particle is present in a sufficient amount to increase the concentration of the pharmaceutical agent by at least 10% in the tissue when administered in the composition, compared to the concentration of the pharmaceutical agent in the tissue when administered as a core particle without the coating.

In another set of embodiments, a method of treating an ocular condition in a subject by repeated administration of a pharmaceutical composition is provided. The method involves
administering two or more doses of a pharmaceutical composition comprising loteprednol etabonate to an eye of a subject, wherein the period between consecutive doses is at least about 4 hours, at least about 6 hours, at least about 8 hours, at least about 12 hours, at least about 36 hours, or at least about 48 hours, wherein the amount of loteprednol etabonate delivered to a tissue of an eye is effective to treat an ocular condition in the subject.

In another set of embodiments, a method of treating an ocular condition in a subject by repeated administration of a pharmaceutical composition is provided. The method involves administering two or more doses of a pharmaceutical composition comprising one or more pharmaceutical agents to an eye of a subject, wherein the period between consecutive doses is at least about 4 hours, at least about 6 hours, at least about 8 hours, at least about 12 hours, at least about 36 hours, or at least about 48 hours. The one or more pharmaceutical agents is selected from the group consisting of loteprednol etabonate, sorafenib, linifanib, MGCD-265, pazopanib, cediranib, axitinib, bromfenac calcium, diclofenac free acid, ketorolac free acid and a combination thereof. The amount of the pharmaceutical agent delivered to a tissue of an eye is effective to treat an ocular condition in the subject.

In another set of embodiments, a pharmaceutical composition suitable for treating an anterior ocular disorder by administration to an eye is provided. The pharmaceutical composition comprises a plurality of coated particles, comprising a core particle comprising a corticosteroid (e.g., loteprednol etabonate), and a coating comprising one or more surface-altering agents surrounding the core particle. The one or more surface-altering agents comprises at least one of: a) a triblock copolymer comprising a hydrophilic block-hydrophobic block-hydrophilic block configuration, wherein the hydrophobic block has a molecular weight of at least about 2 kDa, and the hydrophilic blocks constitute at least about 15 wt % of the triblock copolymer, b) a synthetic polymer having pendant hydroxyl groups on the backbone of the polymer, the polymer having a molecular weight of at least about 1 kDa and less than or equal to about 1000 kDa, wherein the polymer is at least about 30% hydrolyzed and less than about 95% hydrolyzed, or c) a polysorbate. The plurality of coated particles have an average smallest cross-sectional dimension of less than about 1 micron. The coating on the core particle is present in a sufficient amount to increase the concentration of the corticosteroid (e.g., loteprednol etabonate) by at least 50% in an anterior component of the eye selected from the group consisting of a cornea or aqueous humor 30 minutes after administration when administered to the eye, compared to the concentration of the corticosteroid in the tissue when administered as a core particle without the coating.

In another set of embodiments, a method of treating an anterior ocular disorder by administration to an eye is provided. The method involves administering a composition to an eye of a subject, wherein the composition comprises a plurality of coated particles. The plurality of coated particles comprises a core particle comprising a corticosteroid (e.g., loteprednol etabonate), and a coating comprising one or more surface-altering agents surrounding the core particle. The one or more surface-altering agents comprises at least one of a) a triblock copolymer comprising a hydrophilic block-hydrophobic block-hydrophilic block configuration, wherein the hydrophobic block has a molecular weight of at least about 2 kDa, and the hydrophilic blocks constitute at least about 15 wt % of the triblock copolymer, b) a synthetic polymer having pendant hydroxyl groups on the backbone of the polymer, the polymer having a molecular weight of at least about 1 kDa and less than or equal to about 1000 kDa, wherein the polymer is at least about 30% hydrolyzed and less than about 95% hydrolyzed, or c) a polysorbate The method involves sustaining an ophthalmically efficacious level of the corticosteroid (e.g., loteprednol etabonate) in an anterior ocular tissue selected from the group consisting of a palpebral conjunctiva, a bulbar conjunctiva, or a cornea for at least 12 hours after administration.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

FIGS. 3A-3D are histograms showing distribution of trajectory-mean velocity $V_{mean}$ in CVM within an ensemble of nanocrystal particles coated with different surface-altering agents according to one set of embodiments;

FIGS. 9A-9B represent data obtained with two different CVM samples;

FIGS. 13A-13F are representative CVM velocity ($V_{mean}$) distribution histograms for pyrene/nanocrystals obtained with various surface-altering agents (SAMPLE=Pyrene nanoparticles, POSITIVE=200 nm PS-PEG5K, NEGATIVE=200 nm PS—COO); according to one set of embodiments;

FIG. 23A: Rabbits were given one 50 μL dose of 0.5% LE MPP or LE SDS in each eye. FIG. 23B: Rabbits were given one 50 μL dose of 0.5% Lotemax® or LE SDS in each eye. Data for Lotemax® were obtained from a previous experiment performed using the same techniques at the same facility;

FIG. 32 indicates that LE MPPs in the presence of sodium chloride were stable.

FIG. 35A: particle Z-average size of bromfenac calcium (bromfenac-Ca) MPPs diluted to a concentration of 0.09% w/v bromfenac-Ca and 0.09% w/v Pluronic® F127 (F127) and stored at room temperature for 23 days. FIG. 35B: polydispersity index of bromfenac-Ca MPPs diluted to a concentration of 0.09% w/v bromfenac-Ca and 0.09% w/v F127 and stored at room temperature for 23 days. FIG. 35C: particle Z-average size of bromfenac-Ca MPPs diluted to a concentration of 0.09% w/v bromfenac-Ca and 0.5% w/v F127 and stored at room temperature for 7 or 12 days. FIG. 35D: polydispersity index of bromfenac-Ca MPPs diluted to a concentration of 0.09% w/v bromfenac-Ca and 0.5% w/v F127 and stored at room temperature for 7 or 12 days.

FIG. 36A: the rabbits were given one 50 μL dose of 0.5% sorafenib-MPP or 0.5% sorafenib non-MPP control in each eye. Error bars show standard errors of the mean (n=6). FIG. 36B: the rabbits were given one 50 μL dose of 2% linifanib-MPP or 2% linifanib non-MPP control in each eye. Error bars show standard errors of the mean (n=6).

FIG. 37A: the rabbits were given one 50 μL dose of 0.5% pazopanib-MPP in each eye. Error bars show standard errors of the mean (n=6). Cellular $IC_{50}$ is also shown for reference. FIG. 37B: the rabbits were given one 50 μL dose of 2% MGCD-265-MPP in each eye. Error bars show standard errors of the mean (n=6). Cellular IC50 is also shown for reference.

FIG. 38A: the rabbits were given one 50 μL dose of 2% cediranib-MPP in the choroid. Error bars show standard errors of the mean (n=6). Cellular IC50 is also shown for reference. FIG. 38B: the rabbits were given one 50 μL dose of 2% cediranib-MPP in the *retina*. Error bars show standard errors of the mean (n=6). Cellular IC50 is also shown for reference.

FIG. 39A: the rabbits were given one 50 μL dose of 2% axitinib-MPP in the choroid. Error bars show standard errors of the mean (n=6). Cellular IC50 is also shown for reference. FIG. 39B: the rabbits were given one 50 μL dose of 2% axitinib-MPP in the *retina*. Error bars show standard errors of the mean (n=6). Cellular IC50 is also shown for reference.

DETAILED DESCRIPTION

Figure 1:
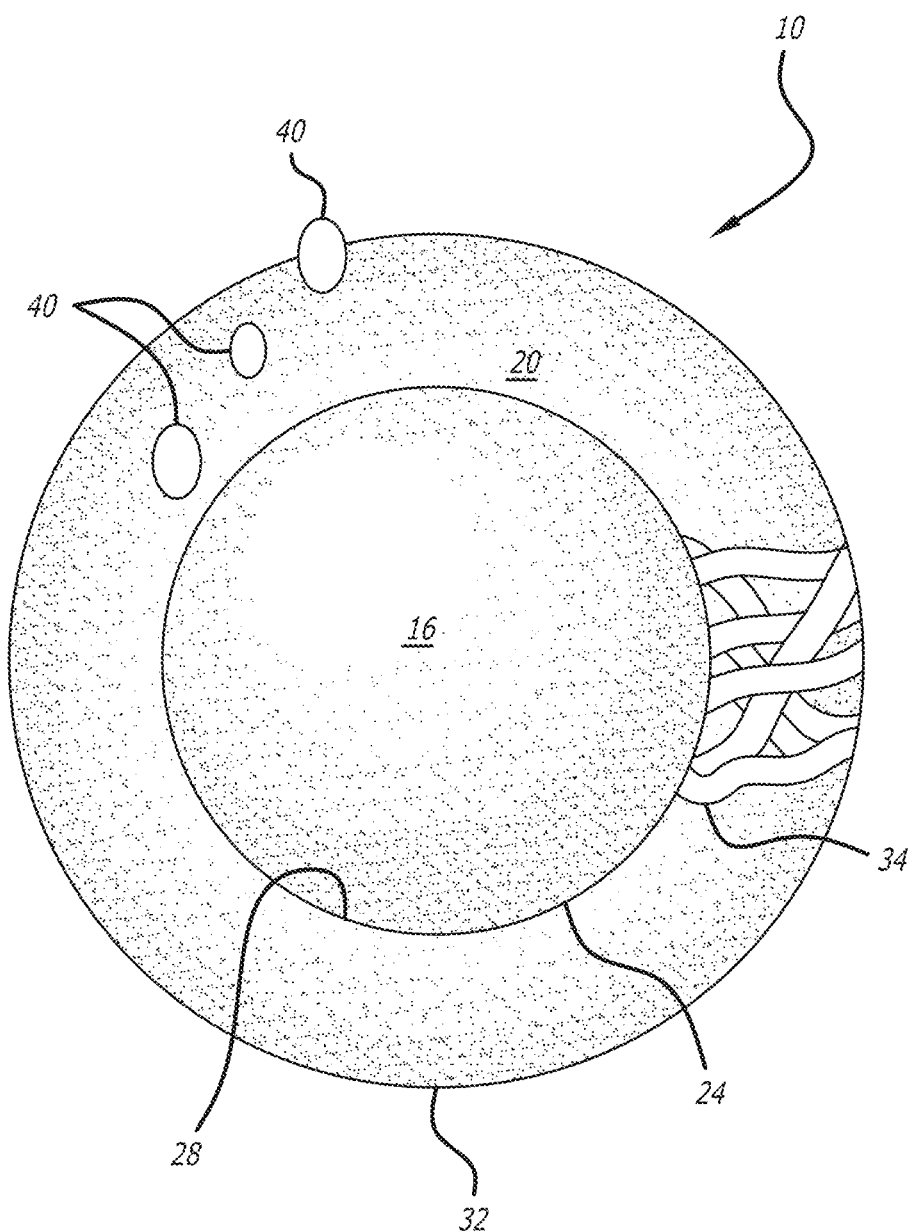
FIG. 1 is a schematic drawing of a mucus-penetrating particle having a coating and a core according to one set of embodiments.

Particles, compositions, and methods that aid particle transport in mucus are provided. The particles, compositions, and methods may be used, in some instances, for ophthalmic and/or other applications. In some embodiments, the compositions and methods may involve modifying the surface coatings of particles, such as particles of pharmaceutical agents that have a low aqueous solubility. Such compositions and methods can be used to achieve efficient transport of particles of pharmaceutical agents though mucus barriers in the body for a wide spectrum of applications, including drug delivery, imaging, and diagnostic applications. In certain embodiments, a pharmaceutical composition including such particles is well-suited for ophthalmic applications, and may be used for delivering pharmaceutical agents to the front of the eye, middle of the eye, and/or the back of the eye.

Particles having efficient transport through mucus barriers may be referred to herein as mucus-penetrating particles (MPPs). Such particles may include surfaces that are modified with one or more surface-altering agents that reduce the adhesion of the particles to mucus, or otherwise increase the transport of the particles through mucus barriers compared to conventional particles or non-MPPs, i.e., particles that do not include such surface-altering agent(s).

In some embodiments, the particles comprise a corticosteroid such as loteprednol etabonate for treating an eye disease or condition. The corticosteroid may be present, for example, in the core of the particle. The particles include a surface-altering agent that modifies the surface of the particles to reduce the adhesion of the particles to mucus and/or to facilitate penetration of the particles through physiological mucus. Compositions including such particles are also provided, including compositions that can be administered topically to the eye. Such compositions are advantageous over marketed formulations, such as Lotemax® or Alrex®, as the compositions described herein are able to more readily penetrate the mucus layer of an ocular tissue to avoid or minimize mucus adhesion and/or rapid mucus clearance. Therefore, the compositions may be more effectively delivered to and may be retained longer in the target issue. As a result, the compositions described herein may be administered at a lower dose and/or less frequently than marketed formulations to achieve similar or superior exposure. Moreover, the relatively low and/or infrequent dosage of the compositions may result in fewer or less severe side effects, a more desirable toxicity profile, and/or improved patient compliance. Other advantages are provided below.

In some embodiments, the particles comprise one or more receptor tyrosine kinase inhibitors (RTKi), such as sorafenib, linifanib, MGCD-265, pazopanib, cediranib, axitinib, or a combination thereof, for treating an eye disease or condition. The one or more RTKi may be present, for example, in the core of the particle. Compositions including such particles are also provided, including compositions that can be administered topically to the eye. For reasons described herein, such compositions may have advantages over certain conventional formulations (e.g., an aqueous suspension of the respective RTKi).

In some embodiments, the particles comprise a non-steroidal anti-inflammatory drug (NSAID), such as a divalent metal salt of bromfenac (e.g., a divalent metal salt of bromfenac, such as bromfenac calcium)), diclofenac (e.g., diclofenac free acid or a divalent or trivalent metal salt thereof, such as an alkaline earth metal salt of diclofenac), or ketorolac (e.g., ketorolac free acid or a divalent or trivalent metal salt thereof, such as an alkaline earth metal salt of ketorolac), for treating an eye disease or condition. The NSAID may be present, for example, in the core of the particle. Compositions including such particles are also provided, including compositions that can be administered topically to the eye. For reasons described herein, such compositions may have advantages over certain conventional formulations (e.g., an aqueous solution of bromfenac sodium).

As described in more detail below, in some embodiments, the particles, compositions and/or formulations described herein may be used to diagnose, prevent, treat or manage diseases or conditions at the back of the eye, such as at the *retina, macula*, choroid, sclera and/or uvea, and/or diseases and conditions at the front and/or middle of the eye, such as at the cornea, conjunctiva (including palpebral and bulbar), iris and ciliary body. In some embodiments, the particles, compositions and/or formulations are designed to be administered topically to the eye. In other embodiments, the particles, compositions and/or formulations are designed to be administered by direct injection into the eye.

Delivering drugs to the eye topically is challenging due to the limited permeability of the cornea and sclera (the tissues exposed to an instillation) and the eye's natural clearance mechanisms: drug solutions, such as in conventional ophthalmic solutions, are typically washed away from the surface of the eye very rapidly by drainage and lachrymation; and drug particles, such as in conventional ophthalmic suspensions, are typically trapped by the rapidly cleared mucus layer of the eye, and hence, are also rapidly cleared. Therefore, conventional ophthalmic solutions and suspensions currently used to treat conditions at the front of the eye are typically administered at high doses and high frequency in order to achieve and sustain efficacy. Such frequent high dosing greatly reduces patient compliance and increases the risk of local adverse effects. Topically delivering drugs to the back of the eye is even more challenging due to the lack of direct exposure to a topical instillation and because of the anatomical and physiological barriers associated with this part of the eye. Consequently, little (if any) drug reaches the back of the eye when administered as conventional topical ophthalmic solutions or suspensions. Therefore, invasive delivery techniques, such as intravitreal or periocular injections, are currently used for conditions at the back of the eye.

In some instances, the particles, compositions and/or formulations described herein that are mucus-penetrating can address these issues associated with delivery to the front of the eye (e.g., dosage frequency) and the back of the eye (e.g., sufficient delivery) since the particles may avoid adhesion to the mucus layer and/or may be more evenly spread across the surface of the eye, thereby avoiding the eye's natural clearance mechanisms and prolonging their residence at the ocular surface. In some embodiments, the particles may effectively penetrate through physiological mucus to facilitate sustained drug release directly to the underlying tissues, as described in more detail below.

In some embodiments, the particles described herein have a core-shell type arrangement. The core may comprise any suitable material such as a solid pharmaceutical agent or a salt thereof having a relatively low aqueous solubility, a polymeric carrier, a lipid, and/or a protein. The core may also comprise a gel or a liquid in some embodiments. The core may be coated with a coating or shell comprising a surface-altering agent that facilitates mobility of the particle in mucus. As described in more detail below, in some embodiments the surface-altering agent may comprise a polymer (e.g., a synthetic or a natural polymer) having pendant hydroxyl groups on the backbone of the polymer. The molecular weight and/or degree of hydrolysis of the polymer may be chosen to impart certain transport characteristics to the particles, such as increased transport through mucus. In certain embodiments, the surface-altering agent may comprise a triblock copolymer comprising a hydrophilic block-hydrophobic block-hydrophilic block configuration. The molecular weights of each of the blocks may be chosen to impart certain transport characteristics to the particles, such as increased transport through mucus.

Non-limiting examples of particles are now provided. As shown in the illustrative embodiment of FIG. 1, a particle 10 includes a core 16 (which may be in the form of a particle, referred to herein as a core particle) and a coating 20 surrounding the core. In one set of embodiments, a substantial portion of the core is formed of one or more solid pharmaceutical agents (e.g., a drug, therapeutic agent, diagnostic agent, imaging agent) that can lead to certain beneficial and/or therapeutic effects. The core may be, for example, a nanocrystal (i.e., a nanocrystal particle) of a pharmaceutical agent. In other embodiments, the core may include a polymeric carrier, optionally with one or more pharmaceutical agents encapsulated or otherwise associated with the core. In yet other cases, the core may include a lipid, a protein, a gel, a liquid, and/or another suitable material to be delivered to a subject. The core includes a surface 24 to which one or more surface-altering agents can be attached. For instance, in some cases, core 16 is surrounded by coating 20, which includes an inner surface 28 and an outer surface 32. The coating may be formed, at least in part, of one or more surface-altering agents 34, such as a polymer (e.g., a block copolymer and/or a polymer having pendant hydroxyl groups), which may associate with surface 24 of the core. Surface-altering agent 34 may be associated with the core particle by, for example, being covalently attached to the core particle, non-covalently attached to the core particle, adsorbed to the core, or attached to the core through ionic interactions, hydrophobic and/or hydrophilic interactions, electrostatic interactions, van der Waals interactions, or combinations thereof. In one set of embodiments, the surface-altering agents, or portions thereof, are chosen to facilitate transport of the particle through a mucosal barrier (e.g., mucus or a mucosal membrane). In certain embodiments described herein, one or more surface-altering agents 34 are oriented in a particular configuration in the coating of the particle. For example, in some embodiments in which a surface-altering agent is a triblock copolymer, such as a triblock copolymer having a hydrophilic block-hydrophobic block-hydrophilic block configuration, a hydrophobic block may be oriented towards the surface of the core, and hydrophilic blocks may be oriented away from the core surface (e.g., towards the exterior of the particle). The hydrophilic blocks may have characteristics that facilitate transport of the particle through a mucosal barrier, as described in more detail below.

Particle 10 may optionally include one or more components 40 such as targeting moieties, proteins, nucleic acids, and bioactive agents which may optionally impart specificity to the particle. For example, a targeting agent or molecule (e.g., a protein, nucleic acid, nucleic acid analog, carbohydrate, or small molecule), if present, may aid in directing the particle to a specific location in the subject's body. The location may be, for example, a tissue, a particular cell type, or a subcellular compartment. One or more components 40, if present, may be associated with the core, the coating, or both; e.g., they may be associated with surface 24 of the core, inner surface 28 of the coating, outer surface 32 of the coating, and/or embedded in the coating. The one or more components 40 may be associated through covalent bonds, absorption, or attached through ionic interactions, hydrophobic and/or hydrophilic interactions, electrostatic interactions, van der Waals interactions, or combinations thereof. In some embodiments, a component may be attached (e.g., covalently) to one or more of the surface-altering agents of the coated particle using methods known to those of ordinary skill in the art.

It should be understood that components and configurations other than those shown in FIG. 1 or described herein may be suitable for certain particles and compositions, and that not all of the components shown in FIG. 1 are necessarily present in some embodiments.

In one set of embodiments, particle 10, when introduced into a subject, may interact with one or more components in the subject such as mucus, cells, tissues, organs, particles, fluids (e.g., blood), portions thereof, and combinations thereof. In some such embodiments, the coating of particle 10 can be designed to include surface-altering agents or other components with properties that allow favorable interactions (e.g., transport, binding, adsorption) with one or more materials from the subject. For example, the coating may include surface-altering agents or other components having a certain hydrophilicity, hydrophobicity, surface charge, functional group, specificity for binding, and/or density to facilitate or reduce particular interactions in the subject. One specific example includes choosing a certain hydrophilicity, hydrophobicity, surface charge, functional group, specificity for binding, and/or density of one or more surface-altering agents to reduce the physical and/or chemical interactions between the particle and mucus of the subject, so as to enhance the mobility of the particle through mucus. Other examples are described in more detail below.

In some embodiments, once a particle is successfully transported across a mucosal barrier (e.g., mucus or a mucosal membrane) in a subject, further interactions between the particle in the subject may take place. Interactions may take place, in some instances, through the coating and/or the core, and may involve, for example, the exchange of materials (e.g., pharmaceutical agents, therapeutic agents, proteins, peptides, polypeptides, nucleic acids, nutrients, e.g.) from the one or more components of the subject to particle 10, and/or from particle 10 to the one or more components of the subject. For example, in some embodiments in which the core is formed of or comprises a pharmaceutical agent, the breakdown, release and/or transport of the pharmaceutical agent from the particle can lead to certain beneficial and/or therapeutic effects in the subject. As such, the particles described herein can be used for the diagnosis, prevention, treatment or management of certain diseases or bodily conditions.

Specific examples for the use of the particles described herein are provided below in the context of being suitable for administration to a mucosal barrier (e.g., mucus or a mucosal membrane) in a subject. It should be appreciated that while many of the embodiments herein are described in this context, and in the context of providing a benefit for diseases and conditions that involve transport of materials across a mucosal barrier, the invention is not limited as such and the particles, compositions, kits, and methods described herein may be used to prevent, treat, or manage other diseases or bodily conditions.

Mucus is a sticky viscoelastic gel that protects against pathogens, toxins, and debris at various points of entry into the body, including the eyes, nose, lungs, gastrointestinal tract, and female reproductive tract. Many synthetic nanoparticles are strongly mucoadhesive and become effectively trapped in the rapidly-cleared peripheral mucus layer, vastly limiting their distribution throughout the mucosal membrane as well as penetration toward the underlying tissue. The residence time of these trapped particles is limited by the turnover rate of the peripheral mucus layer, which, depending on the organ, ranges from seconds to several hours. To ensure effective delivery of particles including pharmaceutical agents (e.g., therapeutic, diagnostic, and/or imaging agents) via mucus membranes, such particles must be able to readily diffuse through the mucus barrier, avoiding mucus adhesion. As described in more detail below, delivery of particles in mucus of the eye has particular challenges.

It has been recently demonstrated that modifying surfaces of polymeric nanoparticles with a mucus-penetrating coating can minimize adhesion to mucus and thus allow rapid particle penetration across mucus barriers. Despite these improvements, only a handful of surface coatings have been shown to facilitate mucus penetration of particles. Accordingly, improvements in compositions and methods involving mucus-penetrating particles for delivery of pharmaceutical agents would be beneficial.

In some embodiments, the compositions and methods described herein involve mucus-penetrating particles without any polymeric carriers, or with minimal use of polymeric carriers. Polymer-based mucus-penetrating particles may have one or more inherent limitations in some embodiments. In particular, in light of drug delivery applications, these limitations may include one or more of the following: A) Low drug encapsulation efficiency and low drug loading: Encapsulation of drugs into polymeric particles is often inefficient, as generally less than 10% of the total amount of drug used gets encapsulated into particles during manufacturing. Additionally, drug loadings above 50% are rarely achieved. B) Convenience of usage: Formulations based on drug-loaded polymeric particles, in general, typically need to be stored as dry powder to avoid premature drug release and, thus, require either point-of-use re-constitution or a sophisticated dosing device. C) Biocompatibility: Accumulation of slowly degrading polymer carriers following repeated dosing and their toxicity over the long term present a major concern for polymeric drug carriers. D) Chemical and physical stability: Polymer degradation may compromise stability of encapsulated drugs. In many encapsulation processes, the drug undergoes a transition from a solution phase to a solid phase, which is not well-controlled in terms of physical form of the emerging solid phase (i.e., amorphous vs. crystalline vs. crystalline polymorphs). This is a concern for multiple aspects of formulation performance, including physical and chemical stability and release kinetics. E) Manufacturing complexity: Manufacturing, especially scalability, of drug-loaded polymeric MPPs is a fairly complex process that may involve multiple steps and a considerable amount of toxic organic solvents.

In some embodiments described herein, the compositions and methods of making particles, including certain compositions and methods for making particles that have increased transport through mucosal barriers, address one or more, or all, of the concerns described above. Specifically, in some embodiments, the compositions and methods do not involve encapsulation into polymeric carriers or involve minimal use of polymeric carriers. Advantageously, by avoiding or minimizing the need to encapsulate pharmaceutical agents (e.g., drugs, imaging or diagnostic agents) into polymeric carriers, certain limitations of polymeric MPPs with respect to drug loading, convenience of usage, biocompatibility, stability, and/or complexity of manufacturing, may be addressed. The methods and compositions described herein may facilitate clinical development of the mucus-penetrating particle technology.

It should be appreciated, however, that in other embodiments, pharmaceutical agents may be associated with polymer carriers via encapsulation or other processes. Thus, the description provided herein is not limited in this respect. For instance, despite the above-mentioned drawbacks of certain mucus-penetrating particles including a polymeric carrier, in certain embodiments such particles may be preferred. For example, it may be preferable to use polymer carriers for controlled release purposes and/or for encapsulating certain pharmaceutical agents that are difficult to formulate into particles. As such, in some embodiments described herein, particles that include a polymer carrier are described.

As described in more detail below, in some embodiments, the compositions and methods involve the use of PVAs that aids particle transport in mucus. The compositions and methods may involve making mucus-penetrating particles (MPPs) by, for example, an emulsification process in the presence of specific PVAs. In certain embodiments, the compositions and methods involve making MPPs from pre-fabricated particles by non-covalent coating with specific PVAs. In other embodiments, the compositions and methods involve making MPPs in the presence of specific PVAs without any polymeric carriers, or with minimal use of polymeric carriers. It should be appreciated, however, that in other embodiments, polymeric carriers can be used.

PVA is a water-soluble non-ionic synthetic polymer. Due to its surface active properties, PVA is widely used in the food and drug industries as a stabilizing agent for emulsions and, in particular, to enable encapsulation of a wide variety of compounds by emulsification techniques. PVA has the "generally recognized as safe" or "GRAS" status with the Food and Drug Administration (FDA), and has been used in auricular, intramuscular, intraocular, intravitreal, iontophoretic, ophthalmic, oral, topical, and transdermal drug products and/or drug delivery systems.

In certain previous studies, many have described PVA as a mucoadhesive polymer, suggesting or reporting that incorporating PVA in the particle formulation process leads to particles that are strongly mucoadhesive. Surprisingly, and contrary to the established opinion that PVA is a mucoadhesive polymer, the inventors have discovered within the context of the invention that compositions and methods utilizing specific PVA grades aid particle transport in mucus and are not mucoadhesive in certain applications described herein. Specifically, mucus-penetrating particles can be prepared by tailoring the degree of hydrolysis and/or molecular weight of the PVA, which was previously unknown. This discovery significantly broadens the arsenal of techniques and ingredients applicable for manufacturing MPPs.

In some embodiments described herein, the compositions and methods of making particles, including certain compositions and methods for making particles that have increased transport through mucosal barriers, address one or more, or all, of the concerns described above.

It should be appreciated that while some of the description herein may relate to the use of PVAs in coatings, in other embodiments, PVAs are not used or are used in conjunction with other polymers. For example, in some embodiments, PEG, Pluronics®, and/or other surfactants (e.g., a polysorbate (e.g., Tween 80®)) may be included in the compositions and methods described herein (in replace of or in addition to PVAs). In other embodiments, other polymers, such as those described in more detail herein, may be used in coatings described herein.

As described in more detail below, in some embodiments, the compositions and methods involve the use of poloxamers that aid particle transport in mucus. Poloxamers are typically nonionic triblock copolymers comprising a central hydrophobic block (e.g., a poly(propylene oxide) block) flanked by two hydrophilic blocks (e.g., poly(ethylene oxide) blocks). Poloxamers have the trade name Pluronic®, examples of which are provided below As described in more detail below, in certain embodiments, the compositions and methods involve the use of polysorbates that aid particle transport in mucus. Polysorbates are typically derived from PEGylated sorbitan (a derivative of sorbitol) esterified with fatty acids. Common brand names for polysorbates include Tween®, Alkest®, Canarcel®. Examples of polysorbates include polyoxyethylene sorbitan monooleate (e.g., Tween 80®), polyoxyethylene sorbitan monostearate (e.g., Tween 60®), polyoxyethylene sorbitan monopalmitate (e.g., Tween 40®), and polyoxyethylene sorbitan monolaurate (e.g., Tween 20®).

Core Particles

As described above in reference to FIG. 1, particle 10 may include a core 16. The core may be formed of any suitable material, such as an organic material, an inorganic material, a polymer, a lipid, a protein or combinations thereof. In one set of embodiments, the core comprises a solid. The solid may be, for example, a crystalline or an amorphous solid, such as a crystalline or amorphous solid pharmaceutical agent (e.g., a therapeutic agent, diagnostic agent, and/or imaging agent), or a salt thereof. In other embodiments, the core may comprise a gel or a liquid (e.g., an oil-in-water or water-in-oil emulsion). In some embodiments, more than one pharmaceutical agents may be present in the core. Specific examples of pharmaceutical agents are provided in more detail below.

The pharmaceutical agent may be present in the core in any suitable amount, e.g., at least about 0.01 wt %, at least about 0.1 wt %, at least about 1 wt %, at least about 5 wt %, at least about 10 wt %, at least about 20 wt %, at least about 30 wt %, at least about 40 wt %, at least about 50 wt %, at least about 60 wt %, at least about 70 wt %, at least about 80 wt %, at least about 85 wt %, at least about 90 wt %, at least about 95 wt %, or at least about 99 wt % of the core. In one embodiment, the core is formed of 100 wt % of the pharmaceutical agent. In some cases, the pharmaceutical agent may be present in the core at less than or equal to about 100 wt %, less than or equal to about 90 wt %, less than or equal to about 80 wt %, less than or equal to about 70 wt %, less than or equal to about 60 wt %, less than or equal to about 50 wt %, less than or equal to about 40 wt %, less than or equal to about 30 wt %, less than or equal to about 20 wt %, less than or equal to about 10 wt %, less than or equal to about 5 wt %, less than or equal to about 2 wt %, or less than or equal to about 1 wt %. Combinations of the above-referenced ranges are also possible (e.g., present in an amount of at least about 80 wt % and less than or equal to about 100 wt %). Other ranges are also possible.

In embodiments in which the core particles comprise relatively high amounts of a pharmaceutical agent (e.g., at least about 50 wt % of the core particle), the core particles generally have an increased loading of the pharmaceutical agent compared to particles that are formed by encapsulating agents into polymeric carriers. This is an advantage for drug delivery applications, since higher drug loadings mean that fewer numbers of particles may be needed to achieve a desired effect compared to the use of particles containing polymeric carriers.

As described herein, in other embodiments in which a relatively high amounts of a polymer or other material forms the core, less amounts of pharmaceutical agent may be present in the core.

The core may be formed of solid materials having various aqueous solubilities (i.e., a solubility in water, optionally with one or more buffers), and/or various solubilities in the solution in which the solid material is being coated with a surface-altering agent. For example, the solid material may have an aqueous solubility (or a solubility in a coating solution) of less than or equal to about 5 mg/mL, less than or equal to about 2 mg/mL, less than or equal to about 1 mg/mL, less than or equal to about 0.5 mg/mL, less than or equal to about 0.1 mg/mL, less than or equal to about 0.05 mg/mL, less than or equal to about 0.01 mg/mL, less than or equal to about 1 µg/mL, less than or equal to about 0.1 µg/mL, less than or equal to about 0.01 µg/mL, less than or equal to about 1 ng/mL, less than or equal to about 0.1 ng/mL, or less than or equal to about 0.01 ng/mL at 25° C. In some embodiments, the solid material may have an aqueous solubility (or a solubility in a coating solution) of at least about 1 µg/mL, at least about 10 µg/mL, at least about 0.1 ng/mL, at least about 1 ng/mL, at least about 10 ng/mL, at least about 0.1 µg/mL, at least about 1 µg/mL, at least about 5 µg/mL, at least about 0.01 mg/mL, at least about 0.05 mg/mL, at least about 0.1 mg/mL, at least about 0.5 mg/mL, at least about 1.0 mg/mL, at least about 2 mg/mL. Combinations of the above-noted ranges are possible (e.g., an aqueous solubility or a solubility in a coating solution of at least about 10 µg/mL and less than or equal to about 1 mg/mL). Other ranges are also possible. The solid material may have these or other ranges of aqueous solubilities at any point throughout the pH range (e.g., from pH 1 to pH 14).

In some embodiments, the core may be formed of a material within one of the ranges of solubilities classified by the U.S. Pharmacopeia Convention: e.g., very soluble: >1,000 mg/mL; freely soluble: 100-1,000 mg/mL; soluble: 33-100 mg/mL; sparingly soluble: 10-33 mg/mL; slightly soluble: 1-10 mg/mL; very slightly soluble: 0.1-1 mg/mL; and practically insoluble: <0.1 mg/mL.

Although a core may be hydrophobic or hydrophilic, in many embodiments described herein, the core is substantially hydrophobic. "Hydrophobic" and "hydrophilic" are given their ordinary meaning in the art and, as will be understood by those skilled in the art, in many instances herein, are relative terms. Relative hydrophobicities and hydrophilicities of materials can be determined by measuring the contact angle of a water droplet on a planar surface of the substance to be measured, e.g., using an instrument such as a contact angle goniometer and a packed powder of the core material.

In some embodiments, a material (e.g., a material forming a particle core) has a contact angle of at least about 20 degrees, at least about 30 degrees, at least about 40 degrees, at least about 50 degrees, at least about 60 degrees, at least about 70 degrees, at least about 80 degrees, at least about 90 degrees, at least about 100 degrees, at least about 110 degrees, at least about 120 degrees, or at least about 130 degrees. In some embodiments, a material has a contact angle of less than or equal to about 160 degrees, less than or equal to about 150 degrees, less than or equal to about 140 degrees, less than or equal to about 130 degrees, less than or equal to about 120 degrees, less than or equal to about 110 degrees, less than or equal to about 100 degrees, less than or equal to about 90 degrees, less than or equal to about 80 degrees, or less than or equal to about 70 degrees. Combinations of the above-referenced ranges are also possible (e.g., a contact angle of at least about 30 degrees and less than or equal to about 120 degrees). Other ranges are also possible.

Contact angle measurements can be made using a variety of techniques; here a static contact angle measurement between a pellet of the starting material which will be used to form the core and a bead of water is referenced. The material used to form the core was received as a fine powder or otherwise was ground into a fine powder using a mortar and pestle. In order to form a surface on which to make measurements, the powder was packed using a 7 mm pellet die set from International Crystal Labs. The material was added to the die and pressure was applied by hand to pack the powder into a pellet, no pellet press or high pressure was used. The pellet was then suspended for testing so that the top and bottom of the pellet (defined as the surface water is added to and the opposite parallel surface respectively) were not in contact with any surface. This was done by not fully removing the pellet from the collar of the die set. The pellet therefore touches the collar on the sides and makes no contact on the top or bottom. For contact angle measurements, water was added to the surface of the pellet until a bead of water with a steady contact angle over 30 seconds was obtained. The water was added into the bead of water by submerging or contacting the tip of the pipette or syringe used for addition to the bead of water. Once a stable bead of water was obtained, an image was taken and the contact angle was measured using standard practices.

In embodiments in which the core comprises an inorganic material (e.g., for use as imaging agents), the inorganic material may include, for example, a metal (e.g., Ag, Au, Pt, Fe, Cr, Co, Ni, Cu, Zn, and other transition metals), a semiconductor (e.g., silicon, silicon compounds and alloys, cadmium selenide, cadmium sulfide, indium arsenide, and indium phosphide), or an insulator (e.g., ceramics such as silicon oxide). The inorganic material may be present in the core in any suitable amount, e.g., at least about 1 wt %, at least about 5 wt %, at least about 10 wt %, at least about 20 wt %, at least about 30 wt %, at least about 40 wt %, at least about 50 wt %, at least about 75 wt %, at least about 90 wt %, or at least about 99 wt %. In one embodiment, the core is formed of 100 wt % inorganic material. In some cases, the inorganic material may be present in the core at less than or equal to about 100 wt %, less than or equal to about 90 wt %, less than or equal to about 80 wt %, less than or equal to about 70 wt %, less than or equal to about 60 wt %, less than or equal to about 50 wt %, less than or equal to about 40 wt %, less than or equal to about 30 wt %, less than or equal to about 20 wt %, less than or equal to about 10 wt %, less than or equal to about 5 wt %, less than or equal to about 2 wt %, or less than or equal to about 1 wt %. Combinations of the above-referenced ranges are also possible (e.g., present in an amount of at least about 1 wt % and less than or equal to about 20 wt %). Other ranges are also possible.

The core may, in some cases, be in the form of a quantum dot, a carbon nanotube, a carbon nanowire, or a carbon nanorod. In some cases, the core comprises, or is formed of, a material that is not of biological origin.

In some embodiments, the core includes one or more organic materials such as a synthetic polymer and/or a natural polymer. Examples of synthetic polymers include non-degradable polymers such as polymethacrylate and degradable polymers such as polylactic acid, polyglycolic acid and copolymers thereof. Examples of natural polymers include hyaluronic acid, chitosan, and collagen. Other examples of polymers that may be suitable for portions of the core include those herein suitable for forming coatings on particles, as described below. In some cases, the one or more polymers present in the core may be used to encapsulate or adsorb one or more pharmaceutical agents.

In certain embodiments, a core may include a pharmaceutical agent comprising a lipid and/or a protein. Other materials are also possible.

If a polymer is present in the core, the polymer may be present in the core in any suitable amount, e.g., less than or equal to about 100 wt %, less than or equal to about 90 wt %, less than or equal to about 80 wt %, less than or equal to about 70 wt %, less than or equal to about 60 wt %, less than or equal to about 50 wt %, less than or equal to about 40 wt %, less than or equal to about 30 wt %, less than or equal to about 20 wt %, less than or equal to about 10 wt %, less than or equal to about 5 wt %, less than or equal to about 2 wt %, or less than or equal to about 1 wt %. In some cases, the polymer may be present in an amount of at least about 1 wt %, at least about 5 wt %, at least about 10 wt %, at least about 20 wt %, at least about 30 wt %, at least about 40 wt %, at least about 50 wt %, at least about 75 wt %, at least about 90 wt %, or at least about 99 wt % in the core. Combinations of the above-referenced ranges are also possible (e.g., present in an amount of at least about 1 wt % and less than or equal to about 20 wt %). Other ranges are also possible. In one set of embodiments, the core is formed is substantially free of a polymeric component.

The core of a particle described herein may include a mixture of more than one polymer. In some embodiments, the core, or at least a portion of the core, includes a mixture of a first polymer and a second polymer. In certain embodiments, the first polymer is a polymer described herein. In certain embodiments, the first polymer is a relatively hydrophobic polymer (e.g., a polymer having a higher hydrophobicity than the second polymer). In certain embodiments, the first polymer is not a polyalkyl ether. In certain embodiments, the first polymer is polylactide (PLA), e.g., 100DL7A MW108K. In certain embodiments, the first polymer is polylactide-co-glycolide (PLGA), e.g., PLGA1A MW4K. In other embodiments, however, the first polymer may be a relatively hydrophilic polymer (e.g., a polymer having a higher hydrophilicity than the second polymer).

In certain embodiments, the second polymer is a block copolymer described herein (e.g., a diblock copolymer or a triblock copolymer). In certain embodiments, the second polymer is a diblock copolymer including a relatively hydrophilic block (e.g., a polyalkyl ether block) and a relatively hydrophobic block (e.g., a non-(polyalkyl ether) block). In certain embodiments, the polyalkyl ether block of the second polymer is PEG (e.g., PEG2K or PEG5K). In certain embodiments, the non-(polyalkyl ether) block of the second polymer is PLA (e.g., 100DL9K, 100DL30, or 100DL95). In certain embodiments, the non-(polyalkyl ether) block of the second polymer is PLGA (e.g., 8515PLGA54K, 7525PLGA15K, or 5050PLGA18K). In certain embodiments, the second polymer is 100DL9K-co-PEG2K. In certain embodiments, the second polymer is 8515PLGA54K-co-PEG2K.

It should be appreciated that while "first" and "second" polymers are described, in some embodiments, a particle or core described herein may include only one such polymer. Additionally, while specific examples of first and second polymers are provided, it should be appreciated that other polymers, such as the polymers listed herein, can be used as first or second polymers.

The first polymer and the relatively hydrophobic block of the second polymer may be the same or different polymer. In some cases, the relatively hydrophilic block of the second polymer is present primarily at or on the surface of the core that includes the first and second polymers. For instance, the relatively hydrophilic block of the second polymer may act as a surface-altering agent as described herein. In some cases, the relatively hydrophobic block of the second polymer and the first polymer are present primarily inside the surface of the core that includes the first and second polymers. Additional details are provided in Example 19.

The relatively hydrophilic block (e.g., a polyalkyl ether block, such as PEG block) of the second polymer may have any suitable molecular weight. In certain embodiments, the molecular weight of the relatively hydrophilic block of the second polymer is at least about 0.1 kDa, at least about 0.2 kDa, at least about 0.5 kDa, at least about 1 kDa, at least about 1.5 kDa, at least about 2 kDa, at least about 2.5 kDa, at least about 3 kDa, at least about 4 kDa, at least about 5 kDa, at least about 6 kDa, at least about 8 kDa, at least about 10 kDa, at least about 20 kDa, at least about 50 kDa, at least about 100 kDa, or at least about 300 kDa. In certain embodiments, the molecular weight of the relatively hydrophilic block of the second polymer is less than or equal to about 300 kDa, less than or equal to about 100 kDa, less than or equal to about 50 kDa, less than or equal to about 20 kDa, less than or equal to about 10 kDa, less than or equal to about 8 kDa, less than or equal to about 6 kDa, at least about 5 kDa, less than or equal to about 4 kDa, less than or equal to about 3 kDa, less than or equal to about 2.5 kDa, less than or equal to about 2 kDa, less than or equal to about 1.5 kDa, less than or equal to about 1 kDa, less than or equal to about 0.5 kDa, less than or equal to about 0.2 kDa, or less than or equal to about 0.1 kDa. Combinations of the above-mentioned ranges are also possible (e.g., at least about 0.5 kDa and less than or equal to about 10 kDa). Other ranges are also possible. In certain embodiments, the molecular weight of the relatively hydrophilic block of the second polymer is about 2 kDa. In certain embodiments, the molecular weight of the relatively hydrophilic block of the second polymer is about 5 kDa.

The relatively hydrophobic block (e.g., a non-(polyalkyl ether) block, such as PLGA or PLA block) of the second polymer may have any suitable molecular weight. In certain embodiments, the relatively hydrophobic block of the second polymer is relatively short in length and/or low in molecular weight. In certain embodiments, the molecular weight of the relatively hydrophobic block of the second polymer is less than or equal to about 300 kDa, less than or equal to about 100 kDa, less than or equal to about 80 kDa, less than or equal to about 60 kDa, less than or equal to about 54 kDa, less than or equal to about 50 kDa, less than or equal to about 40 kDa, less than or equal to about 30 kDa, less than or equal to about 20 kDa, less than or equal to about 15 kDa less than or equal to about 10 kDa, less than or equal to about 5 kDa, less than or equal to about 2 kDa, or less than or equal to about 1 kDa. In certain embodiments, the molecular weight of the PLGA or PLA block of the second polymer is at least about 0.1 kDa, at least about 0.3 kDa, at least about 1 kDa, at least about 2 kDa, at least about 4 kDa, at least about 6 kDa, at least about 7 kDa, at least about 8 kDa, at least about 9 kDa, at least about 10 kDa, at least about 12 kDa, at least about 15 kDa, at least about 20 kDa, at least about 30 kDa, at least about 50 kDa, or at least about 100 kDa. Combinations of the above-mentioned ranges are also possible (e.g., less than or equal to about 20 kDa and at least about 1 kDa). Other ranges are also possible. In certain embodiments, the molecular weight of the relatively hydrophobic block of the second polymer is about 9 kDa.

The relatively hydrophilic block (e.g., a polyalkyl ether block, such as PEG block) of the second polymer may be present in any suitable amount or density at or on the surface of a core described herein. In certain embodiments, the PEG block of the second polymer is present at or on the surface of the core at at least about 0.001, at least about 0.003, at least about 0.03, at least about 0.1 at least about 0.15, at least about 0.18, at least about 0.2, at least about 0.3, at least about 0.5, at least about 1, at least about 3, at least about 30, or at least about 100 PEG chains per nm$^2$ of the surface area of the core. In certain embodiments, the PEG block of the second polymer is present at or on the surface of the core at less than or equal to about 100, less than or equal to about 30, less than or equal to about 10, less than or equal to about 3, less than or equal to about 1, less than or equal to about 0.5, less than or equal to about 0.3, less than or equal to about 0.2, less than or equal to about 0.18, less than or equal to about 0.15, less than or equal to about 0.1, less than or equal to about 0.03, less than or equal to about 0.01, less than or equal to about 0.003, or less than or equal to about 0.001 PEG chains per nm$^2$ of the surface area of the core. Combinations of the above-mentioned ranges are also possible (e.g., at least about 0.03 and less than or equal to about 1 PEG chains per nm$^2$ of the surface area of the core). Other ranges are also possible. In certain embodiments, the PEG block of the second polymer is present at or on the surface of the core at at least about 0.18 PEG chains per nm$^2$ of the surface area of the core.

The relatively hydrophilic block (e.g., a polyalkyl ether block, such as PEG block) of the second polymer may be present in any suitable amount in a particle or core described herein. In certain embodiments, the relatively hydrophilic block of the second polymer is present in the core at less than or equal to about less than or equal to about 90 wt %, less than or equal to about 80 wt %, less than or equal to about 70 wt %, less than or equal to about 60 wt %, less than or equal to about 50 wt %, less than or equal to about 40 wt %, less than or equal to about 30 wt %, less than or equal to about 20 wt %, less than or equal to about 10 wt %, less than or equal to about 5 wt %, less than or equal to about 4 wt %, less than or equal to about 3 wt %, less than or equal to about 2 wt %, less than or equal to about 1 wt %, less than or equal to about 0.5 wt %, less than or equal to about 0.2 wt %, less than or equal to about 0.1 wt %, less than or equal to about 0.05 wt %, less than or equal to about 0.02 wt %, or less than or equal to about 0.01 wt % of the particle or core. In certain embodiments, the relatively hydrophilic block of the second polymer is present in the core at at least about 0.01 wt %, at least about 0.02 wt %, at least about 0.05 wt %, at least about 0.1 wt %, at least about 0.2 wt %, at least about 0.5 wt %, at least about 1 wt %, at least about 2 wt %, at least about 3 wt %, at least about 4 wt %, at least about 5 wt %, at least about 10 wt %, at least about 20 wt %, at least about 30 wt %, at least about 40 wt %, at least about 50 wt %, at least about 60 wt %, at least about 70 wt %, at least about 80 wt %, or at least about 90 wt % of the particle or core. Combinations of the above-mentioned ranges are also possible (e.g., less than or equal to about 10 wt % and at least about 0.5 wt % of the particle or core). Other ranges are also possible. In certain embodiments, the relatively hydrophilic block of the second polymer is present at less than or equal to about 3 wt % of the particle or core.

The relatively hydrophilic block (e.g., a polyalkyl ether block, such as PEG block) and the relatively hydrophobic block (e.g., a non-(polyalkyl ether) block, such as PLGA or PLA block) of the second polymer may be present in the core in any suitable ratio. In certain embodiments, the ratio of the relatively hydrophilic block to relatively hydrophobic block of the second polymers is at least about 1:99, at least about 10:90, at least about 20:80, at least about 30:70, at least about 40:60, at least about 50:50, at least about 60:40, at least about 70:30, at least about 80:20, at least about 90:10, or at least about 99:1 w/w. In certain embodiments, the ratio of the relatively hydrophilic block to relatively hydrophobic block is less than or equal to about 99:1, less than or equal to about 90:10, less than or equal to about 80:20, less than or equal to about 70:30, less than or equal to about 60:40, less than or equal to about 50:50, less than or equal to about 40:60, less than or equal to about 30:70, less than or equal to about 20:80, less than or equal to about 10:90, or less than or equal to about 1:99 w/w. Combinations of the above-mentioned ranges are also possible (e.g., greater than about 70:30 and less than or equal to about 90:10 w/w). Other ranges are also possible. In certain embodiments, the ratio of the relatively hydrophilic block to relatively hydrophobic block is about 20:80 w/w.

The first polymer (e.g., PLA or PLGA) and the second polymer (e.g., PLA-co-PEG or PLGA-co-PEG) may be present in the particle or core in any suitable ratio. In certain embodiments, the ratio of the first polymer to second polymer in the particle or core is at least about 1:99, at least about 10:90, at least about 20:80, at least about 30:70, at least about 40:60, at least about 50:50, at least about 60:40, at least about 65:35, at least about 70:30, at least about 75:25, at least about 80:20, at least about 85:15, at least about 90:10, at least about 95:5, or at least about 99:1 w/w. In certain embodiments, the ratio of the first polymer to second polymer in the particle or core is less than or equal to about 99:1, less than or equal to about 95:5, less than or equal to about 90:10, less than or equal to about 85:15, less than or equal to about 80:20, less than or equal to about 75:25, less than or equal to about 70:30, less than or equal to about 65:35, less than or equal to about 60:40, less than or equal to about 50:50, less than or equal to about 40:60, less than or equal to about 30:70, less than or equal to about 20:80, less than or equal to about 10:90, or less than or equal to about 1:99 w/w. Combinations of the above-mentioned ranges are also possible (e.g., greater than about 70:30 and less than or equal to about 90:10 w/w). Other ranges are also possible. In certain embodiments, the ratio of the first polymer to second polymer in the particle or core is about 70:30 w/w. In certain embodiments, the ratio of the first polymer to second polymer in the particle or core is about 80:20 w/w.

The particle or core comprising a mixture of the first polymer and the second polymer described herein may further include a coating described herein. The coating may be at or on the surface of the particle (e.g., the surface of the first polymer and/or the second polymer). In some embodiments, the coating includes a hydrophilic material. The coating may include one or more surface-altering agents described herein, such as a polymer and/or a surfactant (e.g., a PVA, a poloxamer, a polysorbate (e.g., Tween 80®)).

The core may have any suitable shape and/or size. For instance, the core may be substantially spherical, non-spherical, oval, rod-shaped, pyramidal, cube-like, disk-shaped, wire-like, or irregularly shaped. The core may have a largest or smallest cross-sectional dimension of, for example, less than or equal to about 10 µm, less than or equal to about 5 µm, less than or equal to about 1 µm, less than or equal to about 800 nm, less than or equal to about 700 nm, less than or equal to about 500 nm, less than or equal to 400 nm, less than or equal to 300 nm, less than or equal to about 200 nm, less than or equal to about 100 nm, less than or equal to about 75 nm, less than or equal to about 50 nm, less than or equal to about 40 nm, less than or equal to about 35 nm, less than or equal to about 30 nm, less than or equal to about 25 nm, less than or equal to about 20 nm, less than or equal to about 15 nm, or less than or equal to about 5 nm. In some cases, the core may have a largest or smallest cross-sectional dimension of, for example, at least about 5 nm, at least about 20 nm, at least about 50 nm, at least about 100 nm, at least about 200 nm, at least about 300 nm, at least about 400 nm, at least about 500 nm, at least about 1 µm, or at least about 5 µm. Combinations of the above-referenced ranges are also possible (e.g., a largest or smallest cross-sectional dimension of at least about 50 nm and less than or equal to about 500 nm). Other ranges are also possible. In some embodiments, the sizes of the cores formed by a process described herein have a Gaussian-type distribution. Unless indicated otherwise, the measurements of particle/core sizes herein refer to the smallest cross-sectional dimension.

Those of ordinary skill in the art are familiar with techniques to determine sizes (e.g., smallest or largest cross-sectional dimensions) of particles. Examples of suitable techniques include (DLS), transmission electron microscopy, scanning electron microscopy, electroresistance counting and laser diffraction. Other suitable techniques are known to those or ordinary skill in the art. Although many methods for determining sizes of particles are known, the sizes described herein (e.g., average particle sizes, thicknesses) refer to ones measured by dynamic light scattering.

Methods of Forming Core Particles and Coated Particles

The core particles described herein may be formed by any suitable method. Suitable methods may include, for example, so called top-down techniques, i.e. techniques based on size reduction of relatively large particles into smaller particles (e.g., milling or homogenization) or so called bottom-up techniques, i.e. techniques based on the growth of particles from smaller particles or individual molecules (e.g., precipitation or spray-freezing into liquid).

In some embodiments, core particles may be coated with a coating. For example, core particles may be provided or formed in a first step, and then the particles may be coated in a second step to form coated particles. In other embodiments, core particles may be formed and coated substantially simultaneously (e.g., in a single step). Examples of these and other methods are provided below.

In some embodiments, the coated particles described herein are formed by a method that involves using a formulation process, a milling process, and/or a dilution process. In certain embodiments, a method of forming the particles includes a milling process, optionally with a formulation process and/or a dilution process. A formulation process may be used to form a suspension or solution comprising a core material, one or more surface-altering agents, and other components, such as solvents, tonicity agents, chelating agents, salts, preservatives, anti-microbial agents and/or buffers (e.g., a sodium citrate and citric acid buffer), each of which is as described herein. The formulation process may be performed using a formulation vessel. The core material and other components may be added into the formulation vessel at the same time or different times. A mixture of the core material and/or one or more other components may be stirred and/or shaken, or otherwise agitated in the vessel to facilitate suspending and/or dissolving the components. The temperature and/or pressure of the fluids containing the core material, the other components, and/or the mixture may also be individually increased or decreased to facilitate the suspending and/or dissolving processes. In some embodiments, the core material and other components are processed as described herein in the formulation vessel under an inert atmosphere (e.g., nitrogen or argon) and/or protected from light. The suspension or solution obtained from the formulation vessel may be subsequently subject to a milling process which may be followed by a dilution process.

In some embodiments involving a core comprising a solid material, a milling process may be used to reduce the size of the solid material to form particles in the micrometer to nanometer size range. The milling process may be performed using a mill or other suitable apparatus. Dry and wet milling processes such as jet milling, cryo-milling, ball milling, media milling, sonication, and homogenization are known and can be used in methods described herein. Generally, in a wet milling process, a suspension of the material to be used as the core is agitated with or without excipients to reduce particle size. Dry milling is a process wherein the material to be used as the core is mixed with milling media with or without excipients to reduce particle size. In a cyro-milling process, a suspension of the material to be used as the core is mixed with milling media with or without excipients under cooled temperatures.

After milling or other suitable process for reducing the size of a core material, a dilution process may be used to form and/or modify coated particles from a suspension. The coated particles may comprise a core material, one or more surface-altering agents, and other components, such as solvents, tonicity agents, chelating agents, salts, preservatives, anti-microbial agents, and buffers (e.g., a sodium citrate and citric acid buffer). A dilution process may be used to achieve a target dosing concentration by diluting a solution or suspension of particles that were coated during a milling step, with or without the additional of surface-altering agents and/or other components. In certain embodiments, a dilution process may be used to exchange a first surface-altering agent with a second surface-altering agent from a surface of a particle as described herein.

The dilution process may be performed using a product vessel or any other suitable apparatus. In certain embodiments, the suspension is diluted, i.e., mixed or otherwise processed with a diluent, in the product vessel. The diluent may contain solvents, surface-altering agents, tonicity agents, chelating agents, salts, preservatives, or anti-microbial agents, or a combination thereof, as described herein. The suspension and the diluent may be added into the product vessel at the same time or different times. In certain embodiments when the suspension is obtained from a milling process involving milling media, the milling media may be separated from the suspension before the suspension is added into the product vessel. The suspension, the diluent, or the mixture of the suspension and the diluent may be stirred and/or shaken, or otherwise agitated, to form the coated particles described herein. The temperature and/or pressure of the suspension, the diluent, or the mixture may also be individually increased or decreased to form the coated particles. In some embodiments, the suspension and the diluent are processed in the product vessel under an inert atmosphere (e.g., nitrogen or argon) and/or protected from light.

In some embodiments, the core particles described herein may be produced by milling of a solid material (e.g., a pharmaceutical agent) in the presence of one or more surface-altering agents. Small particles of a solid material may require the presence of one or more surface-altering agents, which may function as a stabilizer in some embodiments, in order to stabilize a suspension of particles without agglomeration or aggregation in a liquid solution. In some such embodiments, the stabilizer may act as a surface-altering agent, forming a coating on the particle.

As described herein, in some embodiments, a method of forming a core particle involves choosing a surface-altering agent that is suitable for both milling and for forming a coating on the particle and rendering the particle mucus penetrating. For example, as described in more detail below, it has been demonstrated that 200-500 nm nanoparticles of a model compound pyrene produced by milling of pyrene in the presence of certain Pluronics® polymers resulted in particles that can penetrate physiological mucus samples at the same rate as well-established PEGylated polymeric MPPs. Interestingly, it was observed that only a subset of Pluronics® polymers tested fit the criteria of being suitable for both milling and for forming a coating on the particle that renders the particle mucus penetrating, as described in more detail below.

In a wet milling process, milling can be performed in a dispersion (e.g., an aqueous dispersion) containing one or more surface-altering agents, a grinding medium, a solid to be milled (e.g., a solid pharmaceutical agent), and a solvent. Any suitable amount of a surface-altering agent can be included in the solvent. In some embodiments, a surface-altering agent may be present in the solvent in an amount of at least about 0.001% (wt % or % weight to volume (w:v)), at least about 0.01%, at least about 0.1%, at least about 0.5%, at least about 1%, at least about 2%, at least about 3%, at least about 4%, at least about 5%, at least about 6%, at least about 7%, at least about 8%, at least about 10%, at least about 12%, at least about 15%, at least about 20%, at least about 40%, at least about 60%, or at least about 80% of the solvent. In some cases, the surface-altering agent may be present in the solvent in an amount of about 100% (e.g., in an instance where the surface-altering agent is the solvent). In other embodiments, the surface-altering agent may be present in the solvent in an amount of less than or equal to about 100%, less than or equal to about 80%, less than or equal to about 60%, less than or equal to about 40%, less than or equal to about 20%, less than or equal to about 15%, less than or equal to about 12%, less than or equal to about 10%, less than or equal to about 8%, less than or equal to about 7%, less than or equal to about 6%, less than or equal to about 5%, less than or equal to about 4%, less than or equal to about 3%, less than or equal to about 2%, or less than or equal to about 1% of the solvent. Combinations of the above-referenced ranges are also possible (e.g., an amount of less than or equal to about 5% and at least about 1% of the solvent). Other ranges are also possible. In certain embodiments, the surface-altering agent is present in the solvent in an amount of about 0.01-2% of the solvent. In certain embodiments, the surface-altering agent is present in the solvent in an amount of about 0.2-20% of the solvent. In certain embodiments, the surface-altering agent is present in the solvent in an amount of about 0.1% of the solvent. In certain embodiments, the surface-altering agent is present in the solvent in an amount of about 0.4% of the solvent. In certain embodiments, the surface-altering agent is present in the solvent in an amount of about 1% of the solvent. In certain embodiments, the surface-altering agent is present in the solvent in an amount of about 2% of the solvent. In certain embodiments, the surface-altering agent is present in the solvent in an amount of about 5% of the solvent. In certain embodiments, the surface-altering agent is present in the solvent in an amount of about 10% of the solvent.

The particular range chosen may influence factors that may affect the ability of the particles to penetrate mucus such as the stability of the coating of the surface-altering agent on the particle surface, the average thickness of the coating of the surface-altering agent on the particles, the orientation of the surface-altering agent on the particles, the density of the surface altering agent on the particles, surface-altering agent:drug ratio, drug concentration, the size, dispersibility, and polydispersity of the particles formed, and the morphology of the particles formed.

The pharmaceutical agent (or salt thereof) may be present in the solvent in any suitable amount. In some embodiments, the pharmaceutical agent (or salt thereof) is present in an amount of at least about 0.001% (wt % or % weight to volume (w:v)), at least about 0.01%, at least about 0.1%, at least about 0.5%, at least about 1%, at least about 2%, at least about 3%, at least about 4%, at least about 5%, at least about 6%, at least about 7%, at least about 8%, at least about 10%, at least about 12%, at least about 15%, at least about 20%, at least about 30%, at least about 40%, at least about 60%, or at least about 80% of the solvent. In some cases, the pharmaceutical agent (or salt thereof) may be present in the solvent in an amount of less than or equal to about 100%, less than or equal to about 90%, less than or equal to about 80%, less than or equal to about 60%, less than or equal to about 40%, less than or equal to about 30%, less than or equal to about 20%, less than or equal to about 15%, less than or equal to about 12%, less than or equal to about 10%, less than or equal to about 8%, less than or equal to about 7%, less than or equal to about 6%, less than or equal to about 5%, less than or equal to about 4%, less than or equal to about 3%, less than or equal to about 2%, or less than or equal to about 1% of the solvent. Combinations of the above-referenced ranges are also possible (e.g., an amount of less than or equal to about 20% and at least about 1% of the solvent). In some embodiments, the pharmaceutical agent is present in the above ranges but in w:v The ratio of surface-altering agent to pharmaceutical agent (or salt thereof) in a solvent may also vary. In some embodiments, the ratio of surface-altering agent to pharmaceutical agent (or salt thereof) may be at least 0.001:1 (weight ratio, molar ratio, or w:v ratio), at least 0.01:1, at least 0.01:1, at least 1:1, at least 2:1, at least 3:1, at least 5:1, at least 10:1, at least 25:1, at least 50:1, at least 100:1, or at least 500:1. In some cases, the ratio of surface-altering agent to pharmaceutical agent (or salt thereof) may be less than or equal to 1000:1 (weight ratio or molar ratio), less than or equal to 500:1, less than or equal to 100:1, less than or equal to 75:1, less than or equal to 50:1, less than or equal to 25:1, less than or equal to 10:1, less than or equal to 5:1, less than or equal to 3:1, less than or equal to 2:1, less than or equal to 1:1, or less than or equal to 0.1:1. Combinations of the above-referenced ranges are possible (e.g., a ratio of at least 5:1 and less than or equal to 50:1). Other ranges are also possible.

Surface-altering agents that may be suitable for use in coatings include, for example, polymers and surfactants. Non-limiting examples of polymers that are suitable for use in coatings as surface-altering agents, as described in more detail below, include poly(vinyl alcohol) and Pluronics®. Non-limiting examples of surfactants that are suitable for use in coatings as surface-altering agents include L-α-phosphatidylcholine (PC), 1,2-dipalmitoylphosphatidylcholine (DPPC), oleic acid, sorbitan trioleate, sorbitan monooleate, sorbitan monolaurate, polyoxylene sorbitan fatty acid esters (Tweens), polysorbates (e.g., polyoxyethylene sorbitan monooleate) (e.g., Tween 80®), polyoxyethylene sorbitan monostearate (e.g., Tween 60®), polyoxyethylene sorbitan monopalmitate (e.g., Tween 40®), polyoxyethylene sorbitan monolaurate (e.g., Tween 20®), natural lecithin, oleyl polyoxyethylene ether, stearyl polyoxyethylene ether, lauryl polyoxyethylene ether, polyoxylene alkyl ethers, block copolymers of oxyethylene and oxypropylene, polyoxyethylene stearates, polyoxyethylene castor oil and their derivatives, Vitamin-PEG and their derivatives, synthetic lecithin, diethylene glycol dioleate, tetrahydrofurfuryl oleate, ethyl oleate, isopropyl myristate, glyceryl monooleate, glyceryl monostearate, glyceryl monoricinoleate, cetyl alcohol, stearyl alcohol, polyethylene glycol, cetyl pyridinium chloride, benzalkonium chloride, olive oil, glyceryl monolaurate, corn oil, cotton seed oil, and sunflower seed oil. Derivatives of the above-noted compounds are also possible. Combinations of the above-noted compounds and others described herein may also be used as surface-altering agents in the inventive particles. As described herein, in some embodiments a surface-altering agent may act as a stabilizer, a surfactant, and/or an emulsifier. In some embodiments, the surface altering agent may aid particle transport in mucus.

It should be appreciated that while in some embodiments the stabilizer used for milling forms a coating on a particle surface, which coating renders particle mucus penetrating, in other embodiments, the stabilizer may be exchanged with one or more other surface-altering agents after the particle has been formed. For example, in one set of methods, a first stabilizer/surface-altering agent may be used during a milling process and may coat a surface of a core particle, and then all or portions of the first stabilizer/surface-altering agent may be exchanged with a second stabilizer/surface-altering agent to coat all or portions of the core particle surface. In some cases, the second stabilizer/surface-altering agent may render the particle mucus penetrating more than the first stabilizer/surface-altering agent. In some embodiments, a core particle having a coating including multiple surface-altering agents may be formed.

Any suitable grinding medium can be used for milling. In some embodiments, a ceramic and/or polymeric material and/or a metal can be used. Examples of suitable materials may include zirconium oxide, silicon carbide, silicon oxide, silicon nitride, zirconium silicate, yttrium oxide, glass, alumina, alpha-alumina, aluminum oxide, polystyrene, poly (methyl methacrylate), titanium, steel. A grinding medium may have any suitable size. For example, the grinding medium may have an average diameter of at least about 0.1 mm, at least about 0.2 mm, at least about 0.5 mm, at least about 0.8 mm, at least about 1 mm, at least about 2 mm, or at least about 5 mm. In some cases, the grinding medium may have an average diameter of less than or equal to about 5 mm, less than or equal to about 2 mm, less than or equal to about 1 mm, less than or equal to about 0.8, less than or equal to about 0.5 mm, or less than or equal to about 0.2 mm. Combinations of the above-referenced ranges are also possible (e.g., an average diameter of at least about 0.5 millimeters and less than or equal to about 1 mm). Other ranges are also possible.

Any suitable solvent may be used for milling. The choice of solvent may depend on factors such as the solid material (e.g., pharmaceutical agent) being milled, the particular type of stabilizer/surface-altering agent being used (e.g., one that may render the particle mucus penetrating), the grinding material be used, among other factors. Suitable solvents may be ones that do not substantially dissolve the solid material or the grinding material, but dissolve the stabilizer/surface-altering agent to a suitable degree. Non-limiting examples of solvents may include water, buffered solutions, other aqueous solutions, alcohols (e.g., ethanol, methanol, butanol), and mixtures thereof that may optionally include other components such as pharmaceutical excipients, polymers, pharmaceutical agents, salts, preservative agents, viscosity modifiers, buffering agents, tonicity modifier, taste masking agents, antioxidants, pH modifier, and other pharmaceutical excipients. In other embodiments, an organic solvent can be used. A pharmaceutical agent may have any suitable solubility in these or other solvents, such as a solubility in one or more of the ranges described above for aqueous solubility or for solubility in a coating solution.

In one aspect, the invention provides a method of forming mucus-penetrating particles (MPP) using a core comprising a pharmaceutical agent in the presence of other components, such surfactants or surface-altering agents, tonicity agents, salts, buffering agents, chelting agents, preservatives, diluents, and/or solvents.

In another embodiment, the invention provides a method of forming MPP using a core comprising loteprednol etabonate in the presence of other components comprising a milling media, such surfactants or surface-altering agents, tonicity agents, salts, buffering agents, chelting agents, preservatives, diluents, and/or solvents.

The method of forming the pharmaceutical agent mucus-penetrating particles comprises a milling step and optionally, dilution step. In the milling step, a coarse aqueous suspension containing about 2-30% pharmaceutical agent is milled in the presence of milling media to produce a nanosuspension of pharmaceutical agent particles sized in the range of about 200-500 nm. In another aspect, the particle size range is about 200-300 nm. In a subsequent dilution step, the obtained nanocrystalline suspension separated from the milling media is mixed in a product vessel with post-milling diluent that can be the same components used in the milling step in varying amounts, or other combinations of components, such as surfactants or surface-altering agents, tonicity agents, salts, buffering agents, chelting agents, preservatives, diluents, and/or solvents.

In one embodiment, the method comprises milling loteprednol etabonate in the presence of milling media comprising a Pluronic or poloxamer (e.g., poloxamer 407, poloxamer 338), glycerin, sodium chloride, disodium edetate (disodium ethylenediaminetetraacetic acid ($Na_2EDTA$) or EDTA), and optionally, trisodium citrate, citric acid, and/or benzalkonium chloride.

In other embodiments, core particles may be formed by an emulsification technique (emulsification). Generally, emulsification techniques may involve dissolving or dispersing a material to be used as the core in a solvent; this solution or dispersion is then emulsified in a second immiscible solvent, thereby forming a plurality of particles comprising the material. Suitable emulsification techniques may include formation of oil-in-water emulsions, water-in-oil emulsions, water-oil-water emulsions, oil-water-oil emulsions, solid-in-oil-in-water emulsions, and solid-in-water-in-oil emulsions, etc., with or without subsequent solvent removal, for example, by evaporation or extraction. Emulsification techniques are versatile and may be useful for preparing core particles comprising pharmaceutical agents having a relatively low aqueous solubility as well as pharmaceutical agents having a relatively high aqueous solubility.

In some embodiments, the core particles described herein may be produced by emulsification in the presence of one or more surface-altering agents. In some such embodiments, the stabilizer may act as a surface-altering agent, forming a coating on the particle (i.e., the emulsification and coating steps may be performed substantially simultaneously).

In some embodiments, a method of forming a core particle by emulsification involves choosing a stabilizer that is suitable for both emulsification and for forming a coating on the particle and rendering the particle mucus penetrating. For example, as described in more detail below, it has been demonstrated that 200-500 nm nanoparticles of a model polymer PLA produced by emulsification in the presence of certain PVA polymers resulted in particles that can penetrate physiological mucus samples at the same rate as well-established PEGylated polymeric MPP. Interestingly, it was observed that only a subset of PVA polymers tested fit the criteria of being suitable for both emulsification and for forming a coating on the particle that renders the particle mucus penetrating, as described in more detail below.

In other embodiments, the particles are first formed using an emulsification technique, following by coating of the particles with a surface-altering agent.

Any suitable solvent and solvent combinations can be used for emulsification. Some examples of solvents which can serve as oil phase are organic solvents such chloroform, dichloromethane, ethyl acetate, ethyl ether, petroleum ether (hexane, heptane), and oils such as peanut oil, cottonseed oil; safflower oil; sesame oil; olive oil; corn oil soybean oil, and silicone oil. Some examples of solvents which can serve as water phase are water and aqueous buffers. Other solvents are also possible.

In other embodiments, core particles may be formed by a precipitation technique. Precipitation techniques (e.g., microprecipitation techniques, nanoprecipitation techniques, crystallization techniques, controlled crystallization techniques) may involve forming a first solution comprising the material to be used as the core (e.g., a pharmaceutical agent) and a solvent, wherein the material is substantially soluble in the solvent. The solution may be added to a second solution comprising another solvent in which the material is substantially insoluble (i.e., an anti-solvent), thereby forming a plurality of particles comprising the material. In some cases, one or more surface-altering agents, surfactants, materials, and/or bioactive agents may be present in the first and/or second solutions. A coating may be formed during the process of precipitating the core (e.g., the precipitating and coating steps may be performed substantially simultaneously). In other embodiments, the particles are first formed using a precipitation technique, following by coating of the particles with a surface-altering agent.

In some embodiments, a precipitation technique may be used to form polymeric core particles with or without a pharmaceutical agent. Generally, a precipitation technique involves dissolving the polymer to be used as the core in a solvent (with or without a pharmaceutical agent present), and the solution is then added to a miscible anti-solvent (with or without excipients present) to form the core particle. In some embodiments, this technique may be useful for preparing, for example, polymeric core particles comprising pharmaceutical agents that are slightly soluble (1-10 mg/L), very slightly soluble (0.1-1 mg/mL) or practically insoluble (<0.1 mg/mL) in aqueous solutions (e.g., agents having a relatively low aqueous solubility).

Any suitable solvent can be used for precipitation. In some embodiments, a suitable solvent for precipitation may include, for example, acetone, acetonitrile, dimethylformamide, dimethylsulfoxide, N-methyl-2-pyrrolidone, 2-pyrrolidone, tetrahydrofuran. Other organic solvents and non-organic solvents can also be used.

Any suitable anti-solvent can be used for precipitation, including the solvents described herein that may be used for milling. In one set of embodiments, an aqueous solution is used (e.g., water, buffered solutions, other aqueous solutions, and alcohols such as ethanol, methanol, butanol), and mixtures thereof that may optionally include other components such as pharmaceutical excipients, polymers, and pharmaceutical agents.

Surface-altering agents for emulsification and precipitation may be polymers or surfactants, including the surface-altering agents described herein that may be used for milling.

Non-limiting examples of suitable polymers suitable for forming all or portions of a core by emulsification or precipitation may include polyamines, polyethers, polyamides, polyesters, polycarbamates, polyureas, polycarbonates, polystyrenes, polyimides, polysulfones, polyurethanes, polyacetylenes, polyethylenes, polyethyleneimines, polyisocyanates, polyacrylates, polymethacrylates, polyacrylonitriles, polyarylates, polypeptides, polynucleotides, and polysaccharides. Non-limiting examples of specific polymers include poly(caprolactone) (PCL), ethylene vinyl acetate polymer (EVA), poly(lactic acid) (PLA), poly(L-lactic acid) (PLLA), poly(glycolic acid) (PGA), poly(lactic acid-co-glycolic acid) (PLGA), poly(L-lactic acid-co-glycolic acid) (PLLGA), poly(D,L-lactide) (PDLA), poly(L-lactide) (PLLA), poly(D,L-lactide-co-caprolactone), poly(D, L-lactide-co-caprolactone-co-glycolide), poly(D, L-lactide-co-PEO-co-D, L-lactide), poly(D,L-lactide-co-PPO-co-D,L-lactide), polyalkyl cyanoacrylate, polyurethane, poly-L-lysine (PLL), hydroxypropyl methacrylate (HPMA), poly (ethylene glycol), poly-L-glutamic acid, poly(hydroxy acids), polyanhydrides, polyorthoesters, poly(ester amides), polyamides, poly(ester ethers), polycarbonates, polyalkylenes such as polyethylene and polypropylene, polyalkylene glycols such as poly(ethylene glycol) (PEG), polyalkylene oxides (PEO), polyalkylene terephthalates such as poly(ethylene terephthalate), polyvinyl alcohols (PVA), polyvinyl ethers, polyvinyl esters such as poly(vinyl acetate), polyvinyl halides such as poly(vinyl chloride) (PVC), polyvinylpyrrolidone, polysiloxanes, polystyrene (PS), polyurethanes, derivatized celluloses such as alkyl celluloses, hydroxyalkyl celluloses, cellulose ethers, cellulose esters, nitro celluloses, hydroxypropylcellulose, carboxymethylcellulose, polymers of acrylic acids, such as poly(methyl(meth)acrylate) (PMMA), poly(ethyl(meth) acrylate), poly(butyl(meth)acrylate), poly(isobutyl(meth) acrylate), poly(hexyl(meth)acrylate), poly(isodecyl(meth) acrylate), poly(lauryl(meth)acrylate), poly(phenyl(meth) acrylate), poly(methyl acrylate), poly(isopropyl acrylate), poly(isobutyl acrylate), poly(octadecyl acrylate) (jointly referred to herein as "polyacrylic acids"), and copolymers and mixtures thereof, polydioxanone and its copolymers, polyhydroxyalkanoates, polypropylene fumarate), polyoxymethylene, poloxamers, poly(ortho)esters, poly(butyric acid), poly(valeric acid), poly(lactide-co-caprolactone), and trimethylene carbonate, polyvinylpyrrolidone, bovine serum albumin, human serum albumin, collagen, DNA, RNA, carboxymethyl cellulose, chitosan, dextran.

Polymers suitable for forming all or portions of a core and/or surface-altering agent may also include a poly(ethylene glycol)-vitamin E conjugate (hereinafter, "PEG-VitE conjugate"). The particles, compositions, and/or formulations including a PEG-VitE conjugate, and methods of making and using the particles, compositions, and/or formulations, are provided in more detail in international PCT application publication WO2012/061703, which is incorporated herein by reference in its entirety for all purposes. In some cases, the molecular weight of the PEG portion of the PEG-VitE conjugate is greater than about 2 kDa. The molecular weight of the PEG portion of the PEG-VitE conjugate may be selected so as to aid in the formation and/or transport of the particle across a mucosal barrier as described herein. In some embodiments, use of a PEG-VitE conjugate with a PEG portion having a molecular weight greater than about 2 kDa may allow for greater penetration of the particles through a mucosal barrier as compared to use of a PEG-VitE conjugate with a PEG portion having a molecular weight less than about 2 kDa. Additionally, in certain embodiments a higher molecular weight PEG portion may facilitate drug encapsulation. The combined ability to act as a surfactant and to reduce mucoadhesion provides important benefits as compared to other commonly used surfactants for drug encapsulation. In some cases, the molecular weight of the PEG portion of the PEG-VitE conjugate is between about 2 kDa and about 8 kDa, or between about 3 kDa and about 7 kDa, or between about 4 kDa and about 6 kDa, or between about 4.5 kDa and about 6.5 kDa, or about 5 kDa.

In some embodiments, a precipitation technique may be used to form particles comprised predominantly of a pharmaceutical agent (e.g., nanocrystals). Generally, such a precipitation technique involves dissolving the pharmaceutical agent to be used as the core in a solvent, which is then added to a miscible anti-solvent with or without excipients to form the core particle. In some embodiments, this technique may be useful for preparing, for example, particles of pharmaceutical agents that are slightly soluble (1-10 mg/L), very slightly soluble (0.1-1 mg/mL) or practically insoluble (<0.1 mg/mL) in aqueous solutions (e.g., agents having a relatively low aqueous solubility).

In some embodiments, precipitation by salt (or complex) formation may be used to form particles (e.g., nanocrystals) of a salt of a pharmaceutical agent. Generally, precipitation by salt formation involves dissolving the material to be used as the core in a solvent with or without excipients followed by addition of a counter-ion or a complexing agent, which forms an insoluble salt or a complex with the pharmaceutical agent to form the core particle. This technique may be useful for preparing particles of pharmaceutical agents that are soluble in aqueous solutions (e.g., agents having a relatively high aqueous solubility). In some embodiments, pharmaceutical agents having one or more charged or ionizable groups can interact with a counter-ion (e.g., a cation or an anion) to form a salt complex.

A variety of counter-ions can be used to form salt complexes, including metals (e.g., alkali metals, alkali earth metals and transition metals). Non-limiting examples of cationic counter-ions include zinc, calcium, aluminum, zinc, barium, and magnesium. Non-limiting examples of anionic counter-ions include phosphate, carbonate, and fatty acids. Counter-ions may be, for example, monovalent, divalent, or trivalent. Other counter-ions are known in the art and can be used in the embodiments described herein. Other ionic and non-ionic complexing agents are also possible.

A variety of different acids may be used in a precipitation process. In some embodiments, a suitable acid may include decanoic acid, hexanoic acid, mucic acid, octanoic acid. In other embodiments, a suitable acid may include acetic acid, adipic acid, L-ascorbic acid, L-aspartic acid, capric acid (decanoic acid), carbonic acid, citric acid, fumaric acid, galactaric acid, D-glucoheptonic acid, D-gluconic acid, D-glucuronic acid, glutamic acid, glutaric acid, glycerophosphoric acid, glycolic acid, hippuric acid, hydrochloric acid, DL-lactic acid, lauric acid, maleic acid, (−)-L-malic acid, palmitic acid, phosphoric acid, sebacic acid, stearic acid, succinic acid, sulfuric acid, (+)-L-tartaric acid, or thiocyanic acid. In other embodiments, a suitable acid may include alginic acid, benzenesulfonic acid, benzoic acid, (+)-camphoric acid, caprylic acid (octanoic acid), cyclamic acid, dodecylsulfuric acid, ethane-1,2-disulfonic acid, ethanesulfonic acid, ethanesulfonic acid, 2-hydroxy-, gentisic acid, glutaric acid, 2-oxo-, isobutyric acid, lactobionic acid, malonic acid, methanesulfonic acid, naphthalene-1,5-disulfonic acid, naphthalene-2-sulfonic acid, 2-naphthoic acid, 1-hydroxy-, nicotinic acid, oleic acid, orotic acid, oxalic acid, pamoic acid, (embonic acid), propionic acid, (−)-L-pyroglutamic acid, or p-toluenesulfonic acid. In yet other embodiments, a suitable acid may include acetic acid, 2,2-dichloro-, benzoic acid, 4-acetamido-, (+)-camphor-10-sulfonic acid, caproic acid (hexanoic acid), cinnamic acid, formic acid, hydrobromic acid, DL-mandelic acid, nitric acid, salicylic acid, salicylic acid, 4-amino-, or undecylenic acid (undec-10-enoic acid). Mixtures of one or more such acids can also be used.

A variety of different bases may be used in a precipitation process. In some embodiments, a suitable base includes ammonia, L-arginine, calcium hydroxide, choline, glucamine, N-methyl-, lysine, magnesium hydroxide, potassium hydroxide, or sodium hydroxide. In other embodiments, a suitable base may include benethamine, benzathine, betaine, deanol, diethylamine, ethanol, 2-(diethylamino)-, hydrabamine, morpholine, 4-(2-hydroxyethyl)-morpholine, pyrrolidine, 1-(2-hydroxyethyl)-, or tromethamine. In other embodiments, a suitable base may include diethanolamine (2,2'-iminobis(ethanol)), ethanolamine (2-aminoethanol), ethylenediamine, IH-imidazole, piperazine, triethanolamine (2,2',2''-nitrilotris(ethanol)), or zinc hydroxide. Mixtures of one or more such bases can also be used.

Any suitable solvent can be used for precipitation by salt formation, including the solvents described herein that may be used for milling. In one set of embodiments, an aqueous solution is used (e.g., water, buffered solutions, other aqueous solutions, alcohols (e.g., ethanol, methanol, butanol), and mixtures thereof that may optionally include other components such as pharmaceutical excipients, polymers, and pharmaceutical agents.

In the precipitation process, the salt may have a lower aqueous solubility (or solubility in the solvent containing the salt) than the pharmaceutical agent in the non-salt form. The aqueous solubility (or solubility in the solvent) of the salt may be, for example, less than or equal to about 5 mg/mL, less than or equal to about 2 mg/mL, less than or equal to about 1 mg/mL, less than or equal to about 0.5 mg/mL, less than or equal to about 0.1 mg/mL, less than or equal to about 0.05 mg/mL, or less than or equal to about 0.01 mg/mL, less than or equal to about 1 µg/mL, less than or equal to about 0.1 µg/mL, less than or equal to about 0.01 µg/mL, less than or equal to about 1 ng/mL, less than or equal to about 0.1 ng/mL, or less than or equal to about 0.01 ng/mL at 25° C. In some embodiments, the salt may have an aqueous solubility (or solubility in the solvent) of at least about 1 µg/mL, at least about 10 µg/mL, at least about 0.1 ng/mL, at least about 1 ng/mL, at least about 10 ng/mL, at least about 0.1 µg/mL, at least about 1 µg/mL, at least about 5 µg/mL, at least about 0.01 mg/mL, at least about 0.05 mg/mL, at least about 0.1 mg/mL, at least about 0.5 mg/mL, at least about 1.0 mg/mL, at least about 2 mg/mL. Combinations of the above-noted ranges are possible (e.g., an aqueous solubility (or solubility in the solvent) of at least about 0.001 mg/mL and less than or equal to about 1 mg/mL). Other ranges are also possible. The salt may have these or other ranges of aqueous solubilities at any point throughout the pH range (e.g., from pH 1 to pH 14).

In some embodiments, the solvent used for precipitation includes one or more surface-altering agents as described herein, and a coating of the one or more surface-altering agents may be formed around the particle as it precipitates out of solution. The surface-altering agent may be present in the solvent at any suitable concentration, such as a concentration of at least about 0.001% (w/v), at least about 0.005% (w/v), at least about 0.01% (w/v), at least about 0.05% (w/v), at least about 0.1% (w/v), at least about 0.5% (w/v), at least about 1% (w/v), or at least about 5% (w/v) in the aqueous solution. In some instances, the surface-altering agent is present in the solvent at a concentration of less than or equal to about 5% (w/v), less than or equal to about 1% (w/v), less than or equal to about 0.5% (w/v), less than or equal to about 0.1% (w/v), less than or equal to about 0.05% (w/v), less than or equal to about 0.01% (w/v), or less than or equal to about 0.005% (w/v). Combinations of the above-referenced ranges are also possible (e.g., a concentration of at least about 0.01 (w/v) and less than or equal to about 1% (w/v). Other ranges are also possible.

Another exemplary method of forming a core particle includes a freeze-drying technique. In this technique, a pharmaceutical agent or salt thereof may be dissolved in an aqueous solution, optionally containing a surface-altering agent. A counter-ion may be added to the solution, and the solution may be immediately flash frozen and freeze dried. Dry powder can be reconstituted in a suitable solvent (e.g., an aqueous solution such as water) at a desired concentration.

A counter-ion may be added to a solvent for freeze-drying in any suitable range. In some cases, the ratio of counter-ion to pharmaceutical agent (e.g., salt) may be at least 0.1:1 (weight ratio or molar ratio), at least 1:1, at least 2:1, at least 3:1, at least 5:1, at least 10:1, at least 25:1, at least 50:1, or at least 100:1. In some cases, the ratio of counter-ion to pharmaceutical agent (e.g., salt) may be less than or equal to 100:1 (weight ratio or molar ratio), less than or equal to 75:1, less than or equal to 50:1, less than or equal to 25:1, less than or equal to 10:1, less than or equal to 5:1, less than or equal to 3:1, less than or equal to 2:1, less than or equal to 1:1, or less than or equal to 0.1:1. Combinations of the above-referenced ranges are possible (e.g., a ratio of at least 5:1 and less than or equal to 50:1). Other ranges are also possible.

If the surface-altering agent is present in the solvent prior to freeze drying, it may be present at any suitable concentration, such as a concentration of at least about 0.001% (w/v), at least about 0.005% (w/v), at least about 0.01% (w/v), at least about 0.05% (w/v), at least about 0.1% (w/v), at least about 0.5% (w/v), at least about 1% (w/v), or at least about 5% (w/v) in the aqueous solution. In some instances, the surface-altering agent is present in the solvent at a concentration of less than or equal to about 5% (w/v), less than or equal to about 1% (w/v), less than or equal to about 0.5% (w/v), less than or equal to about 0.1% (w/v), less than or equal to about 0.05% (w/v), less than or equal to about 0.01% (w/v), or less than or equal to about 0.005% (w/v). Combinations of the above-referenced ranges are also possible (e.g., a concentration of at least about 0.01% (w/v) and less than or equal to about 1% (w/v). Other ranges are also possible.

The concentration of surface-altering agent present in the solvent may be above or below the critical micelle concentration (CMC) of the surface-altering agent, depending on the particular surface-altering agent used. In other embodiments, stable particles can be formed by adding excess counter-ion to a solution containing a pharmaceutical agent. The precipitate can then be washed by various methods such as centrifugation. The resultant slurry may be sonicated. One or more surface-altering agents may be added to stabilize the resultant particles.

Other methods of forming core particles are also possible. Techniques for forming core particles may include, for example, coacervation-phase separation; melt dispersion; interfacial deposition; in situ polymerization; self-assembly of macromolecules (e.g., formation of polyelectrolyte complexes or polyelectrolyte-surfactant complexes); spray-drying and spray-congealing; electro-spray; air suspension coating; pan and spray coating; freeze-drying, air drying, vacuum drying, fluidized-bed drying; precipitation (e.g., nanoprecipitation, microprecipitation); critical fluid extraction; and lithographic approaches (e.g., soft lithography, step and flash imprint lithography, interference lithography, photolithography).

Combinations of the methods described herein and other methods are also possible. For example, in some embodiments, a core of a pharmaceutical agent is first formed by precipitation, and then the size of the core is further reduced by a milling process.

Following formation of particles of a pharmaceutical agent, the particles may be optionally exposed to a solution comprising a (second) surface-altering agent that may associate with and/or coat the particles. In embodiments in which the pharmaceutical agent already includes a coating of a first surface-altering agent, all or portions of a second surface-altering agent may be exchanged with a second stabilizer/surface-altering agent to coat all or portions of the particle surface. In some cases, the second surface-altering agent may render the particle mucus penetrating more than the first surface-altering agent. In other embodiments, a particle having a coating including multiple surface-altering agents may be formed (e.g., in a single layer or in multiple layers). In other embodiments, a particle having multiple coatings (e.g., each coating optionally comprising different surface-altering agents) may be formed. In some cases, the coating is in the form of a monolayer of a surface-altering agent. Other configurations are also possible.

In any of the methods described herein, a particle may be coated with a surface-altering agent by incubating the particle in a solution with the surface-altering agent for a period of at least about 1 minutes, at least about 2 minutes, at least about 5 min., at least about 10 min., at least about 15 min., at least about 20 min., at least about 30 min., at least about 60 min., or more. In some cases, incubation may take place for a period of less than or equal to about 10 hours, less than or equal to about 5 hours, or less than or equal to about 60 min. Combinations of the above referenced ranges are also possible (e.g., an incubation period of less than or equal to 60 min. and at least about 2 min.).

Particle Coatings

As shown in the embodiment illustrated in FIG. 1, core 16 may be surrounded by coating 20 comprising one or more surface-altering agents. In some embodiments, the coating is formed of one or more surface-altering agents or other molecules disposed on the surface of the core. The particular chemical makeup and/or components of the coating and surface-altering agent(s) can be chosen so as to impart certain functionality to the particles, such as enhanced transport through mucosal barriers.

It should be understood that a coating which surrounds a core need not completely surround the core, although such embodiments may be possible. For example, the coating may surround at least about 10%, at least about 30%, at least about 50%, at least about 60%, at least about 70%, at least about 80%, at least about 90%, or at least about 99% of the surface area of a core. In some cases, the coating substantially surrounds a core. In other cases, the coating completely surrounds a core. In other embodiments, a coating surrounds less than or equal to about 100%, less than or equal to about 90%, less than or equal to about 80%, less than or equal to about 70%, less than or equal to about 60%, or less than or equal to about 50% of the surface area of a core. Combinations of the above-referenced ranges are also possible (e.g., surrounding greater than 80% and less than 100% of the surface area of a core).

The components of the coating may be distributed evenly across a surface of the core in some cases, and unevenly in other cases. For example, the coating may include portions (e.g., holes) that do not include any material in some cases. If desired, the coating may be designed to allow penetration and/or transport of certain molecules and components into or out of the coating, but may prevent penetration and/or transport of other molecules and components into or out of the coating. The ability of certain molecules to penetrate and/or be transported into and/or across a coating may depend on, for example, the packing density of the surface-altering agents forming the coating and the chemical and physical properties of the components forming the coating. As described herein, the coating may include one layer of material (e.g., a monolayer), or multilayers of materials in some embodiments. A single type of surface-altering agent may be present, or multiple types of surface-altering agent.

A coating of a particle can have any suitable thickness. For example, a coating may have an average thickness of at least about 1 nm, at least about 5 nm, at least about 10 nm, at least about 30 nm, at least about 50 nm, at least about 100 nm, at least about 200 nm, at least about 500 nm, at least about 1 μm, or at least about 5 μm. In some cases, the average thickness of a coating is less than or equal to about 5 μm, less than or equal to about 1 μm, less than or equal to about 500 nm, less than or equal to about 200 nm, less than or equal to about 100 nm, less than a to about 50 nm, less than or equal to about 30 nm, less than or equal to about 10 nm, or less than or equal to about 5 nm. Combinations of the above-referenced ranges are also possible (e.g., an average thickness of at least about 1 nm and less than or equal to about 100 nm). Other ranges are also possible. For particles having multiple coatings, each coating layer may have one of the thicknesses described above.

In some embodiments, the compositions and methods described herein may allow for the coating of a core particle with hydrophilic surface-altering moieties without requiring covalent linking of the surface-altering moieties to the core surface. In some such embodiments, a core having a hydrophobic surface may be coated with a polymer described herein, thereby causing a plurality of surface-altering moieties to be on the core surface without substantially altering the characteristics of the core itself. For example, the surface altering agent may be adsorbed to the outer surface of the core particle. In other embodiments, however, a surface-altering agent is covalently linked to a core particle.

In certain embodiments in which the surface-altering agent is adsorbed onto a surface of a core, the surface-altering agent may be in equilibrium with other molecules of the surface-altering agent in solution, optionally with other components (e.g., in a composition/formulation). In some cases, the adsorbed surface-altering agent may be present on the surface of the core at a density described herein. The density may be an average density as the surface altering agent is in equilibrium with other components in solution.

The coating and/or surface-altering agent of a particle described herein may comprise any suitable material, such as a hydrophobic material, a hydrophilic material, and/or an amphiphilic material. In some embodiments, the coating includes a polymer. In certain embodiments, the polymer is a synthetic polymer (i.e., a polymer not produced in nature). In other embodiments, the polymer is a natural polymer (e.g., a protein, polysaccharide, rubber). In certain embodiments, the polymer is a surface active polymer. In certain embodiments, the polymer is a non-ionic polymer. In certain embodiments, the polymer is a linear, synthetic non-ionic polymer. In certain embodiments, the polymer is a non-ionic block copolymer. In some embodiments, the polymer may be a copolymer, e.g., where one repeat unit is relatively hydrophobic and another repeat unit is relatively hydrophilic. The copolymer may be, for example, a diblock, triblock, alternating, or random copolymer. The polymer may be charged or uncharged.

In some embodiments, a coating comprises a synthetic polymer having pendant hydroxyl groups on the backbone of the polymer. For example, in certain embodiments, the polymer may include poly(vinyl alcohol), a partially hydrolyzed poly(vinyl acetate) or a copolymer of vinyl alcohol and vinyl acetate. In certain embodiments, a synthetic polymer having pendant hydroxyl groups on the backbone of the polymer may include poly(ethylene glycol)-poly(vinyl acetate)-poly(vinyl alcohol) copolymers, poly(ethylene glycol)-poly(vinyl alcohol) copolymers, poly(propylene oxide)-poly(vinyl alcohol) copolymers, and poly(vinyl alcohol)-poly(acryl amide) copolymers. Without wishing to be bound by theory, a particle including a coating comprising a synthetic polymer having pendant hydroxyl groups on the backbone of the polymer may have reduced mucoadhesion as compared to a control particle due to, at least in part, the display of a plurality of hydroxyl groups on the particle surface. One possible mechanism for the reduced mucoadhesion is that the hydroxyl groups alter the microenvironment of the particle, for example, by ordering water and other molecules in the particle/mucus environment. An additional or alternative possible mechanism is that the hydroxyl groups shield the adhesive domains of the mucin fibers, thereby reducing particle adhesion and speeding up particle transport.

Moreover, the ability of a particle coated with a synthetic polymer having pendant hydroxyl groups on the backbone of the polymer to be mucus penetrating may also depend, at least in part, on the degree of hydrolysis of the polymer. In some embodiments, the hydrophobic portions of the polymer (e.g., portions of the polymer that are not hydrolyzed) may allow the polymer to be adhered to the core surface (e.g., in the case of the core surface being hydrophobic), thus allowing for a strong association between the core and the polymer. Surprisingly, it has been found that in some embodiments involving the surface-altering agent PVA, too high of a degree of hydrolysis does not allow for sufficient adhesion between the PVA and the core (e.g., in the case of the core being hydrophobic), and thus, the particles coated with such a polymer generally do not exhibit sufficient reduced mucoadhesion. In some embodiments, too low of a degree of hydrolysis does not enhance particle transport in mucus, perhaps due to the lower amounts of hydroxyl groups available for altering the microenvironment of the particle and/or shielding the adhesive domains of the mucin fibers.

A synthetic polymer having pendant hydroxyl groups on the backbone of the polymer may have any suitable degree of hydrolysis (and, therefore, varying amounts of hydroxyl groups). The appropriate level of hydrolysis may depend on additional factors such as the molecular weight of the polymer, the composition of the core, the hydrophobicity of the core, etc. In some embodiments, a synthetic polymer (e.g., PVA or partially hydrolyzed poly(vinyl acetate) or a copolymer of vinyl alcohol and vinyl acetate) may be at least about 30% hydrolyzed, at least about 35% hydrolyzed, at least about 40% hydrolyzed, at least about 45% hydrolyzed, at least about 50% hydrolyzed, at least about 55% hydrolyzed, at least about 60% hydrolyzed, at least about 65% hydrolyzed, at least about 70% hydrolyzed, at least about 75% hydrolyzed, at least about 80% hydrolyzed, at least about 85% hydrolyzed, at least about 87% hydrolyzed, at least about 90% hydrolyzed, at least about 95% hydrolyzed, or at least about 98% hydrolyzed. In some embodiments, the synthetic polymer may be less than or equal to about 100% hydrolyzed, less than or equal to about 98% hydrolyzed, less than or equal to about 97% hydrolyzed, less than or equal to about 96% hydrolyzed, less than or equal to about 95% hydrolyzed, less than or equal to about 94% hydrolyzed, less than or equal to about 93% hydrolyzed, less than or equal to about 92% hydrolyzed, less than or equal to about 91% hydrolyzed, less than or equal to about 90% hydrolyzed, less than or equal to about 87% hydrolyzed, less than or equal to about 85% hydrolyzed, less than or equal to about 80% hydrolyzed, less than or equal to about 75% hydrolyzed, less than or equal to about 70% hydrolyzed, or less than or equal to about 60% hydrolyzed. Combinations of the above-mentioned ranges are also possible (e.g., a polymer that is at least about 80% hydrolyzed and less than or equal to about 95% hydrolyzed). Other ranges are also possible.

The molecular weight of a synthetic polymer described herein (e.g., one having pendant hydroxyl groups on the backbone of the polymer) may be selected so as to reduce the mucoadhesion of a core and to ensure sufficient association of the polymer with the core. In certain embodiments, the molecular weight of the synthetic polymer is at least about 1 kDa, at least about 2 kDa, at least about 5 kDa, at least about 8 kDa, at least about 9 kDa, at least about 10 kDa, at least about 12 kDa, at least about 15 kDa at least about 20 kDa, at least about 25 kDa, at least about 30 kDa, at least about 40 kDa, at least about 50 kDa, at least about 60 kDa, at least about 70 kDa, at least about 80 kDa, at least about 90 kDa, at least about 100 kDa at least about 110 kDa, at least about 120 kDa, at least about 130 kDa, at least about 140 kDa, at least about 150 kDa, at least about 200 kDa, at least about 500 kDa, or at least about 1000 kDa. In some embodiments, the molecular weight of the synthetic polymer is less than or equal to about 1000 kDa, less than or equal to about 500 kDa, less than or equal to about 200 kDa, less than or equal to about 180 kDa, less than or equal to about 150 kDa, less than or equal to about 130 kDa, less than or equal to about 120 kDa, less than or equal to about 100 kDa, less than or equal to about 85 kDa, less than or equal to about 70 kDa, less than or equal to about 65 kDa, less than or equal to about 60 kDa, less than or equal to about 50 kDa, or less than or equal to about 40 kDa, less than or equal to about 30 kDa, less than or equal to about 20 kDa, less than or equal to about 15 kDa, or less than or equal to about 10 kDa. Combinations of the above-mentioned ranges are also possible (e.g., a molecular weight of at least about 10 kDa and less than or equal to about 30 kDa). The above-mentioned molecular weight ranges can also be combined with the above-mentioned hydrolysis ranges to form suitable polymers.

In some embodiments, a synthetic polymer described herein is or comprises PVA. PVA is a non-ionic polymer with surface active properties. It is a synthetic polymer typically produced through hydrolysis of poly(vinyl acetate). Partially hydrolyzed PVA is comprised of two types of repeating units: vinyl alcohol units and residual vinyl acetate units. The vinyl alcohol units are relatively hydrophilic; the vinyl acetate units are relatively hydrophobic. In some instances, the sequence distribution of vinyl alcohol units and vinyl acetate units is blocky. For example, a series of vinyl alcohol units may be followed by a series of vinyl acetate units, and followed by more vinyl alcohol units to form a polymer having a mixed block-copolymer type arrangement, with units distributed in a blocky manner. In certain embodiments, the repeat units form a copolymer, e.g., a diblock, triblock, alternating, or random copolymer. Polymers other than PVA may also have these configurations of hydrophilic units and hydrophobic units.

In some embodiments, the hydrophilic units of a synthetic polymer described herein may be substantially present at the outer surface of the particle. For example, the hydrophilic units may form a majority of the outer surface of the coating and may help stabilize the particle in an aqueous solution containing the particle. The hydrophobic units may be substantially present in the interior of the coating and/or at the surface of the core particle, e.g., to facilitate attachment of the coating to the core.

The molar fraction of the relatively hydrophilic units and the relatively hydrophobic units of a synthetic polymer may be selected so as to reduce the mucoadhesion of a core and to ensure sufficient association of the polymer with the core, respectively. As described herein, the molar fraction of the hydrophobic units of the polymer may be chosen such that adequate association of the polymer with the core occurs, thereby increasing the likelihood that the polymer remains adhered to the core. The molar fraction of the relatively hydrophilic units to the relatively hydrophobic units of a synthetic polymer may be, for example, at least 0.5:1, at least 1:1, at least 2:1, at least 3:1, at least 5:1, at least 7:1, at least 10:1, at least 15:1, at least 20:1, at least 25:1, at least 30:1, at least 40:1, at least 50:1, at least 75:1, or at least 100:1. In some embodiments, the molar fraction of the relatively hydrophilic units to the relatively hydrophobic units of a synthetic polymer may be, for example, less than or equal to 100:1, less than or equal to 75:1, less than or equal to 50:1, less than or equal to 40:1, less than or equal to 30:1, less than or equal to 25:1, less than or equal to 20:1, less than or equal to 15:1, less than or equal to 10:1, less than or equal to 7:1, less than or equal to 5:1, less than or equal to 3:1, less than or equal to 2:1, or less than or equal to 1:1. Combinations of the above-referenced ranges are also possible (e.g., a ratio of at least 1:1 and less than or equal to 50:1). Other ranges are also possible.

The molecular weight of the PVA polymer may also be tailored to increase the effectiveness of the polymer to render particles mucus penetrating. Examples of PVA polymers having various molecular weights and degree of hydrolysis are shown in Table 1.

TABLE 1

Grades of PVA. The molecular weight (MW) and hydrolysis degree values were provided by the manufacturers.

| PVA acronym* | MW, kDa | Hydrolysis degree, % |
|---|---|---|
| 2K75 | 2 | 75-79 |
| 9K80 | 9-10 | 80 |
| 13K87 | 13-23 | 87-89 |
| 13K98 | 13-23 | 98 |
| 31K87 | 31-50 | 87-89 |
| 31K98 | 31-50 | 98-99 |
| 57K86 | 57-60 | 86-89 |
| 85K87 | 85-124 | 87-89 |
| 85K99 | 85-124 | 99+ |
| 95K95 | 95 | 95 |
| 105K80 | 104 | 80 |
| 130K87 | 130 | 87-89 |

*PVA acronym explanation: XXKYY, where XX stands for the PVA's lower-end molecular weight in kDa and YY stands for the PVA's lower-end hydrolysis in %.

In certain embodiments, the synthetic polymer is represented by the formula:

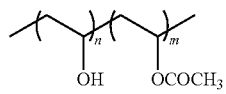

wherein n is an integer between 0 and 22730, inclusive; and m is an integer between 0 and 11630, inclusive. In certain embodiments, n is an integer between 25 and 20600, inclusive. In some embodiments, m is an integer between 5 and 1100, inclusive. In certain embodiments, m is an integer between 0 and 400 inclusive or between 1 and 400 inclusive. It is noted that n and m represent the total content of the vinyl alcohol and vinyl acetate repeat units in the polymer, respectively, rather than the block lengths.

The value of n may vary. In certain embodiments, n is at least 5, at least 10, at least 20, at least 30, at least 50, at least 100, at least 200, at least 300, at least 500, at least 800, at least 1000, at least 1200, at least 1500, at least 1800, at least 2000, at least 2200, at least 2400, at least 2600, at least 3000, at least 5000, at least 10000, at least 15000, at least 20000, or at least 25000. In some cases, n is less than or equal to 30000, less than or equal to 25000, less than or equal to 20000, less than or equal to 25000, less than or equal to 20000, less than or equal to 15000, less than or equal to 10000, less than or equal to 5000, less than or equal to 3000, less than or equal to 2800, less than or equal to 2400, less than or equal to 2000, less than or equal to 1800, less than or equal to 1500, less than or equal to 1200, less than or equal to 1000, less than or equal to 800, less than or equal to 500, less than or equal to 300, less than or equal to 200, less than or equal to 100, or less than or equal to 50. Combinations of the above-referenced ranges are also possible (e.g., n being at least 50 and less than or equal to 2000). Other ranges are also possible.

Similarly, the value of m may vary. For instance, in certain embodiments, m is at least 5, at least 10, at least 20, at least 30, at least 50, at least 70, at least 100, at least 150, at least 200, at least 250, at least 300, at least 350, at least 400, at least 500, at least 800, at least 1000, at least 1200, at least 1500, at least 1800, at least 2000, at least 2200, at least 2400, at least 2600, at least 3000, at least 5000, at least 10000, or at least 15000. In some cases, m is less than or equal to 15000, less than or equal to 10000, less than or equal to 5000, less than or equal to 3000, less than or equal to 2800, less than or equal to 2400, less than or equal to 2000, less than or equal to 1800, less than or equal to 1500, less than or equal to 1200, less than or equal to 1000, less than or equal to 800, less than or equal to 500, less than or equal to 400, less than or equal to 350, less than or equal to 300, less than or equal to 250, less than or equal to 200, less than or equal to 150, less than or equal to 100, less than or equal to 70, less than or equal to 50, less than or equal to 30, less than or equal to 20, or less than or equal to 10. Combinations of the above-referenced ranges are also possible (e.g., m being at least 5 and less than or equal to 200). Other ranges are also possible.

In some embodiments, the particles described herein include a coating comprising a block copolymer having a relatively hydrophilic block and a relatively hydrophobic block. In some cases, the hydrophilic blocks may be substantially present at the outer surface of the particle. For example, the hydrophilic blocks may form a majority of the outer surface of the coating and may help stabilize the particle in an aqueous solution containing the particle. The hydrophobic block may be substantially present in the interior of the coating and/or at the surface of the core particle, e.g., to facilitate attachment of the coating to the core. In some instances, the coating comprises a surface-altering agent including a triblock copolymer, wherein the triblock copolymer comprises a hydrophilic block-hydrophobic block-hydrophilic block configuration. Diblock copolymers having a hydrophilic block-hydrophobic block configuration are also possible. Combinations of block copolymers with other polymers suitable for use as coatings are also possible. Non-linear block configurations are also possible such as in comb, brush, or star copolymers. In some embodiments, the relatively hydrophilic block includes a synthetic polymer having pendant hydroxyl groups on the backbone of the polymer (e.g., PVA).

The molecular weight of the hydrophilic blocks and the hydrophobic blocks of the block copolymers may be selected so as to reduce the mucoadhesion of a core and to ensure sufficient association of the block copolymer with the core, respectively. The molecular weight of the hydrophobic block of the block copolymer may be chosen such that adequate association of the block copolymer with the core occurs, thereby increasing the likelihood that the block copolymer remains adhered to the core.

In certain embodiments, the combined molecular weight of the (one or more) relatively hydrophobic blocks or repeat units of a block copolymer is at least about 0.5 kDa, at least about 1 kDa, at least about 2 kDa, at least about 3 kDa, at least about 4 kDa, at least about 5 kDa, at least about 6 kDa, at least about 10 kDa, at least about 12 kDa, at least about 15 kDa, at least about 20 kDa, or at least about 50 kDa, at least about 60 kDa, at least about 70 kDa, at least about 80 kDa, at least about 90 kDa, at least about 100 kDa at least about 110 kDa, at least about 120 kDa, at least about 130 kDa, at least about 140 kDa, at least about 150 kDa, at least about 200 kDa, at least about 500 kDa, or at least about 1000 kDa. In some embodiments, the combined molecular weight of the (one or more) relatively hydrophobic blocks or repeat units is less than or equal to about 1000 kDa, less than or equal to about 500 kDa, less than or equal to about 200 kDa, less than or equal to about 150 kDa, less than or equal to about 140 kDa, less than or equal to about 130 kDa, less than or equal to about 120 kDa, less than or equal to about 110 kDa, less than or equal to about 100 kDa, less than or equal to about 90 kDa, less than or equal to about 80 kDa, less than or equal to about 50 kDa, less than or equal to about 20 kDa, less than or equal to about 15 kDa, less than or equal to about 13 kDa, less than or equal to about 12 kDa, less than or equal to about 10 kDa, less than or equal to about 8 kDa, or less than or equal to about 6 kDa. Combinations of the above-mentioned ranges are also possible (e.g., at least about 3 kDa and less than or equal to about 15 kDa). Other ranges are also possible.

In some embodiments, the combined (one or more) relatively hydrophilic blocks or repeat units of a block copolymer constitute at least about 15 wt %, at least about 20 wt %, at least about 25 wt %, at least about 30 wt %, at least about 35 wt %, at least about 40 wt %, at least about 45 wt %, at least about 50 wt %, at least about 55 wt %, at least about 60 wt %, at least about 65 wt %, or at least about 70 wt % of the block copolymer. In some embodiments, the combined (one or more) relatively hydrophilic blocks or repeat units of a block copolymer constitute less than or equal to about 90 wt %, less than or equal to about 80 wt %, less than or equal to about 60 wt %, less than or equal to about 50 wt %, or less than or equal to about 40 wt % of the block copolymer. Combinations of the above-referenced ranges are also possible (e.g., at least about 30 wt % and less than or equal to about 80 wt %). Other ranges are also possible.

In some embodiments, the combined molecular weight of the (one or more) relatively hydrophilic blocks or repeat units of the block copolymer may be at least about 0.5 kDa, at least about 1 kDa, at least about 2 kDa, at least about 3 kDa, at least about 4 kDa, at least about 5 kDa, at least about 6 kDa, at least about 10 kDa, at least about 12 kDa, at least about 15 kDa, at least about 20 kDa, or at least about 50 kDa, at least about 60 kDa, at least about 70 kDa, at least about 80 kDa, at least about 90 kDa, at least about 100 kDa at least about 110 kDa, at least about 120 kDa, at least about 130 kDa, at least about 140 kDa, at least about 150 kDa, at least about 200 kDa, at least about 500 kDa, or at least about 1000 kDa. In certain embodiments, the combined molecular weight of the (one or more) relatively hydrophilic blocks or repeat units is less than or equal to about 1000 kDa, less than or equal to about 500 kDa, less than or equal to about 200 kDa, less than or equal to about 150 kDa, less than or equal to about 140 kDa, less than or equal to about 130 kDa, less than or equal to about 120 kDa, less than or equal to about 110 kDa, less than or equal to about 100 kDa, less than or equal to about 90 kDa, less than or equal to about 80 kDa, less than or equal to about 50 kDa, less than or equal to about 20 kDa, less than or equal to about 15 kDa, less than or equal to about 13 kDa, less than or equal to about 12 kDa, less than or equal to about 10 kDa, less than or equal to about 8 kDa, less than or equal to about 6 kDa, less than or equal to about 5 kDa, less than or equal to about 3 kDa, less than or equal to about 2 kDa, or less than or equal to about 1 kDa. Combinations of the above-mentioned ranges are also possible (e.g., at least about 0.5 kDa and less than or equal to about 3 kDa). Other ranges are also possible. In embodiments in which two hydrophilic blocks flank a hydrophobic block, the molecular weights of the two hydrophilic blocks may be substantially the same or different.

In certain embodiments, the polymer of a surface-altering agent includes a polyether portion. In certain embodiments, the polymer includes a polyalkylether portion. In certain embodiments, the polymer includes polyethylene glycol tails. In certain embodiments, the polymer includes a polypropylene glycol central portion. In certain embodiments, the polymer includes polybutylene glycol as the central portion. In certain embodiments, the polymer includes polypentylene glycol as the central portion. In certain embodiments, the polymer includes polyhexylene glycol as the central portion. In certain embodiments, the polymer is a diblock copolymer of one of the polymers described herein. In certain embodiments, the polymer is a triblock copolymer of one of the polymers described herein. As disclosed herein, any recitation of PEG may be replaced with polyethylene oxide (PEO), and any recitation of PEO may be replaced with PEG. In some embodiments, a diblock or triblock copolymer comprises a synthetic polymer having pendant hydroxyl groups on the backbone of the polymer (e.g., PVA) as one or more of the blocks (with varying degrees of hydrolysis and varying molecular weights as described herein). The synthetic polymer blocks may form the central portion or the end portions of the block copolymer.

In certain embodiments, the polymer is a triblock copolymer of a polyalkyl ether (e.g., polyethylene glycol, polypropylene glycol) and another polymer (e.g., a synthetic polymer having pendant hydroxyl groups on the backbone of the polymer (e.g., PVA). In certain embodiments, the polymer is a triblock copolymer of a polyalkyl ether and another polyalkyl ether. In certain embodiments, the polymer is a triblock copolymer of polyethylene glycol and another polyalkyl ether. In certain embodiments, the polymer is a triblock copolymer of polypropylene glycol and another polyalkyl ether. In certain embodiments, the polymer is a triblock copolymer with at least one unit of polyalkyl ether. In certain embodiments, the polymer is a triblock copolymer of two different polyalkyl ethers. In certain embodiments, the polymer is a triblock copolymer including a polyethylene glycol unit. In certain embodiments, the polymer is a triblock copolymer including a polypropylene glycol unit. In certain embodiments, the polymer is a triblock copolymer of a more hydrophobic unit flanked by two more hydrophilic units. In certain embodiments, the hydrophilic units are the same type of polymer. In some embodiments, the hydrophilic units include a synthetic polymer having pendant hydroxyl groups on the backbone of the polymer (e.g., PVA). In certain embodiments, the polymer includes a polypropylene glycol unit flanked by two more hydrophilic units. In certain embodiments, the polymer includes two polyethylene glycol units flanking a more hydrophobic unit. In certain embodiments, the polymer is a triblock copolymer with a polypropylene glycol unit flanked by two polyethylene glycol units. The molecular weights of the two blocks flanking the central block may be substantially the same or different.

In certain embodiments, the polymer is of the formula:

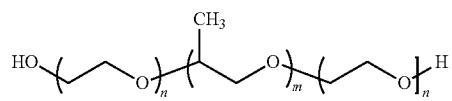

wherein n is an integer between 2 and 1140, inclusive; and m is an integer between 2 and 1730, inclusive. In certain embodiments, n is an integer between 10 and 170, inclusive. In certain embodiments, m is an integer between 5 and 70 inclusive. In certain embodiments, n is at least 2 times m, 3 times m, or 4 times m.

In certain embodiments, the coating includes a surface-altering agent comprising a (poly(ethylene glycol))-(poly(propylene oxide))-(poly(ethylene glycol)) triblock copolymer (hereinafter "PEG-PPO-PEG triblock copolymer"), present in the coating alone or in combination with another polymer such as a synthetic polymer having pendant hydroxyl groups on the backbone of the polymer (e.g., PVA). As described herein, the PEG blocks may be interchanged with PEO blocks in some embodiments. The molecular weights of the PEG (or PEO) and PPO segments of the PEG-PPO-PEG triblock copolymer may be selected so as to reduce the mucoadhesion of the particle, as described herein. Without wishing to be bound by theory, a particle having a coating comprising a PEG-PPO-PEG triblock copolymer may have reduced mucoadhesion as compared to a control particle due to, at least in part, the display of a plurality of PEG (or PEO) segments on the particle surface. The PPO segment may be adhered to the core surface (e.g., in the case of the core surface being hydrophobic), thus allowing for a strong association between the core and the triblock copolymer. In some cases, the PEG-PPO-PEG triblock copolymer is associated with the core through non-covalent interactions. For purposes of comparison, the control particle may be, for example, a carboxylate-modified polystyrene particle of similar size as the coated particle in question.

In certain embodiments, a surface-altering agent includes a polymer comprising a poloxamer, having the trade name Pluronic®. Pluronic® polymers that may be useful in the embodiments described herein include, but are not limited to, F127, F38, F108, F68, F77, F87, F88, F98, L101, L121, L31, L35, L43, L44, L61, L62, L64, L81, L92, N3, P103, P104, P105, P123, P65, P84, and P85.

Examples of molecular weights of certain Pluronic® molecules are shown in Table 2.

TABLE 2

Molecular Weights of Pluronic ® molecules

| Pluronic ® | Average MW | MW PPO | PEO wt % | MW PEO |
|---|---|---|---|---|
| L31 | 1000 | 900 | 10 | 100 |
| L44 | 2000 | 1200 | 40 | 800 |
| L81 | 2667 | 2400 | 10 | 267 |
| L101 | 3333 | 3000 | 10 | 333 |
| P65 | 3600 | 1800 | 50 | 1800 |
| L121 | 4000 | 3600 | 10 | 400 |
| P103 | 4286 | 3000 | 30 | 1286 |
| F38 | 4500 | 900 | 80 | 3600 |
| P123 | 5143 | 3600 | 30 | 1543 |
| P105 | 6000 | 3000 | 50 | 3000 |
| F87 | 8000 | 2400 | 70 | 5600 |
| F68 | 9000 | 1800 | 80 | 7200 |
| F127 | 12000 | 3600 | 70 | 8400 |
| P123 | 5750 | 4030 | 30 | 1730 |

Although other ranges may be possible and useful in certain embodiments described herein, in some embodiments, the hydrophobic block of the PEG-PPO-PEG triblock copolymer has one of the molecular weights described above (e.g., at least about 3 kDa and less than or equal to about 15 kDa), and the combined hydrophilic blocks have a weight percentage with respect to the polymer in one of the ranges described above (e.g., at least about 15 wt %, at least about 20 wt %, at least about 25 wt %, at least about 30 wt %, at least about 50%, or at least about 70% and less than or equal to about 80 wt %). Certain Pluronic® polymers that fall within these criteria include, for example, F127, F108, P105 and P103. Surprisingly, and as described in more detail in the Examples, it was found that these particular Pluronic® polymers rendered certain particles mucus penetrating more than other Pluronic® polymers tested that did not fall within this criteria. Additionally, other agents that did not render particles mucus penetrating (for some certain particle cores) included certain polymers such as polyvinylpyrrolidones (PVP/Kollidon), polyvinyl alcohol-polyethylene glycol graft-copolymer (Kollicoat IR), hydroxypropyl methylcellulose (Methocel); solutol HS 15, Triton X100, tyloxapol, cremophor RH 40; small molecules such as Span 20, Span 80, octyl glucoside, cetyltrimethylammonium bromide (CTAB), sodium dodecyl sulfate (SDS).

It should be appreciated that the ability of a surface-altering agent to render a particle or core mucus penetrating may depend at least in part on the particular core/surface-altering agent combination, including the ability of the surface-altering agent to attach to the core and/or the density of the surface-altering agent on the core/particle surface. As such, in some embodiments a particular surface-altering agent may enhance the mobility of one type of particle or core but may not enhance the mobility of particle or core of another type.

Although much of the description herein may involve coatings comprising a hydrophilic block-hydrophobic block-hydrophilic block configuration (e.g., a PEG-PPO-PEG triblock copolymer) or coatings comprising a synthetic polymer having pendant hydroxyl groups, it should be appreciated that the coatings are not limited to these configurations and materials and that other configurations and materials are possible.

Furthermore, although many of the embodiments described herein involve a single coating, in other embodiments, a particle may include more than one coating (e.g., at least two, three, four, five, or more coatings), and each coating need not be formed of or comprise a mucus penetrating material. In some cases, an intermediate coating (i.e., a coating between the core surface and an outer coating) may include a polymer that facilitates attachment of an outer coating to the core surface. In many embodiments, an outer coating of a particle includes a polymer comprising a material that facilitates the transport of the particle through mucus.

As such, a coating (e.g., an inner coating, an intermediate coating, and/or an outer coating) may include any suitable polymer. In some cases, the polymer may be biocompatible and/or biodegradable. In some cases, the polymeric material may comprise more than one type of polymer (e.g., at least two, three, four, five, or more, polymers). In some cases, a polymer may be a random copolymer or a block copolymer (e.g., a diblock copolymer, a triblock copolymer) as described herein.

Non-limiting examples of suitable polymers may include polyamines, polyethers, polyamides, polyesters, polycarbamates, polyureas, polycarbonates, polystyrenes, polyimides, polysulfones, polyurethanes, polyacetylenes, polyethylenes, polyethyleneimines, polyisocyanates, polyacrylates, polymethacrylates, polyacrylonitriles, and polyarylates. Non-limiting examples of specific polymers include poly(caprolactone) (PCL), ethylene vinyl acetate polymer (EVA), poly(lactic acid) (PLA), poly(L-lactic acid) (PLLA), poly(glycolic acid) (PGA), poly(lactic acid-co-glycolic acid) (PLGA), poly(L-lactic acid-co-glycolic acid) (PLLGA), poly(D,L-lactide) (PDLA), poly(L-lactide) (PLLA), poly(D,L-lactide-co-caprolactone), poly(D,L-lactide-co-caprolactone-co-glycolide), poly(D, L-lactide-co-PEO-co-D, L-lactide), poly(D, L-lactide-co-PPO-co-D,L-lactide), polyalkyl cyanoacrylate, polyurethane, poly-L-lysine (PLL), hydroxypropyl methacrylate (HPMA), poly(ethylene glycol), poly-L-glutamic acid, poly(hydroxy acids), polyanhydrides, polyorthoesters, poly(ester amides), polyamides, poly(ester ethers), polycarbonates, polyalkylenes such as polyethylene and polypropylene, polyalkylene glycols such as poly(ethylene glycol) (PEG), polyalkylene oxides (PEO), polyalkylene terephthalates such as poly(ethylene terephthalate), polyvinyl alcohols (PVA), polyvinyl ethers, polyvinyl esters such as poly(vinyl acetate), polyvinyl halides such as poly(vinyl chloride) (PVC), polyvinylpyrrolidone, polysiloxanes, polystyrene (PS), polyurethanes, derivatized celluloses such as alkyl celluloses, hydroxyalkyl celluloses, cellulose ethers, cellulose esters, nitro celluloses, hydroxypropylcellulose, carboxymethylcellulose, polymers of acrylic acids, such as poly(methyl(meth)acrylate) (PMMA), poly(ethyl(meth)acrylate), poly(butyl(meth)acrylate), poly(isobutyl(meth)acrylate), poly(hexyl(meth)acrylate), poly(isodecyl(meth)acrylate), poly(lauryl(meth)acrylate), poly(phenyl(meth)acrylate), poly(methyl acrylate), poly(isopropyl acrylate), poly(isobutyl acrylate), poly(octadecyl acrylate) (jointly referred to herein as "polyacrylic acids"), and copolymers and mixtures thereof, polydioxanone and its copolymers, polyhydroxyalkanoates, polypropylene fumarate), polyoxymethylene, poloxamers, poly(ortho)esters, poly(butyric acid), poly(valeric acid), poly(lactide-co-caprolactone), and trimethylene carbonate, polyvinylpyrrolidone.

The molecular weight of a polymer may vary. In some embodiments, the molecular weight may be at least about 0.5 kDa, at least about 1 kDa, at least about 2 kDa, at least about 3 kDa, at least about 4 kDa, at least about 5 kDa, at least about 6 kDa, at least about 8 kDa, at least about 10 kDa, at least about 12 kDa, at least about 15 kDa, at least about 20 kDa, at least about 30 kDa, at least about 40 kDa, or at least about 50 kDa. In some embodiments, the molecular weight may be less than or equal to about 50 kDa, less than or equal to about 40 kDa, less than or equal to about 30 kDa, less than or equal to about 20 kDa, less than or equal to about 12 kDa, less than or equal to about 10 kDa, less than or equal to about 8 kDa, less than or equal to about 6 kDa, less than or equal to about 5 kDa, or less than or equal to about 4 kDa. Combinations of the above-referenced ranges are possible (e.g., a molecular weight of at least about 2 kDa and less than or equal to about 15 kDa). Other ranges are also possible. The molecular weight may be determined using any known technique such as light-scattering and gel permeation chromatography. Other methods are known in the art.

In certain embodiments, the polymer is biocompatible, i.e., the polymer does not typically induce an adverse response when inserted or injected into a living subject; for example, it does not include significant inflammation and/or acute rejection of the polymer by the immune system, for instance, via a T-cell-mediated response. It will be recognized, of course, that "biocompatibility" is a relative term, and some degree of immune response is to be expected even for polymers that are highly compatible with living tissue. However, as used herein, "biocompatibility" refers to the acute rejection of material by at least a portion of the immune system, i.e., a non-biocompatible material implanted into a subject provokes an immune response in the subject that is severe enough such that the rejection of the material by the immune system cannot be adequately controlled, and often is of a degree such that the material must be removed from the subject. One simple test to determine biocompatibility is to expose a polymer to cells in vitro; biocompatible polymers are polymers that typically does not result in significant cell death at moderate concentrations, e.g., at concentrations of about 50 micrograms/$10^6$ cells. For instance, a biocompatible polymer may cause less than about 20% cell death when exposed to cells such as fibroblasts or epithelial cells, even if phagocytosed or otherwise uptaken by such cells. In some embodiments, a substance is "biocompatible" if its addition to cells in vitro results in less than or equal to 20% cell death, and their administration in vivo does not induce unwanted inflammation or other such adverse effects.

In certain embodiments, a biocompatible polymer may be biodegradable, i.e., the polymer is able to degrade, chemically and/or biologically (e.g., by the cellular machinery or by hydrolysis), within a physiological environment, such as within the body or when introduced to cells. For instance, the polymer may be one that hydrolyzes spontaneously upon exposure to water (e.g., within a subject), and/or the polymer may degrade upon exposure to heat (e.g., at temperatures of about 37° C.). Degradation of a polymer may occur at varying rates, depending on the polymer or copolymer used. For example, the half-life of the polymer (the time at which 50% of the polymer is degraded into monomers and/or other nonpolymeric moieties) may be on the order of days, weeks, months, or years, depending on the polymer. The polymer may be biologically degraded, e.g., by enzymatic activity or cellular machinery, in some cases, for example, through exposure to a lysozyme (e.g., having relatively low pH). In some cases, the polymer may be broken down into monomers and/or other nonpolymeric moieties that cells can either reuse or dispose of without significant toxic effect on the cells (i.e., fewer than about 20% of the cells are killed when the components are added to cells in vitro). For example, polylactide may be hydrolyzed to form lactic acid, polyglycolide may be hydrolyzed to form glycolic acid, etc.).

Examples of biodegradable polymers include, but are not limited to, poly(ethylene glycol)-poly(propylene oxide)-poly(ethylene glycol) triblock copolymers, poly(lactide) (or poly(lactic acid)), poly(glycolide) (or poly(glycolic acid)), poly(orthoesters), poly(caprolactones), polylysine, poly(ethylene imine), poly(acrylic acid), poly(urethanes), poly(anhydrides), poly(esters), poly(trimethylene carbonate), poly(ethyleneimine), poly(acrylic acid), poly(urethane), poly(beta amino esters) or the like, and copolymers or derivatives of these and/or other polymers, for example, poly(lactide-co-glycolide) (PLGA).

In certain embodiments, a polymer may biodegrade within a period that is acceptable in the desired application. In certain embodiments, such as in vivo therapy, such degradation occurs in a period usually less than about five years, one year, six months, three months, one month, fifteen days, five days, three days, or even one day or less (e.g., 1-4 hours, 4-8 hours, 4-24 hours, 1-24 hours) on exposure to a physiological solution with a pH between 6 and 8 having a temperature of between 25 and 37° C. In other embodiments, the polymer degrades in a period of between about one hour and several weeks, depending on the desired application.

Although coatings and particles described herein may include polymers, in some embodiments, the particles described herein comprise a hydrophobic material that is not a polymer (e.g., a non-polymer) and is not a pharmaceutical agent. For example, all or portions of a particle may be coated with a passivating layer in some embodiments. Non-limiting examples of non-polymeric materials may include certain metals, waxes, and organic materials (e.g., organic silanes, perfluorinated or fluorinated organic materials).

Particles with Reduced Mucoadhesion

As described herein, in some embodiments, a method involves identifying a material such as a particle to which it is desired that its mucoadhesiveness be reduced. Materials in need of increased diffusivity through mucus may be, for example, hydrophobic, have many hydrogen bond donors or acceptors, and/or may be highly charged. In some cases, the material may include a crystalline or amorphous solid material. The material, which may serve as a core, may be coated with a suitable polymer described herein, thereby forming a particle with a plurality of surface-altering moieties on the surface, resulting in reduced mucoadhesion. Particles herein described as having reduced mucoadhesion may alternatively be characterized as having increased transport through mucus, being mobile in mucus, or mucus-penetrating (i.e., mucus-penetrating particles), meaning that the particles are transported through mucus faster than a (negative) control particle. The (negative) control particle may be a particle that is known to be mucoadhesive, e.g., an unmodified particle or core that is not coated with a coating described herein, such as a 200 nm carboxylated polystyrene particle.

In certain embodiments, methods herein include preparing a pharmaceutical composition or formulation of the modified substance, e.g., in a formulation adapted for delivery (e.g., topical delivery) to mucus or a mucosal surface of a subject. The pharmaceutical composition with surface-altering moieties may be delivered to the mucosal surface of a subject, may pass through the mucosal barrier in the subject, and/or prolonged retention and/or increased uniform distribution of the particles at mucosal surfaces, e.g., due to reduced mucoadhesion. As will be known by those of ordinary skill in the art, mucus is a viscoelastic and adhesive substance that traps most foreign particles. Trapped particles are not able to reach the underlying epithelium and/or are quickly eliminated by mucus clearance mechanisms. For a particle to reach the underlying epithelium and/or for a particle to have prolonged retention in the mucosal tissue, the particle must quickly penetrate mucus secretions and/or avoid the mucus clearance mechanisms. If a particle does not adhere substantially to the mucus, the particle may be able to diffuse in the interstitial fluids between mucin fibers and reach the underlying epithelium and/or not be eliminated by the mucus clearance mechanisms. Accordingly, modifying mucoadhesive materials, (e.g., pharmaceutical agents that are hydrophobic) with a material to reduce the mucoadhesion of the particle may allow for efficient delivery of the particles to the underlying epithelium and/or prolonged retention at mucosal surfaces.

Furthermore, in some embodiments, the particles described herein having reduced mucoadhesion facilitate better distribution of the particles at a tissue surface, and/or have a prolonged presence at the tissue surface, compared to particles that are more mucoadhesive. For example, in some cases a luminal space such as the gastrointestinal tract is surrounded by a mucus-coated surface. Mucoadhesive particles delivered to such a space are typically removed from the luminal space and from the mucus-coated surface by the body's natural clearance mechanisms. The particles described herein with reduced mucoadhesion may remain in the luminal space for relatively longer periods compared to the mucoadhesive particles. This prolonged presence may prevent or reduce clearance of the particles, and/or may allow for better distribution of the particles on the tissue surface. The prolonged presence may also affect the particle transport through the luminal space, e.g., the particles may distribute into the mucus layer and may reach the underlying epithelium.

In certain embodiments, a material (e.g., a core) coated with a polymer described herein may pass through mucus or a mucosal barrier in a subject, and/or exhibit prolonged retention and/or increase uniform distribution of the particles at mucosal surfaces, e.g., such substances are cleared more slowly (e.g., at least 2 times, 5 times, 10 times, or even at least 20 times more slowly) from a subject's body as compared to a (negative) control particle. The (negative) control particle may be a particle that is known to be mucoadhesive, e.g., an unmodified particle or core that is not coated with a coating described herein, such as a 200 nm carboxylated polystyrene particle.

In certain embodiments, a particle described herein has certain a relative velocity, $<V_{mean}>_{rel}$, which is defined as follows:

$$<V_{mean}>_{rel} = \frac{<V_{mean}>_{Sample} - <V_{mean}>_{Negative\ control}}{<V_{mean}>_{Positive\ control} - <V_{mean}>_{Negative\ control}} \quad \text{(Equation 1)}$$

where $<V_{mean}>$ is the ensemble average trajectory-mean velocity, $V_{mean}$ is the velocity of an individual particle averaged over its trajectory, the sample is the particle of interest, the negative control is a 200 nm carboxylated polystyrene particle, and the positive control is a 200 nm polystyrene particle densely PEGylated with 2 kDa-5 kDa PEG.

The relative velocity can be measured by a multiple particle tracking technique. For instance, a fluorescent microscope equipped with a CCD camera can be used to capture 15 s movies at a temporal resolution of 66.7 ms (15 frames/s) under 100× magnification from several areas within each sample for each type of particles: sample, negative control, and positive control. The sample, negative and positive controls may be fluorescent particles to observe tracking. Alternatively non-fluorescent particles may be coated with a fluorescent molecule, a fluorescently tagged surface agent or a fluorescently tagged polymer. An advanced image processing software (e.g., Image Pro or MetaMorph) can be used to measure individual trajectories of multiple particles over a time-scale of at least 3.335 s (50 frames).

In some embodiments, a particle described herein has a relative velocity of greater than or equal to about 0.3, greater than or equal to about 0.4, greater than or equal to about 0.5, greater than or equal to about 0.6, greater than or equal to about 0.7, greater than or equal to about 0.8, greater than or equal to about 0.9, greater than or equal to about 1.0, greater than or equal to about 1.1, greater than or equal to about 1.2, greater than or equal to about 1.3, greater than or equal to about 1.4, greater than or equal to about 1.5, greater than or equal to about 1.6, greater than or equal to about 1.7, greater than or equal to about 1.8, greater than or equal to about 1.9 or greater than or equal to about 2.0 in mucus. In some embodiments, a particle described herein has a relative velocity of less than or equal to about 10.0, less than or equal to about 8.0, less than or equal to about 6.0, less than or equal to about 4.0, less than or equal to about 3.0, less than or equal to about 2.0, less than or equal to about 1.9, less than or equal to about 1.8, less than or equal to about 1.7, less than or equal to about 1.6, less than or equal to about 1.5, less than or equal to about 1.4, less than or equal to about 1.3, less than or equal to about 1.2, less than or equal to about 1.1, less than or equal to about 1.0, less than or equal to about 0.9, less than or equal to about 0.8, or less than or equal to about 1.7 in mucus. Combinations of the above-noted ranges are possible (e.g., a relative velocity of greater than or equal to about 0.5 and less than or equal to about 6.0). Other ranges are also possible. The mucus may be, for example, human cervicovaginal mucus.

In certain embodiments, a particle described herein can diffuse through mucus or a mucosal barrier at a greater rate or diffusivity than a control particle or a corresponding particle (e.g., a corresponding particle that is unmodified and/or is not coated with a coating described herein). In some cases, a particle described herein may pass through mucus or a mucosal barrier at a rate of diffusivity that is at least about 10 times, 20 times, 30 times, 50 times, 100 times, 200 times, 500 times, 1000 times, 2000 times, 5000 times, 10000 times, or more, higher than a control particle or a corresponding particle. In some cases, a particle described herein may pass through mucus or a mucosal barrier at a rate of diffusivity that is less than or equal to about 10000 times higher, less than or equal to about 5000 times higher, less than or equal to about 2000 times higher, less than or equal to about 1000 times higher, less than or equal to about 500 times higher, less than or equal to about 200 times higher, less than or equal to about 100 times higher, less than or equal to about 50 times higher, less than or equal to about 30 times higher, less than or equal to about 20 times higher, or less than or equal to about 10 times higher than a control particle or a corresponding particle. Combinations of the above-referenced ranges are also possible (e.g., at least about 10 times and less than or equal to about 1000 times higher than a control particle or a corresponding particle). Other ranges are also possible.

For the purposes of the comparisons described herein, the corresponding particle may be approximately the same size, shape, and/or density as the test particle but lacking the coating that makes the test particle mobile in mucus. In some cases, the measurement is based on a time scale of about 1 second, or about 0.5 second, or about 2 seconds, or about 5 seconds, or about 10 seconds. Those of ordinary skill in the art will be aware of methods for determining the geometric mean square displacement and rate of diffusivity.

In addition, a particle described herein may pass through mucus or a mucosal barrier with a geometric mean squared displacement that is at least about 10 times, 20 times, 30 times, 50 times, 100 times, 200 times, 500 times, 1000 times, 2000 times, 5000 times, 10000 times, or more, higher than a corresponding particle or control particle. In some cases, a particle described herein may pass through mucus or a mucosal barrier with a geometric mean squared displacement that is less than or equal to about 10000 times higher, less than or equal to about 5000 times higher, less than or equal to about 2000 times higher, less than or equal to about 1000 times higher, less than or equal to about 500 times higher, less than or equal to about 200 times higher, less than or equal to about 100 times higher, less than or equal to about 50 times higher, less than or equal to about 30 times higher, less than or equal to about 20 times higher, or less than or equal to about 10 times higher than a control particle or a corresponding particle. Combinations of the above-referenced ranges are also possible (e.g., at least about 10 times and less than or equal to about 1000 times higher than a control particle or a corresponding particle). Other ranges are also possible.

In some embodiments, a particle described herein diffuses through a mucosal barrier at a rate approaching the rate or diffusivity at which said particles can diffuse through water. In some cases, a particle described herein may pass through a mucosal barrier at a rate or diffusivity that is less than or equal to about 1/100, less than or equal to about 1/200, less than or equal to about 1/300, less than or equal to about 1/400, less than or equal to about 1/500, less than or equal to about 1/600, less than or equal to about 1/700, less than or equal to about 1/800, less than or equal to about 1/900, less than or equal to about 1/1000, less than or equal to about 1/2000, less than or equal to about 1/5000, less than or equal to about 1/10,000 the diffusivity that the particle diffuse through water under identical conditions. In some cases, a particle described herein may pass through a mucosal barrier at a rate or diffusivity that is greater than or equal to about 1/10,000, greater than or equal to about 1/5000, greater than or equal to about 1/2000, greater than or equal to about 1/1000, greater than or equal to about 1/900, greater than or equal to about 1/800, greater than or equal to about 1/700, greater than or equal to about 1/600, greater than or equal to about 1/500, greater than or equal to about 1/400, greater than or equal to about 1/300, greater than or equal to about 1/200, or greater than or equal to about 1/100 the diffusivity that the particle diffuse through water under identical conditions. Combinations of the above-referenced ranges are also possible (e.g., greater than or equal to about 1/5000 and less than 1/500 the diffusivity that the particle diffuse through water under identical conditions). Other ranges are also possible. The measurement may be based on a time scale of about 1 second, or about 0.5 second, or about 2 seconds, or about 5 seconds, or about 10 seconds.

In a particular embodiment, a particle described herein may diffuse through human cervicovaginal mucus at a diffusivity that is less than about 1/500 the diffusivity that the particle diffuses through water. In some cases, the measurement is based on a time scale of about 1 second, or about 0.5 second, or about 2 seconds, or about 5 seconds, or about 10 seconds.

In certain embodiments, the present invention provides particles that travel through mucus, such as human cervicovaginal mucus, at certain absolute diffusivities. For example, the particles of described herein may travel at diffusivities of at least about $1 \times 10^{-4}$ µm/s, $2 \times 10^{-4}$ µm/s, $5 \times 10^{-4}$ µm/s, $1 \times 10^{-3}$ µm/s, $2 \times 10^{-3}$ µm/s, $5 \times 10^{-3}$ µm/s, $1 \times 10^{-2}$ µm/s, $2 \times 10^{-2}$ µm/s, $4 \times 10^{-2}$ µm/s, $5 \times 10^{-2}$ µm/s, $6 \times 10^{-2}$ µm/s, $8 \times 10^{-2}$ µm/s, $1 \times 10^{-1}$ µm/s, $2 \times 10^{-1}$ µm/s, $5 \times 10^{-1}$ µm/s, 1 µm/s, or 2 µm/s. In some cases, the particles may travel at diffusivities of less than or equal to about 2 µm/s, less than or equal to about 1 µm/s, less than or equal to about $5 \times 10^{-1}$ µm/s, less than or equal to about $2 \times 10^{-1}$ µm/s, less than or equal to about $1 \times 10^{-1}$ µm/s, less than or equal to about $8 \times 10^{-2}$ µm/s, less than or equal to about $6 \times 10^{-2}$ µm/s, less than or equal to about $5 \times 10^{-2}$ µm/s, less than or equal to about $4 \times 10^{-2}$ µm/s, less than or equal to about $2 \times 10^{-2}$ µm/s, less than or equal to about $1 \times 10^{-2}$ µm/s, less than or equal to about $5 \times 10^{-3}$ µm/s, less than or equal to about $2 \times 10^{-3}$ µm/s, less than or equal to about $1 \times 10^{-3}$ µm/s, less than or equal to about $5 \times 10^{-4}$ µm/s, less than or equal to about $2 \times 10^{-4}$ µm/s, or less than or equal to about $1 \times 10^{-4}$ µm/s. Combinations of the above-referenced ranges are also possible (e.g., greater than or equal to about $2 \times 10^{-4}$ µm/s and less than or equal to about $1 \times 10^{-1}$ µm/s). Other ranges are also possible. In some cases, the measurement is based on a time scale of about 1 second, or about 0.5 second, or about 2 seconds, or about 5 seconds, or about 10 seconds.

It should be appreciated that while many of the mobilities (e.g., relative velocities, diffusivities) described here may be measured in human cervicovaginal mucus, they may be measured in other types of mucus as well.

In certain embodiments, a particle described herein comprises surface-altering moieties at a given density. The surface-altering moieties may be the portions of a surface-altering agent that are, for example, exposed to the solvent containing the particle. As an example, the hydrolyzed units/blocks of PVA may be surface-altering moieties of the surface-altering agent PVA. In another example, the PEG segments may be surface-altering moieties of the surface-altering agent PEG-PPO-PEG. In some cases, the surface-altering moieties and/or surface-altering agents are present at a density of at least about 0.001 units or molecules per $nm^2$, at least about 0.002, at least about 0.005, at least about 0.01, at least about 0.02, at least about 0.05, at least about 0.1, at least about 0.2, at least about 0.5, at least about 1, at least about 2, at least about 5, at least about 10, at least about 20, at least about 50, at least about 100 units or molecules per $nm^2$, or more units or molecules per $nm^2$. In some cases, the surface-altering moieties and/or surface-altering agents are present at a density of less than or equal to about 100 units or molecules per $nm^2$, less than or equal to about 50, less than or equal to about 20, less than or equal to about 10, less than or equal to about 5, less than or equal to about 2, less than or equal to about 1, less than or equal to about 0.5, less than or equal to about 0.2, less than or equal to about 0.1, less than or equal to about 0.05, less than or equal to about 0.02, or less than or equal to about 0.01 units or molecules per $nm^2$. Combinations of the above-referenced ranges are possible (e.g., a density of at least about 0.01 and less than or equal to about 1 units or molecules per $nm^2$). Other ranges are also possible. In some embodiments, the density values described above may be an average density as the surface altering agent is in equilibrium with other components in solution.

Those of ordinary skill in the art will be aware of methods to estimate the average density of surface-altering moieties (see, for example, S. J. Budijono et al., Colloids and Surfaces A: Physicochem. Eng. Aspects 360 (2010) 105-110 and Joshi, et al., *Anal. Chim.* Acta 104 (1979) 153-160, each of which is incorporated herein by reference). For example, as described herein, the average density of surface-altering moieties can be determined using HPLC quantitation and DLS analysis. A suspension of particles for which surface density determination is of interest is first sized using DLS: a small volume is diluted to an appropriate concentration (~100 µg/mL, for example), and the z-average diameter is taken as a representative measurement of particle size. The remaining suspension is then divided into two aliquots. Using HPLC, the first aliquot is assayed for the total concentration of core material and for the total concentration of surface-altering moiety. Again using HPLC the second aliquot is assayed for the concentration of free or unbound surface-altering moiety. In order to get only the free or unbound surface-altering moiety from the second aliquot, the particles, and therefore any bound surface-altering moiety, are removed by ultracentrifugation. By subtracting the concentration of the unbound surface-altering moiety from the total concentration of surface-altering moiety, the concentration of bound surface-altering moiety can be determined. Since the total concentration of core material was also determined from the first aliquot, the mass ratio between the core material and the surface-altering moiety can be determined. Using the molecular weight of the surface-altering moiety the number of surface-altering moiety to mass of core material can be calculated. To turn this number into a surface density measurement, the surface area per mass of core material needs to be calculated. The volume of the particle is approximated as that of a sphere with the diameter obtained from DLS allowing for the calculation of the surface area per mass of core material. In this way the number of surface-altering moieties per surface area can be determined.

In certain embodiments, the particles described herein comprise surface-altering moieties and/or agents that affect the zeta-potential of the particle. The zeta potential of the coated particle may be, for example, at least about −100 mV, at least about −75 mV, at least about −50 mV, at least about −40 mV, at least about −30 mV, at least about −20 mV, at least about −10 mV, at least about −5 mV, at least about 5 mV, at least about 10 mV, at least about 20 mV, at least about 30 mV, at least about 40 mV, at least about 50 mV, at least about 75 mV, or at least about 100 mV. Combinations of the above-referenced ranges are possible (e.g., a zeta-potential of at least about −50 mV and less than or equal to about 50 mV). Other ranges are also possible.

The coated particles described herein may have any suitable shape and/or size. In some embodiments, a coated particle has a shape substantially similar to the shape of the core. In some cases, a coated particle described herein may be a nanoparticle, i.e., the particle has a characteristic dimension of less than about 1 micrometer, where the characteristic dimension of the particle is the diameter of a perfect sphere having the same volume as the particle. In other embodiments, larger sizes are possible (e.g., about 1-10 microns). A plurality of particles, in some embodiments, may also be characterized by an average size (e.g., an average largest cross-sectional dimension, or an average smallest cross-sectional dimension for the plurality of particles). A plurality of particles may have an average size of, for example, less than or equal to about 10 µm, less than or equal to about 5 µm, less than or equal to about 1 µm, less than or equal to about 800 nm, less than or equal to about 700 nm, less than or equal to about 500 nm, less than or equal to about 400 nm, less than or equal to about 300 nm, less than or equal to about 200 nm, less than or equal to about 100 nm, less than or equal to about 75 nm, less than or equal to about 50 nm, less than or equal to about 40 nm, less than or equal to about 35 nm, less than or equal to about 30 nm, less than or equal to about 25 nm, less than or equal to about 20 nm, less than or equal to about 15 nm, or less than or equal to about 5 nm. In some cases, a plurality of particles may have an average size of, for example, at least about 5 nm, at least about 20 nm, at least about 50 nm, at least about 100 nm, at least about 200 nm, at least about 300 nm, at least about 400 nm, at least about 500 nm, at least about 1 µm, at least or at least about 5 µm. Combinations of the above-referenced ranges are also possible (e.g., an average size of at least about 50 nm and less than or equal to about 500 nm). In one embodiment, a plurality of particles have an average size between about 100 nm and 500 nm, 200 nm and 500 nm, 200 nm and 400 nm, or 200 nm and 300 nm. Other ranges are also possible. In some embodiments, the sizes of the cores formed by a process described herein have a Gaussian-type distribution.

Pharmaceutical Agents

In some embodiments, a coated particle comprises at least one pharmaceutical agent. The pharmaceutical agent may be present in the core of the particle and/or present in a coating of the particle (e.g., dispersed throughout the core and/or coating). In some cases, a pharmaceutical agent may be disposed on the surface of the particle (e.g., on an outer surface of a coating, the inner surface of a coating, on a surface of the core). The pharmaceutical agent may be contained within a particle and/or disposed in a portion of the particle using commonly known techniques (e.g., by coating, adsorption, covalent linkage, encapsulation, or other process). In some cases, the pharmaceutical agent may be present in the core of the particle prior to or during coating of the particle. In some cases, the pharmaceutical agent is present during the formation of the core of the particle, as described herein.

Non-limiting examples of pharmaceutical agents include imaging agents, diagnostic agents, therapeutic agents, agents with a detectable label, nucleic acids, nucleic acid analogs, small molecules, peptidomimetics, proteins, peptides, lipids, vaccines, viral vectors, virus, and surfactants.

In some embodiments, a pharmaceutical agent contained in a particle described herein has a therapeutic, diagnostic, or imaging effect in a mucosal tissue to be targeted. Non-limiting examples of mucosal tissues include oral (e.g., including the buccal and esophageal membranes and tonsil surface), ophthalmic, gastrointestinal (e.g., including stomach, small intestine, large intestine, colon, rectum), nasal, respiratory (e.g., including nasal, pharyngeal, tracheal and bronchial membranes), and genital (e.g., including vaginal, cervical and urethral membranes) tissues.

Any suitable number of pharmaceutical agents may be present in a particle described herein. For example, at least 1, at least 2, at least 3, at least 4, at least 5, or more, but generally less than 10, pharmaceutical agents may be present in a particle described herein.

A number of drugs that are mucoadhesive are known in the art and may be used as pharmaceutical agents in the particles described herein (see, for example, Khanvilkar K, Donovan M D, Flanagan D R, Drug transfer through mucus, Advanced Drug Delivery Reviews 48 (2001) 173-193; Bhat P G, Flanagan D R, Donovan M D. Drug diffusion through cystic fibrotic mucus: steady-state permeation, rheologic properties, and glycoprotein morphology, J Pharm Sci, 1996 June; 85(6):624-30). Additional non-limiting examples of pharmaceutical agents include imaging and diagnostic agents (such as radioopaque agents, labeled antibodies, labeled nucleic acid probes, dyes, such as colored or fluorescent dyes, etc.) and adjuvants (radiosensitizers, transfection-enhancing agents, chemotactic agents and chemoattractants, peptides that modulate cell adhesion and/or cell mobility, cell permeabilizing agents, vaccine potentiators, inhibitors of multidrug resistance and/or efflux pumps, etc.).

Additional non-limiting examples of pharmaceutical agents include pazopanib, sorafenib, lapatinib, fluocinolone acetonide, semaxanib, axitinib, tivozanib, cediranib, linifanib, regorafenib, telatinib, vatalanib, MGCD-265, OSI-930, KRN-633, bimatoprost, latanoprost, travoprost, aloxiprin, auranofin, azapropazone, benorylate, diflunisal, etodolac, fenbufen, fenoprofen calcim, flurbiprofen, furosemide, ibuprofen, indomethacin, ketoprofen, loteprednol etabonate, bromfenac beryllium, bromfenac magnesium, bromfenac calcium, bromfenac strontium, bromfenac barium, bromfenac zinc, bromfenac copper(II), diclofenac free acid, diclofenac beryllium, diclofenac magnesium, diclofenac calcium, diclofenac strontium, diclofenac barium, diclofenac zinc, diclofenac copper(II), ketorolac free acid, ketorolac beryllium, ketorolac magnesium, ketorolac calcium, ketorolac strontium, ketorolac barium, ketorolac zinc, ketorolac copper(II), meclofenamic acid, mefenamic acid, nabumetone, naproxen, oxyphenbutazone, phenylbutazone, piroxicam, sulindac, albendazole, bephenium hydroxynaphthoate, cambendazole, dichlorophen, ivermectin, mebendazole, oxamniquine, oxfendazole, oxantel embonate, praziquantel, pyrantel embonate, thiabendazole, amiodarone HCl, disopyramide, flecainide acetate, quinidine sulphate. Anti-bacterial agents: benethamine penicillin, cinoxacin, ciprofloxacin HCl, clarithromycin, clofazimine, cloxacillin, demeclocycline, doxycycline, erythromycin, ethionamide, imipenem, nalidixic acid, nitrofurantoin, rifampicin, spiramycin, sulphabenzamide, sulphadoxine, sulphamerazine, sulphacetamide, sulphadiazine, sulphafurazole, sulphamethoxazole, sulphapyridine, tetracycline, trimethoprim, dicoumarol, dipyridamole, nicoumalone, phenindione, amoxapine, maprotiline HCl, mianserin HCL, nortriptyline HCl, trazodone HCL, trimipramine maleate, acetohexamide, chlorpropamide, glibenclamide, gliclazide, glipizide, tolazamide, tolbutamide, beclamide, carbamazepine, clonazepam, ethotoin, methoin, methsuximide, methylphenobarbitone, oxcarbazepine, paramethadione, phenacemide, phenobarbitone, phenytoin, phensuximide, primidone, sulthiame, valproic acid, amphotericin, butoconazole nitrate, clotrimazole, econazole nitrate, fluconazole, flucytosine, griseofulvin, itraconazole, ketoconazole, miconazole, natamycin, nystatin, sulconazole nitrate, terbinafine HCl, terconazole, tioconazole, undecenoic acid, allopurinol, probenecid, sulphin-pyrazone, amlodipine, benidipine, darodipine, diltiazem HCl, diazoxide, felodipine, guanabenz acetate, isradipine, minoxidil, nicardipine HCl, nifedipine, nimodipine, phenoxybenzamine HCl, prazosin HCL, reserpine, terazosin HCL, amodiaquine, chloroquine, chlorproguanil HCl, halofantrine HCl, mefloquine HCl, roguanil HCl, pyrimethamine, quinine sulphate, dihydroergotamine mesylate, ergotamine tartrate, methysergide maleate, pizotifen maleate, sumatriptan succinate, atropine, benzhexol HCl, biperiden, ethopropazine HCl, hyoscyamine, mepenzolate bromide, oxyphencylcimine HCl, tropicamide, aminoglutethimide, amsacrine, azathioprine, busulphan, chlorambucil, cyclosporin, dacarbazine, estramustine, etoposide, lomustine, melphalan, mercaptopurine, methotrexate, mitomycin, mitotane, mitozantrone, procarbazine HCl, tamoxifen citrate, testolactone, benznidazole, clioquinol, decoquinate, diiodohydroxyquinoline, diloxanide furoate, dinitolmide, furazolidone, metronidazole, nimorazole, nitrofurazone, ornidazole, tinidazole, carbimazole, propylthiouracil, alprazolam, amylobarbitone, barbitone, bentazepam, bromazepam, bromperidol, brotizolam, butobarbitone, carbromal, chlordiazepoxide, chlormethiazole, chlorpromazine, clobazam, clotiazepam, clozapine, diazepam, droperidol, ethinamate, fluanisone, flunitrazepam, fluopromazine, flupenthixol decanoate, fluphenazine decanoate, flurazepam, haloperidol, lorazepam, lormetazepam, medazepam, meprobamate, methaqualone, midazolam, nitrazepam, oxazepam, pentobarbitone, perphenazine pimozide, prochlorperazine, sulpiride, temazepam, thioridazine, triazolam, zopiclone, acebutolol, alprenolol, atenolol, labetalol, metoprolol, nadolol, oxprenolol, pindolol, propranolol, amrinone, digitoxin, digoxin, enoximone, lanatoside C, medigoxin, beclomethasone, betamethasone, budesonide, cortisone acetate, desoxymethasone, dexamethasone, fludrocortisone acetate, flunisolide, fluocortolone, fluticasone propionate, hydrocortisone, methylprednisolone, prednisolone, prednisone, triamcinolone, acetazolamide, amiloride, bendrofluazide, bumetanide, chlorothiazide, chlorthalidone, ethacrynic acid, furosemide, metolazone, spironolactone, triamterene, bromocriptine mesylate, lysuride maleate, bisacodyl, cimetidine, cisapride, diphenoxylate HCl, domperidone, famotidine, loperamide, mesalazine, nizatidine, omeprazole, ondansetron HCL, ranitidine HCl, sulphasalazine, acrivastine, astemizole, cinnarizine, cyclizine, cyproheptadine HCl, dimenhydrinate, flunarizine HCl, loratadine, meclozine HCl, oxatomide, terfenadine, bezafibrate, clofibrate, fenofibrate, gemfibrozil, probucol, amyl nitrate, glyceryl trinitrate, isosorbide dinitrate, isosorbide mononitrate, pentaerythritol tetranitrate, betacarotene, vitamin A, vitamin B 2, vitamin D, vitamin E, vitamin K, codeine, dextropropoxyphene, diamorphine, dihydrocodeine, meptazinol, methadone, morphine, nalbuphine, pentazocine, clomiphene citrate, danazol, ethinyl estradiol, medroxyprogesterone acetate, mestranol, methyltestosterone, norethisterone, norgestrel, estradiol, conjugated oestrogens, progesterone, stanozolol, stilbestrol, testosterone, tibolone, amphetamine, dexamphetamine, dexfenfluramine, fenfluramine, and mazindol.

Uses and Pharmaceutical Compositions

The particles described herein may be employed in any suitable application. In some cases, the particles are part of pharmaceutical compositions (e.g., as described herein), for example, those used to deliver a pharmaceutical agent (e.g., a drug, therapeutic agent, diagnostic agent, imaging agent) through or to mucus or a mucosal surface. A pharmaceutical composition may comprise at least one particle described herein and one or more pharmaceutically acceptable excipients or carriers. The composition may be used in treating, preventing, and/or diagnosing a condition in a subject, wherein the method comprises administering to a subject the pharmaceutical composition. A subject or patient to be treated by the articles and methods described herein may mean either a human or non-human animal, such as primates, mammals, and vertebrates.

Methods involving treating a subject may include preventing a disease, disorder or condition from occurring in the subject which may be predisposed to the disease, disorder and/or condition but has not yet been diagnosed as having it; inhibiting the disease, disorder or condition, e.g., impeding its progress; and relieving the disease, disorder, or condition, e.g., causing regression of the disease, disorder and/or condition. Treating the disease or condition includes ameliorating at least one symptom of the particular disease or condition, even if the underlying pathophysiology is not affected (e.g., such treating the pain of a subject by administration of an analgesic agent even though such agent does not treat the cause of the pain).

In some embodiments, a pharmaceutical composition described herein is delivered to a mucosal surface in a subject and may pass through a mucosal barrier in the subject (e.g., mucus), and/or may exhibit prolonged retention and/or increased uniform distribution of the particles at mucosal surfaces, e.g., due to reduced mucoadhesion. Non-limiting examples of mucosal tissues include oral (e.g., including the buccal and esophageal membranes and tonsil surface), ophthalmic, gastrointestinal (e.g., including stomach, small intestine, large intestine, colon, rectum), nasal, respiratory (e.g., including nasal, pharyngeal, tracheal and bronchial membranes), genital (e.g., including vaginal, cervical and urethral membranes).

Pharmaceutical compositions described herein and for use in accordance with the articles and methods described herein may include a pharmaceutically acceptable excipient or carrier. A pharmaceutically acceptable excipient or pharmaceutically acceptable carrier may include a non-toxic, inert solid, semi-solid or liquid filler, diluent, encapsulating material or formulation auxiliary of any suitable type. Some examples of materials which can serve as pharmaceutically acceptable carriers are sugars such as lactose, glucose, and sucrose; starches such as corn starch and potato starch; cellulose and its derivatives such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols such as propylene glycol; esters such as ethyl oleate and ethyl laurate; agar; detergents such as Tween 80; buffering agents such as magnesium hydroxide and aluminum hydroxide; alginic acid; pyrogen-free water; isotonic saline; Ringer's solution; ethyl alcohol; and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. As would be appreciated by one of skill in this art, the excipients may be chosen based on the route of administration as described below, the pharmaceutical agent being delivered, time course of delivery of the agent, etc.

Pharmaceutical compositions containing the particles described herein may be administered to a subject via any route known in the art. These include, but are not limited to, oral, sublingual, nasal, intradermal, subcutaneous, intramuscular, rectal, vaginal, intravenous, intraarterial, intracisternally, intraperitoneal, intravitreal, periocular, topical (as by powders, creams, ointments, or drops), buccal and inhalational administration. In some embodiments, compositions described herein may be administered parenterally as injections (intravenous, intramuscular, or subcutaneous), drop infusion preparations, or suppositories. As would be appreciated by one of skill in this art, the route of administration and the effective dosage to achieve the desired biological effect may be determined by the agent being administered, the target organ, the preparation being administered, time course of administration, disease being treated, intended use, etc.

As an example, the particles may be included in a pharmaceutical composition to be formulated as a nasal spray, such that the pharmaceutical composition is delivered across a nasal mucus layer. As another example, the particles may be included in a pharmaceutical composition to be formulated as an inhaler, such that the pharmaceutical compositions is delivered across a pulmonary mucus layer. As another example, if compositions are to be administered orally, it may be formulated as tablets, capsules, granules, powders, or syrups. Similarly, the particles may be included in a pharmaceutical composition that is to be delivered via ophthalmic, gastrointestinal, nasal, respiratory, rectal, urethral and/or vaginal tissues.

For application by the ophthalmic mucous membrane route, subject compositions may be formulated as eye drops or eye ointments. These formulations may be prepared by conventional means, and, if desired, the subject compositions may be mixed with any conventional additive, such as a buffering or pH-adjusting agents, tonicity adjusting agents, viscosity modifiers, suspension stabilizers, preservatives, and other pharmaceutical excipients. In addition, in certain embodiments, subject compositions described herein may be lyophilized or subjected to another appropriate drying technique such as spray drying.

In some embodiments, particles described herein that may be administered in inhalant or aerosol formulations comprise one or more pharmaceutical agents, such as adjuvants, diagnostic agents, imaging agents, or therapeutic agents useful in inhalation therapy. The particle size of the particulate medicament should be such as to permit inhalation of substantially all of the medicament into the lungs upon administration of the aerosol formulation and may be, for example, less than about 20 microns, e.g., in the range of about 1 to about 10 microns, e.g., about 1 to about 5 microns, although other ranges are also possible. The particle size of the medicament may be reduced by conventional means, for example by milling or micronisation. Alternatively, the particulate medicament can be administered to the lungs via nebulization of a suspension. The final aerosol formulation may contain, for example, between 0.005-90% w/w, between 0.005-50%, between 0.005-10%, between about 0.005-5% w/w, or between 0.01-1.0% w/w, of medicament relative to the total weight of the formulation. Other ranges are also possible.

It is desirable, but by no means required, that the formulations described herein contain no components which may provoke the degradation of stratospheric ozone. In particular, in some embodiments, propellants are selected that do not contain or do not consist essentially of chlorofluorocarbons such as $CCl_3F$, $CCl_2F_2$, and $CF_3CCl_3$.

The aerosol may comprise propellant. The propellant may optionally contain an adjuvant having a higher polarity and/or a higher boiling point than the propellant. Polar adjuvants which may be used include (e.g., $C_{2-6}$) aliphatic alcohols and polyols such as ethanol, isopropanol, and propylene glycol, preferably ethanol. In general, only small quantities of polar adjuvants (e.g., 0.05-3.0% w/w) may be required to improve the stability of the dispersion—the use of quantities in excess of 5% w/w may tend to dissolve the medicament. Formulations in accordance with the embodiments described herein may contain less than 1% w/w, e.g., about 0.1% w/w, of polar adjuvant. However, the formulations described herein may be substantially free of polar adjuvants, especially ethanol. Suitable volatile adjuvants include saturated hydrocarbons such as propane, n-butane, isobutane, pentane and isopentane and alkyl ethers such as dimethyl ether. In general, up to 50% w/w of the propellant may comprise a volatile adjuvant, for example, up to 30% w/w of a volatile saturated $C_1$-$C_6$ hydrocarbon. Optionally, the aerosol formulations according to the invention may further comprise one or more surfactants. The surfactants can be physiologically acceptable upon administration by inhalation. Within this category are included surfactants such as L-α-phosphatidylcholine (PC), 1,2-dipalmitoylphosphatidylcholine (DPPC), oleic acid, sorbitan trioleate, sorbitan mono-oleate, sorbitan monolaurate, polyoxyethylene sorbitan monolaurate, polyoxyethylene sorbitan monooleate, natural lecithin, oleyl polyoxyethylene ether, stearyl polyoxyethylene ether, lauryl polyoxyethylene ether, block copolymers of oxyethylene and oxypropylene, synthetic lecithin, diethylene glycol dioleate, tetrahydrofurfuryl oleate, ethyl oleate, isopropyl myristate, glyceryl monooleate, glyceryl monostearate, glyceryl monoricinoleate, cetyl alcohol, stearyl alcohol, polyethylene glycol 400, cetyl pyridinium chloride, benzalkonium chloride, olive oil, glyceryl monolaurate, corn oil, cotton seed oil, and sunflower seed oil.

The formulations described herein may be prepared by dispersal of the particles in the selected propellant and/or co-propellant in an appropriate container, e.g., with the aid of sonication. The particles may be suspended in co-propellant and filled into a suitable container. The valve of the container is then sealed into place and the propellant introduced by pressure filling through the valve in the conventional manner. The particles may be thus suspended or dissolved in a liquified propellant, sealed in a container with a metering valve and fitted into an actuator. Such metered dose inhalers are well known in the art. The metering valve may meter 10 to 500 μL and preferably 25 to 150 μL. In certain embodiments, dispersal may be achieved using dry powder inhalers (e.g., spinhaler) for the particles (which remain as dry powders). In other embodiments, nanospheres, may be suspended in an aqueous fluid and nebulized into fine droplets to be aerosolized into the lungs.

Sonic nebulizers may be used because they minimize exposing the agent to shear, which may result in degradation of the particles. Ordinarily, an aqueous aerosol is made by formulating an aqueous solution or suspension of the particles together with conventional pharmaceutically acceptable carriers and stabilizers. The carriers and stabilizers vary with the requirements of the particular composition, but typically include non-ionic surfactants (Tweens, Pluronic®, or polyethylene glycol), innocuous proteins like serum albumin, sorbitan esters, oleic acid, lecithin, amino acids such as glycine, buffers, salts, sugars, or sugar alcohols. Aerosols generally are prepared from isotonic solutions.

Liquid dosage forms for oral administration include pharmaceutically acceptable emulsions, microemulsions, solutions, suspensions, syrups, and elixirs. In addition to the active ingredients (i.e., microparticles, nanoparticles, liposomes, micelles, polynucleotide/lipid complexes), the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension, or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. In certain embodiments, the particles are suspended in a carrier fluid comprising 1% (w/v) sodium carboxymethyl cellulose and 0.1% (v/v) Tween 80.

The injectable formulations can be sterilized, for example, by filtration through a bacteria-retaining filter, or by incorporating sterilizing agents in the form of sterile solid compositions which can be dissolved or dispersed in sterile water or other sterile injectable medium prior to use.

Compositions for rectal or vaginal administration can be suppositories which can be prepared by mixing the particles with suitable non-irritating excipients or carriers such as cocoa butter, polyethylene glycol, or a suppository wax which are solid at ambient temperature but liquid at body temperature and therefore melt in the rectum or vaginal cavity and release the particles.

Solid dosage forms for oral administration include capsules, tablets, pills, powders, and granules. In such solid dosage forms, the particles are mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets, and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Solid compositions of a similar type may also be employed as fillers in soft and hard-filled gelatin capsules using such excipients as lactose or milk sugar as well as high molecular weight polyethylene glycols and the like.

Dosage forms for topical or transdermal administration of an inventive pharmaceutical composition include ointments, pastes, creams, lotions, gels, powders, solutions, sprays, inhalants, or patches. The particles are admixed under sterile conditions with a pharmaceutically acceptable carrier and any needed preservatives or buffers as may be required. Ophthalmic formulation, ear drops, and eye drops are also contemplated as being within the scope of this invention.

The ointments, pastes, creams, and gels may contain, in addition to the particles described herein, excipients such as animal and vegetable fats, oils, waxes, paraffins, starch, tragacanth, cellulose derivatives, polyethylene glycols, silicones, bentonites, silicic acid, talc, and zinc oxide, or mixtures thereof.

Powders and sprays can contain, in addition to the particles described herein, excipients such as lactose, talc, silicic acid, aluminum hydroxide, calcium silicates, and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the microparticles or nanoparticles in a proper medium. Absorption enhancers can also be used to increase the flux of the compound across the skin. The rate can be controlled by either providing a rate controlling membrane or by dispersing the particles in a polymer matrix or gel.

The particles described herein comprising a pharmaceutical agent may be administered to a subject to be delivered in an amount sufficient to deliver to a subject a therapeutically effective amount of an incorporated pharmaceutical agent as part of a diagnostic, prophylactic, or therapeutic treatment. In general, an effective amount of a pharmaceutical agent or component refers to the amount necessary to elicit the desired biological response. The desired concentration of pharmaceutical agent in the particle will depend on numerous factors, including, but not limited to, absorption, inactivation, and excretion rates of the drug as well as the delivery rate of the compound from the subject compositions, the desired biological endpoint, the agent to be delivered, the target tissue, etc. It is to be noted that dosage values may also vary with the severity of the condition to be alleviated. It is to be further understood that for any particular subject, specific dosage regimens should be adjusted over time according to the individual need and the professional judgment of the person administering or supervising the administration of the compositions. Typically, dosing will be determined using techniques known to one skilled in the art.

The concentration and/or amount of any pharmaceutical agent to be administered to a subject may be readily determined by one of ordinary skill in the art. Known methods are also available to assay local tissue concentrations, diffusion rates from particles and local blood flow before and after administration of the therapeutic formulation.

The compositions and/or formulations described herein may have any suitable osmolarity. In some embodiments, a composition and/or formulation described herein may have an osmolarity of at least about 0 mOsm/L, at least about 5 mOsm/L, at least about 25 mOsm/L, at least about 50 mOsm/L, at least about 75 mOsm/L, at least about 100 mOsm/L, at least about 150 mOsm/L, at least about 200 mOsm/L, at least about 250 mOsm/L, or at least about 310 mOsm/L. In certain embodiments, a composition and/or formulation described herein may have an osmolarity of less than or equal to about 310 mOsm/L, less than or equal to about 250 mOsm/L, less than or equal to about 200 mOsm/L, less than or equal to about 150 mOsm/L, less than or equal to about 100 mOsm/L, less than or equal to about 75 mOsm/L, less than or equal to about 50 mOsm/L, less than or equal to about 25 mOsm/L, or less than or equal to about 5 mOsm/L. Combinations of the above-referenced ranges are also possible (e.g., an osmolarity of at least about 0 mOsm/L and less than or equal to about 50 mOsm/L). Other ranges are also possible. The osmolarity of the composition and/or formulation can be varied by changing, for example, the concentration of salts present in the solvent of the composition and/or formulation.

In one set of embodiments, a composition and/or formulation includes a core material comprises a drug, such as loteprednol etabonate, sorafenib, linifanib, MGCD-265, pazopanib, cediranib, axitinib, bromfenac calcium, diclofenac (e.g., diclofenac free acid or a divalent or trivalent metal salt thereof), ketorolac (e.g., ketorolac free acid or a divalent or trivalent metal salt thereof), or other suitable drug described herein. In some embodiments, the ratio of the weight of the drug to the weight of the one or more surface-altering agents (e.g., Pluronic® F127) present in the composition and/or formulation is greater than or equal to about 1:100, greater than or equal to about 1:30, greater than or equal to about 1:10, greater than or equal to about 1:3, greater than or equal to about 1:1, greater than or equal to about 3:1, greater than or equal to about 10:1, greater than or equal to about 30:1, or greater than or equal to about 100:1. In some embodiments, the ratio of the weight of the drug to the weight of the one or more surface-altering agents in a composition and/or formulation is less than or equal to about 100:1, less than or equal to about 30:1, less than or equal to about 10:1, less than or equal to about 3:1, less than or equal to about 1:1, less than or equal to about 1:3: less than or equal to about 1:10, less than or equal to about 1:30, or less than or equal to about 1:100. Combinations of the above-noted ranges are possible (e.g., a ratio of greater than or equal to about 1:1 and less than or equal to about 10:1). Other ranges are also possible. In certain embodiments, the ratio is about 1:1. In certain embodiments, the ratio is about 2:1. In certain embodiments, the ratio is about 10:1.

In some embodiments, a composition and/or formulation may include the above-noted ranges for the ratio of the weight of the drug to the weight of the one or more surface-altering agents during a formation process and/or a dilution process described herein. In certain embodiments, a composition and/or formulation may include the above-noted ranges for the ratio of the weight of the drug to the weight of the one or more surface-altering agents in a final product.

The pharmaceutical agent may be present in the composition and/or formulation in any suitable amount, e.g., at least about 0.01 wt %, at least about 0.1 wt %, at least about 1 wt %, at least about 5 wt %, at least about 10 wt %, at least about 20 wt % of the composition and/or formulation. In some cases, the pharmaceutical agent may be present in the composition and/or formulation at less than or equal to about 30 wt %, less than or equal to about 20 wt %, less than or equal to about 10 wt %, less than or equal to about 5 wt %, less than or equal to about 2 wt %, or less than or equal to about 1 wt %. Combinations of the above-referenced ranges are also possible (e.g., present in an amount of at least about 0.1 wt % and less than or equal to about 10 wt %). Other ranges are also possible. In certain embodiments, the pharmaceutical agent is about 0.1-2 wt % of the composition and/or formulation. In certain embodiments, the pharmaceutical agent is about 2-20 wt % of the composition and/or formulation. In certain embodiments, the pharmaceutical agent is about 0.2 wt % of the composition and/or formulation. In certain embodiments, the pharmaceutical agent is about 0.4 wt % of the composition and/or formulation. In certain embodiments, the pharmaceutical agent is about 1 wt % of the composition and/or formulation. In certain embodiments, the pharmaceutical agent is about 2 wt % of the composition and/or formulation. In certain embodiments, the pharmaceutical agent is about 5 wt % of the composition and/or formulation. In certain embodiments, the pharmaceutical agent is about 10 wt % of the composition and/or formulation.

In one set of embodiments, a composition and/or formulation includes one or more chelating agents. A chelating agent used herein refers to a chemical compound that has the ability to react with a metal ion to form a complex through one or more bonds. The one or more bonds are typically ionic or coordination bonds. The chelating agent can be an inorganic or an organic compound. A metal ion capable of catalyzing certain chemical reactions (e.g., oxidation reactions) may lose its catalytic activity when the metal ion is bound to a chelating agent to form a complex. Therefore, a chelating agent may show preservative properties when it binds to a metal ion. Any suitable chelating agent that has preservative properties can be used, such as phosphonic acids, aminocarboxylic acids, hydroxycarboxylic acids, polyamines, aminoalcohols, and polymeric chelating agents. Specific examples of chelating agents include, but are not limited to, ethylenediaminetetraacetic acid (EDTA), nitrilotriacetic acid (NTA), diethylenetriaminepentacetic acid (DTPA), N-hydroxyethylethylene diaminetriacetic acid (HEDTA), tetraborates, triethylamine diamine, and salts and derivatives thereof. In certain embodiments, the chelating agent is EDTA. In certain embodiments, the chelating agent is a salt of EDTA. In certain embodiments, the chelating agent is disodium EDTA.

A chelating agent may be present at a suitable concentration in a composition and/or formulation including the coated particles described herein. In certain embodiments, the concentration of the chelating agent is greater than or equal to about 0.0003 wt %, greater than or equal to about 0.001 wt %, greater than or equal to about 0.003 wt %, greater than or equal to about 0.01 wt %, greater than or equal to about 0.03 wt %, greater than or equal to about 0.05 wt %, greater than or equal to about 0.1 wt %, greater than or equal to about 0.3 wt %, greater than or equal to about 1 wt %, or greater than or equal to about 3 wt %. In certain embodiments, the concentration of the chelating agent is less than or equal to about 3 wt %, less than or equal to about 1 wt %, less than or equal to about 0.3 wt %, less than or equal to about 0.1 wt %, less than or equal to about 0.05 wt %, less than or equal to about 0.03 wt %, less than or equal to about 0.01 wt %, less than or equal to about 0.003 wt %, less than or equal to about 0.001 wt %, or less than or equal to about 0.0003 wt %. Combinations of the above-noted ranges are possible (e.g., a concentration of greater than or equal to about 0.01 wt % and less than or equal to about 0.3 wt %). Other ranges are also possible. In certain embodiments, the concentration of the chelating agent is about 0.001-0.1 wt %. In certain embodiments, the concentration of the chelating agent is about 0.005 wt %. In certain embodiments, the concentration of the chelating agent is about 0.01 wt %. In certain embodiments, the concentration of the chelating agent is about 0.05 wt %. In certain embodiments, the concentration of the chelating agent is about 0.1 wt %.

In some embodiments, a chelating agent may be present in a composition and/or formulation in one or more of the above-noted ranges during a formation process and/or a dilution process described herein. In certain embodiments, a chelating agent may be present in a composition and/or formulation in one or more of the above-noted ranges in a final product.

In some embodiments, an antimicrobial agent may be included in a composition and/or formulation including the coated particles described herein. An antimicrobial agent used herein refers to a bioactive agent effective in the inhibition of, prevention of, or protection against microorganisms such as bacteria, microbes, fungi, viruses, spores, yeasts, molds, and others generally associated with infections. Examples of antimicrobial agents include cephalosporins, clindamycin, chloramphenicol, carbapenems, minocyclines, rifampin, penicillins, monobactams, quinolones, tetracycline, macrolides, sulfa antibiotics, trimethoprim, fusidic acid, aminoglycosides, amphotericin B, azoles, flucytosine, cilofungin, bactericidal nitrofuran compounds, nanoparticles of metallic silver or an alloy of silver containing about 2.5 wt % copper, silver citrate, silver acetate, silver benzoate, bismuth pyrithione, zinc pyrithione, zinc percarbonates, zinc perborates, bismuth salts, parabens (e.g., methyl-, ethyl-, propyl-, butyl-, and octyl-benzoic acid esters), citric acid, benzalkonium chloride (BAC), rifamycin, and sodium percarbonate.

An antimicrobial agent may be present at a suitable concentration in a composition and/or formulation including the coated particles described herein. In certain embodiments, the concentration of the antimicrobial agent may be greater than or equal to about 0.0003 wt %, greater than or equal to about 0.001 wt %, greater than or equal to about 0.003 wt %, greater than or equal to about 0.01 wt %, greater than or equal to about 0.03 wt %, greater than or equal to about 0.1 wt %, greater than or equal to about 0.3 wt %, greater than or equal to about 1 wt %, or greater than or equal to about 3 wt %. In certain embodiments, the concentration of the antimicrobial agent may be less than or equal to about 3 wt %, less than or equal to about 1 wt %, less than or equal to about 0.3 wt %, less than or equal to about 0.1 wt %, less than or equal to about 0.03 wt %, less than or equal to about 0.01 wt %, less than or equal to about 0.003 wt %, less than or equal to about 0.001 wt %, or less than or equal to about 0.0003 wt %. Combinations of the above-noted ranges are possible (e.g., a concentration of greater than or equal to about 0.001 wt % and less than or equal to about 0.1 wt %). Other ranges are also possible. In certain embodiments, the concentration of the antimicrobial agent is about 0.001-0.05 wt %. In certain embodiments, the concentration of the antimicrobial agent is about 0.002 wt %. In certain embodiments, the concentration of the antimicrobial agent is about 0.005 wt %. In certain embodiments, the concentration of the antimicrobial agent is about 0.01 wt %. In certain embodiments, the concentration of the antimicrobial agent is about 0.02 wt %. In certain embodiments, the concentration of the antimicrobial agent is about 0.05 wt %.

In some embodiments, an antimicrobial agent may be present in a composition and/or formulation in one or more of the above-noted ranges during a formation process and/or a dilution process described herein. In certain embodiments, an antimicrobial agent may be present in a composition and/or formulation in one or more of the above-noted ranges in a final product.

In some embodiments, a tonicity agent may be included in a composition and/or formulation including the coated particles described herein. A tonicity agent used herein refers to a compound or substance that can be used to adjust the composition of a formulation to the desired osmolarity range. In certain embodiments, the desired osmolarity range is an isotonic range compatible with blood. In certain embodiments, the desired osmolarity range is hypotonic. In certain embodiments, the desired osmolarity range is hypertonic. Examples of tonicity agents include glycerin, lactose, mannitol, dextrose, sodium chloride, sodium sulfate, sorbitol, saline-sodium citrate (SSC), and the like. In certain embodiments, a combination of one or more tonicity agents may be used. In certain embodiments, the tonicity agent is glycerin. In certain embodiments, the tonicity agent is sodium chloride.

A tonicity agent (such as one described herein) may be present at a suitable concentration in a composition and/or formulation including the coated particles described herein. In certain embodiments, the concentration of the tonicity agent is greater than or equal to about 0.003 wt %, greater than or equal to about 0.01 wt %, greater than or equal to about 0.03 wt %, greater than or equal to about 0.1 wt %, greater than or equal to about 0.3 wt %, greater than or equal to about 1 wt %, greater than or equal to about 3 wt %, greater than or equal to about 10 wt %, greater than or equal to about 20 wt %, or greater than or equal to about 30 wt %. In certain embodiments, the concentration of the tonicity agent is less than or equal to about 30 wt %, less than or equal to about 10 wt %, less than or equal to about 3 wt %, less than or equal to about 1 wt %, less than or equal to about 0.3 wt %, less than or equal to about 0.1 wt %, less than or equal to about 0.03 wt %, less than or equal to about 0.01 wt %, or less than or equal to about 0.003 wt %. Combinations of the above-noted ranges are possible (e.g., a concentration of greater than or equal to about 0.1 wt % and less than or equal to about 10 wt %). Other ranges are also possible. In certain embodiments, the concentration of the tonicity agent is about 0.1-1%. In certain embodiments, the concentration of the tonicity agent is about 0.5-3%. In certain embodiments, the concentration of the tonicity agent is about 0.25 wt %. In certain embodiments, the concentration of the tonicity agent is about 0.45 wt %. In certain embodiments, the concentration of the tonicity agent is about 0.9 wt %. In certain embodiments, the concentration of the tonicity agent is about 1.2 wt %. In certain embodiments, the concentration of the tonicity agent is about 2.4 wt %. In certain embodiments, the concentration of the tonicity agent is about 5 wt %. In certain embodiments, the tonicity agent comprises glycerin in a concentration of about 0.1 wt %, about 0.2 wt %, about 0.3 wt %, about 0.4 wt %, about 0.5 wt %, about 0.6 wt %, about 0.7 wt %, about 0.8 wt %, about 0.9 wt %, or about 1.0 wt %.

In some embodiments, a tonicity agent may be present in a composition and/or formulation in one or more of the above-noted ranges during a formation process and/or a dilution process described herein. In certain embodiments, a tonicity agent may be present in a composition and/or formulation in one or more of the above-noted ranges in a final product.

In some embodiments, a composition and/or formulation described herein may have an osmolarity of at least about 0 mOsm/L, at least about 5 mOsm/L, at least about 25 mOsm/L, at least about 50 mOsm/L, at least about 75 mOsm/L, at least about 100 mOsm/L, at least about 150 mOsm/L, at least about 200 mOsm/L, at least about 250 mOsm/L, at least about 310 mOsm/L, or at least about 450 mOsm/L. In certain embodiments, a composition and/or formulation described herein may have an osmolarity of less than or equal to about 450 mOsm/L, less than or equal to about 310 mOsm/L, less than or equal to about 250 mOsm/L, less than or equal to about 200 mOsm/L, less than or equal to about 150 mOsm/L, less than or equal to about 100 mOsm/L, less than or equal to about 75 mOsm/L, less than or equal to about 50 mOsm/L, less than or equal to about 25 mOsm/L, or less than or equal to about 5 mOsm/L. Combinations of the above-referenced ranges are also possible (e.g., an osmolarity of at least about 0 mOsm/L and less than or equal to about 50 mOsm/L). Other ranges are also possible.

It is appreciated in the art that the ionic strength of a formulation comprising particles may affect the polydispersity of the particles. Polydispersity is a measure of the heterogeneity of sizes of particles in a formulation. Heterogeneity of particle sizes may be due to differences in individual particle sizes and/or to the presence of aggregation in the formulation. A formulation comprising particles is considered substantially homogeneous or "monodisperse" if the particles have essentially the same size, shape, and/or mass. A formulation comprising particles of various sizes, shapes, and/or masses is deemed heterogeneous or "polydisperse".

The ionic strength of a formulation comprising particles may also affect the colloidal stability of the particles. For example, a relatively high ionic strength of a formulation may cause the particles of the formulation to coagulate and therefore may destabilize the formulation. In some embodiments, a formulation comprising particles is stabilized by repulsive inter-particle forces. For example, the particles may be electrically or electrostatically charged. Two charged particles may repel each other, preventing collision and aggregation. When the repulsive inter-particle forces weaken or become attractive, particles may start to aggregate. For instance, when the ionic strength of the formulation is increased to a certain level, the charges (e.g., negative charges) of the particles may be neutralized by the oppositely charged ions present in the formulation (e.g., $Na^+$ ions in solution). As a result, the particles may collide and bond to each other to form aggregates (e.g., clusters or flocs) of larger sizes. The formed aggregates of particles may also differ in size, and thus the polydispersity of the formulation may also increase. For example, a formulation comprising similarly-sized particles may become a formulation comprising particles having various sizes (e.g., due to aggregation) when the ionic strength of the formulation is increased beyond a certain level. In the course of aggregation, the aggregates may grow in size and eventually settle to the bottom of the container, and the formulation is considered colloidally unstable. Once the particles in a formulation form aggregates, it is usually difficult to disrupt the aggregates into individual particles.

Certain formulations described herein show unexpected properties in that, among other things, the presence of one or more ionic tonicity agents (e.g., a salt such as NaCl) in the formulations at certain concentrations actually decreases or maintains the degree of aggregation of the particles present in the formulations, and/or does not significantly increase aggregation. See, for instance, Example 14. In certain embodiments, the polydispersity of a formulation decreases, is relatively constant, or does not change by an appreciable amount upon addition of one or more ionic tonicity agents into the formulation.

For example, in some embodiments, the polydispersity of a composition and/or formulation is relatively constant in the presence of added ionic strength and/or when the added ionic strength of the composition and/or formulation is kept relatively constant or increased (e.g., during a formation and/or dilution process). In certain embodiments, when the ionic strength increases by at least 50%, the polydispersity increases by less than or equal to about 200%, less than or equal to about 150%, less than or equal to about 100%, less than or equal to about 75%, less than or equal to about 50%, less than or equal to about 30%, less than or equal to about 20%, less than or equal to about 10%, less than or equal to about 3%, or less than or equal to about 1%. In certain embodiments, when the ionic strength is increased by at least 50%, the polydispersity increases by greater than or equal to about 1%, greater than or equal to about 3%, greater than or equal to about 10%, greater than or equal to about 30%, or greater than or equal to about 100%. Combinations of the above-noted ranges are possible (e.g., an increase in polydispersity of less than or equal to 50% and greater than or equal to 1%). Other ranges are also possible.

The ionic strength of a formulation described herein may be controlled (e.g., increased) through a variety of means, such as the addition of one or more ionic tonicity agents (e.g., a salt such as NaCl) to the formulation. In certain embodiments, the ionic strength of a formulation described herein is greater than or equal to about 0.0005 M, greater than or equal to about 0.001 M, greater than or equal to about 0.003 M, greater than or equal to about 0.01 M, greater than or equal to about 0.03 M, greater than or equal to about 0.1 M, greater than or equal to about 0.3 M, greater than or equal to about 1 M, greater than or equal to about 3 M, or greater than or equal to about 10 M. In certain embodiments, the ionic strength of a formulation described herein is less than or equal to about 10 M, less than or equal to about 3 M, less than or equal to about 1 M, less than or equal to about 0.3 M, less than or equal to about 0.1 M, less than or equal to about 0.03 M, less than or equal to about 0.01 M, less than or equal to about 0.003 M, less than or equal to about 0.001 M, or less than or equal to about 0.0005 M. Combinations of the above-noted ranges are possible (e.g., an ionic strength of greater than or equal to about 0.01 M and less than or equal to about 1 M). Other ranges are also possible. In certain embodiments, the ionic strength of a formulation described herein is about 0.1 M. In certain embodiments, the ionic strength of a formulation described herein is about 0.15 M. In certain embodiments, the ionic strength of a formulation described herein is about 0.3 M.

In certain embodiments, the polydispersity of a formulation does not change upon addition of one or more ionic tonicity agents into the formulation. In certain embodiments, the polydispersity does not significantly increase upon addition of one or more ionic tonicity agents into the formulation. In certain embodiments, the polydispersity increases to a level described herein upon addition of one or more ionic tonicity agents into the formulation.

The polydispersity of a formulation described herein may be measured by the polydispersity index (PDI). The PDI is used to describe the width of the particle size distribution and is often calculated from a cumulants analysis of the dynamic light scattering (DLS) measured intensity autocorrelation function. The calculations for these parameters are defined in the standards ISO 13321:1996 E and ISO 22412:2008. The PDI is dimensionless and, when measured by DLS, scaled such that values smaller than 0.05 indicate a highly monodisperse sample while values greater than 0.7 indicate a very broad size distribution. In certain embodiments, the PDI of a formulation and/or composition described herein is less than or equal to about 1, less than or equal to about 0.9, less than or equal to about 0.8, less than or equal to about 0.7, less than or equal to about 0.6, less than or equal to about 0.5, less than or equal to about 0.4, less than or equal to about 0.3, less than or equal to about 0.2, less than or equal to about 0.15, less than or equal to about 0.1, less than or equal to about 0.05, less than or equal to about 0.01, or less than or equal to about 0.005. In certain embodiments, the PDI of a formulation and/or composition described herein is greater than or equal to about 0.005, greater than or equal to about 0.01, greater than or equal to about 0.05, greater than or equal to about 0.1, greater than or equal to about 0.15, greater than or equal to about 0.2, greater than or equal to about 0.3, greater than or equal to about 0.4, greater than or equal to about 0.5, greater than or equal to about 0.6, greater than or equal to about 0.7, greater than or equal to about 0.8, greater than or equal to about 0.9, or greater than or equal to about 1. Combinations of the above-noted ranges are possible (e.g., a PDI of greater than or equal to about 0.1 and less than or equal to about 0.5). Other ranges are also possible. In certain embodiments, the PDI of a formulation is about 0.1. In certain embodiments, the PDI of a formulation is about 0.15. In certain embodiments, the PDI of a formulation is about 0.2.

In certain embodiments, the compositions and/or formulations described herein may be highly dispersible and do not tend to form aggregates. Even when the particles do form aggregates, the aggregates may be easily broken up into individual particles without rigorously agitating the compositions and/or formulations.

Generally, it is desired that a formulation is sterile before or upon administration to a subject. A sterile formulation is essentially free of pathogenic microorganisms, such as bacteria, microbes, fungi, viruses, spores, yeasts, molds, and others generally associated with infections. In some embodiments, compositions and/or formulations including the coated particles described herein may be subject to an aseptic process and/or other sterilization process. An aseptic process typically involves sterilizing the components of a formulation, final formulation, and/or container closure of a drug product through a process such as heat, gamma irradiation, ethylene oxide, or filtration and then combining in a sterile environment. In some cases, an aseptic process is preferred. In other embodiments, terminal sterilization is preferred.

Examples of other sterilization methods include radiation sterilization (e.g., gamma, electron, or x-ray radiation), heat sterilization, sterile filtration, and ethylene oxide sterilization. The terms "radiation" and "irradiation" are used herein interchangeably. Unlike other sterilization methods, radiation sterilization has the advantage of high penetrating ability and instantaneous effects, without the need to control temperature, pressure, vacuum, or humidity in some instances. In certain embodiments, the radiation used to sterilize the coated particles described herein is gamma radiation. Gamma radiation may be applied in an amount sufficient to kill most or substantially all of the microbes in or on the coated particles. The temperature of the coated particles described herein and the rate of radiation may be relatively constant during the entire gamma radiation period. Gamma irradiation may be performed at any suitable temperature (e.g., ambient temperature, about 40° C., between about 30 to about 50° C.). Unless otherwise indicated, measurements of gamma irradiation described herein refer to ones performed at about 40° C.

Figure 22:
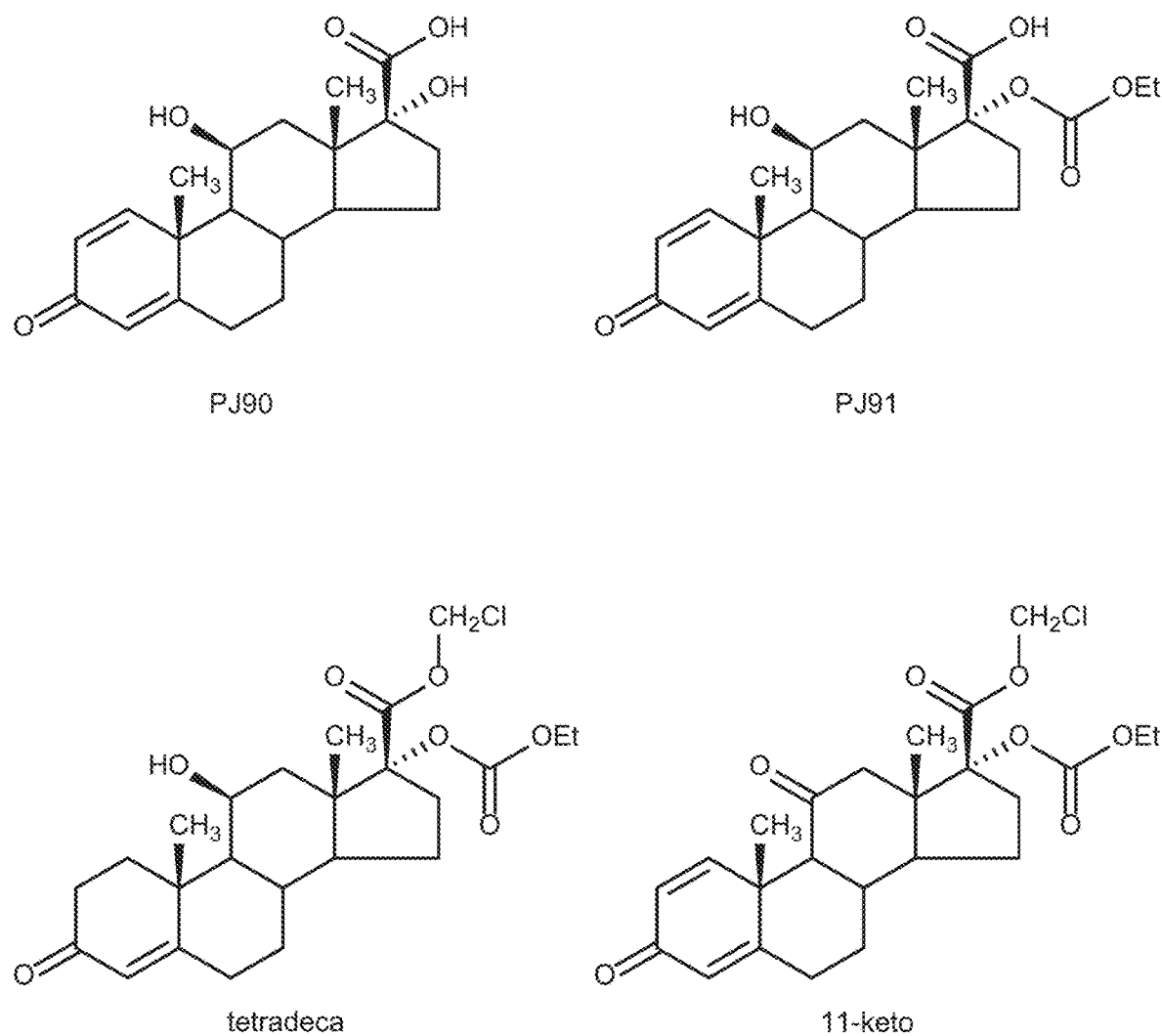
FIG. 22 shows the chemical structures of certain degradants of loteprednol etabonate.

In embodiments in which a sterilization process is used, it may be desired that the process does not: (1) significantly change the particle size of the coated particles described herein; (2) significantly change the integrity of the active ingredient (such as a drug) of the coated particles described herein; and (3) generate unacceptable concentrations of impurities during or following the process. In certain embodiments, the impurities generated during or following the process are degradants of the active ingredient of the coated particles described herein. For example, when the active ingredient is loteprednol etabonate (LE), degradants of LE may include 11β,17α-dihydroxy-3-oxoandrosta-1,4-diene-17-carboxylic acid (PJ-90), 17α-[(ethoxycarbonyl)oxy]-11β-hydroxy-3-oxoandrosta-1,4-diene-17β-carboxylic acid (PJ-91), 17α-[(ethoxycarbonyl)oxy]-11β-hydroxy-3-oxoandrosta-4-ene-17-carboxylic acid chloromethyl ester (tetradeca), and/or 17α-[(ethoxycarbonyl)oxy]-3,11-dioxoandrosta-1,4-diene-17-carboxylic acid chloromethyl ester (11-keto), as shown in FIG. 22.

In certain embodiments, a process used to sterilize a composition and/or formulation described herein results in the presence of one or more degradants in the formulation at less than or equal to about 10 wt % (relative to the weight of the undegraded drug), less than or equal to about 3 wt %, less than or equal to about 2 wt %, less than or equal to about 1.5 wt %, less than or equal to about 1 wt %, less than or equal to about 0.9 wt %, less than or equal to about 0.8 wt %, less than or equal to about 0.7 wt %, less than or equal to about 0.6 wt %, less than or equal to about 0.5 wt %, less than or equal to about 0.4 wt %, less than or equal to about 0.3 wt %, less than or equal to about 0.2 wt %, less than or equal to about 0.15 wt %, less than or equal to about 0.1 wt %, less than or equal to about 0.03 wt %, less than or equal to about 0.01 wt %, less than or equal to about 0.003 wt %, or less than or equal to about 0.001 wt %. In some embodiments, the process results in a degradant in the formulation at greater than or equal to about 0.001 wt %, greater than or equal to about 0.003 wt %, greater than or equal to about 0.01 wt %, greater than or equal to about 0.03 wt %, greater than or equal to about 0.1 wt %, greater than or equal to about 0.3 wt %, greater than or equal to about 1 wt %, greater than or equal to about 3 wt %, or greater than or equal to about 10 wt %. Combinations of the above-referenced ranges are also possible (e.g., less than or equal to about 1 wt % and greater than or equal to about 0.01 wt %). Other ranges are also possible.

In some embodiments, a composition and/or formulation subjected to gamma irradiation includes a degradant having a concentration at one or more of the above-noted ranges. In one set of embodiments, the drug is loteprednol etabonate and the degradant is PJ-90, PJ-91, tetradeca, and/or 11-keto. In certain embodiments, one or more, or each, of the degradants is present in a composition and/or formulation at one or more of the above-noted ranges (e.g., less than or equal to about 1 wt %, less than or equal to about 0.9 wt %, less than or equal to about 0.8 wt %, less than or equal to about 0.7 wt %, less than or equal to about 0.6 wt %, less than or equal to about 0.5 wt %, less than or equal to about 0.4 wt %, less than or equal to about 0.3 wt %, less than or equal to about 0.2 wt %, or less than or equal to about 0.1 wt %). Other ranges are also possible.

In some embodiments, one or more additives are included in the composition and/or formulation to help achieve a relatively low amount of one or more degradants. For example, as described in Example 13, the presence of glycerin in a loteprednol etabonate formulation resulted in relatively low amounts of the degradant tetradeca after the formulation was sterilized with gamma irradiation, compared to a loteprednol etabonate formulation that did not include glycerin.

When gamma irradiation is used in a sterilization process, the cumulative amount of the gamma radiation used may vary. In certain embodiments, the cumulative amount of the gamma radiation is greater than or equal to about 0.1 kGy, greater than or equal to about 0.3 kGy, greater than or equal to about 1 kGy, greater than or equal to about 3 kGy, greater than or equal to about 10 kGy, greater than or equal to about 30 kGy, greater than or equal to about 100 kGy, or greater than or equal to about 300 kGy. In certain embodiments, the cumulative amount of the gamma radiation is less than or equal to about 0.1 kGy, less than or equal to about 0.3 kGy, less than or equal to about 1 kGy, less than or equal to about 3 kGy, less than or equal to about 10 kGy, less than or equal to about 30 kGy, less than or equal to about 100 kGy, or less than or equal to about 300 kGy. Combinations of the above-noted ranges are possible (e.g., greater than or equal to about 1 kGy and less than or equal to about 30 kGy). Other ranges are also possible. In certain embodiments, multiple doses of radiation are utilized to achieve a desired cumulative radiation dosage.

The compositions and/or formulations described herein may have any suitable pH values. The term "pH," unless otherwise provided, refers to pH measured at ambient temperature (e.g., about 20° C., about 23° C., or about 25° C.). The compositions and/or formulations have, for example, an acidic pH, a neutral pH, or a basic pH and may depend on, for example, where the compositions and/or formulations are to be delivered in the body. In certain embodiments, the compositions and/or formulations have a physiological pH. In certain embodiments, the pH value of the compositions and/or formulations is at least about 1, at least about 2, at least about 3, at least about 4, at least about 5, at least about 6, at least about 6.2, at least about 6.4, at least about 6.6, at least about 6.8, at least about 7, at least about 7.2, at least about 7.4, at least about 7.6, at least about 7.8, at least about 8, at least about 8.2, at least about 8.4, at least about 8.6, at least about 8.8, at least about 9, at least about 10, at least about 11, or at least about 12. In certain embodiments, the pH value of the compositions and/or formulations is less than or equal to about 12, less than or equal to about 11, less than or equal to about 10, less than or equal to about 9, less than or equal to about 8.8, less than or equal to about 8.6, less than or equal to about 8.4, less than or equal to about 8.2, less than or equal to about 8, less than or equal to about 7.8, less than or equal to about 7.6, less than or equal to about 7.4, less than or equal to about 7.2, less than or equal to about 7, less than or equal to about 6.8, less than or equal to about 6.6, less than or equal to about 6.4, less than or equal to about 6.2, less than or equal to about 6, less than or equal to about 5, less than or equal to about 4, less than or equal to about 3, less than or equal to about 2, or less than or equal to about 1. Combinations of the above-noted ranges are possible (e.g., a pH value of at least about 5 and less than or equal to about 8.2). Other ranges are also possible. In certain embodiments, the pH value of the compositions and/or formulations described herein is at least about 5 and less than or equal to about 8.

Methods, Compositions and Formulations for the Treatment of Ocular Conditions

Figure 15A:
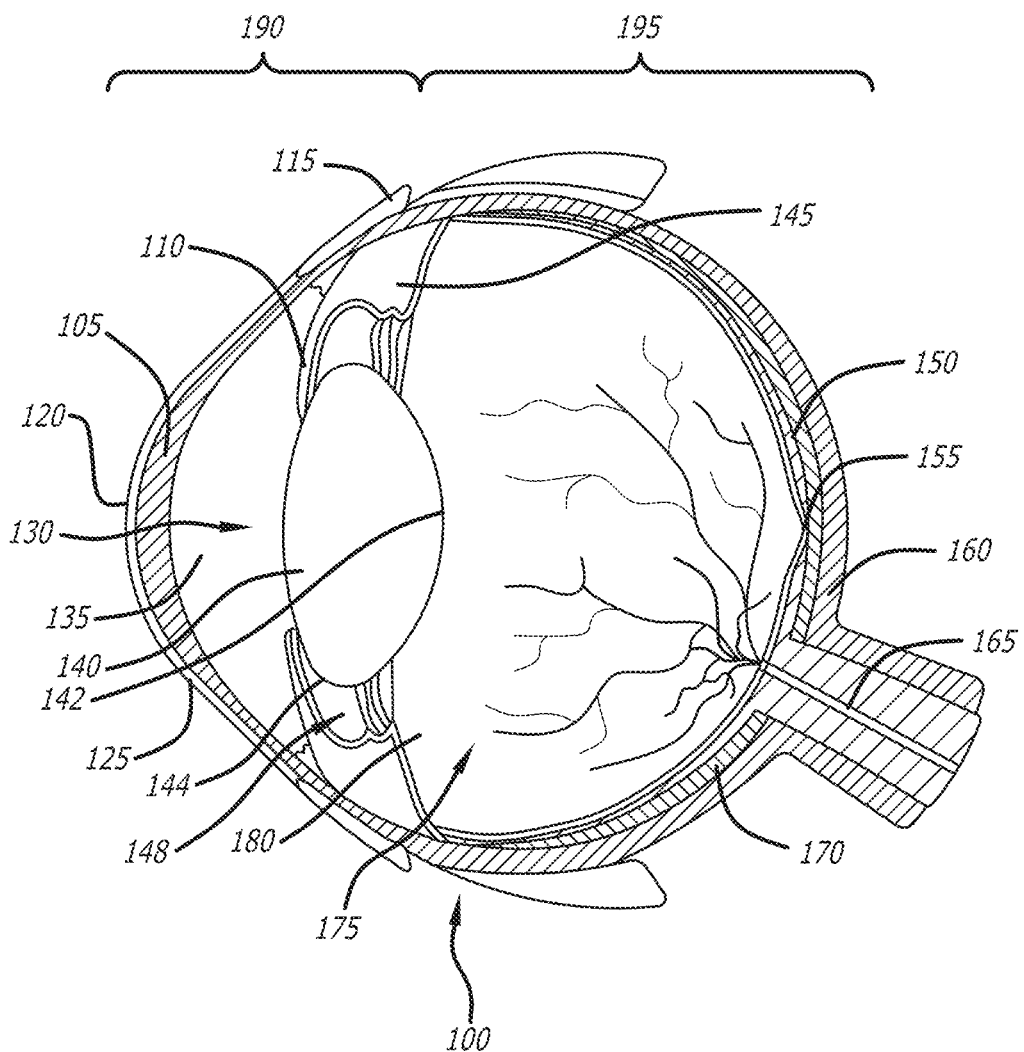
FIGS. 15A-15B are schematic drawings showing the constituent parts (FIG. 15A), including the mucus layers (FIG. 15B), of an eye, according to one set of embodiments.

The mammalian eye is a complex organ comprising an outer covering including the sclera (the tough white portion of the exterior of the eye) and the cornea (the clear outer portion covering the pupil and iris). An exemplary schematic diagram of an eye is shown in FIG. 15A. As shown illustratively in FIG. 15A in a medial cross section, from anterior to posterior, an eye 100 comprises features including, without limitation: a cornea 105, an iris 110 (a curtain-like feature that can open and close in response to ambient light), a conjunctiva 115 (composed of rare stratified columnar epithelium, covering the sclera, and lining the inside of the eyelids), a tear film 120 (which may include an oil layer, a water layer, and a mucous layer (where the mucous layer(s) has several functions such as serving as an anchor for the tear film and helping it adhere to the eye), a corneal epithelium 125 (several layers of cells covering the front of the cornea that act as a barrier to protect the cornea, resist the free flow of fluids from the tears, and prevent bacteria from entering), an anterior chamber 130 (a hollow feature filled with a watery, clear fluid called the aqueous humor 135 and bounded by the cornea in the front and the iris), a lens 140 (a transparent, biconvex structure that, along with the cornea, which helps to refract light to be focused on the *retina*), a ciliary body 145 (a circumferential tissue composed of ciliary muscles and ciliary processes), a ciliary zonule 146 (a ring of fibrous strands connecting the ciliary body with the lens), a posterior chamber 148 (a narrow space bounded by the iris in front and by the ciliary zonule and the ciliary body in back and also contains the aqueous humor, a retina 150, a *macula* 155, a sclera 160, an optic nerve 165 (also known as cranial nerve, transmitting visual information from the *retina* to the brain), a choroid 170, and a vitreous chamber 175 (filled with a viscous fluid called the vitreous humor 180). The vitreous chamber comprises approximately ⅔ of the inner volume of the eye, while the anterior chamber and posterior chamber comprise about ⅓ of the eye's inner volume.

Figure 15B:
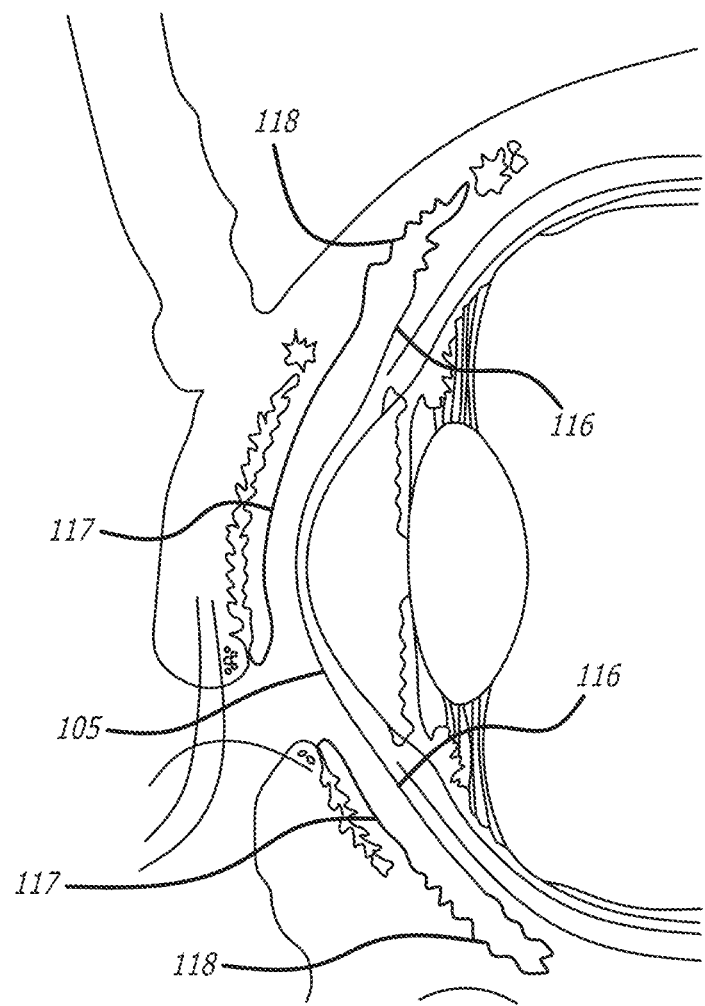

As shown illustratively in FIG. 15B, there area number of mucus layers in the eye, present at a bulbar conjunctiva 116 (covering the eyeball, over the sclera, tightly bound to the underlying sclera, and moving with the eyeball movements), a palpebral conjunctiva 117 (lining the eyelids), a fornix conjunctiva 118 (a loose and flexible tissue forming the junction between the bulbar and palpebral conjunctivas and allowing the free movement of the lids and eyeball), and the cornea. These mucus layers form a complete surface that a topically administered medication contacts. Therefore, the topically administered medication typically has to penetrate through these mucus layers in order to reach the various underneath eye tissues.

As shown illustratively in FIG. 15A, front of the eye, or anterior or anterior segment of the eye, depicted by a bracket 190, generally includes tissues or fluids that are located anterior to a posterior wall 142 of a lens capsule 144 (a clear, membrane-like structure that is elastic and keeps the lens under constant tension) or ciliary muscles. The front of the eye includes, for example, the conjunctiva, the cornea, the iris, the tear film, the anterior chamber, the posterior chamber, the lens and the lens capsule, as well as blood vessels, lymphatics and nerves which vascularize, maintain or innervate an anterior ocular region or site.

As shown illustratively FIG. 15A, the back of the eye, or posterior or posterior segment of the eye, depicted by a bracket 195, generally includes tissues or fluids that are located posterior to posterior wall of the lens capsule or ciliary muscles. The back of the eye includes, for example, the choroid, the sclera (in a position posterior to a plane through the posterior wall of the lens capsule), the vitreous humor, the vitreous chamber, the *retina*, the *macula*, the optic nerve, and the blood vessels and nerves which vascularize or innervate a posterior ocular region or site.

As described in more detail below, in some embodiments, the particles, compositions and/or formulations described herein may be used to diagnose, prevent, treat or manage diseases or conditions at the back of the eye, such as at the *retina, macula*, choroid, sclera and/or uvea.

The *retina* is a 10-layered, delicate nervous tissue membrane of the eye, continuous with the optic nerve, that receives images of external objects and transmits visual impulses through the optic nerve to the brain. The *retina* is soft and semitransparent and contains rhodopsin. It consists of the outer pigmented layer and the nine-layered *retina* proper. These nine layers, starting with the most internal, are the internal limiting membrane, the stratum opticum, the ganglion cell layer, the inner plexiform layer, the inner nuclear layer, the outer plexiform layer, the outer nuclear layer, the external limiting membrane, and the layer of rods and cones. The outer surface of the *retina* is in contact with the choroid; the inner surface with the vitreous body. The *retina* is thinner anteriorly, where it extends nearly as far as the ciliary body, and thicker posteriorly, except for a thin spot in the exact center of the posterior surface where focus is best. The photoreceptors end anteriorly in the jagged or a serrata at the ciliary body, but the membrane of the *retina* extends over the back of the ciliary processes and the iris. The *retina* becomes clouded and opaque if exposed to direct sunlight.

The *macula* or *Macula lutea* is an oval-shaped highly pigmented yellow spot near the center of the *retina* of the human eye. It has a diameter of around 5 mm and is often histologically defined as having two or more layers of ganglion cells. Near its center is the fovea, a small pit that contains the largest concentration of cone cells in the eye and is responsible for central, high resolution vision. The *macula* also contains the parafovea and perifovea. Because the *macula* is yellow in color it absorbs excess blue and ultraviolet light that enter the eye, and acts as a natural sunblock (analogous to sunglasses) for this area of the *retina*. The yellow color comes from its content of lutein and zeaxanthin, which are yellow xanthophyll carotenoids, derived from the diet. Zeaxanthin predominates at the *macula*, while lutein predominates elsewhere in the *retina*. There is some evidence that these carotenoids protect the pigmented region from some types of macular degeneration. Structures in the *macula* are specialized for high acuity vision. Within the *macula* are the fovea and foveola which contain a high density of cones (photoreceptors with high acuity).

The choroid, also known as the choroidea or choroid coat, is the vascular layer of the eye, containing connective tissue, and lying between the *retina* and the sclera. The human choroid is thickest at the far extreme rear of the eye (at 0.2 mm), while in the outlying areas it narrows to 0.1 mm. The choroid provides oxygen and nourishment to the outer layers of the *retina*. Along with the ciliary body and iris, the choroid forms the uveal tract.

The sclera refers to the tough inelastic opaque membrane covering the posterior five sixths of the eyebulb. It maintains the size and form of the bulb and attaches to muscles that move the bulb. Posteriorly it is pierced by the optic nerve and, with the transparent cornea, makes up the outermost of three tunics covering the eyebulb.

The uvea refers to the fibrous tunic beneath the sclera that includes the iris, the ciliary body, and the choroid of the eye.

Ophthalmic therapy may be performed by topically administering compositions, such as eye drops, to the exterior surface of the eye. Eye drops administration is by far the most desired route of drug delivery to the eye due to its convenience, non-invasive nature, localized action, and relative patient comfort. However, drugs administered to the eye topically as solutions (e.g., ophthalmic solutions) may be rapidly cleared from the eye's surface by drainage and lachrymation. Drugs administered to the eye topically as particles (e.g., ophthalmic suspensions) are typically trapped by the mucus layer or tear film in the eye. The eye's natural clearance mechanisms remove the species trapped in such a layer, and hence, drugs trapped in this layer are also rapidly cleared. As a result, achieving desired drug levels in the eye, especially in the posterior portions of the eye, such as the posterior sclera, the uveal tract (located in the vascular middle layer of the eye, constituting the iris, ciliary body, and choroids), the vitreous, the choroid, the *retina*, and the optic nerve head (ON H), or even the inner portions of the cornea, by topical route of administration is often difficult.

Figure 15C:
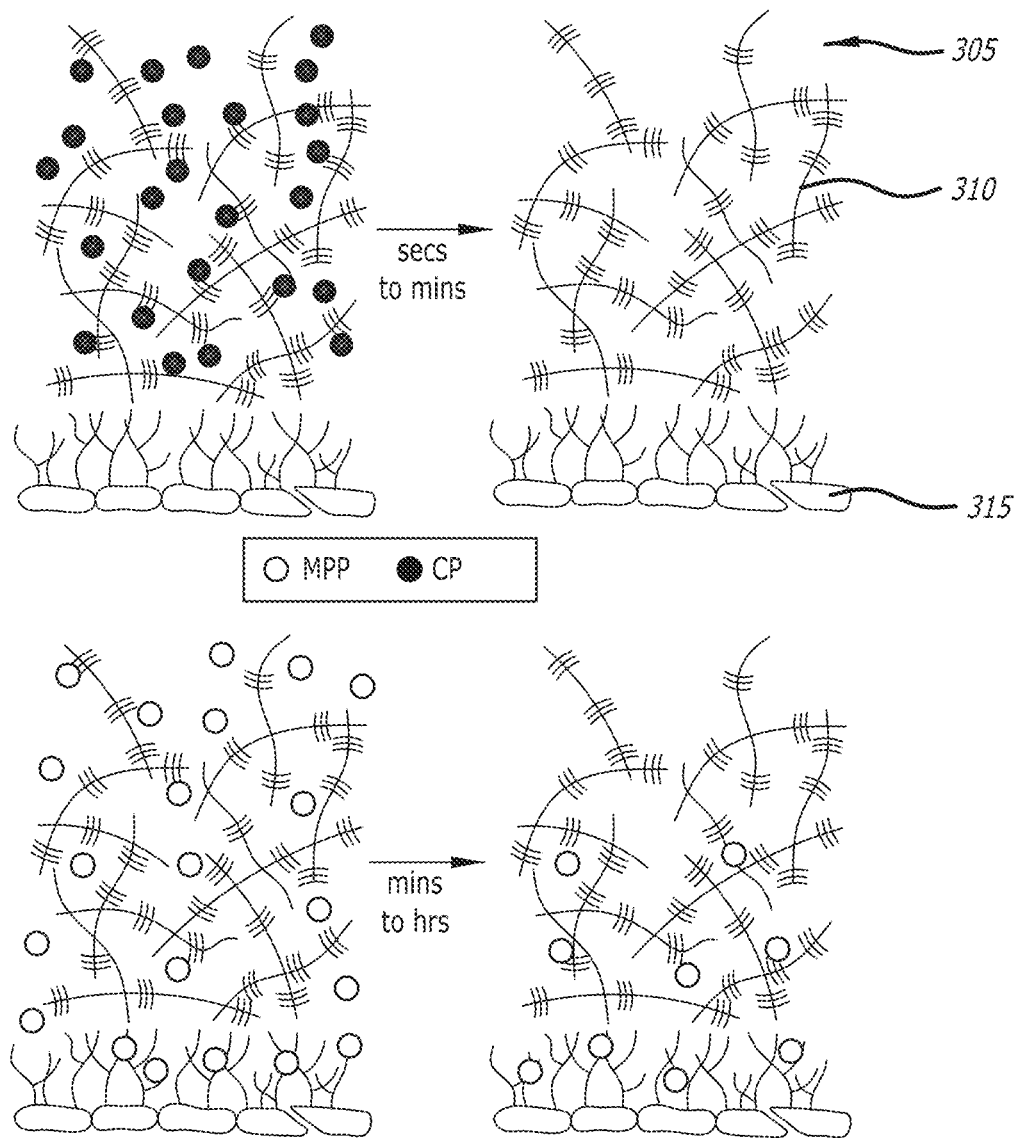
FIG. 15C is a schematic drawing showing MPP and CP in the ocular mucus layer after topical instillation, according to one set of embodiments. The MPP may readily penetrate the outer mucus layer toward the glycocalyx while CP may be immobilized in the outer layer of mucus. The clearance of the outer layer by the body's natural clearance mechanisms may be accompanied by CP removal whereas MPP are retained in the less rapidly cleared glycocalyx, leading to prolonged residence at the ocular surface.

For example, cornea and conjunctiva are naturally covered by a 3-40 μm layer of mucus. As shown illustratively in FIG. 15C, the outer layer is comprised of secreted mucins 310 (cleared rapidly by mucin turnover and blinking), whose primary role is to trap and eliminate allergens, pathogens, and debris (including drug particles) from the aqueous layer 305 of the eye. The inner layer (thickness up to 500 nm) is formed by mucins tethered to epithelium 315 (glycocalyx), which protects the underlying tissue from abrasive stress and are cleared less rapidly. Without wishing to be bound by theory, it is believed that conventional particles (CP; i.e., non-MPP) are trapped in the outer mucus layer and are readily cleared from the ocular surface. Thus, the conventional particles may be cleared before the drugs contained in the particles can be transported to other portions of the eye (e.g., by diffusion or other mechanisms). In contrast, the particles described herein (e.g., MPP) may avoid adhesion to secreted mucins, and thus may penetrate the peripheral mucus layer and reach the slow-clearing glycocalyx, thereby prolonging particle retention and sustaining drug release (FIG. 15C). This suggests that the particles described herein may deliver drugs to underlying tissues (cornea, conjunctiva, etc.) much more efficiently than CP trapped in outer mucus. Furthermore, the formulations described herein may create an even coverage of particles and/or pharmaceutical agent over the whole surface of the eye, where a conventional formulation without the coatings described herein may not spread as evenly due to their immobilization in mucus. Therefore, the formulations described herein may enhance efficacy by more uniform coverage. This in turn, along with higher concentrations, may enhance penetration through mucus.

Moreover, the use of the particles described herein for topical administration may address some of the challenges associated with other modes of delivery to the eye, such as injection methods and the use of topical gels or inserts. Injection methods may be effective for delivering drugs to the posterior portions of the eye, but such methods are invasive and may not be desirable. Other methods of delivery, such as topical gels and/or various inserts, that may help to deliver drug to the eye are less desirable from the patient comfort perspective.

There are other challenges associated with topical administration to the eye. The absorption of pharmaceutical agents into the eye is severely limited by some protective mechanisms that ensure the proper functioning of the eye, and by other concomitant factors, for example: drainage of the instilled solutions; lacrimation and tear turnover; metabolism; tear evaporation; non-productive absorption/adsorption; limited corneal area and poor corneal permeability; and binding by the lacrimal proteins. Therefore, eye drops that can achieve and maintain a high concentration of the pharmaceutical agent for an extended duration at the eye's surface would be desirable.

For example, the drainage of the administered dose via the nasolacrimal system into the nasopharynx and the gastrointestinal tract takes place when the volume of fluid in the eye exceeds the normal lacrimal volume of seven to 10 microlitres. Thus, the portion of the instilled dose (one to two drops, corresponding to 50-100 microlitres) that is not eliminated by spillage from the palpebral fissure may be drained quickly and the contact time of the dose with the absorbing surfaces (cornea and sclera) may be reduced to, for example, a maximum of two minutes.

The lacrimation and the physiological tear turnover (e.g., 16% per minute in humans in normal conditions) can be stimulated and increased by the instillation even of mildly irritating solutions. The net result is a dilution of the applied medication and an acceleration of the loss of the pharmaceutical agent.

Topically administered drug-loaded micro- and nanoparticles have the potential to prolong ocular retention and increase local bioavailability of drugs without causing the discomfort associated with other sustained release formulations such as gels, ointments and inserts. However, a major barrier for such particles is the mucus layer at ocular surfaces (e.g., at the palpebral conjunctiva, bulbar conjunctiva, and cornea; FIG. 15B). This mucus, whose natural role is to clear debris and allergens, effectively traps and rapidly removes virtually all foreign particles, including drug-loaded nanoparticles, from the ocular surface. To prolong drug retention at the ocular surface and deliver the drug closer to the underlying tissue, drug carriers/particles may need to avoid adhesion to the rapidly-clearing mucus. Therefore, drug carriers/particles that can avoid or have reduced adhesion to mucus would be desirable.

For an effective amount of a pharmaceutical agent to be delivered into an eye, high doses and/or frequent dosages may be used. However, high doses of a pharmaceutical agent increase the risk of local and systemic side effects. Moreover, frequent administration is not desirable because of its inconvenience caused to the patient, often resulting in poor compliance. Therefore, improving the mucus penetration of the pharmaceutical agent by using appropriate formulations, such as those described herein, becomes advantageous because an effective concentration of the pharmaceutical agent in the eye can be achieved without the need to use high and/or frequent doses.

Figure 16:
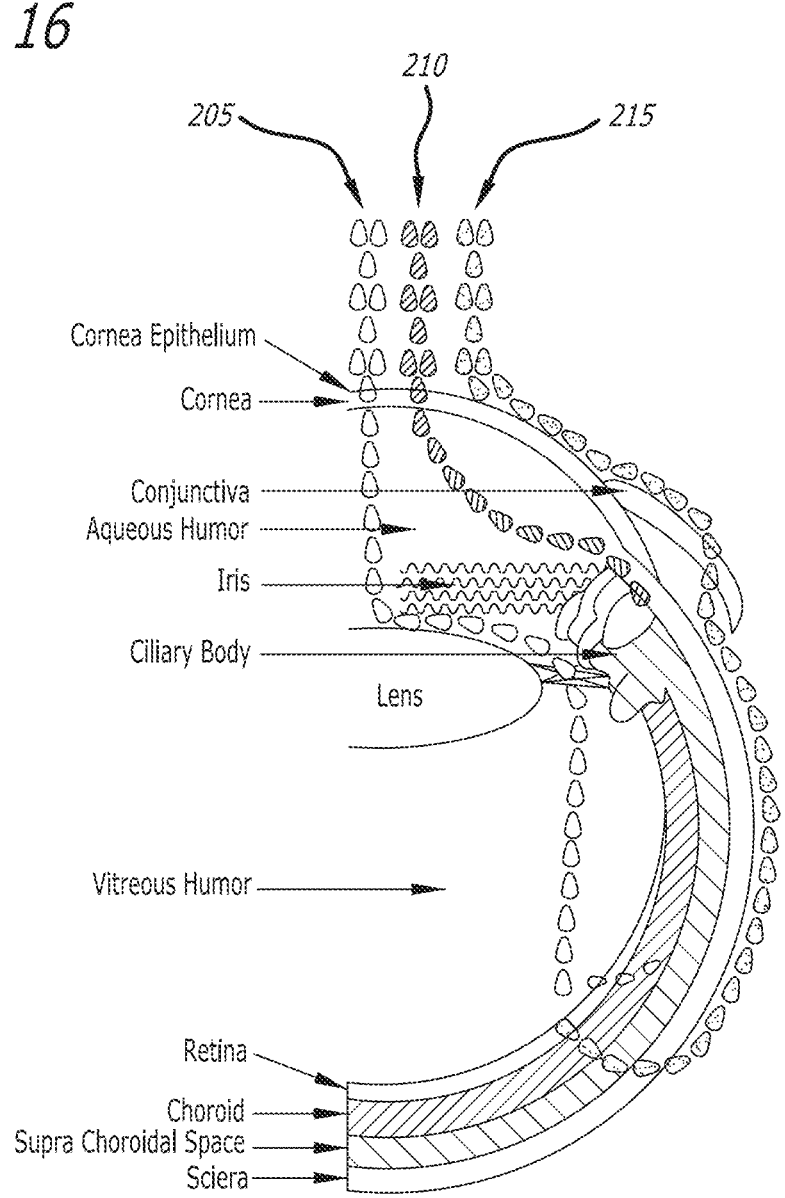
FIG. 16 is a schematic drawing illustrating three main pathways through which a topically applied drug may be transported to the back of the eye, according to one set of embodiments.

Moreover, without wishing to be bound by theory, it is believed that topically administered pharmaceutical agents may be transported to the back of the eye through one or more of three main pathways: 1) the trans-vitreous trans corneal diffusion followed by entry into vitreous and subsequent distribution to ocular tissues (FIG. 16, pathway 205); 2) the uvea-scleral route, i.e., trans-corneal diffusion, passage through the anterior chamber, and drainage via the aqueous humor to the uvea-scleral tissue towards the posterior tissues (FIG. 16, pathway 210); and 3) the periocular route, i.e., permeation through the conjunctiva to access the periocular fluid of the tenon, diffusion around the sclera followed by diffusion across the sclera, choroid, and *retina* (FIG. 16, pathway 215) (Uday B. Kompella and Henry F. Edelhauser; *Drug Product Development for the Back of the Eye*, 1$^{st}$ Ed.; Springer; 2011). Due to anatomic membrane barriers (i.e. cornea, conjunctiva and sclera) and the lachrymal drainage, it can be quite challenging to obtain therapeutic drug concentrations in the posterior parts of the eye after topical drug administration. Reaching the posterior part of the eye is even more challenging task because of the anatomical and physiological barriers associated with this part of the eye. Since those barriers cannot be altered with non-invasive methods, improvements in ophthalmic compositions and formulations that would increase the ocular bioavailability and address other challenges of topical administration to the eye would be beneficial.

The urgency to develop such formulations can be inferred from the fact that the leading causes of vision impairment and blindness are conditions linked to the posterior segment of the eye. These conditions may include, without limitation, age-related ocular degenerative diseases such as, age-related macular degeneration (AMD), proliferative vitreoretinopathy (PVR), retinal ocular condition, retinal damage, macular edema (e.g., cystoid macular edema (CME) or (diabetic macular edema (DME)), and endophthalmitis. Glaucoma, which is often thought of as a condition of the anterior chamber affecting the flow (and thus, the intraocular pressure (IOP)) of aqueous humor, also has a posterior segment component. In fact, certain forms of glaucoma are not characterized by high IOP, but mainly by retinal degeneration alone.

In certain embodiments, these and other conditions may be treated, diagnosed, prevented, or managed using the mucus-penetrating particles, compositions and formulations described herein. For example, topical administration of eye drops containing mucus-penetrating particles may be used to effectively deliver an anti-AMD drug to the back of the eye and treat AMD without subjecting the patient to an invasive procedure such as an intravitreal injection. Or, for example, topical administration of eye drops containing mucus-penetrating particles loaded with an anti-inflammatory drug (e.g. corticosteroid or NSIAD) can be used for the treatment of ocular inflammation at a reduced dosing frequency.

The particles, compositions, and methods described herein may address the challenges described herein associated with the delivery of pharmaceutical agents to the anterior and/or posterior portions of the eye at least in part due to the mucus-penetrating properties of the particles. Without wishing to be bound by theory, it is believed that the particles described herein having mucus-penetrating properties are able to avoid adhesion to, and effectively penetrate through, the mucus coating the eye. As the particles penetrate through the mucus layer of an eye tissue (e.g., palpebral conjunctiva, bulbar conjunctiva, cornea, or tear film), they avoid rapid clearance by the body's natural clearance mechanisms and achieve prolonged retention at the front of the eye. The particles may then be dissolved and/or may release a pharmaceutical agent as the particles and/or pharmaceutical agents are transported towards the back of the eye, e.g., by one of the mechanisms described in FIG. 16. By contrast, particles or drugs that are not mucus penetrating may adhere to mucus, and may be rapidly cleared by the body's natural clearance mechanisms such that insufficient amounts of the particles or drugs remain at the front of the eye shortly after administration. Thus, relatively low amounts of the particles or drugs may be available for being transported to the back of the eye (e.g., by diffusion or other mechanisms). For example, as described in more detail in Examples 3 and 8, the marketed ophthalmic suspension Lotemax®, which includes particles of the pharmaceutical agent loteprednol etabonate (LE) that do not effectively penetrate mucus, was compared with LE particles having a coating of Pluronic® F127. This drug is typically used for treating inflammation of tissues at the front of the eye. Surprisingly, when particles of the pharmaceutical agent LE were coated with a coating of Pluronic® F127, Tween 80®, or certain PVAs rendering them mucus-penetrating, not only was delivery to the ocular surface at the front of the eye (e.g., cornea, iris/ciliary body, aqueous humor) enhanced markedly as described in Examples 3 and 34, but delivery to the middle and back of the eye (e.g., *retina*, choroid, and sclera) was also enhanced as described in Example 8. These results were unexpected, in particular, because LE has not been previously shown to penetrate to the back of the eye when dosed topically as an eye drop. Moreover, conventional wisdom would suggest that LE particles coated with Pluronic® F127 would be rapidly washed away from the ocular surface by lachrymation since many have previously reported that nanosized drug particles are highly soluble in the solution in which they are contained and, thus, are expected to behave more like a conventional solution incapable of sustained release. It should be appreciated that while much of the description herein refers to treating, diagnosing, preventing, or managing tissues in the posterior portions of the eye or the back of the eye, the methods, compositions and formulations described herein are not so limited, and that other portions of the eye may benefit from the methods, compositions and formulations described herein.

In one aspect, the present invention provides a formulation or pharmaceutical composition for administration to an eye of a subject, comprising a plurality of coated particles, wherein the coated particles comprise a particle core comprising loteprednol etabonate and a coating comprising poloxamer 407 (Pluronic F127) surrounding the particle core, and pharmaceutically acceptable excipients, wherein said pharmaceutically acceptable excipients comprise glycerin, sodium chloride, disodium edetate, citric acid, and benzalkonium chloride. The formulation or pharmaceutical composition may further comprise one or more buffering agents, wherein the bufferent agent is trisodium citrate, citric acid, or a combination thereof.

In one aspect, the present invention provides a formulation or pharmaceutical composition of loteprednol etabonate, wherein the formulation or pharmaceutical composition comprises 0.25% w/v loteprednol etabonate, 0.125% w/v poloxamer 407, and 0.6% w/v glycerin. The formulation may also comprise sodium chloride, trisodium citrate dihydrate, disodium edetate dihydrate, citric acid, and benzalkonium chloride. The formulation or pharmaceutical composition may further comprise purified water. In one embodiment, the formulation or pharmaceutical composition is a suspension.

In another aspect, the present invention provides a formulation or pharmaceutical composition of loteprednol etabonate, wherein the formulation or pharmaceutical composition comprises 1.0% w/v loteprednol etabonate, 0.5% w/v poloxamer 407, and 0.6% w/v glycerin. The formulation may also comprise sodium chloride, trisodium citrate dihydrate, disodium edetate dihydrate, citric acid, and benzalkonium chloride. The formulation or pharmaceutical composition may further comprise purified water. In one embodiment, the formulation or pharmaceutical composition is a suspension.

Additionally, described in Examples 21 and 29-33 are particles and compositions including an RTK inhibitor (e.g., sorafenib, linifanib, MGCD-265, pazopanib, cediranib, and axitinib), which demonstrate enhanced exposure of the RTK inhibitor at the back of the eye.

Portions of the eye that may be targeted or treated by the methods, compositions, and formulations described herein are now described in more detail.

In some embodiments, the methods, particles, compositions, and/or formulations described herein may be used to target and/or treat the conjunctiva of a subject. The conjunctiva refers to the mucous membrane lining the inner surfaces of the eyelids and anterior part of the sclera. The palpebral conjunctiva lines the inner surface of the eyelids and is thick, opaque, and highly vascular. The bulbar conjunctiva is loosely connected, thin, and transparent, covering the sclera or the anterior third of the eye.

In certain embodiments, the methods, particles, compositions, and/or formulations described herein may be used to target and/or treat the all or portions of the cornea of a subject. The cornea refers to the convex, transparent anterior part of the eye, comprising one sixth of the outermost tunic of the eye bulb. It allows light to pass through it to the lens. The cornea is a fibrous structure with five layers: the anterior corneal epithelium, continuous with that of the conjunctiva; the anterior limiting layer (Bowman's membrane); the substantial propria; the posterior limiting layer (Descemet's membrane); and the endothelium of the anterior chamber (keratoderma). It is dense, uniform in thickness, and non-vascular, and it projects like a dome beyond the sclera, which forms the other five sixths of the eye's outermost tunic. The degree of corneal curvature varies among different individuals and in the same person at different ages; the curvature is more pronounced in youth than in advanced age.

In some embodiments, the methods, particles, compositions, and/or formulations described herein may be used to target and/or treat portions within the posterior portion or back of the eye, such as the *retina*, the choroid, and/or the sclera, of a subject. Starting from the inside of the eye and going towards the back, the three main layers at the back of the eye are the *retina*, which contains the nerves; the choroid, which contains the blood supply; and the sclera, which is the white of the eye.

In some embodiments, the methods, particles, compositions, and/or formulations described herein may be used to treat, diagnose, prevent, or manage an ocular condition, i.e., a disease, ailment, or condition that affects or involves the eye or one or more of the parts or regions of the eye. Broadly speaking, the eye includes the eyeball and the tissues and fluids which constitute the eyeball, the periocular muscles (such as the oblique and rectus muscles) and the portion of the optic nerve which is within or adjacent to the eyeball.

In some embodiments, the methods, particles, compositions, and/or formulations described herein may be used to treat, diagnose, prevent, or manage an ocular condition at the front of the eye of a subject. In general, a front of the eye (or anterior or anterior segment) ocular condition is a disease, ailment or condition which affects or involves a tissue or a fluid at the front of the eye, as described herein. A front of the eye ocular condition includes a disease, ailment or condition, such as for example, post-surgical inflammation; uveitis; infections; aphakia; pseudophakia; astigmatism; blepharospasm; blepharitis; cataract; conjunctival diseases; conjunctivitis; corneal diseases; corneal ulcer; dry eye syndromes; eyelid diseases; lacrimal apparatus diseases; lacrimal duct obstruction; myopia; presbyopia; pupil disorders; corneal neovascularization; refractive disorders and strabismus. Glaucoma can be considered to be a front of the eye ocular condition in some embodiments because a clinical goal of glaucoma treatment can be to reduce a hypertension of aqueous fluid in the anterior chamber of the eye (i.e., reduce intraocular pressure).

In some embodiments, the methods, particles, compositions, and/or formulations described herein may be used to treat, diagnose, prevent, or manage an ocular condition at the back of the eye of a subject. In general, a back of the eye or posterior ocular condition is a disease, ailment, or condition which primarily affects or involves a tissue or fluid at the back of the eye, as described herein. A posterior ocular condition can include a disease, ailment, or condition, such as intraocular melanoma; acute macular neuroretinopathy; Behcet's disease; choroidal neovascularization; uveitis; diabetic uveitis; histoplasmosis; infections, such as fungal or viral-caused infections; macular degeneration, such as acute macular degeneration, nonexudative age related macular degeneration and exudative age related macular degeneration; edema, such as macular edema (e.g., cystoid macular edema (CME) and diabetic macular edema (DME)); multifocal choroiditis; ocular trauma which affects a posterior ocular site or location; ocular tumors; retinal disorders, such as central retinal vein occlusion, diabetic retinopathy (including proliferative diabetic retinopathy), proliferative vitreoretinopathy (PVR), retinal arterial occlusive disease, retinal detachment, uveitic retinal disease; sympathetic opthalmia; Vogt Koyanagi-Harada (VKH) syndrome; uveal diffusion; a posterior ocular condition caused by or influenced by an ocular laser treatment; posterior ocular conditions caused by or influenced by a photodynamic therapy, photocoagulation, radiation retinopathy, epiretinal membrane disorders, branch retinal vein occlusion, anterior ischemic optic neuropathy, non-retinopathy diabetic retinal dysfunction, retinitis pigmentosa, retinoblastoma, and glaucoma. Glaucoma can be considered a posterior ocular condition in some embodiments because the therapeutic goal is to prevent the loss of or reduce the occurrence of loss of vision due to damage to or loss of retinal cells or optic nerve cells (i.e., neuroprotection).

In some embodiments, the methods, particles, compositions, and/or formulations described herein may be used to treat, diagnose, prevent, or manage dry eye in a subject. In one embodiment, the methods, particles, compositions, and/or formulations comprising loteprednol etabonate described herein may be used to treat, diagnose, prevent, or manage dry eye in a subject. Dry eye is a condition in which there are insufficient tears to lubricate and nourish the eye. Tears are necessary for maintaining the health of the front surface of the eye and for providing clear vision. People with dry eyes either do not produce enough tears or have a poor quality of tears. Dry eye is a common and often chronic problem, particularly in older adults.

With each blink of the eyelids, tears are spread across the front surface of the eye, known as the cornea. Tears provide lubrication, reduce the risk of eye infection, wash away foreign matter in the eye, and keep the surface of the eyes smooth and clear. Excess tears in the eyes flow into small drainage ducts, in the inner corners of the eyelids, which drain in the back of the nose. Tears are produced by several glands (e.g., lacrimal gland) in and around the eyelids. Tear production tends to diminish with age, with various medical conditions, or as a side effect of certain medicines. Environmental conditions such as wind and dry climates can also affect tear volume by increasing tear evaporation. When the normal amount of tear production decreases or tears evaporate too quickly from the eyes, symptoms of dry eye can develop.

The most common form of dry eyes is due to an inadequate amount of the water layer of tears. This condition, called keratoconjunctivitis sicca (KCS), is also referred to as dry eye syndrome.

Treatments for dry eyes aim to restore or maintain the normal amount of tears in the eye to minimize dryness and related discomfort and to maintain eye health. These goals may be achieved through different pathways, such as increasing the lacrimal glands' tear production, regulating conjunctiva's mucin production, and suppressing inflammation of eye tissues. For example, Restasis® (0.05% cyclosporine) is an immunosuppressant that lowers the activity of T cells in the conjunctiva and lacrimal gland. Challenges in developing new treatment of dry eyes include identifying underlying diseases and causes, length of time to see results (3-6 months), and the fact that treatment may only work in 10-15% of dry eye population. Drug delivery may also be a challenge. Although the eye tissues targeted in the treatment of dry eyes are at the front of the eye, a fraction of a topically administered pharmaceutical agent may still be immobilized by the mucus in the conjunctiva, tear film, and cornea). In some embodiments, the particles, formulations, and compositions described herein may address these issues by facilitating effective delivery of pharmaceutical agents to the appropriate tissues, promoting more even and/or widespread coverage of the particles across the eye surface, and/or avoiding or minimizing clearance of the particle/pharmaceutical agent.

In some embodiments, the methods, particles, compositions, and/or formulations described herein may be used to treat, diagnose, prevent, or manage inflammation in the eye of a subject. Inflammation is associated with a variety of ocular disorders. Inflammation may also result from a number of ophthalmic surgical procedures, including cataract surgery. Corticosteroids are often used as ocular anti-inflammatory agents, however, they typically require frequent dosing.

To prevent post-surgical inflammation, steroids or NSAIDs (non-steroidal anti-inflammatory drugs) may be given prophylactically. Current treatment of post-surgical inflammation includes steroids (e.g., Lotemax® (0.5% loteprednol etabonate), Durezol® (0.05% difluprednate), Pred Mild® (0.12% prednisolone acetate), and Omnipred® (1% prednisolone acetate)) and NSAIDs (e.g., Bromday® (0.09% bromfenac), Nevanac® (0.1% nepafenac), Acular LS® (0.4% ketorolac tromethamine), Acuvail® (0.45% ketorolac tromethamine)), Toradol® (ketorolac tromethamine), Sprix® (ketorolac tromethamine), Voltaren® (0.1% diclofenac), Aclonac® (diclofenac), and Cataflam® (diclofenac). One of the greatest challenges for the treatment of post-surgical inflammation is compliance inasmuch as, due to the rapid clearance of eye drops from the surface of the eye, most currently marketed steroid or NSAID eye drops must be administered multiple times a day to achieve and sustain therapeutic effect. In some embodiments, the particles, compositions, and/or formulations described herein may include one or more of these steroidal pharmaceutical agents. For example, as described in more detail in the Examples, particles of Loteprednol Etabonate, the ingredient of Lotemax®, that included certain polymeric coatings described herein produced markedly higher drug levels in various ocular tissues in New Zealand white rabbits, compared to an equivalent dose of the commercial formulation that did not include a suitable polymeric coating. This data suggests that the coated particles may be administered fewer times a day to achieve and sustain therapeutic effect compared to commercial formulations.

A number of topical NSAID formulations (e.g., Bromday® (0.09% bromfenac)) are available in the market. Table 17 provides a list of these formulations, their respective trade names, active pharmaceutical ingredients (APIs), dosing concentration, and dosing frequency. The majority of these formulations (i.e., Bromday®, Flurbiprofen®, Acular®, and Voltaren®) are supplied as solutions in which the active ingredient is completely dissolved.

It has been found that bromfenac is susceptible to degradation in solution via lactam formation, especially below neutral pH (Table 18). Data in Table 18 show that more degradant of bromfenac was observed when the pH of an aqueous solution containing bromfenac sodium was lowered (e.g., from pH 7.8 to 5.8).

To enhance topical delivery of bromfenac, which in turn may translate into a lower dose for improved safety or enhanced therapy for conditions in the middle and back of the eye, it may be desirable to formulate bromfenac as a suspension of MPPs comprising a bromfenac core. Additionally, formulating bromfenac as a suspension of MPPs may allow for an increase in the concentration of bromfenac in the formulation without substantially increasing the concentration of degradants (e.g., compared to an aqueous solution of bromfenac). However, it is difficult to formulate bromfenac sodium as a solid or crystalline particle due to its relatively high water solubility. Bromfenac free acid (bromfenac FA) may also be difficult to develop into a shelf-stable MPP suspension formulation in some embodiments, e.g., due to significant degradation of bromfenac FA in the presence of aqueous Pluronic® F127 (Table 19).

TABLE 17

Currently available products featuring topically-delivered NSAIDs.

| Trade name | Manufacturer | API | Concentration of API (% w/v) | Treatment frequency (drops per day) | Dosage form |
|---|---|---|---|---|---|
| Bromday ® | Bausch & Lomb | bromfenac sodium | 0.09 | 1 | solution |
| Ocufen ® | Allergan | flurbiprofen | 0.03 | 4 | solution |
| Acular ®, Acular LS ®, Acuvail ® | Allergan | ketorolac tromethamine | 0.4-0.5 | 2-4 | solution |
| Voltaren ® | Novartis | diclofenac sodium | 0.1 | 4 | solution |
| Nevanac ® | Alcon | nepafenac | 0.1 | 3 | suspension |

The products listed are prescribed for administration post-surgery, with the exception of Ocufen ® which is administered within 2 hr prior to surgery.

TABLE 18

Chemical degradation of
bromfenac sodium at various pH.*

| pH | % peak area |
| --- | --- |
| 5.8 | 3.16 |
| 6.8 | 0.05 |
| 7.8 | 0 |

*The chemical stability of bromfenac sodium was determined as % chromatographic peak area for the lactam degradant of bromfenac after 0.02% aqueous solutions of bromfenac sodium were stored for 5 days at room temperature.

TABLE 19

Chemical degradation of bromfenac free acid in unbuffered aqueous suspensions in the presence of Pluronic ® F127.*

| Concentration of Pluronic ® F127 (% w/v) | Concentration of Bromfenac FA (% w/v) | % peak area |
| --- | --- | --- |
| 0.50 | 0.5 | 12.0 (day 14) |
| 5 | 5 | 10.2 (day 5) |

*The chemical stability of bromfenac free acid was determined as % chromatographic peak area for the lactam degradant of bromfenac after an aqueous suspension of bromfenac free acid was stored for 5 or 14 days at room temperature.

As described herein, it is desirable to develop a composition comprising an NSAID (e.g., bromfenac, diclofenac, ketorolac, or a salt thereof) that is stable at a suitable pH for topical administration to the eye. In some embodiments, such compositions include solid or crystalline particles of bromfenac, diclofenac, ketorolac, or a salt thereof, that can effectively penetrate mucus. The particles may include one or more surface-altering agents described herein (e.g., a poloxamer, a polysorbate (e.g., Tween 80®), PVA) that can reduce mucoadhesion of the particles.

In some embodiments, the particles, compositions, and/or formulations described herein include a divalent metal salt of bromfenac, such as a divalent metal salt of bromfenac. For instance, the divalent metal salt of bromfenac may be relatively water insoluble and may include, for example, bromfenac beryllium, bromfenac magnesium, bromfenac calcium, bromfenac strontium, bromfenac barium, bromfenac zinc, or bromfenac copper(II). In some embodiments, the particles including a divalent metal salt of bromfenac may have an aqueous solubility in a range described herein (e.g., at least about 0.001 mg/mL and less than or equal to about 1 mg/mL).

In certain embodiments, the particles, compositions, and/or formulations described herein include diclofenac FA. In certain embodiments, the particles, compositions, and/or formulations described herein include a metal salt of diclofenac, such as an alkaline earth metal salt of diclofenac. In certain embodiments, the particles, compositions, and/or formulations described herein include ketorolac FA. In certain embodiments, the particles, compositions, and/or formulations described herein include a metal salt of ketorolac, such as an alkaline earth metal salt of ketorolac. Trivalent metal salts of such compounds are also possible.

The divalent metal salts of bromfenac described herein (e.g., bromfenac calcium) are less water soluble and more hydrophobic than bromfenac sodium and/or other monovalent salts of bromfenac. For example, the aqueous solubility of bromfenac calcium at 25° C. is about 0.15 mg/mL. Compared to the more water soluble and hydrophilic bromfenac sodium, the divalent metal salts of bromfenac may be more suitable to be processed into MPPs using the methods described herein (e.g., milling and/or precipitation). The divalent metal salts of bromfenac are present in the MPPs mostly in solid (e.g., crystalline) form and, therefore, may be less prone to degradation and more chemically stable. Additionally, relatively high concentrations of the divalent metal salts of bromfenac in a composition and/or formulation including MPPs of the divalent metal salts of bromfenac are not limited by the aqueous solubility and/or the formation of degradants of the divalent metal salts of bromfenac. Therefore, the particles, compositions, and/or formulations described herein comprising a divalent metal salt of bromfenac may allow for higher concentrations of bromfenac in the compositions or formulations compared to the free acid form which is dissolved in solution. In some embodiments, such particles, compositions, and/or formulations allow for higher concentrations of bromfenac in ocular tissues after administration to the eye.

For similar reasons discussed herein with respect to bromfenac calcium and the free acid form of bromfenac, the less water soluble and hydrophilic diclofenac FA and a metal salt thereof (e.g., divalent or trivalent metal salts) may be more suitable for being processed into particles, compositions, and/or formulations that are mucus penetrating compared to diclofenac sodium and/or other monovalent salts of diclofenac. Similarly, ketorolac FA and a metal salt thereof (e.g., divalent or trivalent metal salts), which are less water soluble and hydrophilic than ketorolac tromethamine and/or other monovalent salts of ketorolac, may be formed into mucus penetrating particles, compositions, and/or formulations. Moreover, since diclofenac FA or ketorolac FA, or a divalent or trivalent metal salt thereof, may not be limited by their aqueous solubilities, these compounds may be present in a higher concentration in the particles, compositions, and/or formulations described herein compared to aqueous formulations of diclofenac sodium or ketorolac tromethamine, respectively.

In certain embodiments, a pharmaceutical agent described herein (e.g., an NSAID such as a divalent metal salt of bromfenac (e.g., bromfenac calcium), diclofenac FA, a metal salt of diclofenac (e.g., divalent or trivalent metal salts), ketorolac FA, or a metal salt of ketorolac (e.g., divalent or trivalent metal salts); a receptor tyrosine kinase (RTK) inhibitor, such as sorafenib, linifanib, MGCD-265, pazopanib, cediranib, and axitinib; or a corticosteroid, such as LE) is present in a composition and/or formulation described herein at at least about 0.001%, at least about 0.003%, at least about 0.01%, at least about 0.02%, at least about 0.05%, at least about 0.1%, at least about 0.2%, at least about 0.3%, at least about 0.4%, at least about 0.5%, at least about 0.6%, at least about 0.8%, at least about 1%, at least about 1.5%, at least about 2%, at least about 3%, at least about 4%, at least about 5%, at least about 6%, at least about 8%, at least about 10%, at least about 20%, at least about 30%, at least about 40%, or at least about 50%, w/v. In certain embodiments, the pharmaceutical agent is present in a composition and/or formulation described herein at less than or equal to about 50%, less than or equal to about 40%, less than or equal to about 30%, less than or equal to about 20%, less than or equal to about 10%, less than or equal to about 8%, less than or equal to about 6%, less than or equal to about 5%, less than or equal to about 4%, less than or equal to about 3%, less than or equal to about 2%, less than or equal to about 1.5%, less than or equal to about 1%, less than or equal to about 0.8%, less than or equal to about 0.6%, less than or equal to about 0.5%, less than or equal to about 0.4%, less than or equal to about 0.3%, less than or equal to about 0.2%, less than or equal to about 0.1% less than or equal to about 0.05%, less than or equal to about 0.02%, less than or equal to about 0.01%, less than or equal to about 0.003%, or less than or equal to about 0.001%, w/v. Combinations of the above-referenced ranges are also possible (e.g., at least about 0.5% and less than or equal to 5% w/v). Other ranges are also possible.

In certain embodiments, a divalent metal salt of bromfenac (e.g., bromfenac calcium) is present in a composition and/or formulation described herein at about 0.09% w/v or greater. In certain embodiments, the divalent metal salt of bromfenac (e.g., bromfenac calcium) is present in a composition and/or formulation described herein at about 0.5% w/v or greater. In certain embodiments, diclofenac FA or ketorolac FA, or a metal salt thereof (e.g., divalent or trivalent metal salt), is present in a composition and/or formulation described herein at about 0.5% w/v or greater.

In some embodiments, the compositions and/or formulations including MPPs of divalent metal salts of bromfenac or other pharmaceutical agents described herein may have a pH that is not irritating to the eye, such as a mildly basic pH (e.g., pH 8), physiological pH (i.e., about pH 7.4), a substantially neutral pH (e.g., about pH 7), a mildly acidic pH (e.g., about pH 5-6), or ranges thereof (e.g., about pH 5-7, or 6-7). At these pHs, the MPPs, compositions, and/or formulations may be chemically and colloidally stable and may achieve therapeutically and/or prophylactically effective drug levels for a longer duration in ocular tissues compared to certain marketed formulations. The benefits described herein may further lead to a lower required dose for improved safety of this treatment and/or enhanced topical delivery for treating conditions in the middle and back of the eye compared to certain marketed formulations.

In some embodiments, the methods, particles, compositions, and/or formulations described herein may be used to treat, diagnose, prevent, or manage blepharitis in a subject. Blepharitis is a common eye disorder affecting people of all ages, and is an inflammation of the eyelid that results in itchy, red, irritated eyelids and dandruff-like scales on the eyelashes. The disorder can be caused by bacteria or a skin condition (e.g., dandruff or acne rosacea). Blepharitis symptoms include dry eyes, a gritty sensation or burning in the eyes, itching, swollen and red eyelids, excessive tearing, and crusty eyelids. In more severe cases, blepharitis can cause blurry vision and inflammation of other eye tissue, particularly the cornea.

In one embodiment, the methods, particles, compositions, and/or formulations comprising loteprednol etabonate described herein may be used to treat, diagnose, prevent, or manage blepharitis in a subject.

In some embodiments, the methods, particles, compositions, and/or formulations described herein may be used to treat, diagnose, prevent, or manage glaucoma in a subject. Glaucoma is an eye disease in which the optic nerve is damaged in a characteristic pattern. This can permanently damage vision in the affected eye and lead to blindness if left untreated. It is normally associated with increased fluid pressure in the eye (aqueous humour). The term ocular hypertension is used for people with consistently raised IOP without any associated optic nerve damage. Conversely, the term normal tension or low tension glaucoma is used for those with optic nerve damage and associated visual field loss but normal or low IOP.

The nerve damage involves loss of retinal ganglion cells in a characteristic pattern. There are many different subtypes of glaucoma, but they can all be considered to be a type of optic neuropathy. Raised intraocular pressure (e.g., above 21 mmHg or 2.8 kPa) is the most important and only modifiable risk factor for glaucoma. However, some may have high eye pressure for years and never develop damage, while others can develop nerve damage at a relatively low pressure. Untreated glaucoma can lead to permanent damage of the optic nerve and resultant visual field loss, which over time can progress to blindness.

Current treatment of glaucoma may include the use of prostaglandin analogs which increase aqueous humor outflow (e.g., Xalatan® (0.005% latanoprost), Lumigan® (0.03% and 0.01% bimatoprost), and Travatan Z® (0.004% travoprost)); beta-blockers which decreases aqueous humor production (e.g., Timoptic® (0.5% and 0.25% timolol)); alpha agonists which both decrease aqueous humor production and increase outflow (e.g., Alphagan® (0.1% and 0.15% brimonidine tartrate)); carbonic anhydrase inhibitors which decreases aqueous humor production (e.g., Trusopt® (2% dorzolamide)); and cholinergics (miotic) which increase conventional outflow (e.g., Isopto® (1%, 2%, and 4% pilocarpine)). In some embodiments, the particles, formulations, and compositions described herein may address the issues described above by facilitating effective delivery of pharmaceutical agents to the appropriate tissues and avoiding or minimizing clearance of the pharmaceutical agent. For example, the particles, compositions, and/or formulations described herein may include one or more of these or other prostaglandin analogs, beta-blockers, alpha agonists, carbonic anhydrase inhibitors and cholinergics, and may include a coating described herein to facilitate penetration of the particle through mucus and allow effective delivery of the pharmaceutical agent.

In some embodiments, the methods, particles, compositions, and/or formulations described herein may be used to treat, diagnose, prevent, or manage uveitis in a subject. Uveitis is inflammation of the uvea, the vascular layer of the eye sandwiched between the *retina* and the white of the eye (sclera). The uvea extends toward the front of the eye and consists of the iris, choroid layer and ciliary body. The most common type of uveitis is an inflammation of the iris called iritis (anterior uveitis). Uveitis may also occur at the posterior segment of the eye (e.g., at the choroid). Inflammation of the uvea can be recurring and can cause serious problems such as blindness if left untreated (accounts for 10% of blindness globally). Early diagnosis and treatment are important to prevent the complications of uveitis.

Current treatment of uveitis includes eye drops (e.g., TobraDex® (0.1% dexamethasone/0.3% tobramycin) and Zylet® (0.5% loteprednol etabonate/0.3% tobramycin)); intravitreal injections of "gel suspension" in sodium hyaluronate (e.g., Trivaris® (8% triamcinolone acetonide)); intravitreal injection of "aqueous suspension" in carboxymethylcellulose and Tween 80 (e.g., Triesence® (4% triamcinolone acetonide)); and implants (e.g., Retisert® (0.59 mg fluocinolone acetonide) and Ozurdex® (0.7 mg dexamethasone)). Oral steroids and NSAIDS are also employed. Challenges in developing new treatment of uveitis include non-invasive delivery for posterior uveitis, clearance due to high vascularization of the uvea, side effects of long term steroid use such as increased IOP and cataracts. In some embodiments, the particles, compositions, and/or formulations described herein may include one or more of these drugs, which may be administered topically to a subject.

In some embodiments, the methods, particles, compositions, and/or formulations described herein may be used to treat, diagnose, prevent, or manage age-related macular degeneration (AMD) in a subject. AMD is a medical condition which usually affects older adults and results in a loss of vision in the center of the visual field (the *macula*) because of damage to the *retina*. It occurs in "dry" and "wet"

forms. It is a major cause of blindness and visual impairment in older adults (>50 years). Macular degeneration can make it difficult or impossible to read or recognize faces, although enough peripheral vision remains to allow other activities of daily life. The *macula* is the central area of the *retina*, which provides the most detailed central vision. In the dry (non-exudative) form, cellular debris called drusen accumulate between the *retina* and the choroid, and the *retina* can become detached. In the wet (exudative) form, which is more severe, blood vessels grow up from the choroid behind the *retina*, and the *retina* can also become detached. It can be treated with laser coagulation, and with medication that stops and sometimes reverses the growth of blood vessels. Although some macular dystrophies affecting younger individuals are sometimes referred to as macular degeneration, the term generally refers to age-related macular degeneration (AMD or ARMD).

Age-related macular degeneration begins with characteristic yellow deposits (drusen) in the *macula*, between the retinal pigment epithelium and the underlying choroid. Most people with these early changes (referred to as age-related maculopathy) have good vision. People with drusen can go on to develop advanced AMD. The risk is considerably higher when the drusen are large and numerous and associated with disturbance in the pigmented cell layer under the *macula*. Recent research suggests that large and soft drusen are related to elevated cholesterol deposits and may respond to cholesterol-lowering agents.

Potential treatment of AMD includes used of pharmaceutical agents such as verteporfin (e.g., Chlorin®, Visudyne®), thalidomide (e.g., Ambiodry®, Synovir®, Thalomid®), talaporfin sodium (e.g., Aptocine®, Laserphyrin®, Litx®), ranibizumab (e.g., Lucentis®), pegaptanib octasodium (e.g., Macugen®, Macuverse®), isopropyl unoprostone (e.g., Ocuseva®, Rescula®), interferon beta (e.g., Feron®), fluocinolone acetonide (e.g., Envision TD®, Retisert®), everolimus (e.g., Afinitor®, Certican®, Votubia®, Zortress®), eculizumab (e.g., Solaris®, Soliris®), dexamethasone (e.g., Osurdex®, Ozurdex®, Posurdex®, Surodex®), canakinumab (e.g., Ilaris®), bromfenac (Bromday®), ophthalmic (e.g., Bronac®, Bronuck®, Xibrom®, Yellox®), brimonidine (e.g., Alphagan®, Bromoxidine®, Enidin®), anecortave acetate (e.g., Retaane®, Edex®, Prostavasin®, Rigidur®, Vasoprost®, Viridal®), aflibercept ophthalmic solution (e.g., Eyelea®, Eylea®, VEGF-Trap-Eye®), ocriplasmin (e.g., Iluvien®, Medidur®, Medidur FA®), sirolimus (e.g., Perceiva®), NT-501, KH-902, fosbretabulin tromethamine (e.g., Zybrestat®), AL-8309, aganirsen (e.g., Norvess®), volociximab (e.g., Opthotec®), triamcinolone (e.g., Icon Bioscience), TRC-105, Burixafor (e.g., TG-0054), TB-403 (e.g., R-7334), squalamine (e.g., Evizon®), SB-623, S-646240, RTP-801i-14 (e.g., PF-4523655), RG-7417 (e.g., FCFD-45145), AL-78898A (e.g., POT-4), PG-11047 (e.g., CGC-11047), pazopanib hydrochloride, sonepcizumab (e.g., Asonep®, Sphingomab®), padeliporfin (e.g., Stakel®), OT-551, ontecizumab, NOX-A12, hCNS-SC, Neu-2000, NAFB001, MA09-hRPE, LFG-316, iCo-007 (e.g., ISIS-13650), hl-con1, GSK-933776A, GS-6624 (e.g., AB-0024), ESBA-1008, epitalon, E-10030 (e.g., ARC-127), dalantercept, MP-0112, CNTO-2476, CERE-120, AAV-NTN, CCX-168, Brimonidine-DDS, bevasiranib sodium (e.g., Cand5), bertilimumab, AVA-101, ALG-1001, AL-39324, AGN-150998, ACU-4429, A6 (e.g., Paralit®), TT-30, sFLT-01 gene therapy, RetinoStat®, PRS-050 (e.g., Angiocal®), PF-4382923, Palomid-529, MC-1101, GW-824575, Dz13 (e.g., TRC-093), D93, CDX-1135 (e.g., TP10), ATL-1103, ARC-1905, XV-615, wet-AMD antibodies (e.g., pSivida), VEGF/rGel, VAR-10200, VAL-566-620-MULTI, TKI, TK-001, STP-601, dry AMD stem cell therapy (e.g., EyeCyte), OpRegen, SMT-D004, SAR-397769, RTU-007, RST-001, RGNX-004, RFE-007-CAI, retinal degeneration programme (e.g., Orphagen), retinal cells (e.g., ISCO), ReN003, PRM-167, ProDex, Photoswitches (e.g., Photoswitch Biosciences), Parkinson's therapy, OMS-721, OC-10x, NV. AT.08, NT-503, NAFB002, NADPH oxidase inhibitors (e.g., Alimera Sciences), MC-2002, lycium anti-angiogenic proteoglycan, IXSVEGF, integrin inhibitors, GW-771806, GBS-007, Eos-013, EC-400, dry-AMD therapy (e.g., Neuron Systems), CGEN-25017, CERE-140, AP-202, AMD therapy (e.g., Valens Therapeutics), AMD therapy (e.g., Amarna Therapeutics), AMD RNAi therapy (e.g., RXi), ALK-001, AMD therapy (e.g., Aciont), AC-301, 4-IPP, zinc-monocysteine complexes (e.g., Adeona), vatalanib, TG-100-344, prinomastat, PMX-53, Neovastat, mecamylamine, JSM-6427, JPE-1375, CereCRIB, BA-285, ATX-S10, AG-13958, verteporfin/alphavß3 conjugate, VEGF/rGel, VEGF-saporin, VEGF-R2 antagonist (e.g., Allostera), VEGF inhibitors (e.g., Santen), VEGF antagonists (e.g., Ark), Vangiolux®, Triphenylmethanes (e.g., Alimera), TG-100-801, TG-100-572, TA-106, T2-TrpRS, SU-0879, stem cell therapy (e.g., Pfizer and UCL), SOD mimetics (e.g., Inotek), SHEF-1, rostaporfin (e.g., Photrex®, Purlytin®, SnET2), RNA interference (e.g., Idera and Merck), rhCFHp (e.g., Optherion), retino-NPY, retinitis pigmentosa therapy (e.g., Mimetogen), AMD gene therapy (e.g., Novartis), retinal gene therapy (e.g., Genzyme), AMD gene therapy (e.g., Copernicus), retinal dystrophy ther (e.g., Fovea and Genzyme), Ramot project No. K-734B, PRS-055, porcine RPE cells (e.g., GenVec), PMI-002, PLG-101 (e.g., BiCentis®), PJ-34, PI3K conjugates (e.g., Semafore), PhotoPoint, Pharmaprojects No. 6526, pegaptanib sodium (e.g., SurModics®), PEDF ZFP TF, PEDF gene therapy (e.g., GenVec), PDS-1.0, PAN-90806, Opt-21, OPK-HVB-010, OPK-HVB-004, Ophthalmologicals (e.g., Cell NetwoRx), ophthalmic compounds (e.g., AstraZeneca and Alcon), OcuXan, NTC-200, NT-502, NOVA-21012, Neurosolve®, neuroprotective (e.g., BDSI), MEDI-548, MCT-355, McEye®, LentiVue®, LYN-002, LX-213, lutetium texaphyrin (e.g., Antrin®), LG-339 inhibitors (e.g., Lexicon), KDR kinase inhibitors (e.g., Merck), ISV-616, INDUS-815C, ICAM-1 aptamer (e.g., Eyetech), hedgehog antagonists (e.g., Opthalmo), GTx-822, GS-102, Granzyme B/VEGF®, gene therapy (e.g., EyeGate), GCS-100 analogue programme, FOV-RD-27, fibroblast growth factor (e.g., Ramot), fenretinide, F-200 (e.g., Eos-200-F), Panzem SR®, ETX-6991, ETX-6201, EG-3306, Dz-13, disulfiram (e.g., ORA-102), Diclofenac (e.g., Ophthalmopharma), ACU-02, CLT-010, CLT-009, CLT-008, CLT-007, CLT-006, CLT-005, CLT-004, CLT-003 (e.g., Chirovis®), CLT-001, Cethrin® (e.g., BA-210), celecoxib, CD91 antagonist (e.g., Ophthalmophar), CB-42, BNC-4, bestrophin, batimastat, BA-1049, AVT-2, AVT-1, atu012, Ape1 programme (e.g., ApeX-2), anti-VEGF (e.g., Gryphon), AMD ZFPs (e.g., ToolGen), AMD therapy (e.g., Optherion), AMD therapy (e.g., ItherX), dry AMD therapy (e.g., Opko), AMD therapy (e.g., CSL), AMD therapies (e.g., Pharmacopeia and Allergan), AMD therapeutic protein (e.g., ItherX), AMD RNAi therapy (e.g., BioMolecular Therapeutics), AM-1101, ALN-VEG01, AK-1003, AGN-211745, ACU-XSP-001 (e.g., Excellair®), ACU-HTR-028, ACU-HHY-011, ACT-MD (e.g., NewNeural), ABCA4 modulators (e.g., Active Pass), A36 (e.g., Angstrom), 267268 (e.g., SB-267268), bevacizumab (e.g., Avastin®), aflibercept (e.g., Eylea®), 131-I-TM-601, vandetanib (e.g., Caprelsa®, Zactima®, Zictifa®), sunitinib malate (e.g., Sutene®, Sutent®), sorafenib (e.g., Nexavar®), pazopanib (e.g., Armala®, Patorma®, Votrient®), axitinib (e.g., Inlyta®), tivozanib, XL-647, RAF-265, pegdinetanib (e.g., Angiocept®), pazopanib, MGCD-265, icrucumab, foretinib, ENMD-2076, BMS-690514, regorafenib, ramucirumab, plitidepsin (e.g., Aplidin®), orantinib, nintedanib (e.g., Vargatef®), motesanib, midostaurin, linifanib, telatinib, lenvatinib, elpamotide, dovitinib, cediranib (e.g., Recentin®), JI-101, cabozantinib, brivanib, apatinib, Angiozyme®, X-82, SSR-106462, rebastinib, PF-337210, IMC-3C5, CYC116, AL-3818, VEGFR2 inhibitor (e.g., AB Science), VEGF/rGel (e.g., Clayton Biotechnologies), TLK-60596, TLK-60404, R84 antibody (e.g., Peregrine), MG-516, FLT4 kinase inhibitors (e.g., Sareum), flt-4 kinase inhibitors, Sareum, DCC-2618, CH-330331, XL-999, XL-820, vatalanib, SU-14813, semaxanib, KRN-633, CEP-7055, CEP-5214, ZK-CDK, ZK-261991, YM-359445, YM-231146, VEGFR2 kinase inhibitors (e.g., Takeda), VEGFR-2 kinase inhibitors (e.g., Hanmi), VEGFR-2 antagonist (e.g., Affymax), VEGF/rGel (e.g., Targa), VEGF-TK inhibitors (e.g., AstraZeneca), tyrosine kinase inhibitors (e.g., Abbott), tyrosine kinase inhibitors (e.g., Abbott), Tie-2 kinase inhibitors (e.g., GSK), SU-0879, SP-5.2, sorafenib bead (e.g., Nexavar® bead), SAR-131675, Ro-4383596, R-1530, Pharmaprojects No. 6059, OSI-930, OSI-817, OSI-632, MED-A300, L-000021649, KM-2550, kinase inhibitors (e.g., MethylGene), kinase inhibitors (e.g., Amgen), Ki-8751, KDR kinase inhibitors (e.g., Celltech), KDR kinase inhibitors (e.g., Merck), KDR kinase inhibitors (e.g., Amgen), KDR inhibitors (e.g., Abbott), KDR inhibitor (e.g., LGLS), JNJ-17029259, IMC-1C11, Flt 3/4 anticancer (e.g., Sentinel), EG-3306, DP-2514, DCC-2157, CDP-791, CB-173, c-kit inhibitors (e.g., Deciphera), BIW-8556, anti-cancers (e.g., Bracco and Dyax), anti-Flt-1 MAbs (e.g., ImClone), AGN-211745, AEE-788, and AB-434.

Laser therapy is also available for wet AMD. Small molecule anti-VEGF therapies are being investigated, but none are currently approved. Challenges in developing new treatment of AMD include identifying treatments, delivery to the *macula*, side effects and patient compliance with intravitreal injection.

In addition to other bodily conditions described herein, in some embodiments, the methods, particles, compositions, and/or formulations described herein may be used to treat, diagnose, prevent, or manage macular edema (e.g., cystoid macular edema (CME) or (diabetic macular edema (DME)) in a subject. CME is a disorder which affects the central *retina* or *macula* of the eye. When this condition is present, multiple cyst-like (cystoid) areas of fluid appear in the *macula* and cause retinal swelling or edema. CME may accompany a variety of diseases such as retinal vein occlusion, uveitis, and/or diabetes. CME commonly occurs after cataract surgery.

Currently treatment of CME includes administration of an NSAID (such as bromfenac (e.g., Bromday®)). The NSAID may be co-administered topically or intravitreally with a corticosteroid. Severe and persistent cases of CME are usually treated by intravitreal injection of corticosteroids, which is an invasive and costly procedure.

DME occurs when blood vessels in the *retina* of patients with diabetes begin to leak into the *macula*, the part of the eye responsible for detailed central vision. These leaks cause the *macula* to thicken and swell, progressively distorting acute vision. While the swelling may not lead to blindness, the effect can cause a severe loss in central vision.

Currently treatment of DME includes Lucentis® (ranibizumab) injections that are inconvenient and invasive.

Another treatment of DME is laser photocoagulation. Laser photocoagulation is a retinal procedure in which a laser is used to cauterize leaky blood vessels or to apply a pattern of burns to reduce edema. This procedure has undesirable side effects including partial loss of peripheral and night vision.

Due to the drawbacks described above, there is a need for an improved formulation for the treatment and/or prevention of macular edema (e.g., CME or DME). The particles, compositions, and/or formulations described herein including an NSAID (e.g., bromfenac calcium) are stable at a pH suitable for topical administration to the eye and may address the issues described above with respect to current methods of treatment for macular edema. (See, for example, Examples 27-28). Likewise, it is expected that the particles, compositions, and/or formulations described herein including other pharmaceutical agents (e.g. loteprednol etabonate) may also be effective in the treatment, prevention and/or management of macular edema (e.g., CME or DME)

The particles, compositions, and/or formulations described herein may be delivered into the eye by a variety of routes including, without limitation, orally in any acceptable form (e.g., tablet, liquid, capsule, powder, and the like); topically in any acceptable form (e.g., patch, eye drops, creams, gels, nebulization, punctal plug, drug eluting contact, iontophoresis, and ointments); by injection in any acceptable form (e.g., intravenous, intraperitoneal, intramuscular, subcutaneous, parenteral, and epidural); and by implant or the use of reservoirs (e.g., subcutaneous pump, intrathecal pump, suppository, biodegradable delivery system, non-biodegradable delivery system and other implanted extended or slow release device or formulation).

Partly because the administration of particles, compositions, and/or formulations into the eye by injections is invasive (causing discomfort for the patient and can also lead to complications that are even more serious than the disease being treated) and oral doses often lead to low distribution of the particles, compositions, and/or formulations into the eye, topical delivery may be preferred in some embodiments. The key benefits of topical delivery include non-invasive character, localized action with reduced systemic exposure, relative patient comfort, and ease of administration.

Compliance is an issue which stems from a wide variety of factors, from patients' difficulty remembering to take drops, to trouble in physically administering drops, to unpleasant side effects. Other issues include rapid clearance of drug and systemic exposure.

As described herein, in some embodiments, the particles, compositions, and/or formulations may be administered topically to an eye of the subject, and a pharmaceutical agent may be delivered to a posterior part of the eye (e.g. to *retina*, choroid, vitreous, and optic nerve). The particles, compositions, and/or formulations may be used to treat, diagnose, prevent, or manage a disorder such as age-related macular degeneration, diabetic retinopathy, retinal venous occlusions, retinal arterial occlusion, macular edema, postoperative inflammation, uveitis retinitis, proliferative vitreoretinopathy and glaucoma.

In certain embodiments, the particles, compositions, and methods described herein are useful in the imaging of the eye. In certain embodiments, the particles, compositions, and methods described herein are useful in the diagnosis of an ocular condition.

In some embodiments, ophthalmic delivery of a pharmaceutical composition described herein includes delivery to an ocular surface, to the lacrimal glands or lacrimal drainage system, to the eyelids, to the anterior segment of the eye, to the posterior segment of the eye, and/or to the periocular space. In certain embodiments, a pharmaceutical composition described herein can be delivered to the cornea, iris/ciliary body, aqueous humor, vitreous humor, *retina*, choroid and/or sclera. The therapeutic effect of delivering a pharmaceutical composition described herein may be improved compared to the effect of delivering of particles that are not identified herein as mucus penetrating.

In some embodiments, the pharmaceutical agent that is delivered into the eye by the particles, compositions, and/or methods described herein may be a corticosteroid. In certain embodiments, the pharmaceutical agent is loteprednol etabonate. In certain embodiments, the pharmaceutical agent includes one or more of hydrocortisone, cortisone, tixocortol, prednisolone, methylprednisolone, prednisone, triamcinolone, mometasone, amcinonide, budesonide, desonide, fluocinonide, fluocinolone, halcinonide, betamethasone, dexamethasone, fluocortolone, hydrocortisone, aclometasone, prednicarbate, clobetasone, clobetasol, fluprednidene, glucocorticoid, mineralocorticoid, aldosterone, deoxycorticosterone, fludrocortisone, halobetasol, diflorasone, desoximetasone, fluticasone, flurandrenolide, alclometasone, diflucortolone, flunisolide, and beclomethasone.

In certain embodiments, the particles, compositions, and methods described herein are useful in the delivery of a corticosteroid, such as one described above, into the eye for the treatment of inflammation of the eye. In certain embodiments, the particles, compositions, and methods are useful in the delivery of a corticosteroid into the eye for the treatment of macular degeneration, macular edema, other retinal disorders, or other conditions described herein.

In some embodiments, the pharmaceutical agent that is delivered into the eye by the particles, compositions, and methods described herein may be a non-steroidal anti-inflammatory drug (NSAID). In certain embodiments, the pharmaceutical agent is a divalent metal salt of bromfenac (e.g., bromfenac calcium). In certain embodiments, the pharmaceutical agent is diclofenac (e.g., diclofenac free acid or a divalent or trivalent metal salt thereof). In certain embodiments, the pharmaceutical agent is ketorolac (e.g., ketorolac free acid or a divalent or trivalent metal salt thereof). In certain embodiments, the pharmaceutical agent is a salicylate (e.g., aspirin (acetylsalicylic acid), diflunisal, or salsalate). In certain embodiments, the pharmaceutical agent is a propionic acid derivative (e.g., ibuprofen, naproxen, fenoprofen, ketoprofen, dexketoprofen, flurbiprofen, oxaprozin, and loxoprofen). In certain embodiments, the pharmaceutical agent is an acetic acid derivative (e.g., indomethacin, sulindac, etodolac, ketorolac, diclofenac, and nabumetone). In certain embodiments, the pharmaceutical agent is an enolic acid (oxicam) derivative (e.g., piroxicam, meloxicam, tenoxicam, droxicam, lornoxicam, and isoxicam). In certain embodiments, the pharmaceutical agent is a fenamic acid derivative (fenamate) (e.g., mefenamic acid, meclofenamic acid, flufenamic acid, and tolfenamic acid). In certain embodiments, the pharmaceutical agent is a cyclooxygenase (cox) inhibitor, such as a cox-1 or cox-2 inhibitor (e.g., bromfenac calcium). In certain embodiments, the pharmaceutical agent is a selective cox-2 inhibitor (coxib) (e.g., celecoxib, rofecoxib, valdecoxib, parecoxib, lumiracoxib, etoricoxib, and firocoxib). In certain embodiments, the pharmaceutical agent is a sulphonanilide (e.g., nimesulide). In certain embodiments, the pharmaceutical agent is licofelone.

In certain embodiments, the particles, compositions, and methods described herein are useful in the delivery of an NSAID, such as one described above, into the eye for the treatment of inflammation of the eye or other conditions described herein. In some embodiments, the pharmaceutical agent that is delivered into the eye by the particles, compositions, and methods described herein may be an angiogenesis inhibitor. In certain embodiments, the pharmaceutical agent is an endogenous angiogenesis inhibitor (e.g., VEGFR-1 (e.g., pazopanib (Votrient®), cediranib (Recentin®), tivozanib (AV-951), axitinib (Inlyta®), semaxanib), HER2 (lapatinib (Tykerb®, Tyverb®)), linifanib (ABT-869), MGCD-265, and KRN-633), VEGFR-2 (e.g., regorafenib (BAY 73-4506), telatinib (BAY 57-9352), vatalanib (PTK787, PTK/ZK), MGCD-265, OSI-930, and KRN-633), NRP-1, angiopoietin 2, TSP-1, TSP-2, angiostatin, endostatin, vasostatin, calreticulin, platelet factor-4, TIMP, CDAI, Meth-1, Meth-2, IFN-α, IFN-β, IFN-γ, CXCL10, IL-4, IL-12, IL-18, prothrombin (kringle domain-2), antithrombin III fragment, prolactin, VEGI, SPARC, osteopontin, maspin, canstatin, a proliferin-related protein, sorafenib (Nexavar®)), and restin). In certain embodiments, the pharmaceutical agent is an exogenous angiogenesis inhibitor (e.g., bevacizumab, itraconazole, carboxyamidotriazole, TNP-470, CM101, IFN-α, IL-12, platelet factor-4, suramin, SU5416, thrombospondin, VEGFR antagonist, an angiostatic steroid+heparin, a cartilage-derived angiogenesis inhibitory factor, a matrix metalloproteinase inhibitor, angiostatin, endostatin, 2-methoxyestradiol, tecogalan, tetrathiomolybdate, thalidomide, thrombospondin, prolactin, a $\alpha_v\beta_3$ inhibitor, linomide, and tasquinimod).

In certain embodiments, the particles, compositions, and methods described herein are useful in the delivery of an angiogenesis inhibitor, such as those described above, into the eye for the treatment of macular degeneration, other retinal disorders, or other conditions described herein. In some embodiments, the pharmaceutical agent that is delivered into the eye by the particles, compositions, and methods described herein may be a prostaglandin analog. In certain embodiments, the pharmaceutical agent is latanoprost, travoprost, unoprostone, or bimatoprost.

In some embodiments, the pharmaceutical agent in a particle, composition and/or formulation described herein is an RTK inhibitor. In certain embodiments, the pharmaceutical agent is sorafenib. For example, as described in more detail in Examples 21, 25, and 29, administration of particles of sorafenib that included certain surface-altering agents described herein resulted in markedly higher sorafenib levels in various ocular tissues (e.g., tissues at the back of the eye) in rabbits, compared to an equivalent dose of particles of sorafenib that do not include a suitable surface-altering agent.

In certain embodiments, the pharmaceutical agent in a particle, composition and/or formulation described herein is linifanib. For example, as described in more detail in the Example 29, administration of MPPs containing linifanib enhanced the exposure of linifanib at the back of the eye of rabbits.

In certain embodiments, the pharmaceutical agent in a particle, composition and/or formulation described herein is MGCD-265. For example, as described in more detail in the Example 30, administration of MPPs containing MGCD-265 resulted in therapeutically-relevant levels of MGCD-265 at the back of the eye of rabbits.

In certain embodiments, the pharmaceutical agent in a particle, composition and/or formulation described herein is pazopanib. For example, as described in more detail in the Example 30, administration of MPPs containing pazopanib generated therapeutically relevant levels of pazopanib at the back of the eye of rabbits.

In certain embodiments, the pharmaceutical agent in a particle, composition and/or formulation described herein is cediranib. For example, as described in more detail in the Example 31, a single topical administration of cediranib-MPPs produced therapeutically relevant cediranib levels at the back of the eye of rabbits for 24 hours.

In certain embodiments, the pharmaceutical agent in a particle, composition and/or formulation described herein is axitinib. For example, as described in more detail in the Examples 32 and 33, a single topical administration of axitinib-MPP resulted in therapeutically relevant axitinib levels at the back of the eye of rabbits for 24 hours, and axitinib-MPP reduced vascular leakage in a rabbit VEGF (vascular endothelial growth factor receptor)-challenge model.

The results described above and herein suggest that the particles, compositions, and/or formulations described herein may be administered topically to achieve and sustain therapeutic effect in treating AMD, other retinal disorders, or other conditions described herein, compared to certain marketed formulations such as those which must be injected into the eye.

In certain embodiments, the particles, compositions, and methods described herein are useful in the delivery of a prostaglandin analog, such as one described above, into the eye for the treatment of glaucoma or other condition described herein.

In some embodiments, the pharmaceutical agent that is delivered into the eye by the particles, compositions, and methods described herein may be a beta blocker. In certain embodiments, the pharmaceutical agent is a non-selective beta blocker (e.g., alprenolol, bucindolol, carteolol, carvedilol, labetalol, nadolol, oxprenolol, penbutolol, pindolol, propranolol, sotalol, timolol, and eucommia bark). In certain embodiments, the pharmaceutical agent is a $\beta_1$-selective blocker (e.g., acebutolol, atenolol, betaxolol, bisoprolol, celiprolol, esmolol, metoprolol, and nebivolol). In certain embodiments, the pharmaceutical agent is a $\beta_2$-selective blocker (e.g., butaxamine and ICI-118,551). In certain embodiments, the pharmaceutical agent is a $\beta_3$-selective blocker (e.g., SR 59230A).

In certain embodiments, the particles, compositions, and methods described herein are useful in the delivery of a beta blocker, such as one described above, into the eye for the treatment of glaucoma or other condition described herein.

In certain embodiments, the pharmaceutical agent that is delivered into the eye by the particles, compositions, and methods of the present invention may be a carbonic anhydrase inhibitor. In certain embodiments, the pharmaceutical agent is acetazolamide, brinzolamide, dorzolamide, dorzolamide and timolol, or methazolamide.

In certain embodiments, the particles, compositions, and methods described herein are useful in the delivery of a carbonic anhydrase inhibitor, such as those described above, into the eye for the treatment of glaucoma or other conditions described herein. As described herein, in some embodiments, the particles, compositions, and/or formulations described herein can improve or increase ocular bioavailability, defined as the area under the curve (AUC) of drug concentration in an ocular tissue of interest against time after administration, of a pharmaceutical agent that is administered topically to an eye of a subject compared to certain existing particles, compositions, and/or formulations. In some embodiments, the ocular bioavailability of the pharmaceutical agent may increase due to, at least in part, a coating on core particles comprising the pharmaceutical agent that renders the particles mucus penetrating, compared to particles of the pharmaceutical agent of similar size as the coated particle in question, but which does not include the coating.

In some embodiments, the particles, compositions, and/or formulations described herein increase the ocular bioavailability of a pharmaceutical agent by at least about 10%, at least about 20%, at least about 30%, at least about 40%, at least about 50%, at least about 60%, at least about 70%, at least about 80%, at least about 90%, at least about 100%, at least about 150%, at least about 200%, at least about 5 fold, at least about 10 fold, at least about 20 fold, at least about 50 fold, at least about 100 fold, at least about 500 fold, or at least about 1000 fold. In certain the particles, compositions, and/or formulations described herein increase the ocular bioavailability of a pharmaceutical agent by less than or equal to about 1000 fold, less than or equal to about 500 fold, less than or equal to about 100 fold, less than or equal to about 50 fold, less than or equal to about 20 fold, less than or equal to about 10 fold, less than or equal to about 5 fold, less than or equal to about 200%, less than or equal to about 150%, less than or equal to about 100%, less than or equal to about 90%, less than or equal to about 80%, less than or equal to about 70%, less than or equal to about 60%, less than or equal to about 50%, less than or equal to about 40%, less than or equal to about 30%, less than or equal to about 20%, or less than or equal to about 10%. Combinations of the above-referenced ranges are also possible (e.g., an increase of at least about 10% and less than or equal to about 10 fold). Other ranges are also possible. In some instances, the AUC of a pharmaceutical agent increases at a tissue and/or fluid in the front of the eye. In other instances, the AUC of a pharmaceutical agent increases at a tissue and/or fluid in the back of the eye.

In general, an increase in ocular bioavailability may be calculated by taking the difference in the AUC measured in an ocular tissue of interest (e.g., in aqueous humor) between those of a test composition and a control composition, and dividing the difference by the bioavailability of the control composition. A test composition may include particles comprising a pharmaceutical agent, and the particles may be characterized as being mucus penetrating (e.g., having a relative velocity in mucus of greater than about 0.5, or another other relative velocity described herein). A control composition may include particles comprising the same pharmaceutical agent as that present in the test composition, the particles having a substantially similar size as those of the test composition, but which are not mucus penetrating (e.g., having a relative velocity in mucus of less than or equal to about 0.5, or another other relative velocity described herein).

Ocular bioavailability of a pharmaceutical agent may be measured in an appropriate animal model (e.g. in a New Zealand white rabbit model). The concentration of a pharmaceutical agent and, when appropriate, its metabolite(s), in appropriate ocular tissues or fluids is measured as a function of time after administration.

Other methods of measuring ocular bioavailability of a pharmaceutical agent are possible.

As described herein, in some embodiments, the concentration of a pharmaceutical agent in an ocular tissue and/or fluid may be increased when the pharmaceutical agent is delivered (e.g., via topical administration to the eye) using the particles, compositions, and/or formulations described herein compared to when the pharmaceutical agent is delivered using certain existing particles, compositions, and/or formulations that contain the same the pharmaceutical agent (or compared to the delivery of the same pharmaceutical agent (e.g., of similar size) as the coated particle in question, but which does not include the coating). In certain embodiments, a dose of the particles, compositions, and/or formulations is administered, followed by the measurement of the concentration of the pharmaceutical agent in a tissue and/or fluid of the eye. For purposes of comparison, the amount of the pharmaceutical agent included in the administered dose of the particles, compositions, and/or formulations described herein may be similar or substantially equal to the amount of the pharmaceutical agent included in the administered dose of the existing particles, compositions, and/or formulations. In certain embodiments, the concentration of the pharmaceutical agent in a tissue and/or fluid of the eye is measured at a certain time subsequent to the administration ("time post-dose") of a dose of the particles, compositions, and/or formulations described herein or of the existing particles, compositions, and/or formulations. In certain embodiments, the time when the concentration is measured is about 1 min, about 10 min, about 30 min, about 1 h, about 2 h, about 3 h, about 4 h, about 5 h, about 6 h, about 7 h, about 8 h, about 9 h, about 10 h, about 11 h, about 12 h, about 18 h, about 24 h, about 36 h, or about 48 h, post-dose.

In some embodiments, the concentration of the pharmaceutical agent in a tissue and/or fluid may increase due to, at least in part, a coating on core particles comprising the pharmaceutical agent that renders the particles mucus penetrating, compared to particles of the same pharmaceutical agent (e.g., of similar size) as the coated particle in question, but which does not include the coating. In some embodiments, the particles, compositions, and/or formulations described herein increases the concentration of a pharmaceutical agent in a tissue and/or fluid by at least about 10%, at least about 20%, at least about 30%, at least about 40%, at least about 50%, at least about 60%, at least about 70%, at least about 80%, at least about 90%, at least about 100%, at least about 200%, at least about 300%, at least about 400%, at least about 500%, or at least about 10 fold, at least about 20 fold, at least about 50 fold, at least about 100 fold, at least about 1000 fold, at least about $10^4$ fold, at least about $10^5$ fold, or at least about $10^6$ fold. In some cases, the particles, compositions, and/or formulations described herein increases the concentration of a pharmaceutical agent in a tissue and/or fluid by less than or equal to about $10^6$ fold, less than or equal to about $10^5$ fold, less than or equal to about $10^4$ fold, 1000 fold, less than or equal to about 100 fold, less than or equal to about 10 fold, less than or equal to about 500%, less than or equal to about 400%, less than or equal to about 300%, less than or equal to about 200%, less than or equal to about 100%, less than or equal to about 90%, less than or equal to about 80%, less than or equal to about 70%, less than or equal to about 60%, less than or equal to about 50%, less than or equal to about 40%, less than or equal to about 30%, less than or equal to about 20%, or less than or equal to about 10%. Combinations of the above-referenced ranges are also possible (e.g., an increase of greater than or equal to about 10% and less than or equal to about 90%). Other ranges are also possible. In some instances, the concentration of a pharmaceutical agent increases at a tissue and/or fluid in the front of the eye. In other instances, the concentration of a pharmaceutical agent increases at a tissue and/or fluid in the back of the eye.

The ocular concentration of a pharmaceutical agent, and, when appropriate, its metabolite(s), in appropriate ocular fluids or tissues may be measured as a function of time in vivo using an appropriate animal model. One method of determining the ocular concentration of a pharmaceutical agent involves dissecting of the eye to isolate tissues of interest (e.g., in a animal model comparable to the subject). The concentration of the pharmaceutical agent in the tissues of interest is then determined by HPLC or LC/MS analysis.

In certain embodiments, the period of time between administration of the particles described herein and obtaining a sample for measurement of concentration or AUC is less than about 1 hour, less than or equal to about 2 hours, less than or equal to about 3 hours, less than or equal to about 4 hours, less than or equal to about 6 hours, less than or equal to about 12 hours, less than or equal to about 36 hours, or less than or equal to about 48 hours. In certain embodiments, the period of time is at least about 1 hour, at least about 2 hours, at least about 3 hours, at least about 4 hours, at least about 6 hours, at least about 8 hours, at least about 12 hours, at least about 36 hours, or at least about 48 hours. Combinations of the above-referenced ranges are also possible (e.g., a period of time between consecutive doses of greater than or equal to about 3 hours and less than or equal to about 12 hours). Other ranges are also possible.

Other methods of measuring the concentration of a pharmaceutical agent in an eye of a subject or an animal model are also possible. In some embodiments, the concentration of a pharmaceutical agent may be measured in the eye of the subject directly or indirectly (e.g., taking a sample of fluid, such as vitreous humor, from an eye of the subject).

In general, an increase in concentration of a pharmaceutical agent in an ocular site may be calculated by taking the difference in concentration measured between those of a test composition and a control composition, and dividing the difference by the concentration of the control composition. A test composition may include particles comprising a pharmaceutical agent, and the particles may be characterized as being mucus penetrating (e.g., having a relative velocity of greater than about 0.5, or another other relative velocity described herein). A control composition may include particles comprising the same pharmaceutical agent as that present in the test composition, the particles having a substantially similar size as those of the test composition, but which are not mucus penetrating (e.g., having a relative velocity of less than about 0.5, or another other relative velocity described herein).

As described herein, in some embodiments, the particles, compositions, and/or formulations described herein, or a component thereof, is present in a sufficient amount to increase the bioavailability and/or concentration of a pharmaceutical agent in an ocular tissue, compared to the pharmaceutical agent administered to the ocular tissue in the absence of the particles, compositions, and formulations described herein, or a component thereof.

The ocular tissue may be an ocular tissue described herein, such as an anterior ocular tissue (e.g., a palpebral conjunctiva, a bulbar conjunctiva, or a cornea). The pharmaceutical agent may be any suitable agent as described herein, such as a corticosteroid (e.g., loteprednol etabonate), an RTK inhibitor (e.g., sorafenib, linifanib, MGCD-265, pazopanib, cediranib, and axitinib), an NSAID (e.g., bromfenac calcium), or a cox inhibitor (e.g., bromfenac calcium). In certain embodiments, the core particle of a formulation comprising a pharmaceutical agent is present in a sufficient amount to increase the bioavailability and/or concentration of the pharmaceutical agent in an ocular tissue. In certain embodiments, the coating on the core particle of a formulation comprising a pharmaceutical agent is present in a sufficient amount to increase the bioavailability and/or concentration of the pharmaceutical agent in an ocular tissue. In certain embodiments, the coating on the core particle of a formulation comprising a pharmaceutical agent is present in a sufficient amount to increase the concentration of the pharmaceutical agent in an ocular tissue after at least 10 minutes, at least 20 minutes, at least 30 minutes, at least 1 hour, at least 2 hours, at least 3 hours, at least 4 hours, at least 6 hours, at least 9 hours, at least 12 hours, at least 18 hours, or at least 24 hours after administration of the formulation to the ocular tissue. In certain embodiments, the coating on the core particle of a formulation comprising a pharmaceutical agent is present in a sufficient amount to increase the concentration of the pharmaceutical agent in an ocular tissue after less than or equal to 24 hours, less than or equal to 18 hours, less than or equal to 12 hours, less than or equal to 9 hours, less than or equal to 6 hours, less than or equal to 4 hours, less than or equal to 3 hours, less than or equal to 2 hours, less than or equal to 1 hour, less than or equal to 30 minutes, less than or equal to 20 minutes, or less than or equal to 10 minutes after administration of the formulation to the ocular tissue. Combinations of the above-referenced ranges are also possible (e.g., the concentration of the pharmaceutical agent increases after at least 10 minutes and less than or equal to 2 hours). Other ranges are also possible. In certain embodiments, the coating on the core particle of a formulation comprising a pharmaceutical agent is present in a sufficient amount to increase the concentration of the pharmaceutical agent in an ocular tissue after about 30 minutes after administration of the formulation to the ocular tissue.

As described herein, in some embodiments, the particles, compositions, and/or formulations described herein can be administered topically to an eye of a subject in various forms of doses. For example, the particles, compositions, and/or formulations described herein may be administered in a single unit dose or repeatedly administered in a plurality of single unit doses. A unit dose is a discrete amount of the particles, compositions, and/or formulations described herein comprising a predetermined amount of a pharmaceutical agent. In some embodiments, fewer numbers of doses (e.g., ½, ⅓, or ¼ the number doses) are required using the particles described herein having a mucus-penetrating coating compared to particles that do not have such a coating.

The exact amount of the particles, compositions, and/or formulations described herein required to achieve a therapeutically or prophylactically effective amount will vary from subject to subject, depending, for example, on species, age, and general condition of a subject, severity of the side effects or disorder, identity of the particular compound, mode of administration, and the like. The particles, compositions, and/or formulations described herein can be delivered using repeated administrations where there is a period of time between consecutive doses. Repeated administration may be advantageous because it may allow the eye to be exposed to a therapeutically or prophylactically effective amount of a pharmaceutical agent for a period of time that is sufficiently long for the ocular condition to be treated, prevented, or managed. In certain embodiments, the period of time between consecutive doses is less than or equal to about 1 hour, less than or equal to about 2 hours, less than or equal to about 3 hours, less than or equal to about 4 hours, less than or equal to about 6 hours, less than or equal to about 12 hours, less than or equal to about 36 hours, or less than or equal to about 48 hours. In certain embodiments, the period of time between consecutive doses is at least about 1 hour, at least about 2 hours, at least about 3 hours, at least about 4 hours, at least about 6 hours, at least about 12 hours, at least about 36 hours, or at least about 48 hours. Combinations of the above-referenced ranges are also possible (e.g., a period of time between consecutive doses of greater than or equal to about 3 hours and less than or equal to about 12 hours). Other ranges are also possible.

Delivery of the particles, compositions, and/or formulations described herein to an ocular tissue may result in ophthalmically efficacious drug levels in the ocular tissue for an extended period of time after administration (e.g., topical administration or administration by direct injection). An ophthalmically efficacious level of a drug refers to an amount sufficient to elicit the desired biological response of an ocular tissue, i.e., treating an ocular disease. As will be appreciated by those skilled in this art, the ophthalmically efficacious level of a drug may vary depending on such factors as the desired biological endpoint, the pharmacokinetics of the drug, the ocular disease being treated, the mode of administration, and the age and health of the subject. In certain embodiments, the ophthalmically efficacious level of a drug is an amount of the drug, alone or in combination with other therapies, which provides a therapeutic benefit in the treatment of the ocular condition. The ophthalmically efficacious level of a drug can encompass a level that improves overall therapy, reduces or avoids symptoms or causes of the ocular condition, or enhances the therapeutic efficacy of another therapeutic agent.

In some embodiments, an ophthalmically efficacious drug level may be gauged, at least in part, by the maximum concentration ($C_{max}$) of the pharmaceutical agent in the ocular tissue after administration. In some cases, delivery of the particles, compositions, and/or formulations comprising a pharmaceutical agent as described herein to an ocular tissue may result in a higher $C_{max}$ of the pharmaceutical agent in the ocular tissue after administration, compared to marketed particles, compositions, and formulations at similar doses. In certain embodiments, the $C_{max}$ obtained from an administration of the particles, compositions, and/or formulations described herein is at least about 3%, at least about 10%, at least about 30%, at least about 100%, at least about 200%, at least about 300%, at least about 400%, at least about 500%, at least about 1000%, or at least about 3000%, higher than the $C_{max}$ obtained from an administration of the marketed particles, compositions, and/or formulations. In certain embodiments, the $C_{max}$ obtained from an administration of the particles, compositions, and/or formulations described herein is less than or equal to about 3000%, less than or equal to about 1000%, less than or equal to about 500%, less than or equal to about 400%, less than or equal to about 300%, less than or equal to about 200%, less than or equal to about 100%, less than or equal to about 30%, less than or equal to about 10%, or less than or equal to about 3%, higher than the $C_{max}$ obtained from an administration of the marketed particles, compositions, and/or formulations. Combinations of the above-referenced ranges are also possible (e.g., an increase in $C_{max}$ at least about 30% and less than or equal to about 500%). Other ranges are also possible.

In some embodiments, the ophthalmically efficacious drug levels are gauged, at least in part, by minimally efficacious concentrations of the drug, e.g., $IC_{50}$ or $IC_{90}$, as known in the art.

In certain embodiments in which ophthalmically efficacious drug levels (or $C_{max}$, $IC_{50}$, or $IC_{90}$) are present in the ocular tissue for an extended period of time after administration, the extended period of time after administration can range from hours to days. In certain embodiments, the extended period of time after administration is at least 1 hour, at least 2 hours, at least 4 hours, at least 6 hours, at least 9 hours, at least 12 hours, at least 1 day, at least 2 days, at least 3 days, at least 4 days, at least 5 days, at least 6 days, or at least 1 week. In certain embodiments, the extended period of time after administration is less than or equal to 1 week, less than or equal to 6 days, less than or equal to 5 days, less than or equal to 4 days, less than or equal to 3 days, less than or equal to 2 days, less than or equal to 1 day, less than or equal to 12 hours, less than or equal to 9 hours, less than or equal to 6 hours, less than or equal to 4 hours, less than or equal to 2 hours, less than or equal to 1 hour. Combinations of the above-referenced ranges are also possible (e.g., an extended period of time of at least about 4 hours and less than or equal to about 1 week). Other ranges are also possible.

In certain embodiments, the particles, compositions, and/or formulations described herein may be at dosage levels sufficient to deliver an effective amount of a pharmaceutical agent to an eye of a subject to obtain a desired therapeutic or prophylactic effect. In certain embodiments, an effective amount of a pharmaceutical agent that is delivered to an appropriate eye tissue is at least about $10^{-3}$ ng/g, at least about $10^{-2}$ ng/g, at least about $10^{-1}$ ng/g, at least about 1 ng/g, at least about $10^1$ ng/g, at least about $10^2$ ng/g, at least about $10^3$ ng/g, at least about $10^4$ ng/g, at least about $10^5$ ng/g, or at least about $10^6$ ng/g of tissue weight. In certain embodiments, an effective amount of a pharmaceutical agent that is delivered to the eye is less than or equal to about $10^6$ ng/g, less than or equal to about $10^5$ ng/g, less than or equal to about $10^4$ ng/g, less than or equal to about $10^3$ ng/g, less than or equal to about $10^2$ ng/g, less than or equal to about $10^1$ ng/g, less than or equal to about 1 ng/g, less than or equal to about $10^{-1}$ ng/g, less than or equal to about $10^{-2}$ ng/g, or less than or equal to about $10^{-3}$ ng/g of tissue weight. Combinations of the above-referenced ranges are also possible (e.g., an effective amount of a pharmaceutical agent of at least about $10^{-2}$ ng/g and less than or equal to about $10^3$ ng/g of tissue weight). Other ranges are also possible. In certain embodiments, the particles, compositions, and/or formulations described herein may be at dosage levels sufficient to deliver an effective amount of a pharmaceutical agent to the back of an eye of a subject to obtain a desired therapeutic or prophylactic effect.

It will be appreciated that dose ranges as described herein provide guidance for the administration of provided particles, compositions, and/or formulations to an adult. The amount to be administered to, for example, a child or an adolescent can be determined by a medical practitioner or person skilled in the art and can be lower or the same as that administered to an adult.

The particles, compositions, and/or formulations described herein may be topically administered by any method, for example, as by drops, powders, ointments, or creams. Other topical administration approaches or forms are also possible.

In certain embodiments, the compositions and/or formulations described herein are packaged as a ready to use shelf stable suspension. Eye drop formulations are traditionally liquid formulations (solutions or suspensions) which can be packaged in dropper bottles (which dispense a standard drop volume of liquid) or in individual use droppers (typically used for preservative free drops; used once and disposed). These formulations are ready to use and can be self-administered. In some cases the bottle should be shaken before use to ensure homogeneity of the formulation, but no other preparation may be necessary. This may be the simplest and most convenient method of ocular delivery. The compositions and/or formulations described herein can be packaged in the same way as traditional eye drop formulations. They can be stored in suspension and may retain the characteristics which allow the particles to avoid adhesion to mucus.

The pharmaceutical agent may be one of those pharmaceutical agents described herein. In certain embodiments, the pharmaceutical agent is an NSAID, an RTK inhibitor, a cox inhibitor, a corticosteroid, an angiogenesis inhibitor, a prostaglandin analog, a beta blocker, or a carbonic anhydrase inhibitor. In certain embodiments, the pharmaceutical agent is loteprednol etabonate. In certain embodiments, the pharmaceutical agent is sorafenib. In certain embodiments, the pharmaceutical agent is linifanib. In certain embodiments, the pharmaceutical agent is MGCD-265. In certain embodiments, the pharmaceutical agent is pazopanib. In certain embodiments, the pharmaceutical agent is cediranib. In certain embodiments, the pharmaceutical agent is axitinib. In certain embodiments, the pharmaceutical agent is a divalent metal salt of bromfenac (e.g., bromfenac calcium). In certain embodiments, the pharmaceutical agent is bromfenac beryllium, bromfenac magnesium, bromfenac strontium, or bromfenac barium, bromfenac zinc, or bromfenac copper(II). Other pharmaceutical agents are also possible.

These and other aspects of the present invention will be further appreciated upon consideration of the following Examples, which are intended to illustrate certain particular embodiments of the invention but are not intended to limit its scope, as defined by the claims.

EXAMPLES

Example 1

The following describes a non-limiting example of a method of forming non-polymeric solid particles into mucus-penetrating particles. Pyrene, a hydrophobic naturally fluorescent compound, was used as the core particle and was prepared by a milling process in the presence of various surface-altering agents. The surface-altering agents formed coatings around the core particles. Different surface-altering agents were evaluated to determine effectiveness of the coated particles in penetrating mucus.

Pyrene was milled in aqueous dispersions in the presence of various surface-altering agents to determine whether certain surface-altering agents can: 1) aid particle size reduction to several hundreds of nanometers and 2) physically (non-covalently) coat the surface of generated nanoparticles with a mucoinert coating that would minimize particle interactions with mucus constituents and prevent mucus adhesion. In these experiments, the surface-altering agents acted as a coating around the core particles, and the resulting particles were tested for their mobility in mucus, although in other embodiments, the surface-altering agents may be exchanged with other surface-altering agents that can increase mobility of the particles in mucus. The surface-altering agents tested included a variety of polymers, oligomers, and small molecules listed in Table 2, including pharmaceutically relevant excipients such as poly(ethylene oxide)-poly(propylene oxide)-poly(ethylene oxide) block copolymers (Pluronics®), polyvinylpyrrolidones (Kollidon), and hydroxypropyl methylcellulose (Methocel), etc.

TABLE 2

Surface-altering agents tested with Pyrene as a model compound.

| Stabilizer | Acronym or Trade Name | Grade or Molecular Weight | Chemical Structure |
|---|---|---|---|
| Polymeric surface-altering agents | | | |
| Poly(ethylene oxide)-poly(propylene oxide)-poly(ethylene oxide) block copolymers | Pluronic® | F127, F108, F68, F87, F38, P123, P105, P103, P65, L121, L101, L81, L44, L31 | (structure shown) |
| Polyvinylpyrrolidine | PVP | Kollidon 17 (9K), Kollidon 25 (26K), Kollindon 30 (43K) | (structure shown) |
| PVA-poly(ethylene glycol) graft-copolymer | | Kollicoat IR | (structure shown) |
| Hydroxypropyl methylcellulose | HPMS | Methocel E50, Methocel K100 | (structure shown) |
| Oligomeric surface-altering agents | | | |
| Tween 20 | | | (structure shown) $w + x + y + z = 20$ |
| Tween 80 | | | (structure shown) $w + x + y + z = 20$ |

TABLE 2-continued
Surface-altering agents tested with Pyrene as a model compound.
| Stabilizer | Acronym or Trade Name | Grade or Molecular Weight | Chemical Structure |
|---|---|---|---|
| Solutol HS 15 | | | 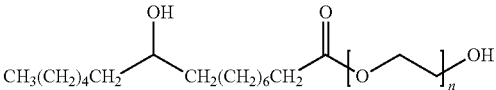 |
| Triton X100 | | | 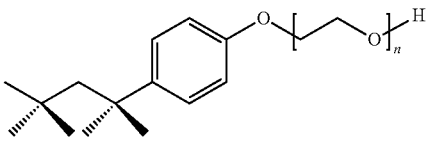 |
| Tyloxapol | | | 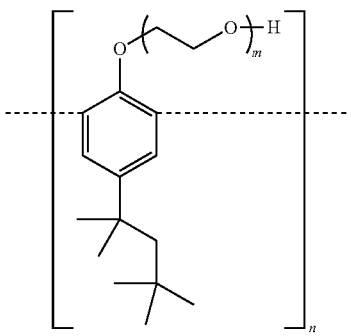 |
| Cremophor RH 40 | | | |
Small molecule surface-altering agents
| | | | |
|---|---|---|---|
| Span 20 | | | 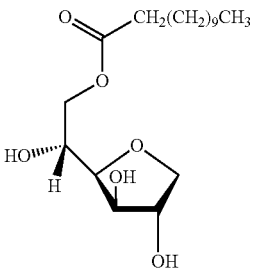 |
| Span 80 | | | 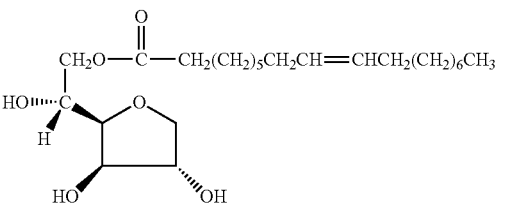 |
| Octyl glucoside | | | 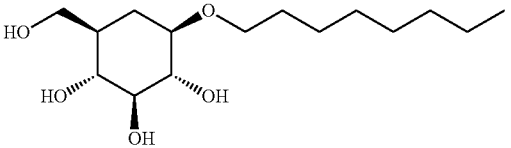 [SMILES: CCCCCCCCO[C@@H]1C[C@H](CO)[C@@H](O)[C@H](O)[C@H]1O] |
| Cetytrimethylammonium bromide (CTAB) | | | 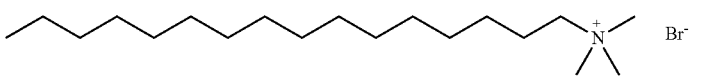 |
| Sodium dodecyl sulfate (SDS) | | | 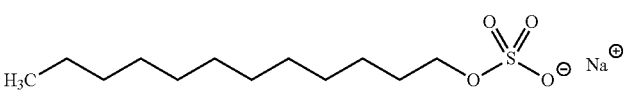 [SMILES: CCCCCCCCCCCCOS(=O)(=O)[O-] ; [Na+]] |

An aqueous dispersion containing pyrene and one of the surface-altering agents listed above was milled with milling media until particle size was reduced below 500 nm. Table 3 lists particle size characteristics of pyrene particles obtained by milling in the presence of the various surface-altering agents. Particle size was measured by dynamic light scattering. When Pluronics® L101, L81, L44, L31, Span 20, Span 80, or Octyl glucoside were used as surface-altering agents, stable nanosuspensions could not be obtained. Therefore, these surface-altering agents were excluded from further investigation due to their inability to effectively aid particle size reduction.

TABLE 3

Particle size measured by DLS in nanosuspensions obtained by milling of Pyrene with various surface-altering agents.

| Stabilizer | N-Ave. D (nm) |
| --- | --- |
| Pluronic ® F127 | 239 |
| Pluronic ® F108 | 267 |
| Pluronic ® P105 | 303 |
| Pluronic ® P103 | 319 |
| Pluronic ® P123 | 348 |
| Pluronic ® L121 | 418 |
| Pluronic ® F68 | 353 |
| Pluronic ® P65 | 329 |
| Pluronic ® F87 | 342 |
| Pluronic ® F38 | 298 |
| Pluronic ® L101 | not measurable* |
| Pluronic ® L81 | not measurable* |
| Pluronic ® L44 | not measurable* |
| Pluronic ® L31 | not measurable* |
| PVA 13K | 314 |
| PVA 31K | 220 |
| PVA 85K | 236 |
| Kollicoat IR | 192 |
| Kollidon 17 (PVP 9K) | 163 |
| Kollidon 25 (PVP 26K) | 210 |
| Kollindon 30 (PVP 43K) | 185 |
| Methocel E50 | 160 |
| Methocel K100 | 216 |
| Tween 20 | 381 |
| Tween 80 | 322 |
| Solutol HS | 378 |
| Triton X100 | 305 |
| Tyloxapol | 234 |
| Cremophor RH40 | 373 |
| SDS | 377 |
| CTAB | 354 |
| Span 20 | not measurable* |
| Span 80 | not measurable* |
| Octyl glucoside | not measurable* |

*milling with Pluronics ® L101, L81, L44, L31, Span 20, Span 80, Octyl glucoside failed to effectively reduce pyrene particle size and produce stable nanosuspensions.

The mobility and distribution of pyrene nanoparticles from the produced nanosuspensions in human cervicovaginal mucus (CVM) were characterized using fluorescence microscopy and multiple particle tracking software. In a typical experiment, ≤0.5 uL of a nanosuspension (diluted if necessary to the surfactant concentration of ~1%) was added to 20 µl of fresh CVM along with controls. Conventional nanoparticles (200 nm yellow-green fluorescent carboxylate-modified polystyrene microspheres from Invitrogen) were used as a negative control to confirm the barrier properties of the CVM samples. Red fluorescent polystyrene nanoparticles covalently coated with PEG 5 kDa were used as a positive control with well-established MPP behavior. Using a fluorescent microscope equipped with a CCD camera, 15 s movies were captured at a temporal resolution of 66.7 ms (15 frames/s) under 100× magnification from several areas within each sample for each type of particles: sample (pyrene), negative control, and positive control (natural blue fluorescence of pyrene allowed observing of pyrene nanoparticles separately from the controls). Next, using an advanced image processing software, individual trajectories of multiple particles were measured over a time-scale of at least 3.335 s (50 frames). Resulting transport data are presented here in the form of trajectory-mean velocity $V_{mean}$, i.e., velocity of an individual particle averaged over its trajectory, and ensemble-average velocity $<V_{mean}>$, i.e., $V_{mean}$ averaged over an ensemble of particles. To enable easy comparison between different samples and normalize velocity data with respect to natural variability in penetrability of CVM samples, relative sample velocity $<V_{mean}>_{rel}$, was determined according to the formula shown in Equation 1.

Prior to quantifying mobility of the produced pyrene nanoparticles, their spatial distribution in the mucus sample was assessed by microscopy at low magnifications (10×, 40×). It was found that pyrene/Methocel nanosuspensions did not achieve uniform distribution in CVM and strongly aggregated into domains much larger than the mucus mesh size (data not shown). Such aggregation is indicative of mucoadhesive behavior and effectively prevents mucus penetration. Therefore, further quantitative analysis of particle mobility was deemed unnecessary. Similarly to the positive control, all other tested pyrene/stabilizer systems achieved a fairly uniform distribution in CVM. Multiple particle tracking confirmed that in all tested samples the negative controls were highly constrained, while the positive controls were highly mobile as demonstrated by $<V_{mean}>$ for the positive controls being significantly greater than those for the negative controls (Table 4).

TABLE 4

Ensemble-average velocity $<V_{mean}>$ (um/s) and relative sample velocity $<V_{mean}>_{rel}$ for pyrene/stabilizer nanoparticles (sample) and controls in CVM.

| | Negative Control | | Positive Control | | Sample | | Sample (relative) | |
| --- | --- | --- | --- | --- | --- | --- | --- | --- |
| Stabilizer | $<V_{mean}>$ | SD | $<V_{mean}>$ | SD | $<V_{mean}>$ | SD | $<V_{mean}>_{rel}$ | SD |
| Pluronic F127 | 0.58 | 0.18 | 5.97 | 0.54 | 6.25 | 0.72 | 1.05 | 0.18 |
| Pluronic F108 | 0.43 | 0.64 | 5.04 | 1.88 | 4.99 | 1.47 | 0.99 | 0.55 |
| Pluronic P105 | 0.56 | 0.52 | 4.38 | 1.36 | 4.47 | 2.11 | 1.02 | 0.69 |
| Pluronic P103 | 0.58 | 0.77 | 4.5 | 2.01 | 4.24 | 1.95 | 0.93 | 0.74 |
| Pluronic P123 | 0.56 | 0.44 | 4.56 | 1.44 | 3.99 | 1.66 | 0.86 | 0.54 |
| Pluronic L121 | 0.42 | 0.3 | 4.27 | 2.04 | 0.81 | 0.51 | 0.10 | 0.16 |
| Pluronic F68 | 0.56 | 0.52 | 4.38 | 1.36 | 0.81 | 0.7 | 0.07 | 0.23 |
| Pluronic P65 | 0.26 | 0.25 | 4.52 | 2.15 | 0.53 | 0.56 | 0.06 | 0.15 |
| Pluronic F87 | 0.95 | 1.6 | 5.06 | 1.34 | 0.74 | 0.78 | −0.05 | −0.43 |
| Pluronic F38 | 0.26 | 0.1 | 5.73 | 0.84 | 0.54 | 0.29 | 0.05 | 0.06 |
| Kollicoat IR | 0.62 | 0.62 | 5.39 | 0.55 | 0.92 | 0.81 | 0.06 | 0.22 |

TABLE 4-continued

Ensemble-average velocity <$V_{mean}$> (um/s) and relative sample velocity <$V_{mean}$>$_{rel}$ for pyrene/stabilizer nanoparticles (sample) and controls in CVM.

| Stabilizer | Negative Control <$V_{mean}$> | SD | Positive Control <$V_{mean}$> | SD | Sample <$V_{mean}$> | SD | Sample (relative) <$V_{mean}$>$_{rel}$ | SD |
|---|---|---|---|---|---|---|---|---|
| Kollidon 17 | 1.69 | 1.8 | 5.43 | 0.98 | 0.82 | 0.59 | −0.23 | −0.52 |
| Kollidon 25 | 0.41 | 0.34 | 5.04 | 0.64 | 1.29 | 1.09 | 0.19 | 0.25 |
| Kollindon 30 | 0.4 | 0.2 | 4.28 | 0.57 | 0.35 | 0.11 | −0.01 | 0.06 |
| Methocel E50** | | | | | | | | |
| Methocel K100** | | | | | | | | |
| Tween 20 | 0.77 | 0.93 | 5.35 | 1.76 | 1.58 | 2.02 | 0.18 | 0.49 |
| Tween 80 | 0.46 | 0.34 | 3.35 | 1.89 | 0.94 | 0.5 | 0.17 | 0.24 |
| Solutol HS | 0.42 | 0.13 | 3.49 | 0.5 | 0.8 | 0.6 | 0.12 | 0.20 |
| Triton X100 | 0.26 | 0.13 | 4.06 | 1.11 | 0.61 | 0.19 | 0.09 | 0.07 |
| Tyloxapol | 0.5 | 0.5 | 3.94 | 0.58 | 0.42 | 0.23 | −0.02 | −0.16 |
| Cremophor RH40 | 0.48 | 0.21 | 3.2 | 0.97 | 0.49 | 0.24 | 0.00 | 0.12 |
| SDS | 0.3 | 0.12 | 5.99 | 0.84 | 0.34 | 0.15 | 0.01 | 0.03 |
| CTAB | 0.39 | 0.09 | 4.75 | 1.79 | 0.32 | 0.31 | −0.02 | −0.07 |

*Did not produce stable nanosuspensions, hence not mucus-penetrating (velocity in CVM not measured)
**Aggregated in CVM, hence not mucus-penetrating (velocity in CVM not measured)

Figure 2A:
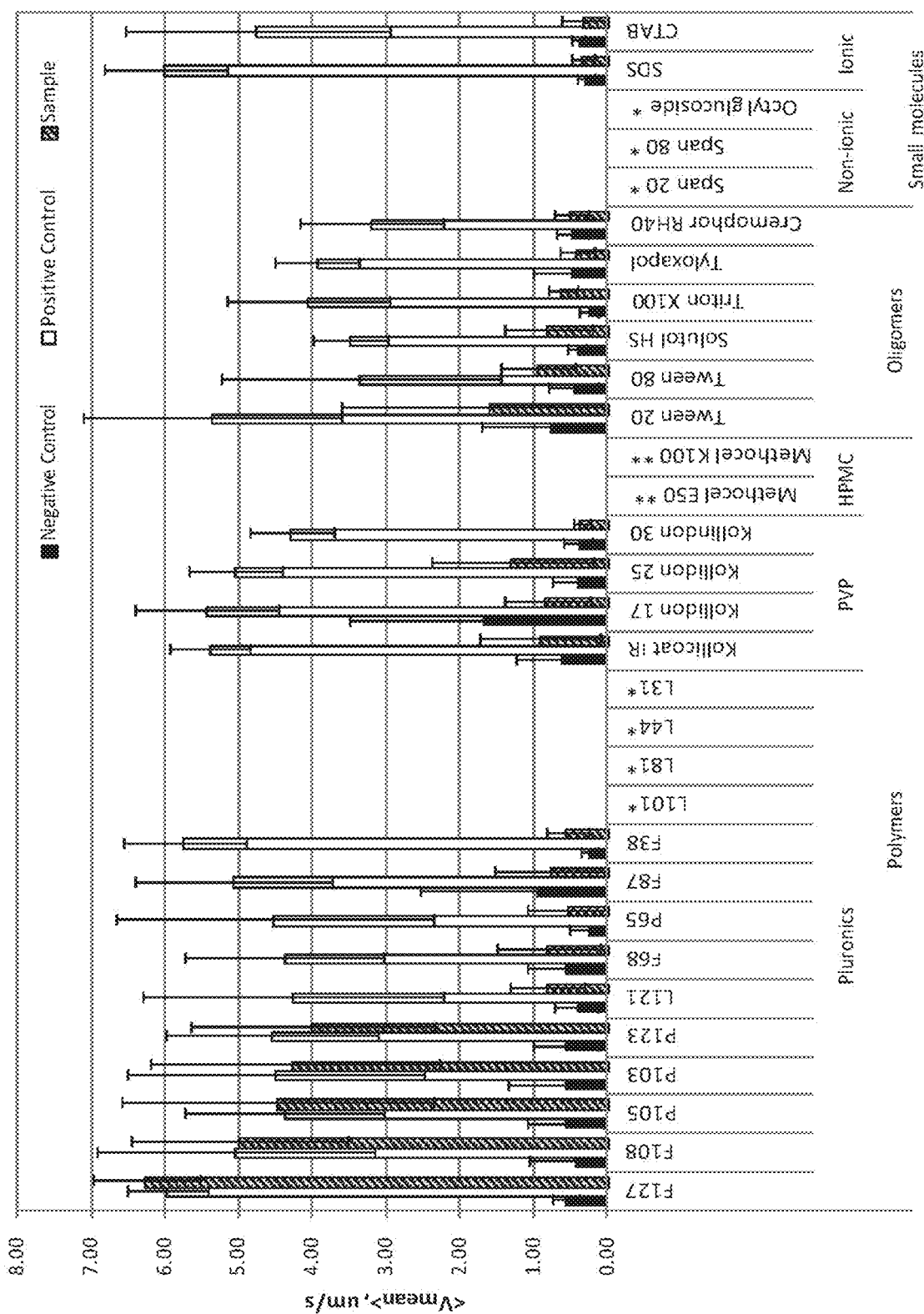
FIG. 2A is a plot showing the ensemble averaged velocity $<V_{mean}>$ in human cervicovaginal mucus (CVM) for 200 nm carboxylated polystyrene particles (negative control), 200 nm PEGylated polystyrene particles (positive control), and nanocrystal particles (sample) made by milling and coated with different surface-altering agents according to one set of embodiments.

It was discovered that nanoparticles obtained in the presence of certain (but, importantly, not all) surface-altering agents migrate through CVM at the same rate or nearly the same velocity as the positive control. Specifically, pyrene nanoparticles stabilized with Pluronics® F127, F108, P123, P105, and P103 exhibited <$V_{mean}$> that exceeded those of the negative controls by approximately an order of magnitude and were indistinguishable, within experimental error, from those of the positive controls, as shown in Table 4 and FIG. 2A. For these samples, <$V_{mean}$>$_{rel}$ values exceeded 0.5, as shown in FIG. 2B.

Figure 2B:
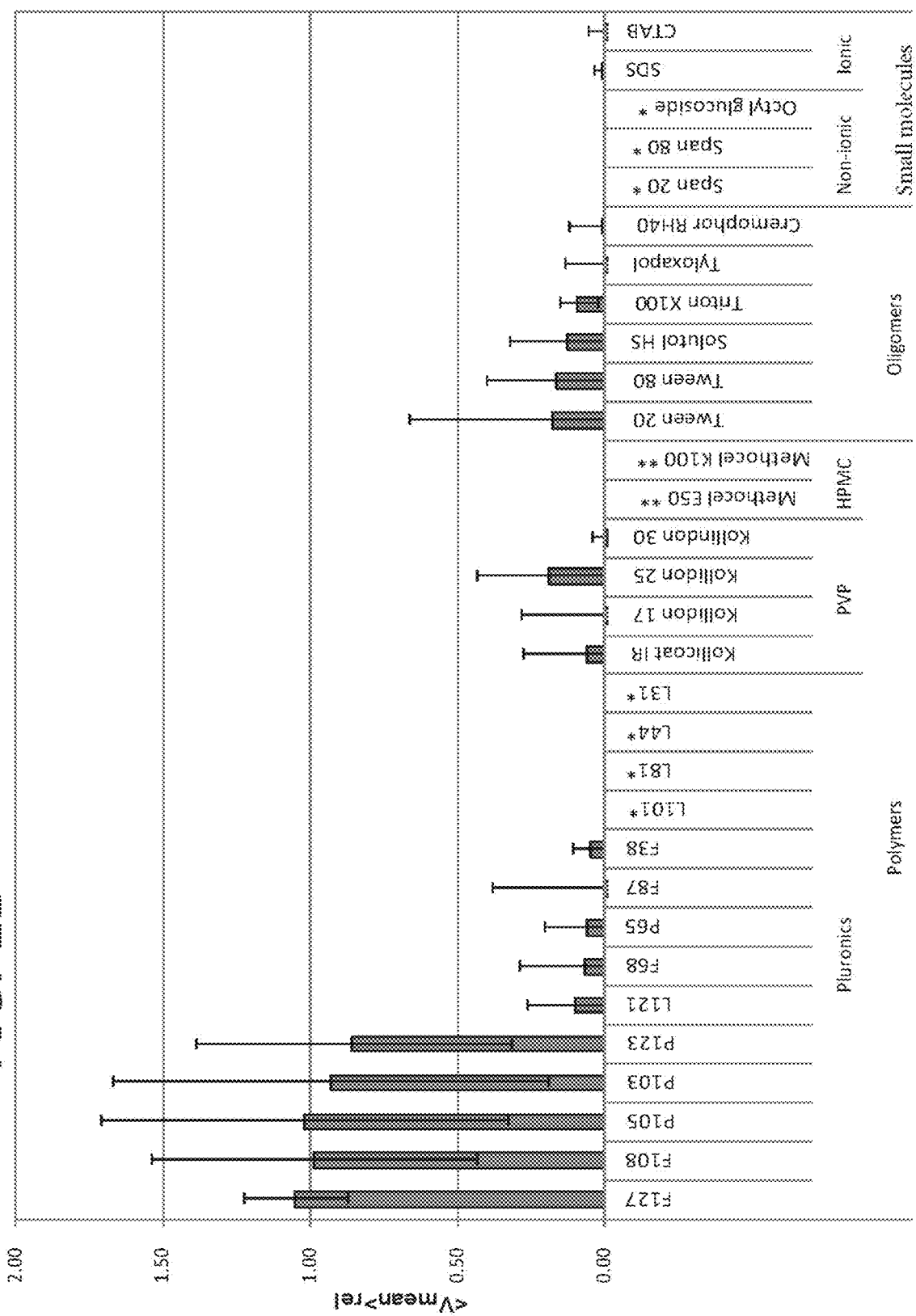
FIG. 2B is a plot showing the relative velocity $<V_{mean}>_{rel}$ in CVM for nanocrystal particles made by milling and coated with different surface-altering agents according to one set of embodiments.
Figure 3A:
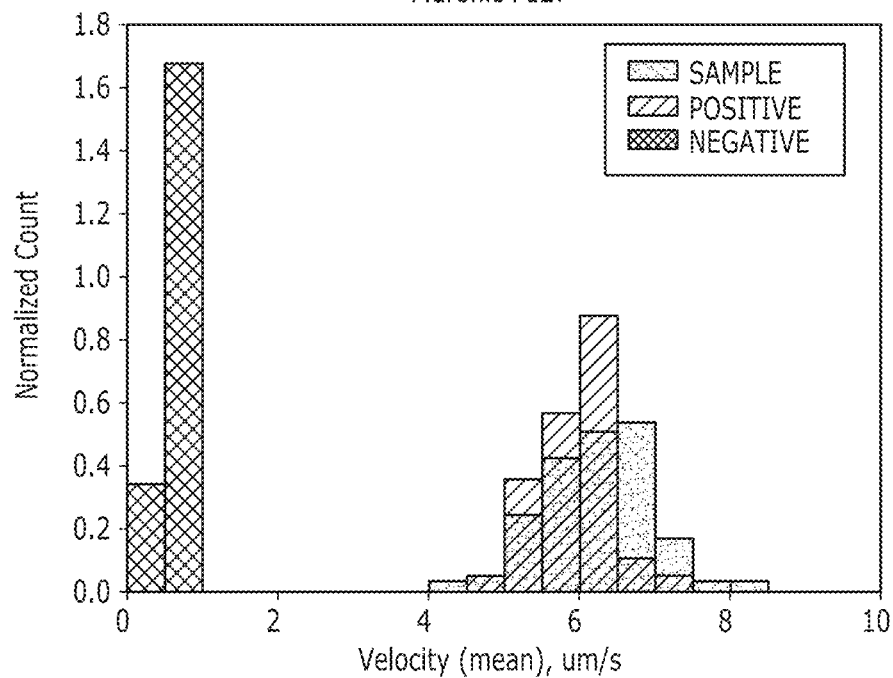
Figure 3B:
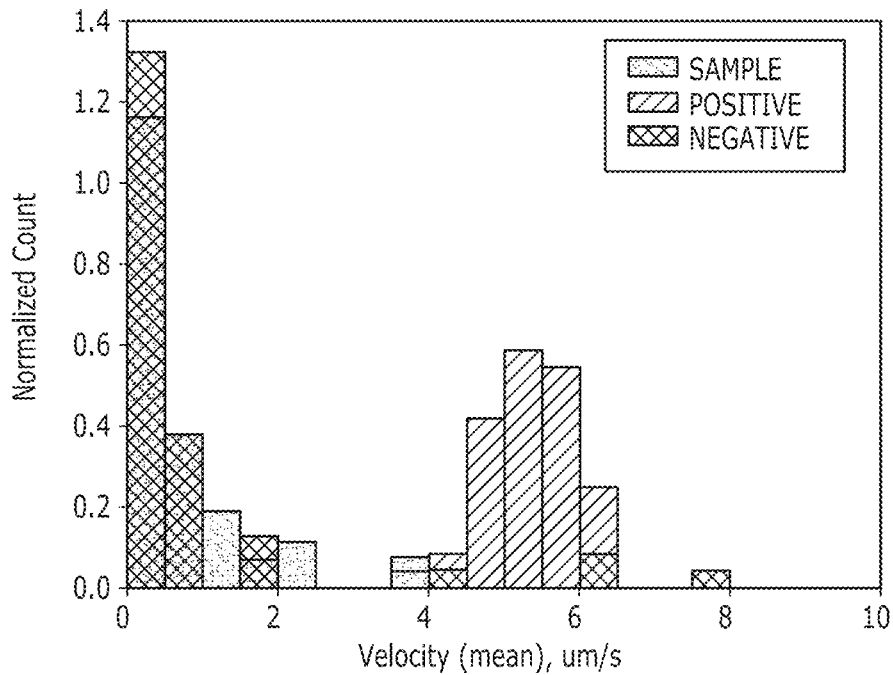

On the other hand, pyrene nanoparticles obtained with the other surface-altering agents were predominantly or completely immobilized as demonstrated by respective <$V_{mean}$>$_{rel}$ values of no greater than 0.4 and, with most surface-altering agents, no greater than 0.1 (Table 4 and FIG. 2B). Additionally, FIGS. 3A-3D are histograms showing distribution of $V_{mean}$ within an ensemble of particles. These histograms illustrate muco-diffusive behavior of samples stabilized with Pluronic® F127 and Pluronic® F108 (similar histograms were obtained for samples stabilized with Pluronic® P123, P105, and P103, but are not shown here) as opposed to muco-adhesive behavior of samples stabilized with Pluronic® 87, and Kollidon 25 (chosen as representative muco-adhesive samples).

Figure 4:
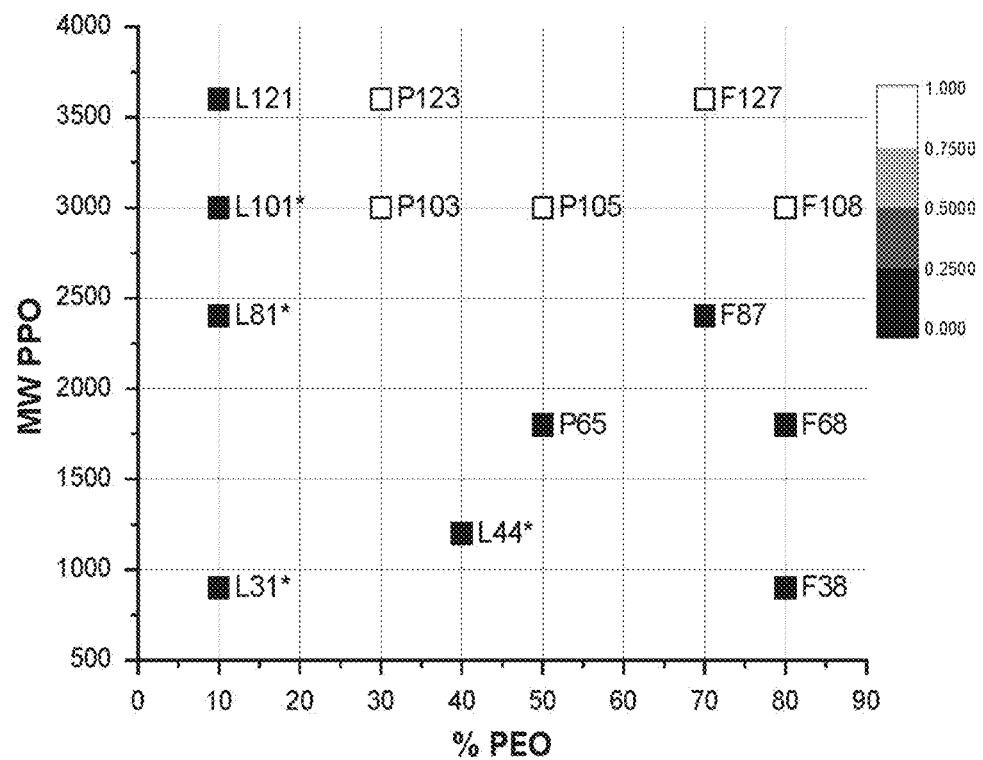
FIG. 4 is a plot showing $<V_{mean}>_{rel}$ in CVM for nanocrystal particles coated with different PEO-PPO-PEO Pluronic® triblock copolymers, mapped with respect to molecular weight of the PPO block and the PEO weight content (%), according to one set of embodiments.

To identify the characteristics of Pluronics® that render pyrene nanocrystals mucus penetrating, <$V_{mean}$>$_{rel}$ of the Pyrene/Pluronic® nanocrystals was mapped with respect to molecular weight of the PPO block and the PEO weight content (%) of the Pluronics® used (FIG. 4). It was concluded that at least those Pluronics® that have the PPO block of at least 3 kDa and the PEO content of at least about 30 wt % rendered the nanocrystals mucus-penetrating. Without wishing to be bound by any theory, it is believed that the hydrophobic PPO block can provide effective association with the surface of the core particles if the molecular weight of that block is sufficient (e.g., at least about 3 kDa in some embodiments); while the hydrophilic PEO blocks are present at the surface of the coated particles and can shield the coated particles from adhesive interactions with mucin fibers if the PEO content of the Pluronic® is sufficient (e.g., at least 30 wt % in some embodiments). As described herein, in some embodiments the PEO content of the surface-altering agent may be chosen to be greater than or equal to about 10 wt % (e.g., at least about 15 wt %, or at least about 20 wt %), as a 10 wt % PEO portion rendered the particles mucoadhesive.

Example 2

This example describes the formation of mucus-penetrating particles using various non-polymeric solid particles.

The technique described in Example 1 was applied to other non-polymeric solid particles to show the versatility of the approach. F127 was used as the surface-altering agent for coating a variety of active pharmaceuticals used as core particles. Sodium dodecyl sulfate (SDS) was chosen as a negative control so that each drug was compared to a similarly sized nanoparticle of the same compound. An aqueous dispersion containing the pharmaceutical agent and Pluronic® F127 or SDS was milled with milling media until particle size was reduced below 300 nm. Table 5 lists the particle sizes for a representative selection of drugs that were milled using this method.

TABLE 5

Particle sizes for a representative selection of drugs milled in the presence of SDS and F127.

| Drug | Stabilizer | Z-Ave D (nm) | PDI |
|---|---|---|---|
| Fluticasone propionate | F127 | 203 | 0.114 |
| | SDS | 202 | 0.193 |
| Furosemide | F127 | 217 | 0.119 |
| | SDS | 200 | 0.146 |
| Itraconazole | F127 | 155 | 0.158 |
| | SDS | 168 | 0.163 |
| Prednisolone | F127 | 273 | 0.090 |
| | SDS | 245 | 0.120 |
| Loteprednol etabonate | F127 | 241 | 0.123 |
| | SDS | 241 | 0.130 |
| Budesonide | F127 | 173 | 0.112 |
| | SDS | 194 | 0.135 |
| Indomethacin | F127 | 225 | 0.123 |
| | SDS | 216 | 0.154 |

Figure 5:
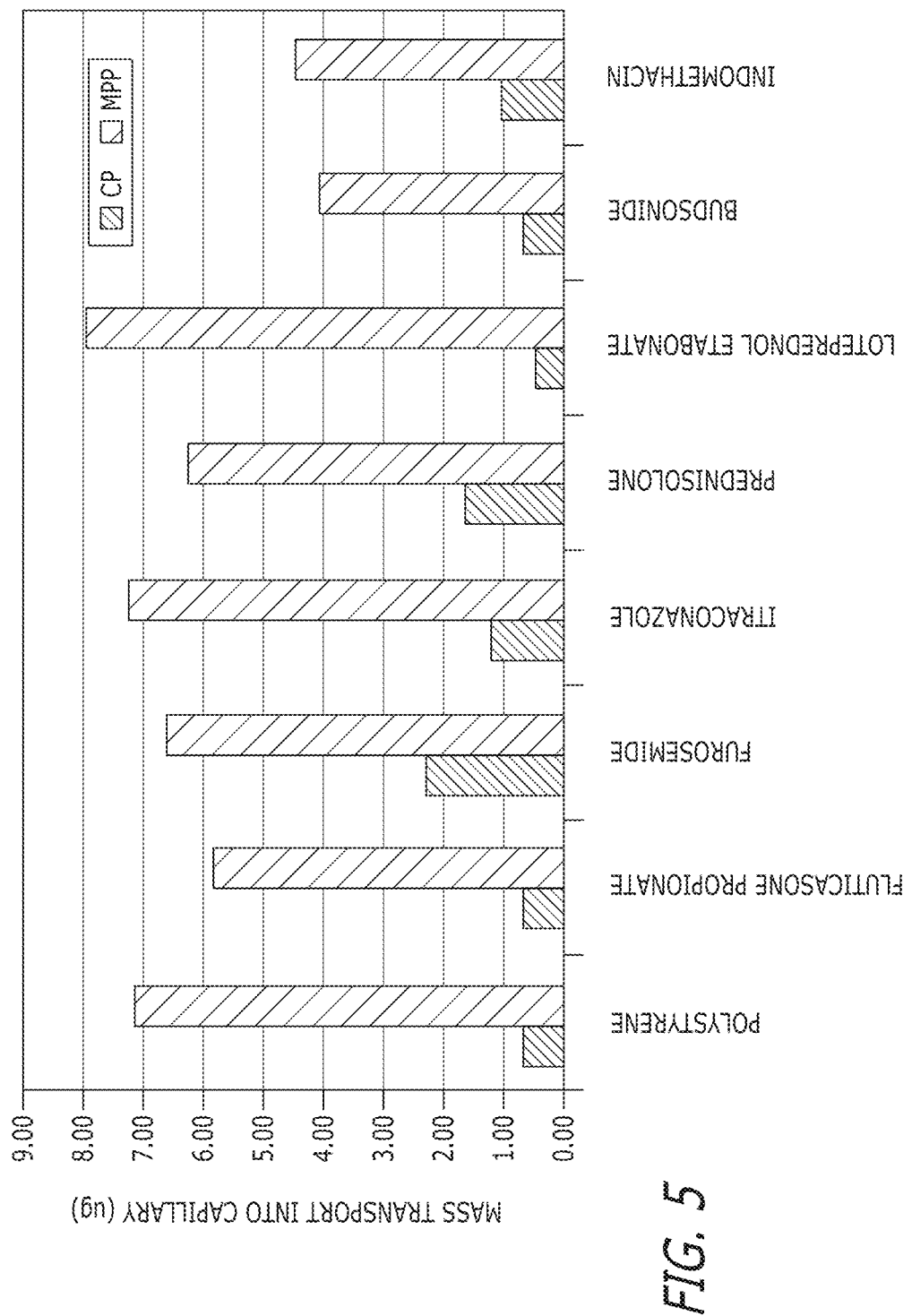
FIG. 5 is a plot showing the mass transport through CVM for solid particles having different core materials that are coated with either Pluronic® F127 (MPP, mucus-penetrating particles) or sodium dodecyl sulfate (CP, conventional particles, a negative control), according to one set of embodiments.

In order to measure the ability of drug nanoparticles to penetrate mucus a new assay was developed which measures the mass transport of nanoparticles into a mucus sample. Most drugs are not naturally fluorescent and are therefore difficult to measure with particle tracking microscopy techniques. The newly-developed bulk transport assay does not require the analyzed particles to be fluorescent or labeled with dye. In this method, 20 µL of CVM is collected in a capillary tube and one end is sealed with clay. The open end of the capillary tube is then submerged in 20 µL of an aqueous suspension of particles which is 0.5% w/v drug. After the desired time, typically 18 hours, the capillary tube is removed from the suspension and the outside is wiped clean. The capillary containing the mucus sample is placed in an ultracentrifuge tube. Extraction media is added to the tube and incubated for 1 hour while mixing which removes the mucus from the capillary tube and extracts the drug from the mucus. The sample is then spun to remove mucins and other non-soluble components. The amount of drug in the extracted sample can then be quantified using HPLC. The results of these experiments are in good agreement with those of the microscopy method, showing clear differentiation in transport between mucus penetrating particles and conventional particles. The transport results for a representative selection of drugs are shown in FIG. 5. These results corroborate microscopy/particle tracking findings with Pyrene and demonstrate the extension to common active pharmaceutical compounds; coating non-polymeric solid nanoparticles with F127 enhances mucus penetration.

In Examples 1-2, 4-6, and 10, cervicovaginal mucus (CVM) samples were obtained from healthy females volunteers age 18 years or older. CVM was collected by inserting a Softcup® menstrual collection cup into the vaginal tract as described by the product literature for between 30 seconds and 2 minutes. After removal the CVM was then collected from the Softcup® by gentle centrifugation at ~30×G to ~120×G in a 50 mL centrifuge tube. In Example 1, CVM was used undiluted and fresh (stored for no longer than 7 days under refrigerated conditions). Barrier and transport of all CVM samples used in Example 1 were verified with negative (200 nm carboxylated polystyrene particles) and positive (200 nm polystyrene particles modified with PEG 5K) controls. In Example 2, CVM was lyophilized and reconstituted. In Example 2, mucus was frozen at −50° C. and then lyophilized to dryness. Samples were then stored at −50° C. Before use, the mucus was reconstituted by grinding the solid into a fine powder using a mortar and pestle followed by water addition to a final volume equal to the original volume to 2 times the original volume. The reconstituted mucus was then incubated at 4° C. for 12 hours and used as described in Example 2. Barrier and transport of all CVM samples used in Example 2 were verified with negative (200 nm carboxylated polystyrene particles) and positive (F127 coated 200 nm polystyrene particles) controls.

Example 3

This example describes the formation of mucus-penetrating particles using a core comprising the drug loteprednol etabonate (LE).

Figure 6A:
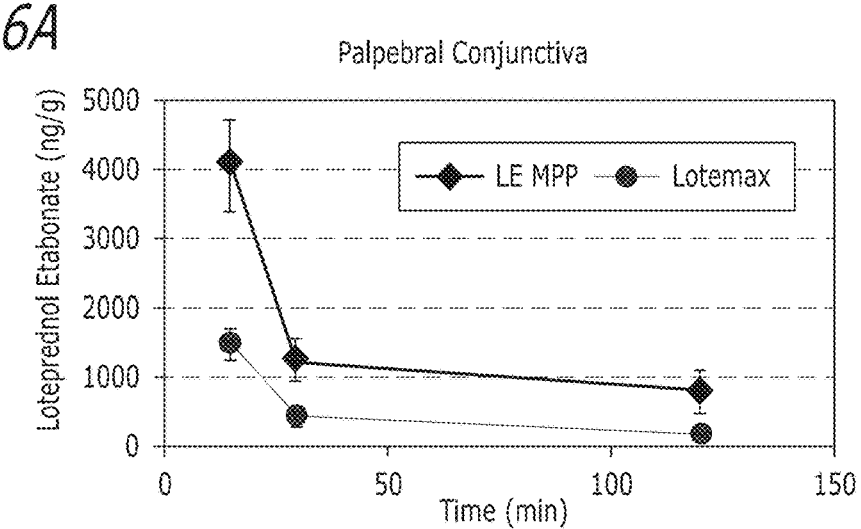
FIGS. 6A-6C show drug levels of loteprednol etabonate in the palpebral conjunctiva (FIG. 6A), bulbar conjunctiva (FIG. 6B), and cornea (FIG. 6C) of New Zealand white rabbits after administration of commercial prescription loteprednol etabonate, Lotemax®, or particles of loteprednol etabonate that were coated with Pluronic® F127, according to one set of embodiments.
Figure 6B:
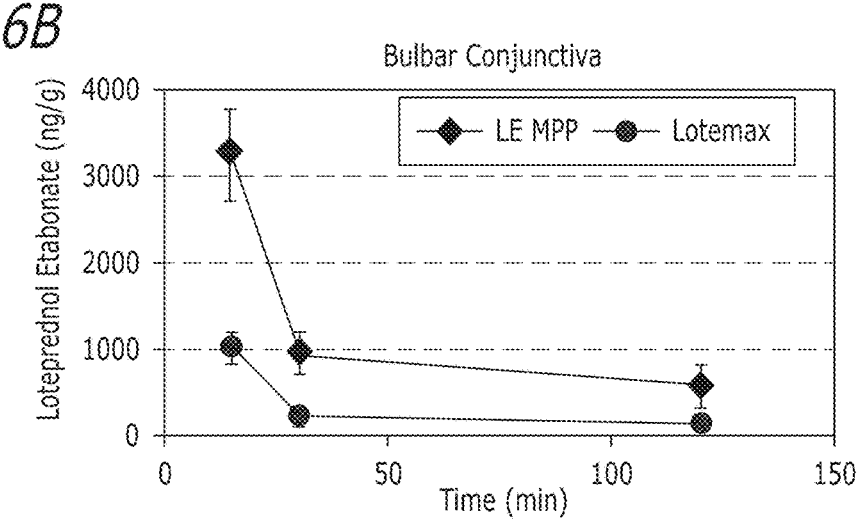
Figure 6C:
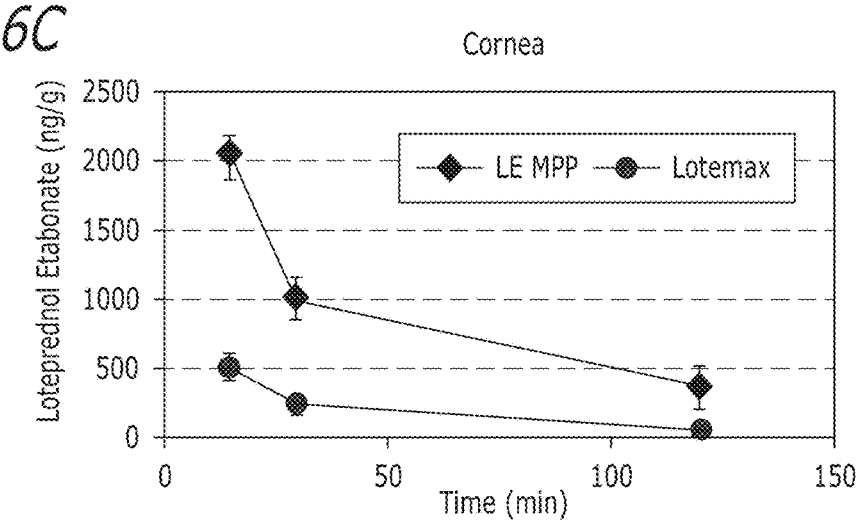

In order to demonstrate the value of enhanced mucus penetration in the delivery of non-polymeric solid particles, an MPP formulation of loteprednol etabonate (LE MPP; LE particles coated with Pluronic® F127 made by the method described in Example 2) was compared to the currently marketed formulation, Lotemax®. Lotemax® is a steroid eye drop approved for the treatment of surface ocular inflammation. Conventional particles, such as those in Lotemax®, are extensively trapped by the peripheral rapidly-cleared mucus layer in the eye and, hence, are also rapidly cleared. LE MPPs are able to avoid adhesion to, and effectively penetrate through, mucus to facilitate sustained drug release directly to underlying tissues. Enhancing drug exposure at the target site would allow the overall dose to be reduced, increasing patient compliance and safety. In vivo, a single topical instillation of LE MPP to New Zealand white rabbits produced significantly higher drug levels in palpebral conjunctiva, bulbar conjunctiva, and cornea compared to an equivalent dose of Lotemax® (FIGS. 6A-6C). At 2 hours LE levels from MPP are 6, 3, and 8 times higher than from Lotemax® (palpebral, bulbar, and cornea, respectively). Notably, LE levels from MPP are approximately 2 times higher at 2 hours than levels from Lotemax® at 30 minutes. These results demonstrate the enhanced exposure achievable with the MPP technology over the commercial formulation.

Example 4

The following describes a non-limiting example of a method of forming mucus-penetrating particles from prefabricated polymeric particles by physical adsorption of certain poly(vinyl alcohol) polymers (PVA). Carboxylated polystyrene nanoparticles (PSCOO) were used as the prefabricated particle/core particle with a well-established strongly mucoadhesive behavior. The PVAs acted as surface-altering agents forming coatings around the core particles. PVA of various molecular weights (MW) and hydrolysis degrees were evaluated to determine effectiveness of the coated particles in penetrating mucus.

PSCOO particles were incubated in aqueous solution in the presence of various PVA polymers to determine whether certain PVAs can physically (non-covalently) coat the core particle with a mucoinert coating that would minimize particle interactions with mucus constituents and lead to rapid particle penetration in mucus. In these experiments, the PVA acted as a coating around the core particles, and the resulting particles were tested for their mobility in mucus, although in other embodiments, PVA may be exchanged with other surface-altering agents that can increase mobility of the particles in mucus. The PVAs tested ranged in the average molecular weight from 2 kDa to 130 kDa and in the average hydrolysis degree from 75% to 99+%. The PVAs that were tested are listed in Table 1, shown above.

The particle modification process was as follows: 200 nm carboxylated-modified red fluorescent polystyrene nanoparticles (PSCOO) were purchased from Invitrogen. The PSCOO particles (0.4-0.5 wt %) were incubated in an aqueous PVA solution (0.4-0.5 wt %) for at least 1 hour at room temperature.

The mobility and distribution of the modified nanoparticles in human cervicovaginal mucus (CVM) were characterized using fluorescence microscopy and multiple particle tracking software. In a typical experiment, ≤0.5 µL of an incubated nanosuspension (diluted ~10× with 0.5 wt % aqueous solution of a corresponding PVA) was added to 20 µl of fresh CVM along with controls. Conventional nanoparticles (200 nm blue fluorescent carboxylate-modified polystyrene microspheres from Invitrogen) were used as a negative control to confirm the barrier properties of the CVM samples. Yellow-green fluorescent polystyrene nanoparticles covalently coated with PEG 2 kDa were used as a positive control with well-established MPP behavior. Using a fluorescent microscope equipped with a CCD camera, 15 s movies were captured at a temporal resolution of 66.7 ms (15 frames/s) under 100× magnification from several areas within each sample for each type of particles: sample (observed through a Texas Red filter set), negative control (observed through a DAPI filter set), and positive control (observed through a FITC filter set). Next, using an advanced image processing software, individual trajectories of multiple particles were measured over a time-scale of at least 3.335 s (50 frames). Resulting transport data are presented here in the form of trajectory-mean velocity $V_{mean}$, i.e., velocity of an individual particle averaged over its trajectory, and ensemble-average velocity $<V_{mean}>$, i.e., $V_{mean}$ averaged over an ensemble of particles. To enable easy comparison between different samples and normalize velocity data with respect to natural variability in penetrability of CVM samples, ensemble-average (absolute) velocity is then converted to relative sample velocity $<V_{mean}>_{rel}$ according to the formula shown in Equation 1. Multiple particle tracking confirmed that in all tested CVM samples the negative controls were constrained, while the positive controls were mobile as demonstrated by the differences in $<V_{mean}>$ for the positive and negative controls (Table 6).

the coated particles render them hydrophilic and can shield the coated particles from adhesive interactions with mucus.

To further confirm the ability of the specific PVA grades to convert mucoadhesive particles into mucus-penetrating particles by physical adsorption, PSCOO nanoparticles incubated with the various PVAs were tested using the bulk transport assay. In this method, 20 μL of CVM was collected in a capillary tube and one end is sealed with clay. The open end of the capillary tube is then submerged in 20 μL of an aqueous suspension of particles which is 0.5% w/v drug. After the desired time, typically 18 hours, the capillary tube is removed from the suspension and the outside is wiped clean. The capillary containing the mucus sample is placed in an ultracentrifuge tube. Extraction media is added to the tube and incubated for 1 hour while mixing which removes the mucus from the capillary tube and extracts the drug from

TABLE 6

Transport of nanoparticles incubated with various PVA (sample) and controls in CVM: Ensemble-average velocity $<V_{mean}>$ (μm/s) and relative sample velocity $<V_{mean}>_{rel}$.

| Stabilizer | Negative Control | | Positive Control | | Sample | | Sample (relative) | |
| --- | --- | --- | --- | --- | --- | --- | --- | --- |
| | $<V_{mean}>$ | SD | $<V_{mean}>$ | SD | $<V_{mean}>$ | SD | $<V_{mean}>_{rel}$ | SD |
| PVA2K75 | 1.39 | 0.33 | 3.3 | 0.68 | 3.44 | 0.7 | 1.07 | 0.59 |
| PVA9K80 | 0.4 | 0.08 | 5.13 | 1.16 | 4.88 | 1.74 | 0.95 | 0.44 |
| PVA13K87 | 0.56 | 0.61 | 5.23 | 1.24 | 4.92 | 1.77 | 0.93 | 0.49 |
| PVA31K87 | 0.53 | 0.63 | 4.48 | 1.38 | 3.69 | 1.94 | 0.80 | 0.60 |
| PVA57K86 | 0.5 | 0.25 | 5.74 | 1.11 | 4.76 | 0.91 | 0.81 | 0.25 |
| PVA85K87 | 0.29 | 0.28 | 4.25 | 0.97 | 4.01 | 0.71 | 0.94 | 0.31 |
| PVA105K80 | 0.98 | 0.52 | 5.44 | 0.86 | 4.93 | 0.66 | 0.89 | 0.27 |
| PVA130K87 | 1.41 | 0.56 | 3.75 | 0.82 | 3.57 | 0.6 | 0.92 | 0.53 |
| PVA95K95 | 0.51 | 0.36 | 3.19 | 0.68 | 0.45 | 0.19 | −0.02 | −0.15 |
| PVA13K98 | 0.43 | 0.17 | 3.42 | 1.65 | 0.5 | 0.76 | 0.02 | 0.26 |
| PVA31K98 | 0.41 | 0.23 | 6.03 | 1.19 | 0.26 | 0.14 | −0.03 | −0.05 |
| PVA85K99 | 0.28 | 0.1 | 4.7 | 0.82 | 0.53 | 0.77 | 0.06 | 0.18 |

Figure 7A:
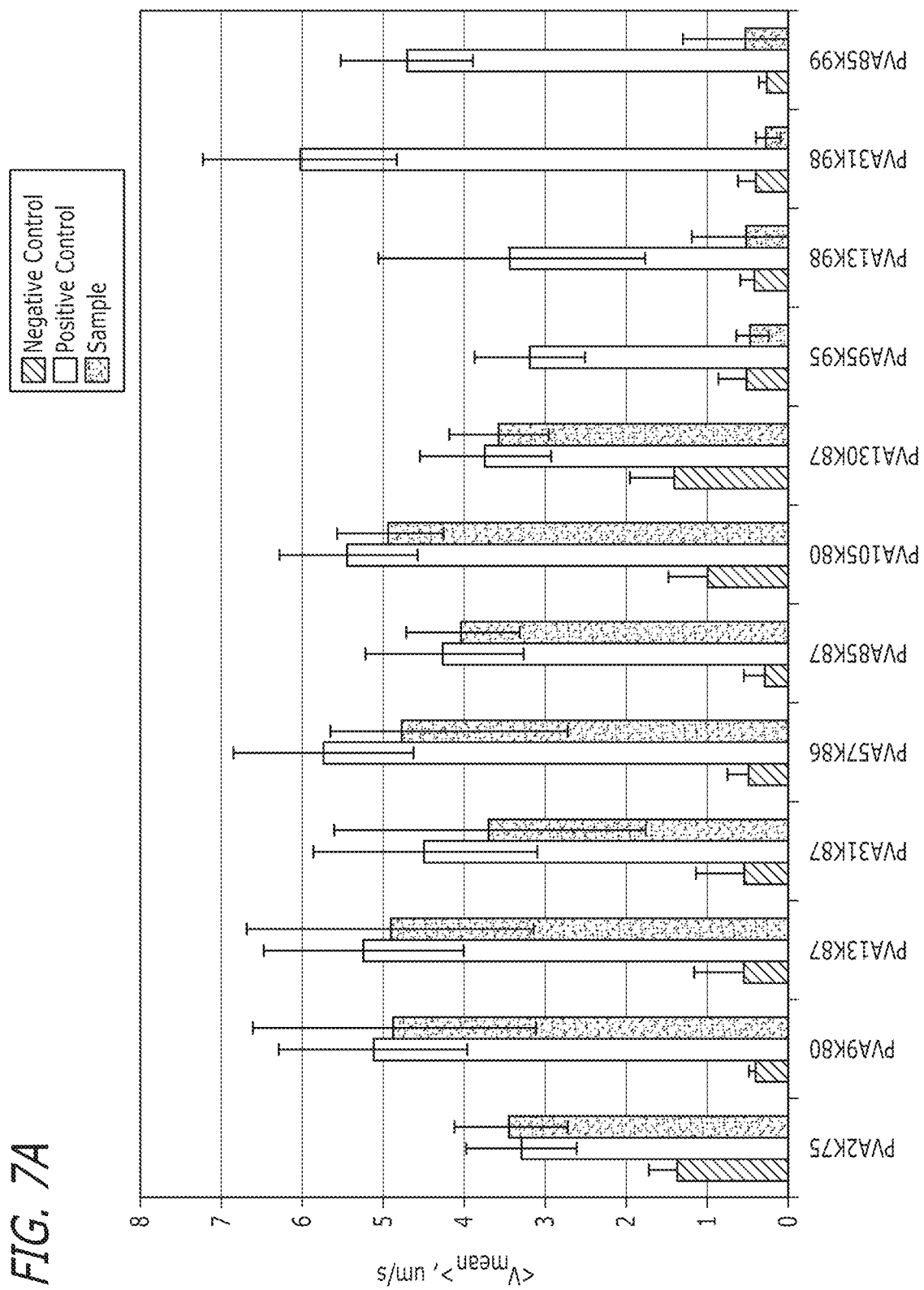
FIG. 7A is a plot showing the ensemble averaged velocity $<V_{mean}>$ in human cervicovaginal mucus (CVM) for PSCOO⁻ particles coated with various poly(vinyl alcohols) (PVAs) according to one set of embodiments.

It was discovered that nanoparticles incubated in the presence of certain (but, interestingly, not all) PVA transported through CVM at the same rate or nearly the same velocity as the positive control. Specifically, the particles stabilized with PVA2K75, PVA9K80, PVA13K87, PVA31K87, PVA57K86, PVA85K87, PVA105K80, and PVA130K87 exhibited $<V_{mean}>$ that significantly exceeded those of the negative controls and were indistinguishable, within experimental error, from those of the positive controls. The results are shown in Table 6 and FIG. 7A. For these samples, $<V_{mean}>_{rel}$ values exceeded 0.5, as shown in FIG. 7B.

Figure 7B:
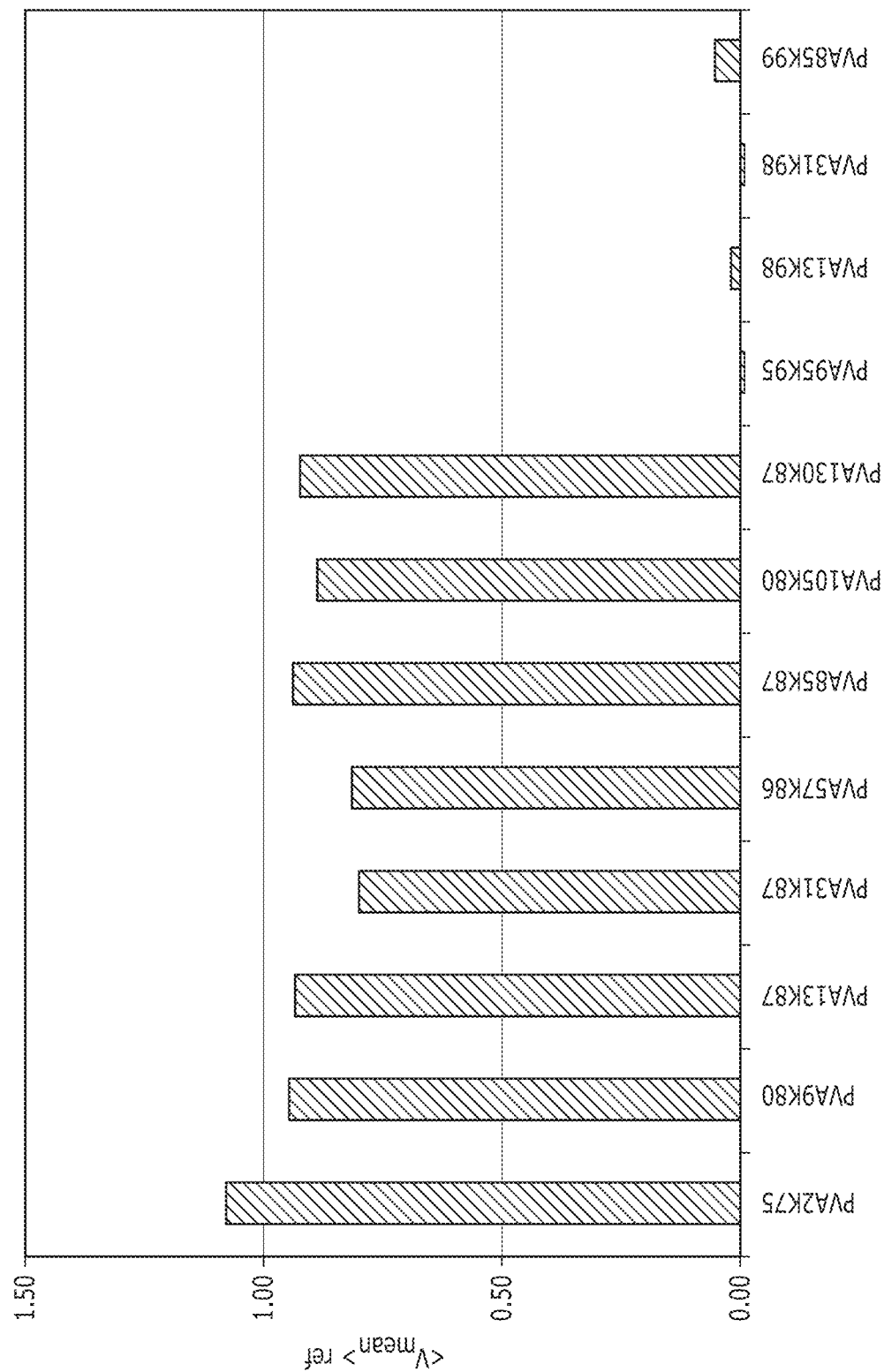
FIG. 7B is a plot showing the relative velocity $<V_{mean}>_{rel}$ in CVM for PSCOO⁻ particles coated with various PVAs according to one set of embodiments.

On the other hand, nanoparticles incubated with PVA95K95, PVA13K98, PVA31K98, and PVA85K99 were predominantly or completely immobilized as demonstrated by respective $<V_{mean}>_{rel}$ values of no greater than 0.1 (Table 6 and FIG. 7B).

Figure 8:
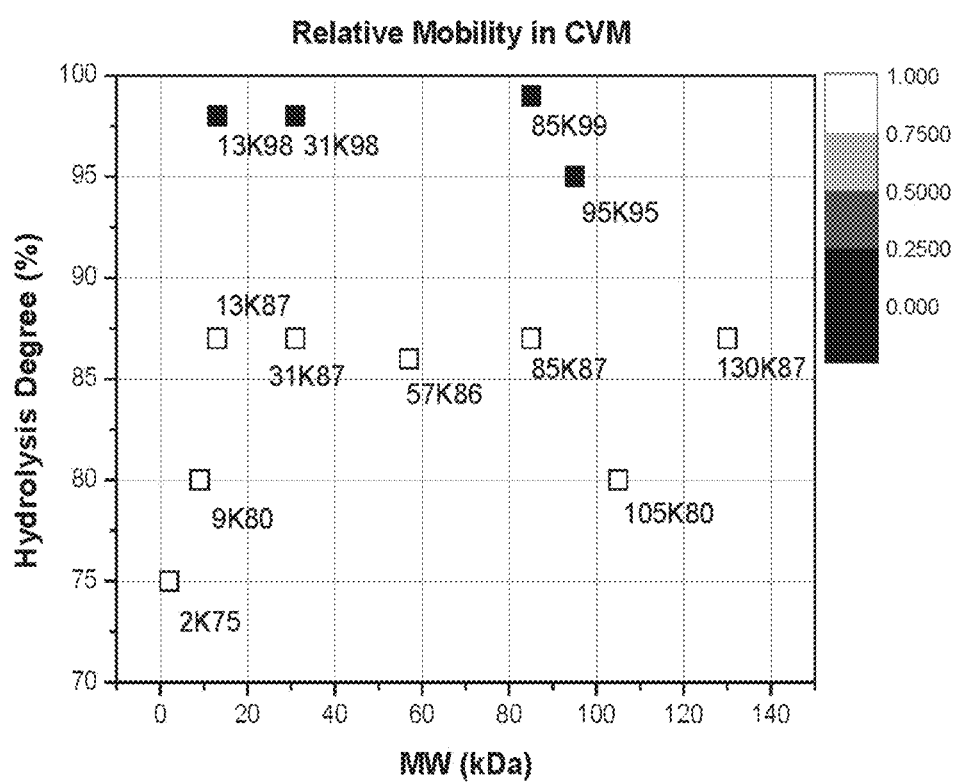
FIG. 8 is a plot showing relative velocity $<V_{mean}>_{rel}$ in CVM for PSCOO⁻ particles incubated with various PVAs mapped according to the PVA's molecular weight and degree of hydrolysis, according to one set of embodiments. Each data point represents $<V_{mean}>_{rel}$ for the particles stabilized with a specific PVA.
Figure 9A:
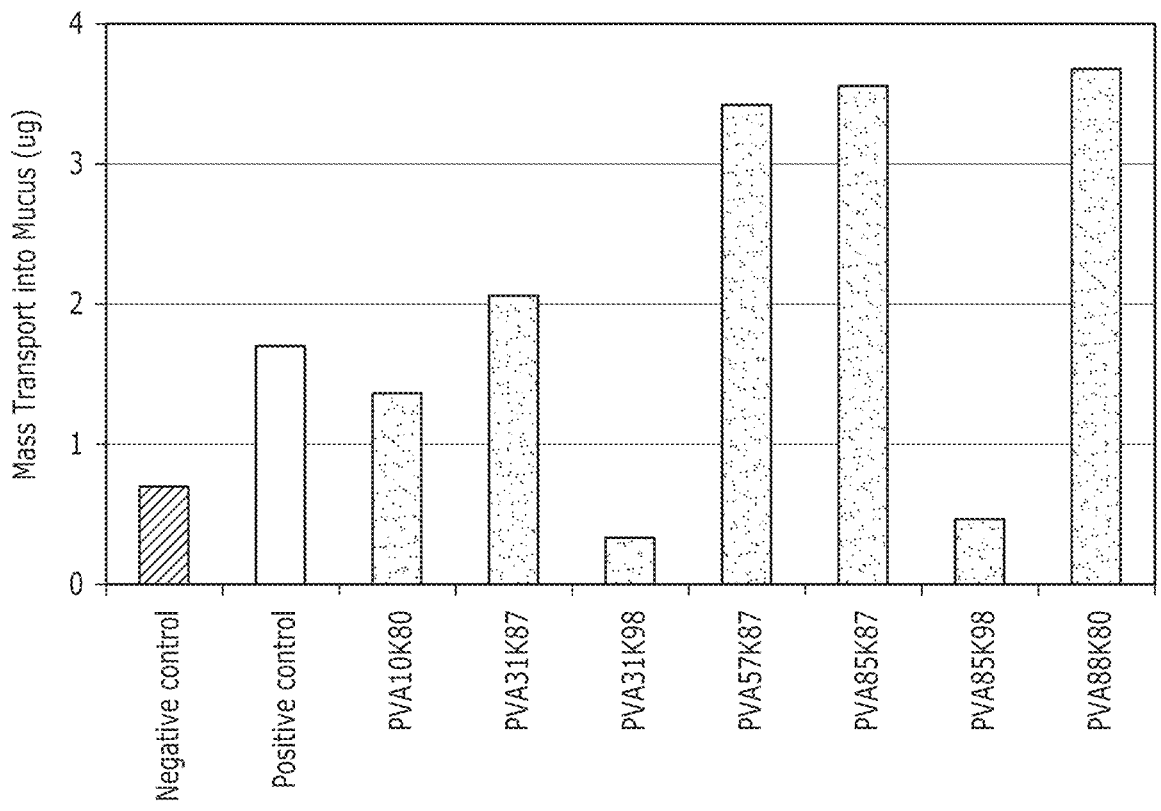
FIGS. 9A-9B are plots showing bulk transport in CVM in vitro of PSCOO nanoparticles coated with various PVAs, according to one set of embodiments. Negative controls are uncoated 200 nm PSCOO particles; Positive controls are 200 nm PSCOO particles coated with Pluronic® F127.
Figure 9B:
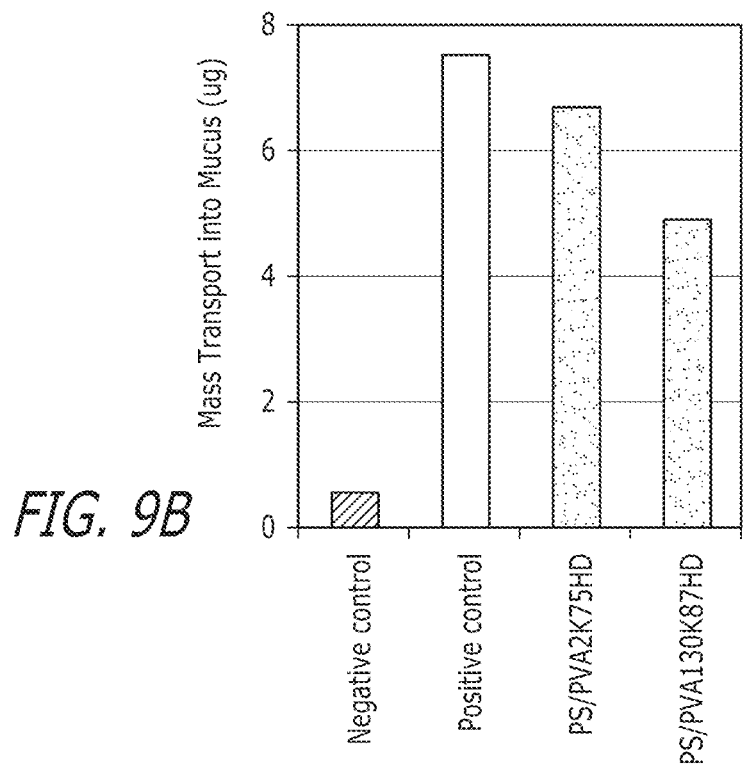

To identify the characteristics of the PVA that render particles mucus penetrating, $<V_{mean}>_{rel}$ of the nanoparticles prepared by incubation with the various PVAs was mapped with respect to MW and hydrolysis degree of the PVAs used (FIG. 8). It was concluded that at least those PVAs that have the hydrolysis degree of less than 95% rendered the nanocrystals mucus-penetrating. Without wishing to be bound by any theory, it is believed that the unhydrolyzed (vinyl acetate) units of PVA can provide effective hydrophobic association with the surface of the core particles if the content of these segments in the PVA is sufficient (e.g., greater than 5% in some embodiments); while the hydrophilic (vinyl alcohol) units of PVA present at the surface of the mucus. The sample is then spun to remove mucins and other non-soluble components. The amount of drug in the extracted sample can then be quantified using HPLC. The results of these experiments are in good agreement with those of the microscopy method, showing clear differentiation in transport between positive (mucus-penetrating particles) and negative controls (conventional particles). The bulk transport results for PSCOO nanoparticles incubated with the various PVAs are shown in FIG. 9. These results corroborate microscopy/particle tracking findings with PSCOO nanoparticles incubated with the various PVAs and demonstrate the incubating nanoparticles with partially hydrolyzed PVAs enhances mucus penetration.

Example 5

The following describes a non-limiting example of a method of forming mucus-penetrating particles by an emulsification process in the presence of certain poly(vinyl alcohol) polymers (PVA). Polylactide (PLA), a biodegradable pharmaceutically relevant polymer was used as a material to form the core particle via an oil-in-water emulsification process. The PVAs acted as emulsion surface-altering agents and surface-altering agents forming coatings around the produced core particles. PVA of various molecular weights (MW) and hydrolysis degrees were evaluated to determine effectiveness of the formed particles in penetrating mucus.

PLA solution in dichloromethane was emulsified in aqueous solution in the presence of various PVA to determine whether certain PVAs can physically (non-covalently) coat the surface of generated nanoparticles with a coating that would lead to rapid particle penetration in mucus. In these experiments, the PVA acted as an surfactant that forms a stabilizing coating around droplets of emulsified organic phase that, upon solidification, form the core particles The resulting particles were tested for their mobility in mucus, although in other embodiments, PVA may be exchanged with other surface-altering agents that can increase mobility of the particles in mucus. The PVAs tested ranged in the average molecular weight from 2 kDa to 130 kDa and in the average hydrolysis degree from 75% to 99+%. The PVAs that were tested are listed in Table 1, shown above.

The emulsification-solvent evaporation process was as follows: Approximately 0.5 mL of 20-40 mg/ml solution of PLA (Polylactide grade 100DL7A, purchased from Surmodics) in dichloromethane was emulsified in approximately 4 mL of an aqueous PVA solution (0.5-2 wt %) by sonication to obtain a stable emulsion with the target number-average particle size of <500 nm. Obtained emulsions were immediately subjected to exhaustive rotary evaporation under reduced pressure at room temperature to remove the organic solvent. Obtained suspensions were filtered through 1 micron glass fiber filters to remove any agglomerates. Table 7 lists the particle size characteristics of the nanosuspensions obtained by this emulsification procedure with the various PVA. In all cases, a fluorescent organic dye Nile Red was added to the emulsified organic phase to fluorescently label the resulting particles.

TABLE 7

Particle size measured by DLS in nanosuspensions obtained by the emulsification process with various PVA.

| PVA Grade | Z-Ave D (nm) | N-Ave D (nm) |
| --- | --- | --- |
| PVA2K75 | 186 | 156 |
| PVA10K80 | 208 | 173 |
| PVA13K98 | 245 | 205 |
| PVA31K87 | 266 | 214 |
| PVA31K98 | 245 | 228 |
| PVA85K87 | 356 | 301 |
| PVA85K99 | 446 | 277 |

TABLE 7-continued

Particle size measured by DLS in nanosuspensions obtained by the emulsification process with various PVA.

| PVA Grade | Z-Ave D (nm) | N-Ave D (nm) |
| --- | --- | --- |
| PVA95K95 | 354 | 301 |
| PVA105K80 | 361 | 300 |
| PVA130K87 | 293 | 243 |

The mobility and distribution of the produced nanoparticles in human cervicovaginal mucus (CVM) were characterized using fluorescence microscopy and multiple particle tracking software. In a typical experiment, ≤0.5 uL of a nanosuspension (diluted if necessary to the PVA concentration of ~0.5%) was added to 20 μl of fresh CVM along with controls. Conventional nanoparticles (200 nm blue fluorescent carboxylate-modified polystyrene microspheres from Invitrogen) were used as a negative control to confirm the barrier properties of the CVM samples. Yellow-green fluorescent polystyrene nanoparticles covalently coated with PEG 2 kDa were used as a positive control with well-established MPP behavior. Using a fluorescent microscope equipped with a CCD camera, 15 s movies were captured at a temporal resolution of 66.7 ms (15 frames/s) under 100× magnification from several areas within each sample for each type of particles: sample (observed through a Texas Red filter set due to the encapsulated Nile Red), negative control (observed through a DAPI filter set), and positive control (observed through a FITC filter set). Next, using an advanced image processing software, individual trajectories of multiple particles were measured over a time-scale of at least 3.335 s (50 frames). Resulting transport data are presented here in the form of trajectory-mean velocity $V_{mean}$, i.e., velocity of an individual particle averaged over its trajectory, and ensemble-average velocity $<V_{mean}>$, i.e., $V_{mean}$ averaged over an ensemble of particles. To enable easy comparison between different samples and normalize velocity data with respect to natural variability in penetrability of CVM samples, ensemble-average (absolute) velocity is then converted to relative sample velocity $<V_{mean}>_{rel}$ according to the formula shown in Equation 1. Multiple particle tracking confirmed that in all tested CVM samples the negative controls were constrained, while the positive controls were mobile as demonstrated by the differences in $<V_{mean}>$ for the positive and negative controls (Table 8).

TABLE 8

Transport of PLA nanoparticles obtained by the emulsification process with various PVAs (sample) and controls in CVM: Ensemble-average velocity $<V_{mean}>$ (um/s) and relative sample velocity $<V_{mean}>_{rel}$.

| Stabilizer | Negative Control | | Positive Control | | Sample | | Sample (relative) | |
| --- | --- | --- | --- | --- | --- | --- | --- | --- |
| | $<V_{mean}>$ | SD | $<V_{mean}>$ | SD | $<V_{mean}>$ | SD | $<V_{mean}>_{rel}$ | SD |
| PVA2K75 | 0.95 | 0.64 | 5.5 | 0.92 | 5.51 | 1.2 | 1.00 | 0.39 |
| PVA9K80 | 0.72 | 0.47 | 5.61 | 0.79 | 4.6 | 1.5 | 0.79 | 0.35 |
| PVA31K87 | 0.63 | 0.60 | 4.94 | 1.50 | 3.36 | 1.84 | 0.63 | 0.51 |
| PVA85K87 | 0.57 | 0.4 | 4.49 | 1.21 | 2.9 | 1.56 | 0.59 | 0.45 |
| PVA105K80 | 0.69 | 0.56 | 4.85 | 1.54 | 3.55 | 1.26 | 0.69 | 0.43 |
| PVA130K87 | 0.95 | 0.54 | 4.98 | 1.25 | 3.46 | 1.23 | 0.62 | 0.39 |
| PVA95K95 | 1.39 | 1.28 | 5.72 | 1.57 | 1.63 | 1.5 | 0.06 | 0.46 |
| PVA13K98 | 1.02 | 0.49 | 5.09 | 0.99 | 2.61 | 1.54 | 0.39 | 0.41 |
| PVA31K98 | 1.09 | 0.6 | 5.09 | 0.9 | 2.6 | 1.13 | 0.38 | 0.34 |
| PVA85K99 | 0.47 | 0.33 | 5.04 | 2.2 | 0.81 | 0.77 | 0.07 | 0.19 |

Figure 10A:
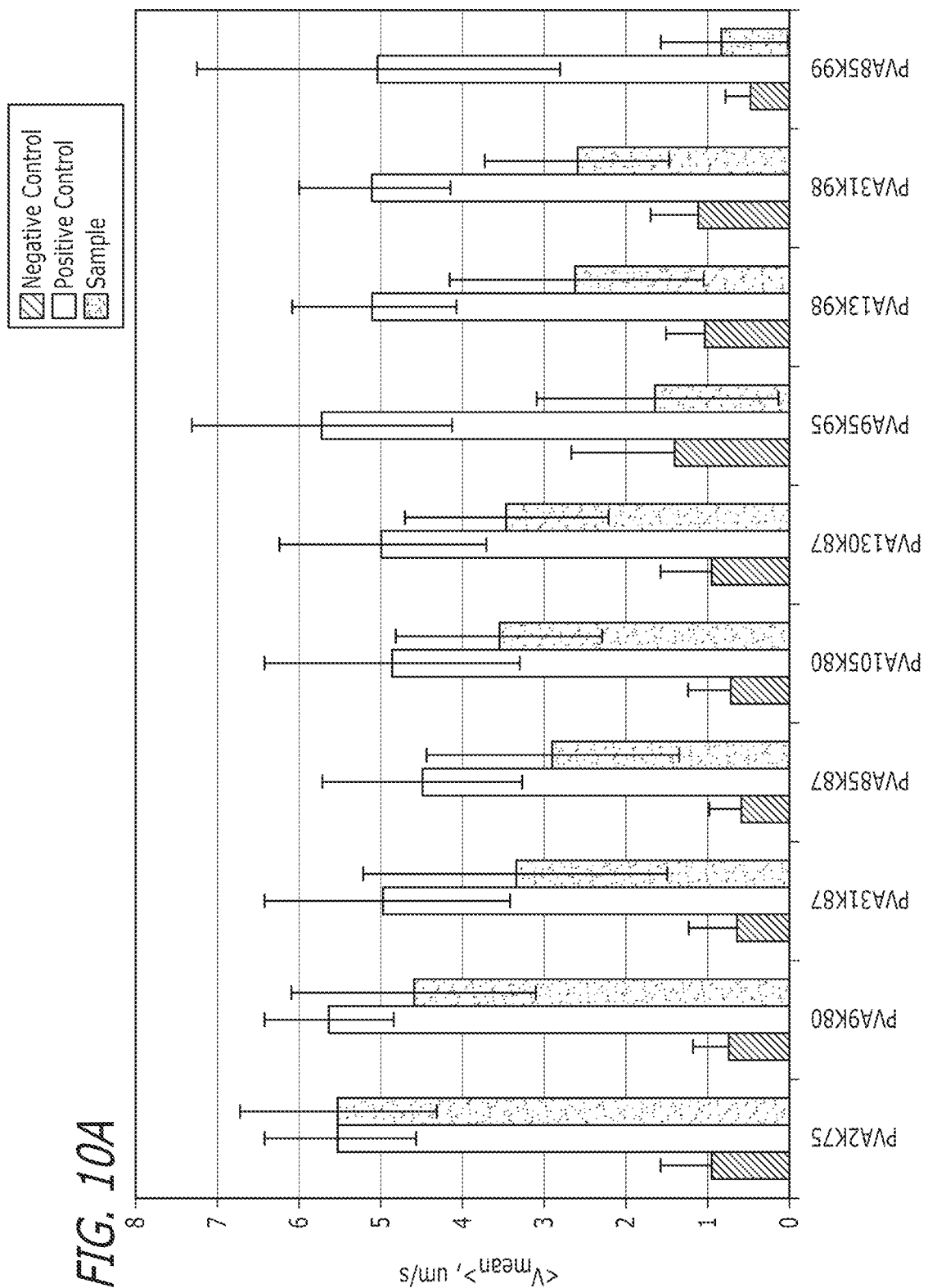
FIGS. 10A-10B are plots showing ensemble-average velocity $<V_{mean}>$ (FIG. 10A) and relative sample velocity $<V_{mean}>_{rel}$ (FIG. 10B) for poly(lactic acid) (PLA) nanoparticles (sample) prepared by emulsification with various PVAs as measured by multiple-particle tracking in CVM, according to one set of embodiments.

It was discovered that nanoparticles prepared in the presence of certain (but, interestingly, not all) PVA transported through CVM at the same rate or nearly the same velocity as the positive control. Specifically, the particles stabilized with PVA2K75, PVA9K80, PVA13K87, PVA31K87, PVA85K87, PVA105K80, and PVA130K87 exhibited $<V_{mean}>$ that significantly exceeded those of the negative controls and were indistinguishable, within experimental error, from those of the positive controls, as shown in Table 8 and FIG. 10A. For these samples, $<V_{mean}>_{rel}$ values exceeded 0.5, as shown in FIG. 10B.

Figure 10B:
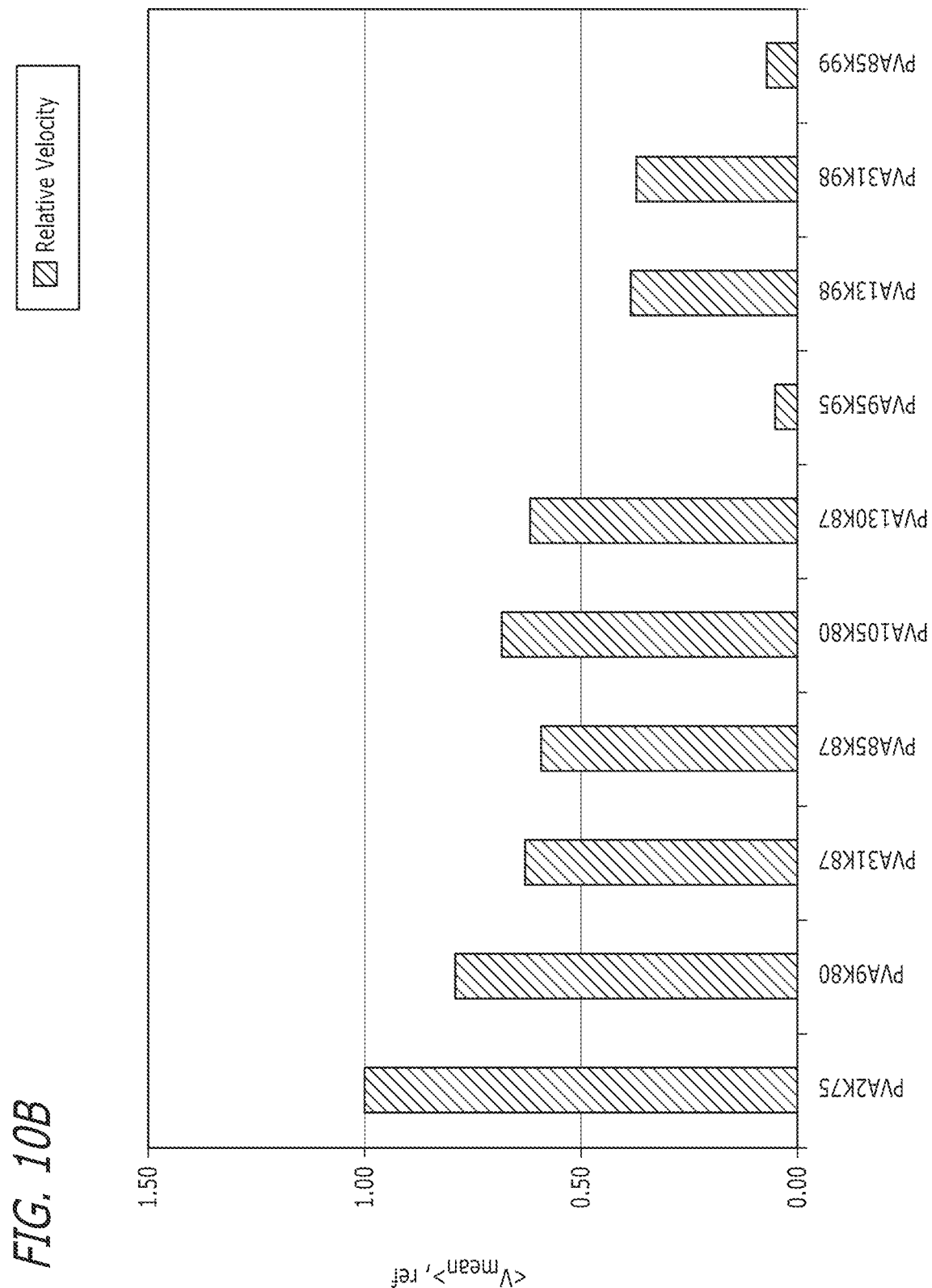
Figure 11:
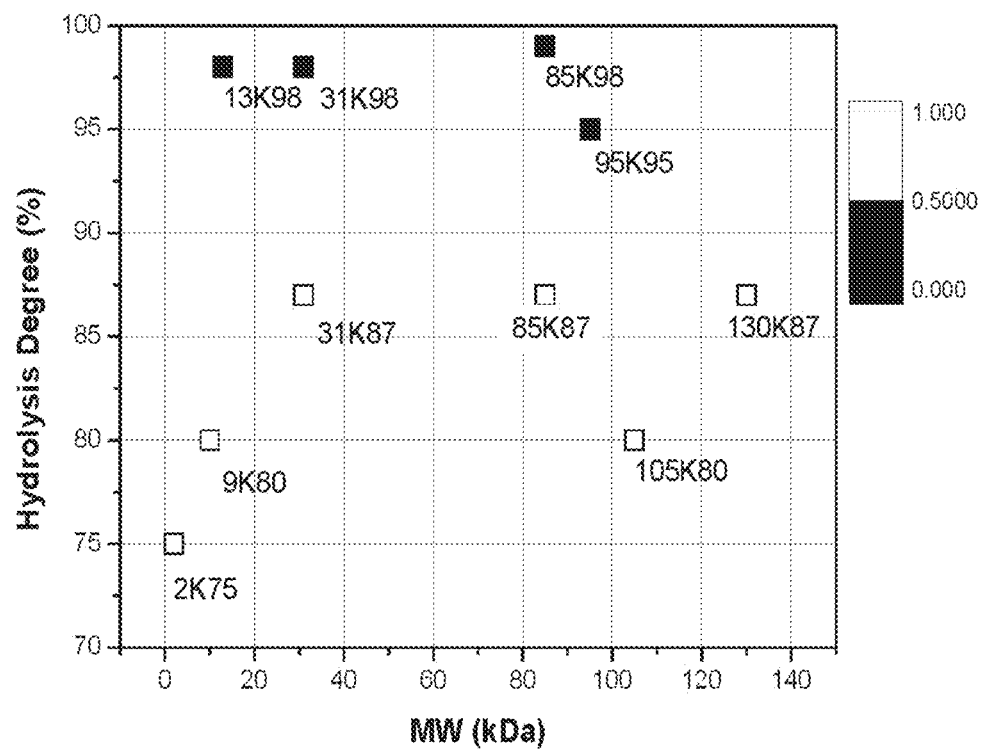
FIG. 11 is a plot showing relative velocity $<V_{mean}>_{rel}$ in CVM for PLA nanoparticles prepared by emulsification with various PVA's mapped according to the PVA's molecular weight and degree of hydrolysis, according to one set of embodiments. Each data point represents $<V_{mean}>_{rel}$ of the particles stabilized with a specific PVA.

On the other hand, pyrene nanoparticles obtained with PVA95K95, PVA13K98, PVA31K98, and PVA85K99 were predominantly or completely immobilized as demonstrated by respective $<V_{mean}>_{rel}$ values of no greater than 0.4 (Table 8 and FIG. 10B). To identify the characteristics of the PVA that render particles mucus penetrating, $<V_{mean}>_{rel}$ of the nanoparticles prepared with the various PVAs was mapped with respect to MW and hydrolysis degree of the PVAs used (Table 6 and FIG. 7B). It was concluded that at least those PVAs that have the hydrolysis degree of less than 95% rendered the nanocrystals mucus-penetrating. Without wishing to be bound by any theory, it is believed that the unhydrolyzed (vinyl acetate) units of PVA can provide effective hydrophobic association with the surface of the core particles if the content of these segments in the PVA is sufficient (e.g., greater than 5% in some embodiments); while the hydrophilic (vinyl alcohol) units of PVA present at the surface of the coated particles render them hydrophilic and can shield the coated particles from adhesive interactions with mucus.

Example 6

The following describes a non-limiting example of a method of forming mucus-penetrating non-polymeric solid particles by milling in the presence of certain poly(vinyl alcohol) polymers (PVA). Pyrene, a model hydrophobic compound, was used as the core particle processed by a milling. The PVA acted as milling aids facilitating particle size reduction of the core particles and surface-altering agents forming coatings around the core particles. PVA of various molecular weights (MW) and hydrolysis degrees were evaluated to determine effectiveness of the milled particles in penetrating mucus.

Pyrene was milled in aqueous dispersions in the presence of various PVA to determine whether PVAs of certain MW and hydrolysis degree can: 1) aid particle size reduction to several hundreds of nanometers and 2) physically (non-covalently) coat the surface of generated nanoparticles with a mucoinert coating that would minimize particle interactions with mucus constituents and prevent mucus adhesion. In these experiments, the PVA acted as a coating around the core particles, and the resulting particles were tested for their mobility in mucus. The PVAs tested ranged in the average molecular weight from 2 kDa to 130 kDa and in the average hydrolysis degree from 75% to 99+%. The PVAs that were tested are listed in Table 1, shown above. A variety of other polymers, oligomers, and small molecules listed in Table, including pharmaceutically relevant excipients such as polyvinylpyrrolidones (Kollidon), hydroxypropyl methylcellulose (Methocel), Tween, Span, etc., were tested in a similar manner.

TABLE 9

Other surface-altering agents tested with pyrene as a model compound.

| Chemical Family | Grades |
| --- | --- |
| Polyvinylpyrrolidone (PVP) | Kollidon 17 |
| | Kollidon 25 |
| | Kollindon 30 |
| PVA-poly(ethylene glycol) graft-copolymer | Kollicoat IR |
| Hydroxypropyl methylcellulose (HPMC) | Methocel E50 |
| | Methocel K100 |
| Non-ionic polyoxyethylene surfactants | Solutol HS 15 |
| | Span 20 |
| | Span 80 |
| | Triton X100 |
| | Tween 20 |
| | Tween 80 |
| | Tyloxapol |
| Non-ionic small molecule surfactants | Octyl glucoside |
| Ionic small molecule surfactants | Cetytrimethylammonium bromide (CTAB) |
| | Sodium dodecyl sulfate (SDS) |

An aqueous dispersion containing pyrene and one of the surface-altering agents listed above was stirred with milling media until particle size was reduced below 500 nm (as measured by dynamic light scattering). Table 10 lists particle size characteristics of pyrene particles obtained by milling in the presence of the various surface-altering agents. When Span 20, Span 80, or Octyl glucoside was used as surface-altering agents, stable nanosuspensions could not be obtained. Therefore, these surface-altering agents were excluded from further investigation due to their inability to effectively aid particle size reduction.

TABLE 10

Particle size measured by DLS in nanosuspensions obtained by milling of pyrene with various surface-altering agents.

| Stabilizer | Z-Ave D (nm) | N-Ave D (nm) |
| --- | --- | --- |
| PVA2K75 | 340 | 301 |
| PVA9K80 | 380 | 337 |
| PVA13K87 | 375 | 326 |
| PVA13K98 | 396 | 314 |
| PVA31K87 | 430 | 373 |
| PVA31K98 | 344 | 220 |
| PVA85K87 | 543 | 434 |
| PVA85K99 | 381 | 236 |
| PVA95K95 | 534 | 392 |
| PVA130K87 | 496 | 450 |
| Kollidon 17 | 237 | 163 |
| Kollidon 25 | 307 | 210 |
| Kollindon 30 | 255 | 185 |
| Kollicoat IR | 364 | 192 |
| Methocel E50 | 244 | 160 |
| Methocel K100 | 375 | 216 |
| Tween 20 | 567 | 381 |
| Tween 80 | 553 | 322 |
| Solutol HS | 576 | 378 |
| Triton X100 | 410 | 305 |
| Tyloxapol | 334 | 234 |
| Cremophor RH40 | 404 | 373 |
| Span 20 | not measurable* | |
| Span 80 | not measurable* | |
| Octyl glucoside | not measurable* | |
| SDS | 603 | 377 |
| CTAB | 432 | 354 |

*milling with Span 20, Span 80, Octyl glucoside failed to effectively reduce pyrene particle size and produce stable nanosuspensions.

The mobility and distribution of the produced pyrene nanoparticles in human cervicovaginal mucus (CVM) were characterized using fluorescence microscopy and multiple particle tracking software. In a typical experiment, ≤0.5 uL of a nanosuspension (diluted if necessary to the surfactant concentration of ~1%) was added to 20 µl of fresh CVM along with controls. Conventional nanoparticles (200 nm yellow-green fluorescent carboxylate-modified polystyrene microspheres from Invitrogen) were used as a negative control to confirm the barrier properties of the CVM samples. Red fluorescent polystyrene nanoparticles covalently coated with PEG 5 kDa were used as a positive control with well-established MPP behavior. Using a fluorescent size (data not shown). Such aggregation is indicative of mucoadhesive behavior and effectively prevents mucus penetration. Therefore, further quantitative analysis of particle mobility was deemed unnecessary. Similarly to the positive control, all other tested pyrene/stabilizer systems achieved a fairly uniform distribution in CVM. Multiple particle tracking confirmed that in all tested CVM samples the negative controls were constrained, while the positive controls were mobile as demonstrated by the differences in $<V_{mean}>$ for the positive and negative controls (Table).

TABLE 11

Transport of pyrene nanoparticles (sample) obtained with various surface-altering agents and controls in CVM: Ensemble-average velocity $<V_{mean}>$ (um/s) and relative sample velocity $<V_{mean}>_{rel}$.

| Stabilizer | Negative Control | | Positive Control | | Sample | | Sample (relative) | |
|---|---|---|---|---|---|---|---|---|
| | $<V_{mean}>$ | SD | $<V_{mean}>$ | SD | $<V_{mean}>$ | SD | $<V_{mean}>_{rel}$ | SD |
| PVA2K75 | 0.4 | 0.24 | 5.73 | 0.73 | 4.73 | 1.08 | 0.81 | 0.24 |
| PVA9K80 | 0.36 | 0.20 | 6.00 | 0.70 | 6.19 | 1.13 | 1.03 | 0.24 |
| PVA13K87 | 1.01 | 1.21 | 5.09 | 0.98 | 4.54 | 1.03 | 0.87 | 0.51 |
| PVA31K87 | 1.28 | 1.14 | 4.88 | 0.6 | 4.57 | 1.123 | 0.91 | 0.55 |
| PVA85K87 | 1.05 | 0.9 | 4.1 | 0.57 | 3.3 | 0.98 | 0.74 | 0.51 |
| PVA130K87 | 0.51 | 0.82 | 5.29 | 0.73 | 4.12 | 1.49 | 0.76 | 0.40 |
| PVA95K95 | 0.4 | 0.27 | 4.53 | 1.03 | 0.67 | 0.6 | 0.07 | 0.16 |
| PVA13K98 | 0.61 | 0.42 | 2.13 | 0.99 | 1.29 | 0.57 | 0.45 | 0.56 |
| PVA31K98 | 0.68 | 0.87 | 5.77 | 1.24 | 2.69 | 2.02 | 0.39 | 0.45 |
| PVA85K99 | 0.43 | 0.23 | 5.42 | 0.97 | 2.23 | 1.60 | 0.36 | 0.33 |
| Kollicoat IR | 0.62 | 0.62 | 5.39 | 0.55 | 0.92 | 0.81 | 0.06 | 0.22 |
| Kollidon 17 | 1.69 | 1.8 | 5.43 | 0.98 | 0.82 | 0.59 | −0.23 | −0.52 |
| Kollidon 25 | 0.41 | 0.34 | 5.04 | 0.64 | 1.29 | 1.09 | 0.19 | 0.25 |
| Kollindon 30 | 0.4 | 0.2 | 4.28 | 0.57 | 0.35 | 0.11 | −0.01 | 0.06 |
| Methocel E50* | | | | | | | | |
| Methocel K100* | | | | | | | | |
| Tween 20 | 0.77 | 0.93 | 5.35 | 1.76 | 1.58 | 2.02 | 0.18 | 0.49 |
| Tween 80 | 0.46 | 0.34 | 3.35 | 1.89 | 0.94 | 0.5 | 0.17 | 0.24 |
| Solutol HS | 0.42 | 0.13 | 3.49 | 0.5 | 0.8 | 0.6 | 0.12 | 0.20 |
| Triton X100 | 0.26 | 0.13 | 4.06 | 1.11 | 0.61 | 0.19 | 0.09 | 0.07 |
| Tyloxapol | 0.5 | 0.5 | 3.94 | 0.58 | 0.42 | 0.23 | −0.02 | −0.16 |
| Cremophor RH40 | 0.48 | 0.21 | 3.2 | 0.97 | 0.49 | 0.24 | 0.00 | 0.12 |
| SDS | 0.3 | 0.12 | 5.99 | 0.84 | 0.34 | 0.15 | 0.01 | 0.03 |
| CTAB | 0.39 | 0.09 | 4.75 | 1.79 | 0.32 | 0.31 | −0.02 | −0.07 |

*Aggregated in CVM, hence not mucus-penetrating (velocity in CVM not measured)

microscope equipped with a CCD camera, 15 s movies were captured at a temporal resolution of 66.7 ms (15 frames/s) under 100× magnification from several areas within each sample for each type of particles: sample (pyrene), negative control, and positive control (natural blue fluorescence of pyrene allowed observing of pyrene nanoparticles separately from the controls). Next, using an advanced image processing software, individual trajectories of multiple particles were measured over a time-scale of at least 3.335 s (50 frames). Resulting transport data are presented here in the form of trajectory-mean velocity $V_{mean}$, i.e., velocity of an individual particle averaged over its trajectory, and ensemble-average velocity $<V_{mean}>$, i.e., $V_{mean}$ averaged over an ensemble of particles. To enable easy comparison between different samples and normalize velocity data with respect to natural variability in penetrability of CVM samples, ensemble-average (absolute) velocity is then converted to relative sample velocity $<V_{mean}>_{rel}$ according to the formula shown in Equation 1.

Figure 12A:
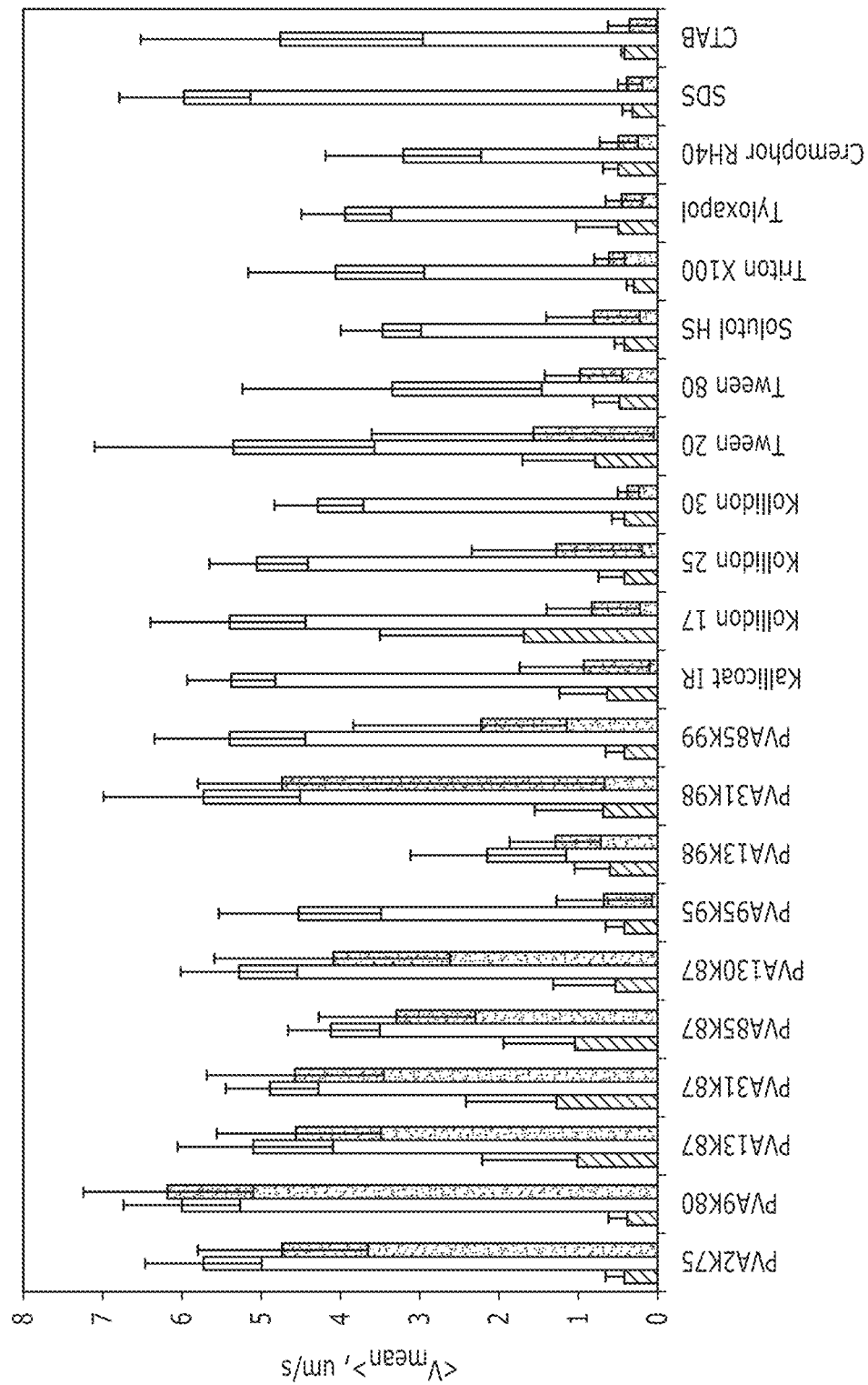
FIGS. 12A-12B are plots showing ensemble-average velocity $<V_{mean}>$ (FIG. 12A) and relative sample velocity $<V_{mean}>_{rel}$ (FIG. 12B) for pyrene nanoparticles (sample) and controls as measured by multiple-particle tracking in CVM, according to one set of embodiments.

Prior to quantifying mobility of pyrene particles, their spatial distribution in the mucus sample was assessed visually. It was found that pyrene/Methocel nanosuspensions did not achieve uniform distribution in CVM and strongly aggregated into domains much larger than the mucus mesh It was discovered that nanoparticles obtained in the presence of certain (but, interestingly, not all) PVA transported through CVM at the same rate or nearly the same velocity as the positive control. Specifically, pyrene nanoparticles stabilized with PVA2K75, PVA9K80, PVA13K87, PVA31K87, PVA85K87, and PVA130K87 exhibited $<V_{mean}>$ that significantly exceeded those of the negative controls and were indistinguishable, within experimental error, from those of the positive controls, as shown in Table 11 and FIG. 12A. For these samples, $<V_{mean}>_{rel}$ values exceeded 0.5, as shown in FIG. 12B.

Figure 12B:
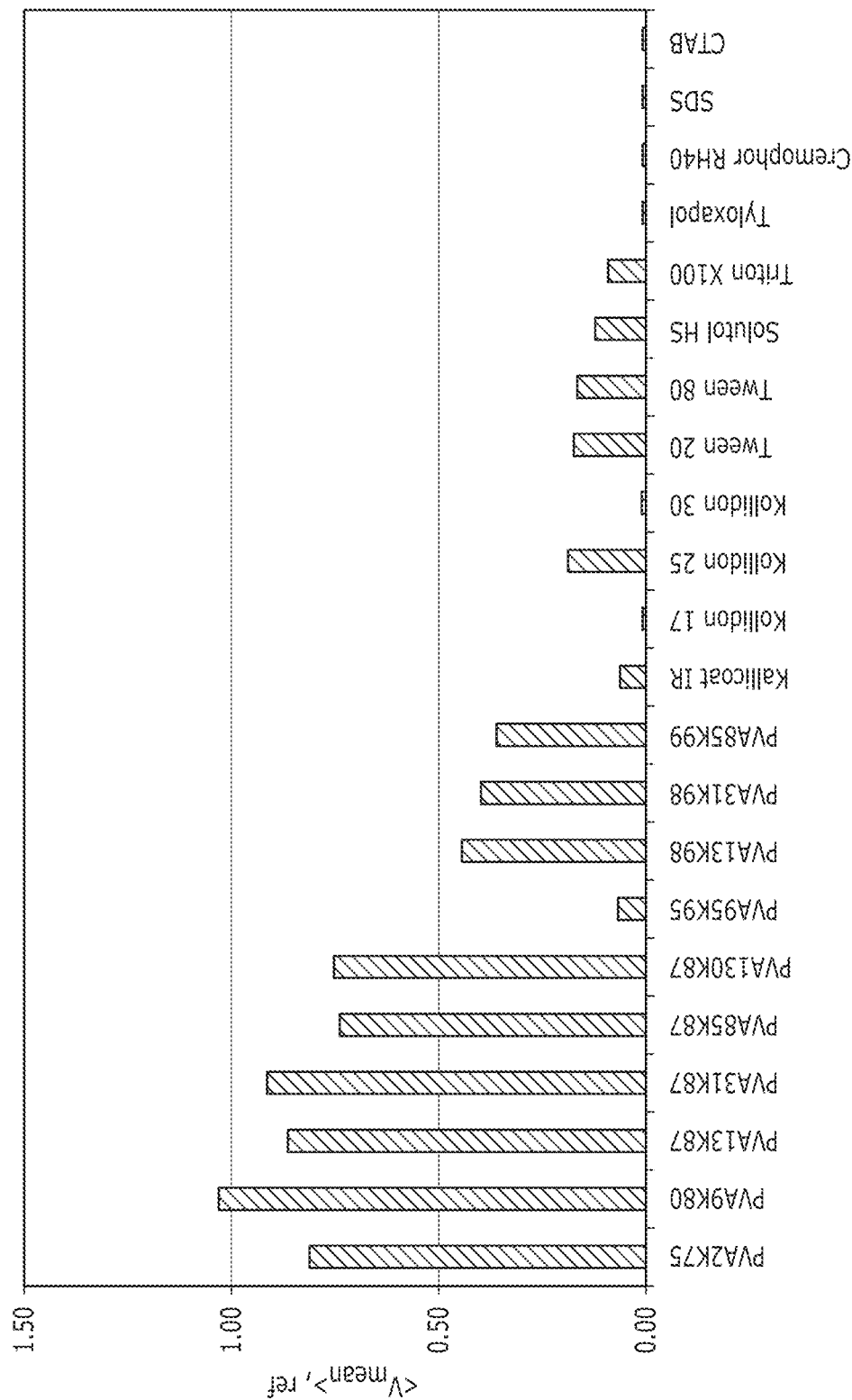
Figure 13C:
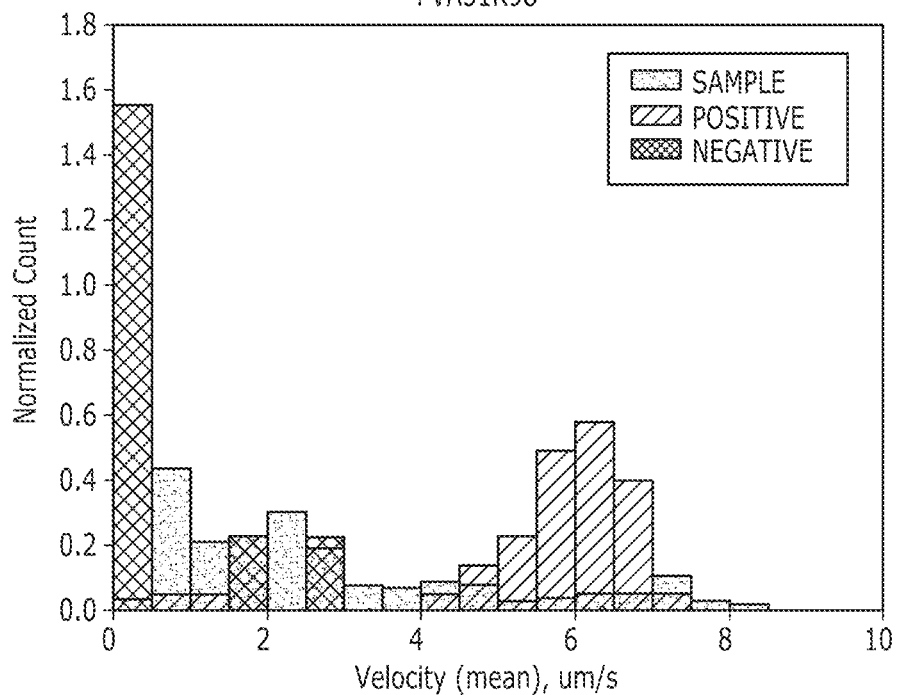
Figure 13D:
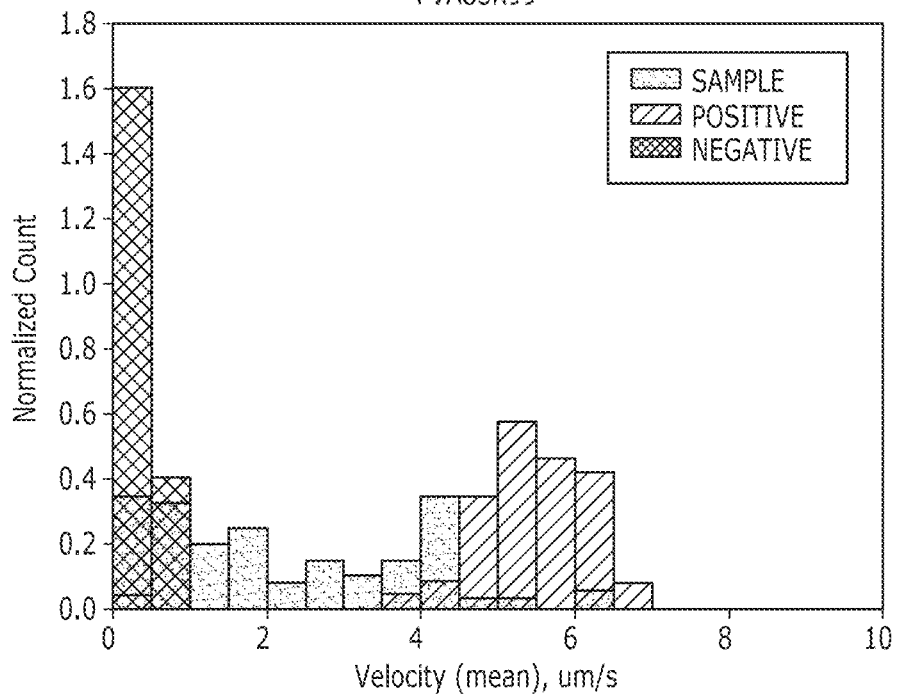
Figure 13E:
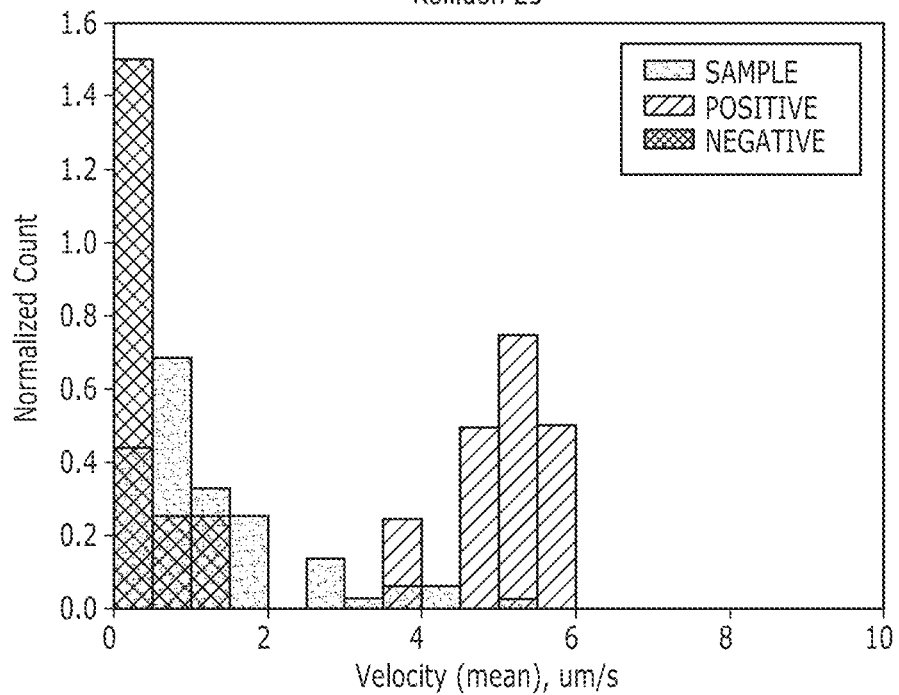
Figure 13F:
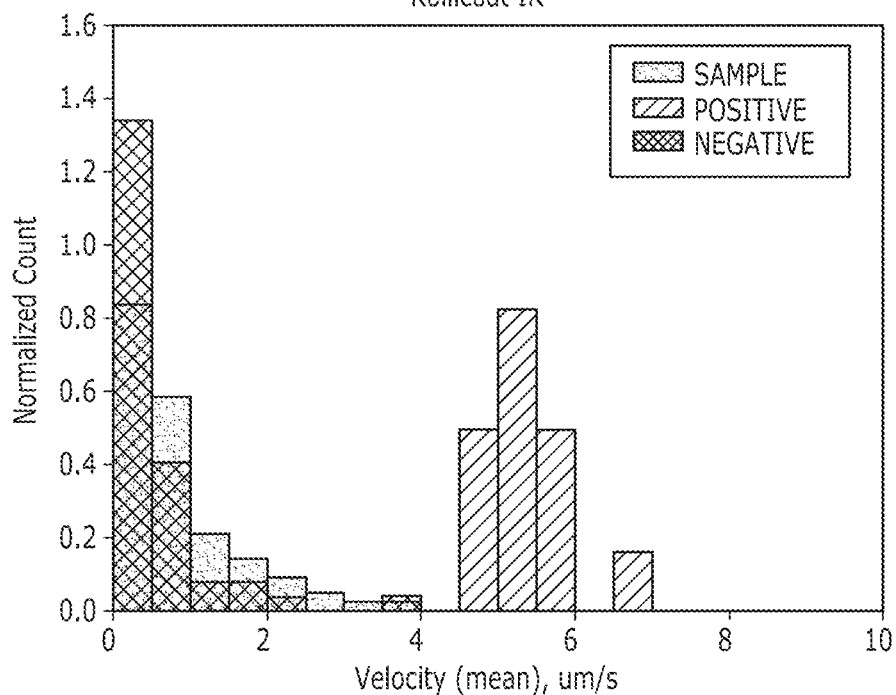

On the other hand, pyrene nanoparticles obtained with the other surface-altering agents, including PVA95K95, PVA13K98, PVA31K98, and PVA85K99, were predominantly or completely immobilized as demonstrated by respective $<V_{mean}>_{rel}$ values of no greater than 0.5 and, with most surface-altering agents, no greater than 0.4 (Table 11 and FIG. 12B). Additionally, FIGS. 13A-13F are histograms showing distribution of $V_{mean}$ within an ensemble of particles. These histograms illustrate muco-diffusive behavior of samples stabilized with PVA2K75 and PVA9K80 (similar histograms were obtained for samples stabilized with PVA13K87, PVA31K87, PVA85K87, and PVA130K87, but are not shown here) as opposed to muco-adhesive behavior of samples stabilized with PVA31K98, PVA85K99, Kollidon 25, and Kollicoat IR (chosen as representative mucoadhesive samples).

Figure 14:
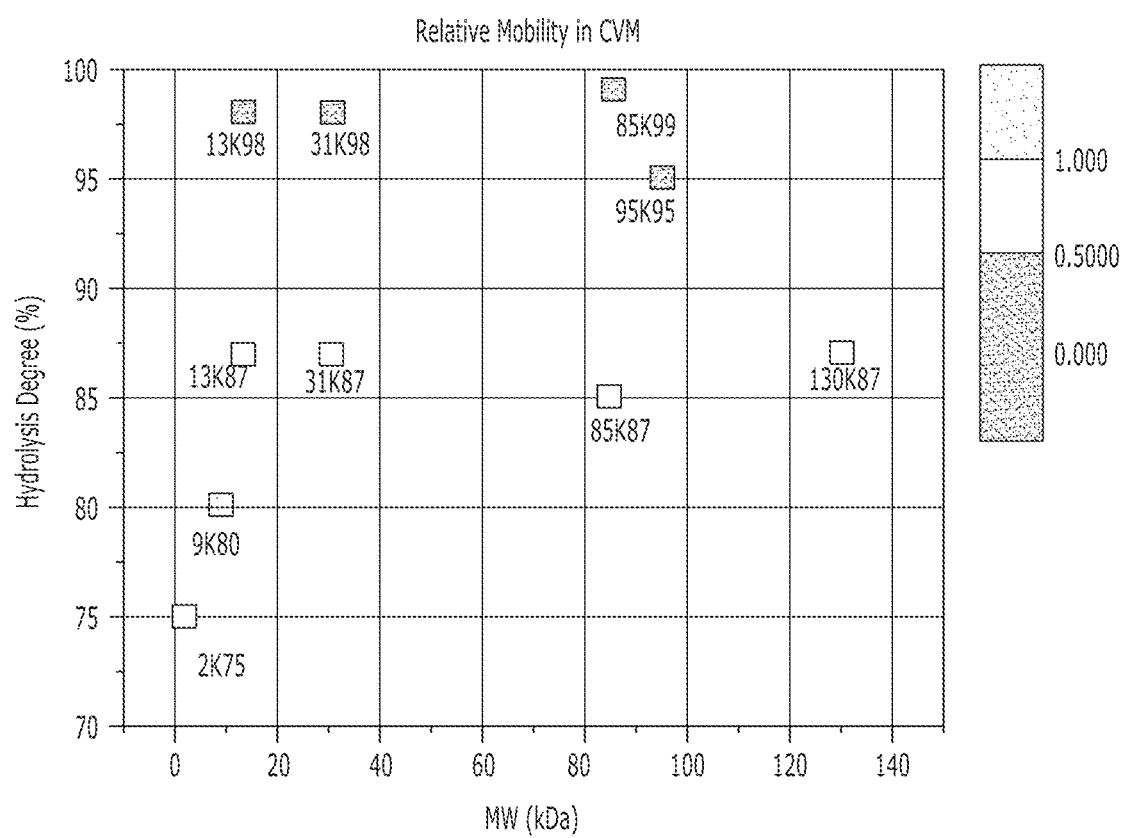
FIG. 14 is a plot of relative velocity $<V_{mean}>_{rel}$ for pyrene nanocrystals coated with PVA in CVM mapped according to the PVA's molecular weight and degree of hydrolysis according to one set of embodiments.

To identify the characteristics of the PVA that render pyrene nanocrystals mucus penetrating, $<V_{mean}>_{rel}$ of the pyrene nanocrystals stabilized with various PVAs was mapped with respect to MW and hydrolysis degree of the PVAs used (FIG. 14). It was concluded that at least those PVAs that have the hydrolysis degree of less than 95% rendered the nanocrystals mucus-penetrating. Without wishing to be bound by any theory, it is believed that the unhydrolyzed (vinyl acetate) segments of PVA can provide effective hydrophobic association with the surface of the core particles if the content of these segments in the PVA is sufficient (e.g., greater than 5% in some embodiments); while the hydrophilic (vinyl alcohol) segments of PVA present at the surface of the coated particles render them hydrophilic and can shield the coated particles from adhesive interactions with mucus.

Example 7

This example shows an improved ophthalmic delivery of a pharmaceutical agent from mucus-penetrating particles comprised of a polymeric core encapsulating the pharmaceutical agent and mucus-penetrating particles comprised of a drug core without any polymeric carrier.

Figure 17A:
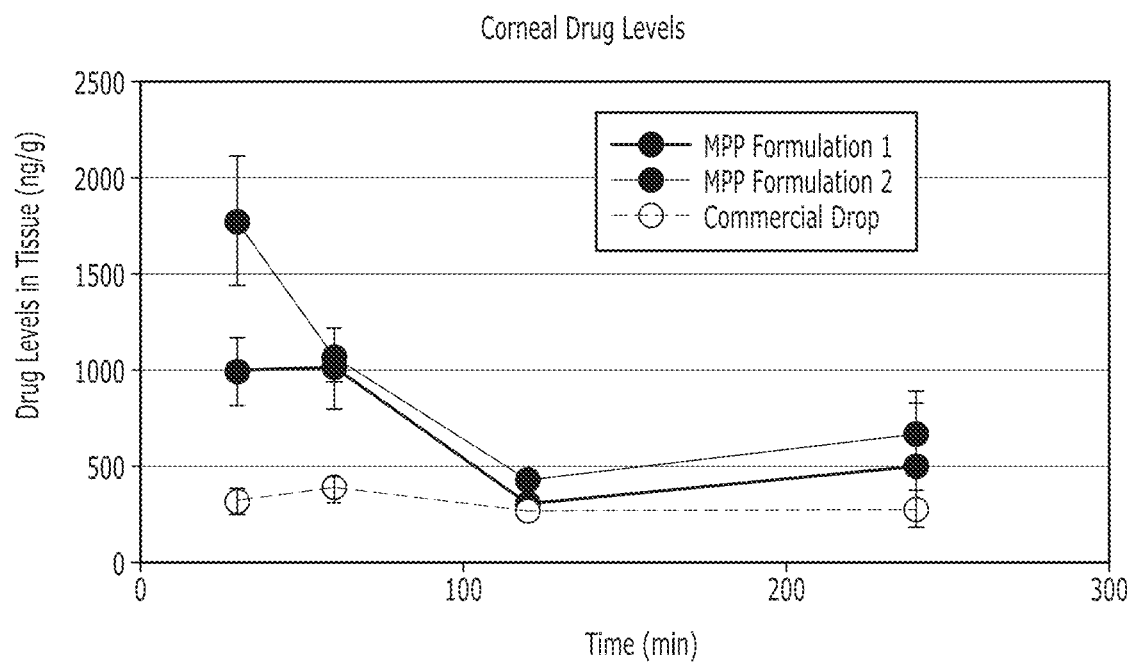
FIGS. 17A-17B are plots showing that the levels of loteprednol etabonate (LE) in the cornea after an administration of LE MPP formulations are higher than the levels of LE after an administration of a commercial formulation in an ocular PK study, according to one set of embodiments. Equivalent drug doses were topically administered to the eyes of NZW rabbit at t=0.
Figure 17B:
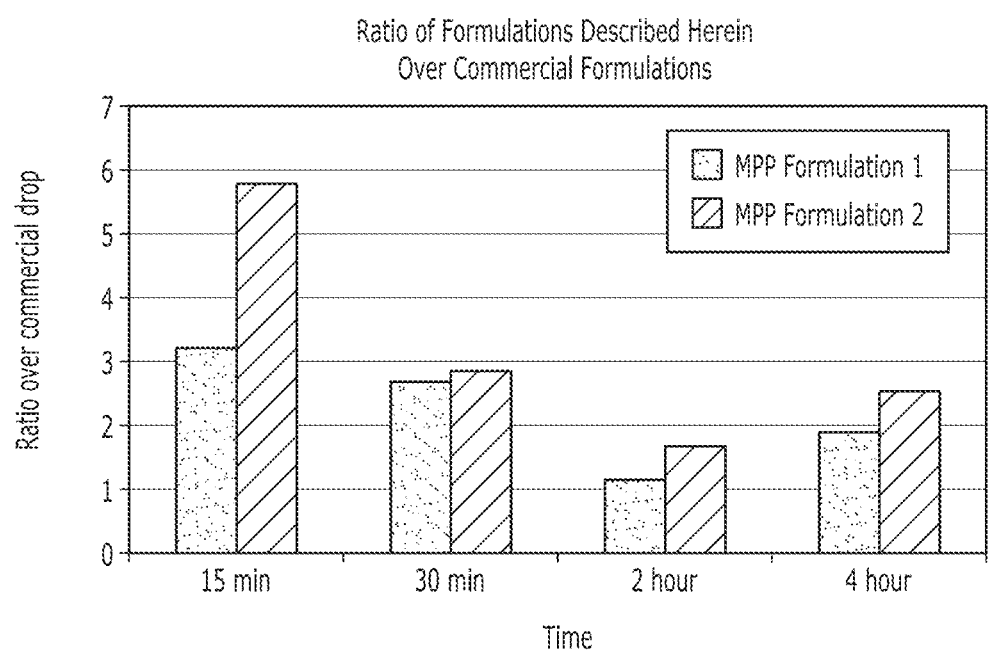

In order to demonstrate the value of enhanced mucus penetration in the delivery of pharmaceutical agents to the eye, concentrations of loteprednol etabonate in the cornea of New Zealand White Rabbits were measured following a single equivalent dose of Lotemax® (the currently marketed ophthalmic suspension of loteprednol etabonate (LE), a soft steroid indicated for the treatment of ocular inflammation), MPP1 (mucus-penetrating particles comprised of a polymeric core encapsulating LE), and MPP2 (mucus-penetrating particles comprised of the LE core). MPP1 particles were made by nanoprecipitation of loteprednol etabonate with poly(lactide) (100DL2A from Surmodics) from a solution in acetone into an aqueous solution. MPP2 particles were made by the method described in Example 2. Both MPP1 and MPP2 particles were coated with Pluronic® F127. As shown in FIG. 17A and FIG. 17B, MPP1 and MPP2 formulations resulted in higher drug levels in the cornea compared to those from the commercial drop having the same concentration of particles as that of the MPP formulations. Without wishing to be bound by any theory, it is believed that conventional particles, such as those in Lotemax®, are extensively trapped by the peripheral rapidly-cleared mucus layer in the eye and, hence, are rapidly cleared; while the MPP particles are able to avoid adhesion to mucus and, hence, achieve prolonged residence at the ocular surface and facilitate sustained drug release directly to underlying tissues.

Example 8

This example shows an improved delivery of a pharmaceutical agent from mucus-penetrating particles coated with Pluronic® F127 to the back of the eye, including the *retina*, choroid and sclera, which is not seen with conventional particles. Delivery to the cornea and iris was also improved for particles coated with Pluronic® F127 compared conventional particles.

Figure 18:
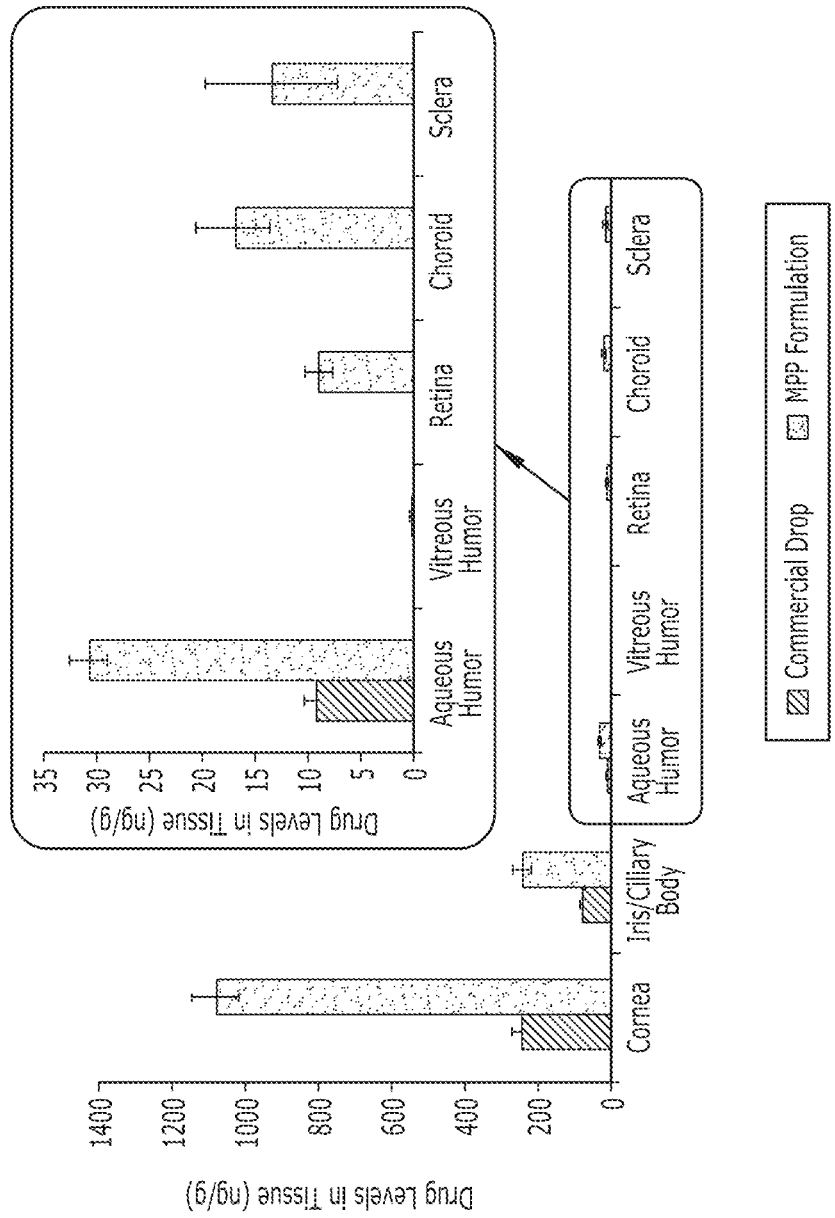
FIG. 18 is a plot showing distribution of MPP (loteprednol etabonate nanocrystals coated with Pluronic® F127) in ocular tissues in vivo 30 minutes after eye drop instillation, according to one set of embodiments. Rabbits were given one 50 μL dose of 0.5% loteprednol etabonate MPP formulation or a commercial drop, Lotemax®, in each eye. Retina, choroid, and sclera are sampled where the human *macula* would be located. Error bars show standard errors of the mean (SEM, n=6)

In order to demonstrate the value of enhanced mucus penetration in the delivery of non-polymeric solid particles, an MPP formulation of loteprednol etabonate (LE MPP; LE particles coated with Pluronic® F127 made by the method described in Example 2) was compared to the currently marketed formulation, Lotemax®. Lotemax® is a steroid eye drop approved for the treatment of ocular inflammation. Conventional particles, such as those in Lotemax®, are extensively trapped by the peripheral rapidly-cleared mucus layer in the eye and, hence, are rapidly cleared. LE MPP are able to avoid adhesion to, and effectively penetrate through, mucus to facilitate sustained drug release directly to underlying tissues. Not only is delivery to the ocular surface enhanced as described in Example 3, but delivery to the middle and back of the eye is also enhanced. In vivo, a single topical instillation of LE MPP to New Zealand white rabbits produced significantly higher drug levels in cornea, iris/ciliary body, aqueous humor, *retina*, choroid, and sclera compared to an equivalent dose of Lotemax® (FIG. 18). Current commercial eye drops are used in the treatment of anterior ocular disorders, but are not effective in treating posterior disorders because drug does not reach the back of the eye. Here the *retina*, choroid and sclera are sampled using an 8 mm punch where the human *macula* would be located. In the back of the eye LE levels are below the limit of detection for Lotemax®, while LE MPP deliver detectable levels of LE to *retina*, choroid, and sclera. These results demonstrate the utility of the non-polymeric solid MPP approach over conventional approaches.

Example 9

This example describes the measurement of the density of Pluronic® F127 on the surface of particles comprising a nanocrystal core of a pharmaceutical agent.

Figure 19:
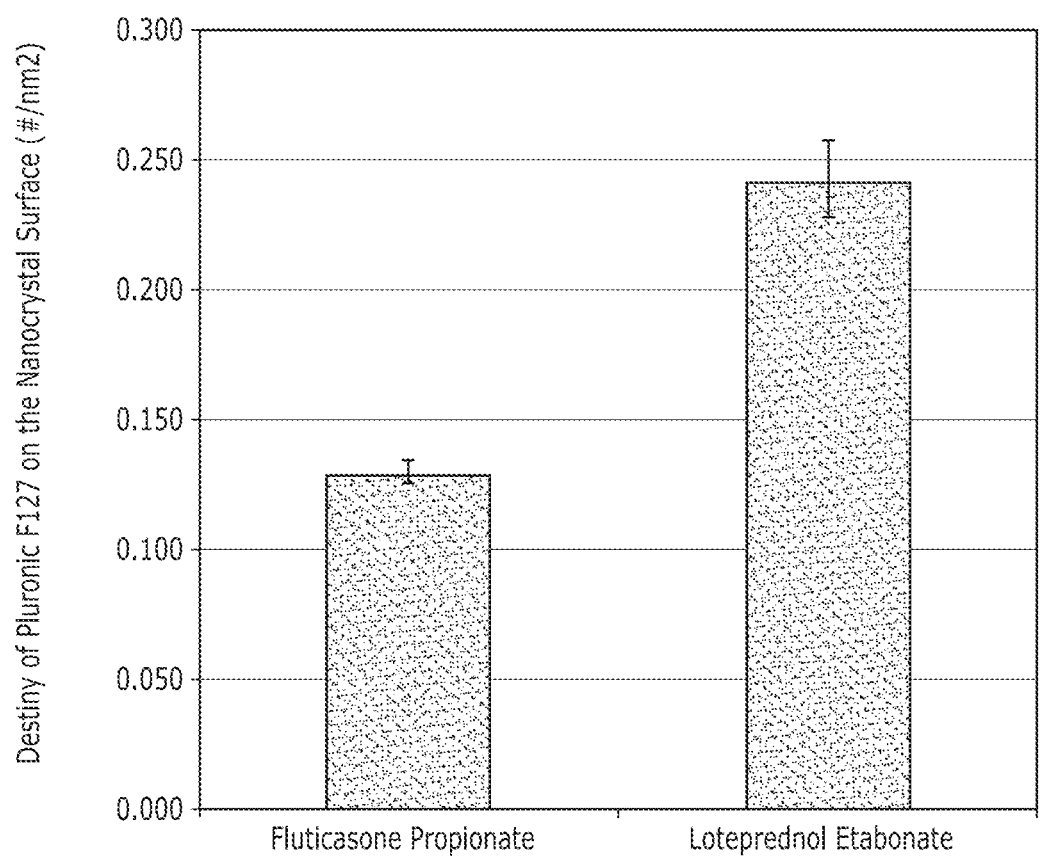
FIG. 19 is a bar graph showing the density of Pluronic® F127 on the surface of fluticasone propionate and loteprednol etabonate nanocrystals, according to one set of embodiments.

An aqueous dispersion containing a pharmaceutical agent and Pluronic® F127 was milled with milling media until particle size was reduced below 300 nm. A small volume from the milled suspension was diluted to an appropriate concentration (~100 µg/mL, for example) and the z-average diameter was taken as a representative measurement of particle size. The remaining suspension was then divided into two aliquots. Using HPLC, the first aliquot was assayed for the total concentration of drug (here, loteprednol etabonate or fluticasone propionate) and for the total concentration of surface-altering moiety (here, Pluronic® F127). Again using HPLC the second aliquot was assayed for the concentration of free or unbound surface-altering moiety. In order to get only the free or unbound surface-altering moiety from the second aliquot, the particles, and therefore any bound surface-altering moiety, were removed by ultracentrifugation. By subtracting the concentration of the unbound surface-altering moiety from the total concentration of surface-altering moiety, the concentration of bound surface-altering moiety was determined. Since the total concentration of drug was also determined from the first aliquot, the mass ratio between the core material and the surface-altering moiety can be determined. Using the molecular weight of the surface-altering moiety, the number of surface-altering moiety to mass of core material can be calculated. To turn this number into a surface density measurement, the surface area per mass of core material needs to be calculated. The volume of the particle is approximated as that of a sphere with the diameter obtained from DLS allowing for the calculation of the surface area per mass of core material. In this way the number of surface-altering moieties per surface area is determined. FIG. 19 shows the results of surface-moiety density determination for loteprednol Itabonate and fluticasone propionate.

Example 10

The following describes a non-limiting example of a method of forming mucus-penetrating particles using a core comprising the drug loteprednol etabonate (LE) by milling in the presence of various Pluronic® surface-altering agents.

LE was milled as an aqueous suspension with milling media and in the presence of a stabilizer. Pluronics of various grades (listed in Table 12) were tested as surface-altering agents in order to determine whether certain Pluronic grades can: 1) aid reduction of particle size of LE to the submicron range and 2) physically (non-covalently) coat the surface of generated LE nanoparticles with a mucoinert coating that would minimize particle interactions with mucus constituents and prevent mucus adhesion. In these experiments, the Pluronics acted as a coating around the core particles, and the resulting particles were tested for their mobility in mucus, although in other embodiments, the surface-altering agents may be exchanged with other surface-altering agents that can increase mobility of the particles in mucus.

The milling process was carried out until LE particles were small and polydispersity was low (i.e., z-average particle diameter below 500 nm and polydispersity index <0.20 as measured by dynamic light scattering). Table 12 lists particle size characteristics of LE particles obtained by milling in the presence of the various Pluronics®. Particle size was measured by dynamic light scattering. Milling of LE in the presence of Pluronic® L31, L35, L44 or L81 failed to produce stable nanosuspensions. Therefore, these Pluronics were excluded from further investigation due to their inability to effectively aid particle size reduction.

The mobility of LE nanoparticles from the produced nanosuspensions in fresh undiluted human cervicovaginal mucus (CVM) was characterized by dark-field microscopy using a CytoViva® High Resolution Illumination System which allows visualization of fluorescent and non-fluorescent nano-sized objects. In a typical experiment, 0.5 µL of a nanosuspension was added to 20 µL of undiluted CVM pre-deposited into a 20 µL well on a microscope slide. Using a CCD camera, 15 s movies were captured at a temporal resolution of 66.7 ms (15 frames/s) under 100× magnification from several randomly selected areas within each sample. Mobility of particles in the movies was scored on a scale from 0 to 3 in order of increasing mobility, in a single-blind experiment by independent observers. The scoring criterion is as follows: 0-0.5 immobile; 0.51-1.5 slightly mobile; 1.51-2.5 moderately mobile; and 2.51-3.0 very mobile.

Figure 20:
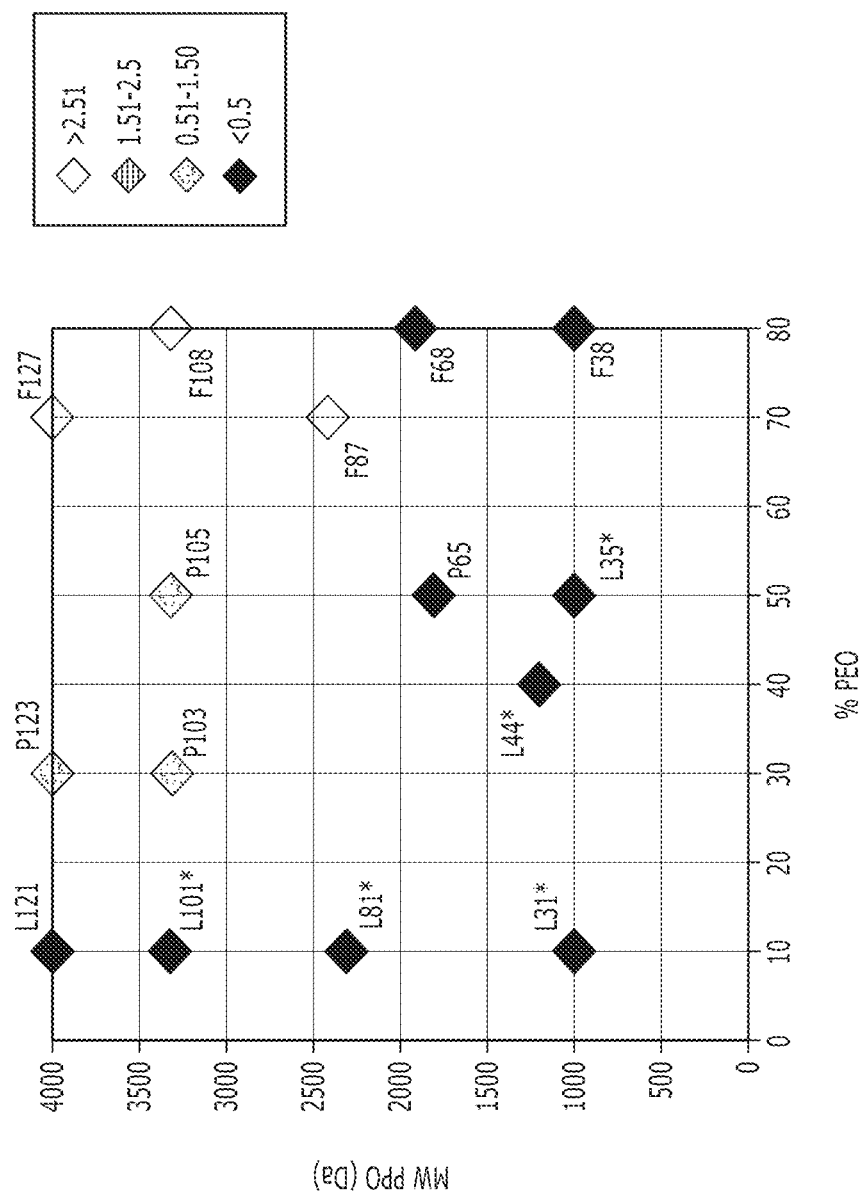
FIG. 20 is a plot showing CVM mobility scores for loteprednol etabonate nanoparticles obtained by milling in the presence of different PEO-PPO-PEO Pluronic® triblock copolymers, mapped with respect to molecular weight of the PPO block and the PEO weight content (%), according to one set of embodiments. The scoring criterion is as follows: 0-0.5 immobile; 0.51-1.5 slightly mobile; 1.51-2.5 moderately mobile; and 2.51-3.0 very mobile. Samples that failed to produce stable nanosuspensions are demarked with * and considered immobile (mobility score <0.5)

The average mobility scores for each LE/Pluronic sample are plotted in FIG. 20 as a function of the molecular weight of the PPO component (MW PPO) and the weight percentage of the PEO component (% PEO) of the Pluronic® polymer. It was discovered that LE milled in the presence of Pluronic® F87, F108, and F127 resulted in particles that are very mobile in CVM (mobility score >2.51). This corresponds to Pluronic® polymers with physical properties of MW PPO≥2.3 kDa and % PEO≥70%. LE nanocrystals milled in Pluronic® P103, P105, and P123 are moderately mobile (mobility score 1.51-2.50). The corresponding physical properties of this Pluronic® class is MW PPO≥3.3 kDa and 30%≤% PEO≤70%. Pluronic® L121, P65, F38, and F68 produced LE nanocrystals that were not mobile (mobility score <0.50). This group of Pluronic® polymers constitutes those with MW PPO≤1.9 kDa and % PEO≤10%. Pluronic® L31, L35, L44, or L81, whose physical properties also fall into the previous-mentioned MW PPO and % PEO categories, failed to produce small and monodisperse particles and are considered immobile (mobility score <0.50) in the analysis.

Without wishing to be bound by any theory, it is believed that the hydrophobic PPO block can provide effective association with the surface of the core LE particles if the molecular weight of that block is sufficient (e.g., at least about 2.3 kDa in some embodiments); while the hydrophilic PEO blocks are present at the surface of the coated LE particles and can shield the coated LE particles from adhesive interactions with mucin fibers if the PEO content of the Pluronic® is sufficient (e.g., at least 30 wt % in some embodiments). As described herein, in some embodiments the PEO content of the surface-altering agent may be chosen to be greater than or equal to about 10 wt % (e.g., at least about 15 wt % or at least about 20 wt %), as a 10 wt % PEO portion rendered the particles mucoadhesive.

Interestingly, the molecular weight of the PPO block needed to provide high mobility (mobility score >2.51) when LE was used as the core was at least about 2.3 kDa, compared to 3 kDa for when pyrene was used as the core. This data suggests that the surface altering agent (e.g., the molecular weight of the PPO block) may be varied, depending on the core to be coated, to tailor the mobility of the particle.

TABLE 12

Particle size measured by Dynamic Light Scattering (DLS) in nanosuspensions obtained by milling of LE with various Pluronic ® surface-altering agents.

| Pluronic ® grade | Z-average diameter (nm) | Polydispersity index |
|---|---|---|
| L31* | not measurable* | not measurable* |
| L35* | not measurable* | not measurable* |
| L44* | not measurable* | not measurable* |
| L81* | not measurable* | not measurable* |
| L101* | not measurable* | not measurable* |
| L121 | 343 | 0.18 |
| P65 | 224 | 0.06 |
| P103 | 251 | 0.08 |
| P105 | 356 | 0.19 |
| P123 | 281 | 0.12 |
| F38 | 233 | 0.10 |
| F68 | 404 | 0.13 |
| F87 | 316 | 0.07 |
| F108 | 294 | 0.12 |
| F127 | 404 | 0.13 |

*denotes samples that failed to effectively reduce LE particle size and produce stable nanosuspensions. For these samples, Z-Ave diameter was greater than at least 1 µm and not measurable with DLS.

Example 11

The following describes a non-limiting example of a method of forming mucus-penetrating particles (MPP) using a core comprising the drug loteprednol etabonate (LE) in the presence of other components, such as Pluronic®, glycerin, sodium chloride (NaCl), disodium ethylenediaminetetraacetic acid (Na₂EDTA), and benzalkonium chloride (BAC).

The method of forming the loteprednol etabonate mucus-penetrating particles (LE MPP) involved two consecutive steps: milling and dilution. In the milling step, a coarse aqueous suspension containing about 2-20% loteprednol etabonate (coarse or micronized crystals), about 0.2-20% Pluronic® F127, about 0.5-3% glycerin, about 0.1-1% sodium chloride, and about 0.001-0.1% EDTA was milled in the presence of milling media to produce a nanosuspension of loteprednol etabonate particles sized in the range of 200-300 nm.

In the subsequent dilution step, the obtained nanocrystalline suspension separated from the milling media was mixed in a product vessel with post-milling diluent containing about 0.5-3% glycerin, about 0.1-1% sodium chloride, about 0.001-0.1% EDTA, and about 0.001-0.05% BAC. This method produced a composition including about 0.1-2% loteprednol etabonate, about 0.01-2% Pluronic® F127, about 0.5-3% glycerin, about 0.1-1% sodium chloride, about 0.001-0.1% EDTA, and about 0.001-0.05% BAC.

Example 12

The following describes a non-limiting example of the effect of Pluronic® F127 on the mucus penetrating properties of the formulations.

Figure 21:
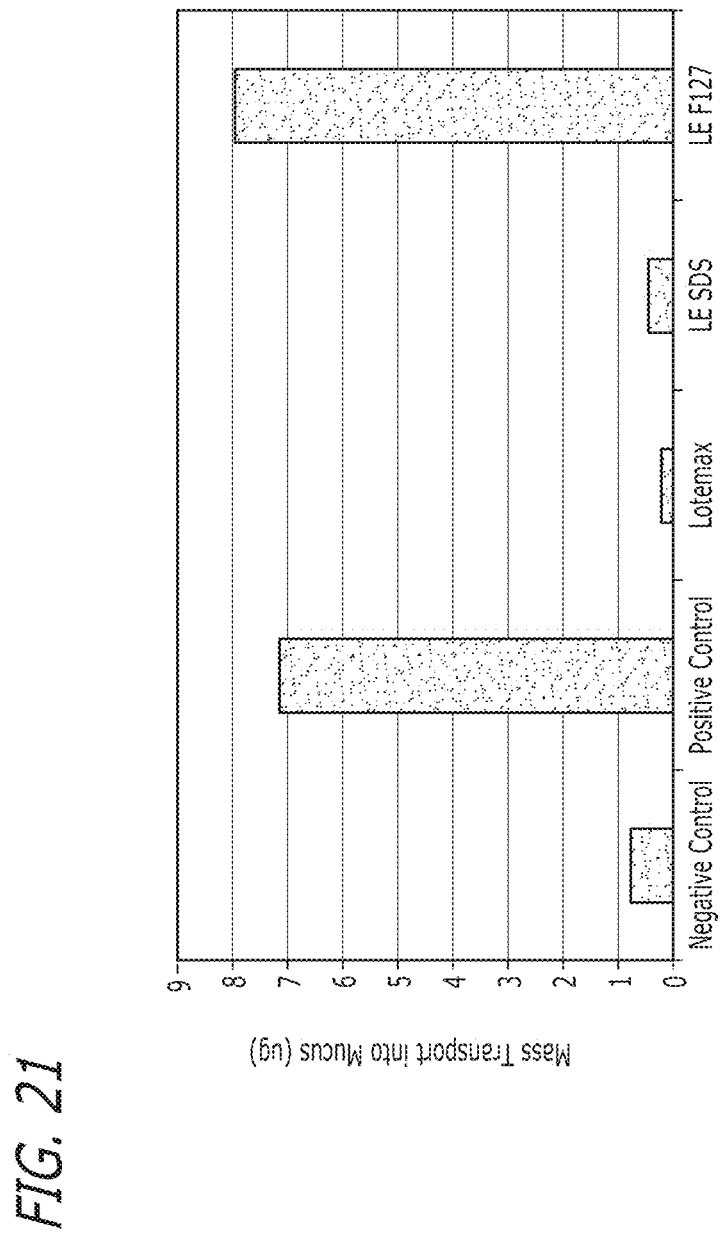
FIG. 21 is a plot showing the mass-transport-into-mucus data of the following formulations: mucus penetrating particles comprising loteprednol etabonate and Pluronic® F127 (LE F127), particles comprising Loteprednol Etabonate and sodium dodecyl sulfate (LE SDS), and marketed formulation Lotemax®. The ratio of loteprednol etabonate to Pluronic® F127 1:1 wt % while the ratio of loteprednol etabonate to SDS is 50:1 wt %. Untreated 200 nm carboxylated polystyrene spheres and 200 nm carboxylated polystyrene spheres treated with Pluronic® F127 were employed as the negative and positive control, respectively.

The formulations were formed using methods similar to the method described in Example 10. FIG. 21 shows mass-transport-into-mucus data of the following formulations: particles comprising loteprednol etabonate and Pluronic® F127 (LE F127), particles comprising loteprednol etabonate and sodium dodecyl sulfate but not Pluronic® F127 (LE SDS), and marketed formulation Lotemax®. The ratio of loteprednol etabonate to Pluronic® F127 1:1 wt % and the ratio of loteprednol etabonate to SDS is 50:1 wt %. The mass transport was measured according to the procedure described in Example 2. The results shown in FIG. 21 indicate that the mucus penetrating properties of LE F127 were approximately 20 times greater compared to LE SDS and approximately 40 times greater compared to Lotemax®. It is believed that an ophthalmic formulation of a drug including a loteprednol etabonate core and a coating of F127 may enhance the ocular exposure of the drug.

Example 13

This non-limiting example shows that loteprednol etabonate (LE) MPPs may be gamma-irradiated for terminal sterilization without adversely affecting the LE MPPs' particle stability, chemical stability, and pharmacokinetics and that glycerin gives chemical protection to the LE MPPs against gamma irradiation.

Gamma irradiation of a formulation can cause chemical degradation and free radical generation and is a concern especially in aqueous formulations. LE is a soft steroid designed to metabolize via the hydrolytic or enzymatic cleavage of two ester bonds into PJ-91 and PJ-90. When LE is exposed to gamma irradiation, 17α-[(ethoxycarbonyl)oxy]-11β-hydroxy-3-oxoandrosta-4-ene-17-carboxylic acid chloromethyl ester (tetradeca) and 17α-[(ethoxycarbonyl)oxy]-3,11-dioxoandrosta-1,4-diene-17-carboxylic acid chloromethyl ester (11-keto) are formed. When LE is gamma-irradiated, 11-keto appears in small amounts, whereas the amount of tetradeca rapidly increases to above 1%.

The formulations comprising LE and different concentrations of glycerin were formed using methods similar to the methods described in Examples 10-11. Table 13 shows the concentrations of certain degradants of LE after the formulations were exposed to gamma radiation. The concentrations of the degradants were measured immediately after being subjected to gamma irradiation ("Gamma irradiated initial") and 4 weeks after being subjected to gamma irradiation ("gamma irradiated after 4 weeks") using a Cobalt 60 gamma irradiation source at a dose of 25 kGy. In LE MPPs with no glycerin, the amount of tetradeca increased by 18-fold after the gamma irradiation of the LE MPPs. In contrast, after gamma irradiation little tetradeca was formed in the LE MPPs with 1.2% or 2.4% glycerin. Surprisingly, the levels of PJ-91 and PJ-90 were decreased in all cases. Although 11-keto was observed after the gamma irradiation, the level of 11-keto did not exceed 0.2%. The results show that much less tetradeca is produced upon gamma radiation when glycerin is present in the formulations. Different concentrations of glycerin were used (e.g., 1.2 wt % and 2.4 wt %), and the resulting formulations generated similar levels of tetradeca after exposure to gamma radiation. These results are unexpected and suggest that glycerin, commonly used as a tonicity agent, may give chemical protection to the formulations during gamma radiation.

TABLE 13

Concentrations of LE and certain degradants of LE after LE formulations were exposed to 25 kGy of gamma radiation.*

| Formulation composition | Time of gamma radiation | Concentration (wt %) | | | | |
| --- | --- | --- | --- | --- | --- | --- |
| | | PJ-90 | PJ-91 | LE | Tetradeca | 11-keto |
| LE, F127, NaCl, EDTA, BAC | Not irradiated | 0.48 | 0.97 | 97.22 | 0.08 | 0.04 |
| | Gamma irradiated initial | 0.07 | 0.45 | 96.51 | 1.45 | 0.13 |
| | Gamma irradiated after 4 weeks | 0.07 | 0.46 | 96.55 | 1.49 | 0.16 |
| LE, F127, 2.4% Glycerin, EDTA, BAC | Not irradiated | 0.48 | 0.87 | 97.21 | 0.08 | 0.05 |
| | Gamma irradiated initial | 0.31 | 0.70 | 97.28 | 0.10 | 0.15 |
| | Gamma irradiated after 4 weeks | 0.36 | 0.81 | 97.24 | 0.11 | 0.16 |
| LE, F127, 1.2% Glycerin, NaCl, EDTA, BAC | Not irradiated | 0.38 | 0.78 | 97.93 | 0.06 | 0.09 |
| | Gamma irradiated initial | 0.29 | 0.48 | 98.04 | 0.09 | 0.16 |
| | Gamma irradiated after 2 weeks | 0.28 | 0.50 | 97.80 | 0.15 | 0.20 |

*LE MPPs employed in this Example were lab scale batches and may be less pure than batches used in other Examples described herein.

Figure 33A:
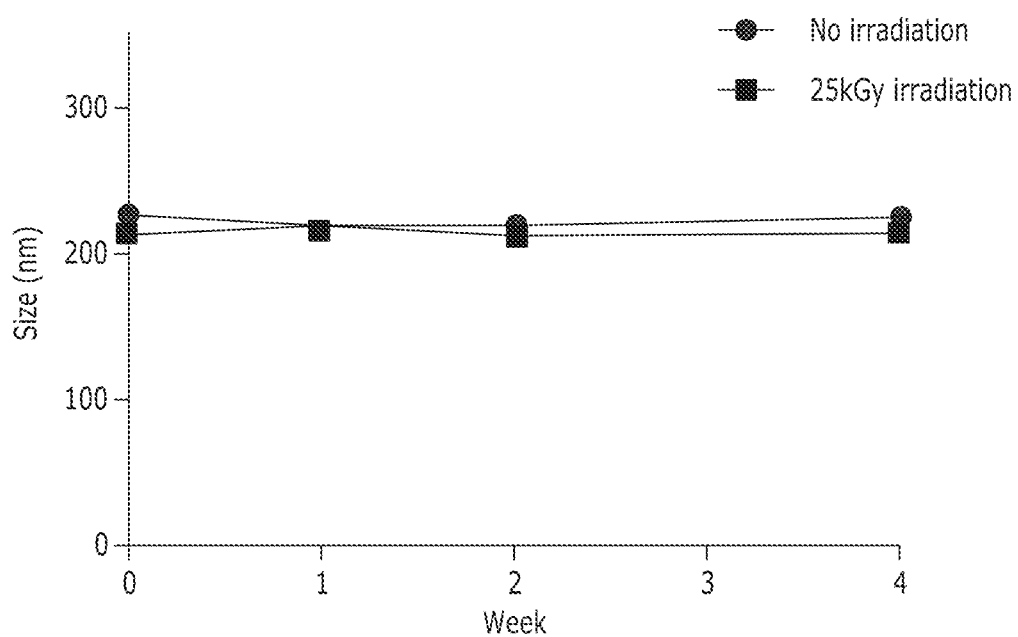
FIG. 33A is a plot showing the particle stability of LE MPPs. Two samples of LE MPPs were monitored by dynamic light scattering (DLS). One sample had been exposed to 25 kGy of gamma irradiation, and the other sample had not been exposed to gamma irradiation.

In addition to the chemical stability of a particle formulation, the physical stability of the formulation is also of high importance. As shown in FIG. 33A, LE MPP formulations containing sodium chloride and glycerin showed no change in particle size over a month after exposure to 25 kGy of gamma irradiation.

Figure 33B:
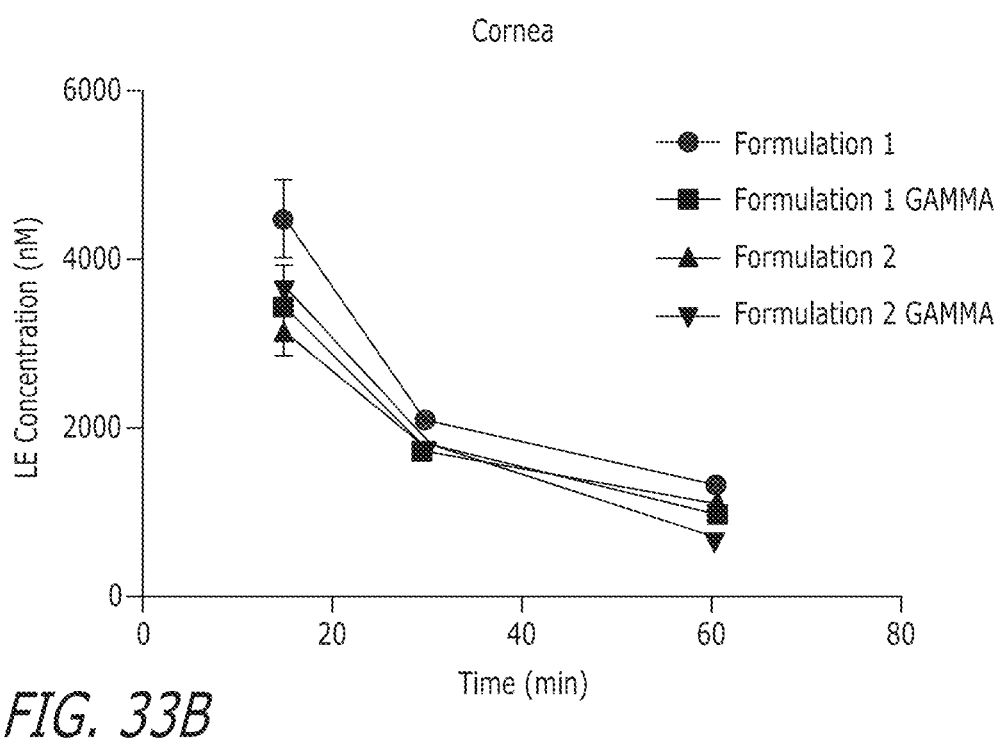
FIG. 33B is a plot showing the pharmacokinetics of LE in the cornea of New Zealand white rabbits in vivo. The rabbits were given one 50 μL dose of LE MPPs including 0.4% LE in each eye of the rabbit. Error bars show standard errors of the mean (n=6).

The effects of gamma irradiation on the pharmacokinetics (PK) of LE MPPs was also studied to investigate whether the performance of the LE MPPs was unaffected by gamma irradiation. In vivo, a single topical instillation of LE MPPs, which had been gamma irradiated at 25 kGy (Formulation 1 GAMMA, Formulation 2 GAMMA), to New Zealand white rabbits produced the same LE levels in the cornea of the rabbits as did LE MPPs that had not been exposed to gamma irradiation (Formulation 1, Formulation 2; FIG. 33B). In FIG. 33B, Formulation 1 (and Formulation 1 GAMMA) included a higher level of Pluronic® F127 than Formulation 2 (and Formulation 2 GAMMA). These results demonstrate that LE MPPs can be terminally sterilized by gamma irradiation without adverse effects on the particle stability, API (active pharmaceutical ingredient) chemical stability, or PK of the LE MPPs.

Example 14

This non-limiting example shows that NaCl is beneficial to the stability of an LE MPP formulation described herein during dilution of the formulation with water.

The formulations comprising LE and one or more tonicity agents (e.g., NaCl, Tyloxapol, glycerin, and SSC (an aqueous solution of sodium citrate and about 1% NaCl)) were formed using methods similar to the method described in Examples 10-11. Table 14 shows the particle size and polydispersity index (PDI) of the LE formulations measured by Dynamic Light Scattering (DLS) before and after a 10-fold dilution of the formulations with water. In entries 1, 4, and 5, where the formulations do not include NaCl, the particle size (measured by diameter) increased by about 2-3 fold upon dilution of the formulation with water, most likely due to aggregation of the particles. In entries 4 and 5, the PDI also increased by about 2-3 fold. In contrast, in entries 2, 3, 6, and 7, where the formulations included NaCl, the particle size remained relatively constant upon dilution of the formulation with water. In entries 2, 3, and 7, there was also no significant increase in PDI. These results were unexpected because the addition of NaCl (a tonicity agent) to a particle formulation increases the ionic strength of the formulation, and is generally known to destabilize the particle formulation by causing aggregation of particles. The opposite effect was observed here.

TABLE 14

Particle size and polydispersity index (PDI) of LE formulations measured by Dynamic Light Scattering (DLS) before and after a 10-fold dilution with water.

| | | Before dilution | | After dilution | |
|---|---|---|---|---|---|
| Entry | Formulation composition | Diameter (nm) | PDI | Diameter (nm) | PDI |
| 1 | 1-5% LE, 1-5% F127 | 208 | 0.148 | 395 | 0.156 |
| 2 | 1-5% LE, 1-5% F127, 0.9% NaCl, 0.05% EDTA, 0.01% BAC | 188 | 0.102 | 187 | 0.122 |
| 3 | 1-5% LE, 1-5% F127, 0.9% NaCl, 0.1% Tyloxapol, 0.05% EDTA, 0.01% BAC | 190 | 0.128 | 193 | 0.139 |
| 4 | 1-5% LE, 1-5% F127, 2.4% Glycerin, 0.05% EDTA, 0.01% BAC | 197 | 0.133 | 514 | 0.409 |
| 5 | 1-5% LE, 1-5% F127, 2.4% Glycerin, 0.1% Tyloxapol, 0.05% EDTA, 0.01% BAC | 191 | 0.116 | 389 | 0.337 |
| 6 | 1-5% LE, 1-5% F127, SSC, 0.05% EDTA, 0.01% BAC | 212 | 0.096 | 244 | 0.176 |
| 7 | 1-5% LE, 1-5% F127, SSC, 0.1% Tyloxapol, 0.05% EDTA, 0.01% BAC | 212 | 0.100 | 246 | 0.095 |

Example 15

This non-limiting example shows that LE MPPs resulted in increased exposure when administered topically to an eye, compared to similarly sized non-MPPs.

Figure 23A:
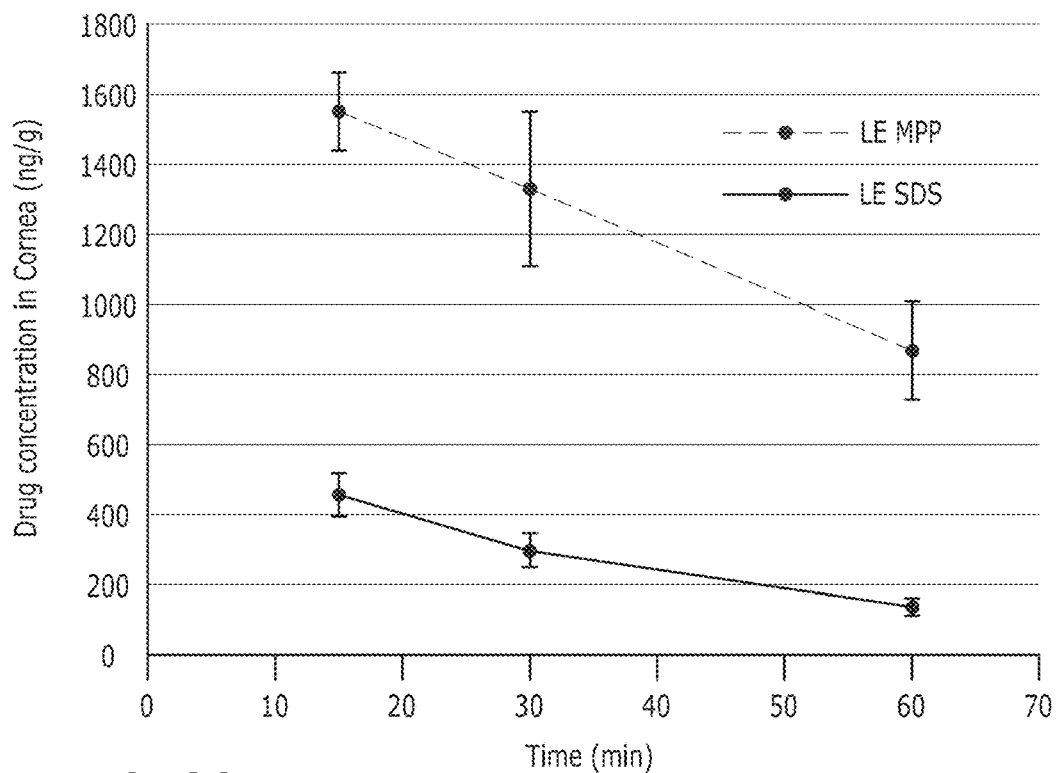
FIGS. 23A-23B are plots showing the pharmacokinetics (PK) of LE in ocular tissues in vivo. Error bars show standard errors of the mean (n=6).
Figure 23B:
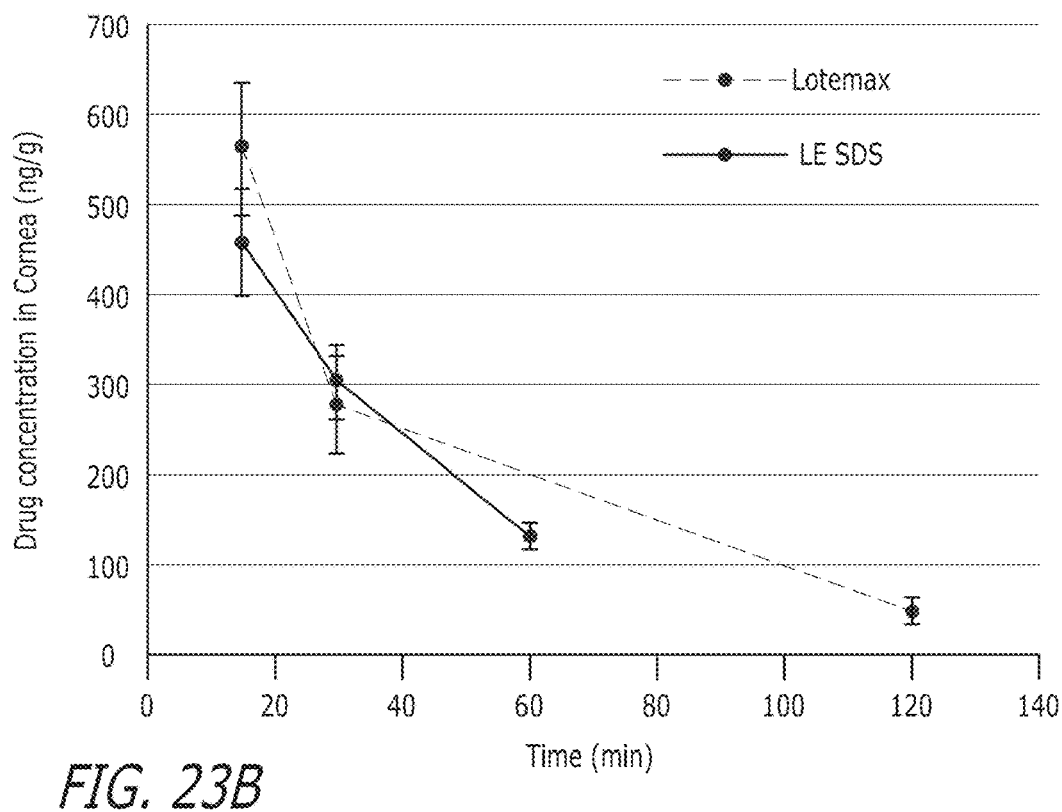

LE MPPs were compared to LE SDS particles, similarly sized non-MPPs (Table 15). LE SDS particles are produced using methods similar to the methods described in Examples 10-11, except that the particles are coated with sodium dodecyl sulfate (SDS). Conventional particles, such as those coated in SDS, are extensively trapped by the peripheral rapidly-cleared mucus layer in the eye and are rapidly cleared. LE MPPs are able to avoid adhesion to, and effectively penetrate through, mucus to facilitate sustained drug release directly to underlying tissues. In vivo, a single topical instillation of LE MPPs to New Zealand white rabbits produced a 4.4-fold enhancement in the AUC of LE concentration in the cornea, compared to an equivalent dose of LE SDS, despite both being similarly sized nanoparticles (FIG. 23A). Additionally, despite the different particle sizes of LE SDS and Lotemax®, which is a commercially available microparticle, the concentrations of LE obtained from rabbits dosed with LE SDS were statistically equivalent to the concentrations of LE obtained from rabbits dosed with Lotemax® (FIG. 23B). These results demonstrate that the MPP's capability to enhance the exposure, in the eye, of a drug that is formulated with the MPP is not solely due to the small particle size of the MPP.

TABLE 15

Particle size and polydispersity index (PDI) of LE SDS and LE MPP measured by Dynamic Light Scattering (DLS).

| Sample | Diameter (nm) | PDI |
|---|---|---|
| LE SDS | 240 | 0.143 |
| LE MPP | 241 | 0.096 |

Example 16

This non-limiting example shows that LE MPPs resulted in increased exposure when administered topically to an eye, compared to Lotemax® coated with Pluronic® F127.

Figure 24:
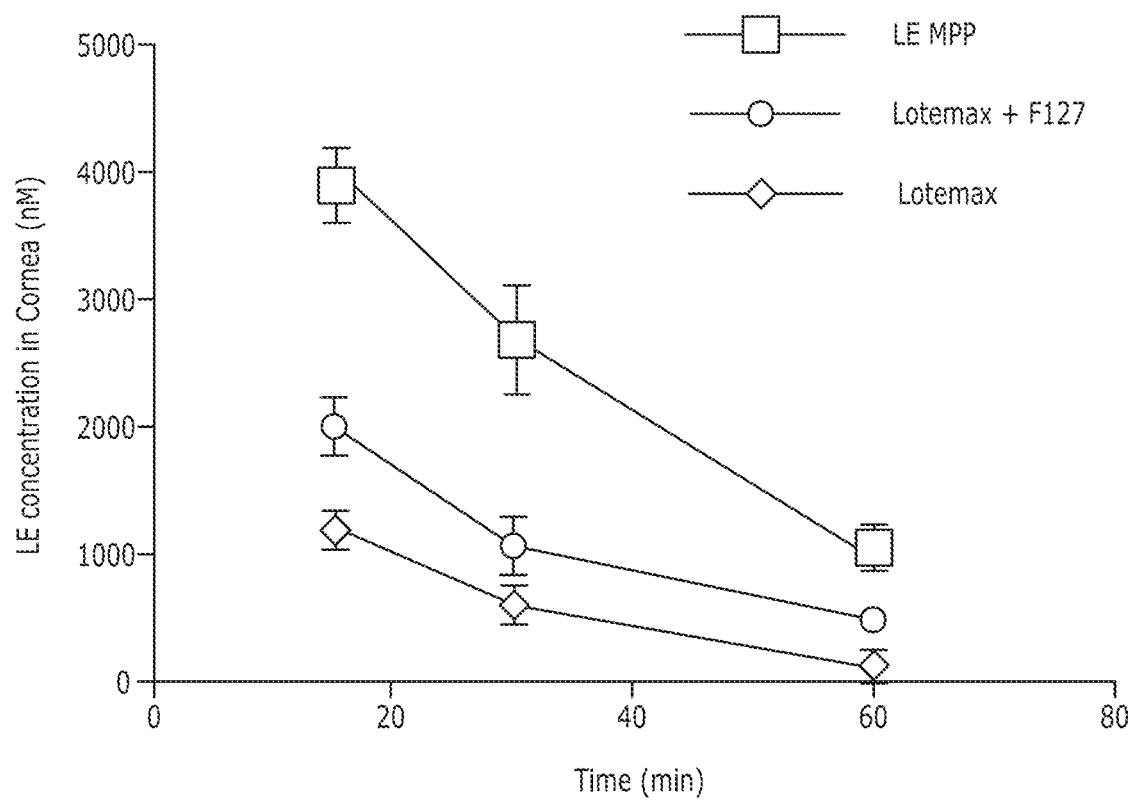
FIG. 24 is a plot showing the pharmacokinetics of LE in ocular tissues in vivo. Rabbits were given one 50 μL dose of 0.5% Lotemax®, Lotemax®+F127, or LE MPPs in each eye. Error bars show standard errors of the mean (n=6). Data for Lotemax® were obtained from a previous experiment performed using the same techniques at the same facility.
Figure 26G:
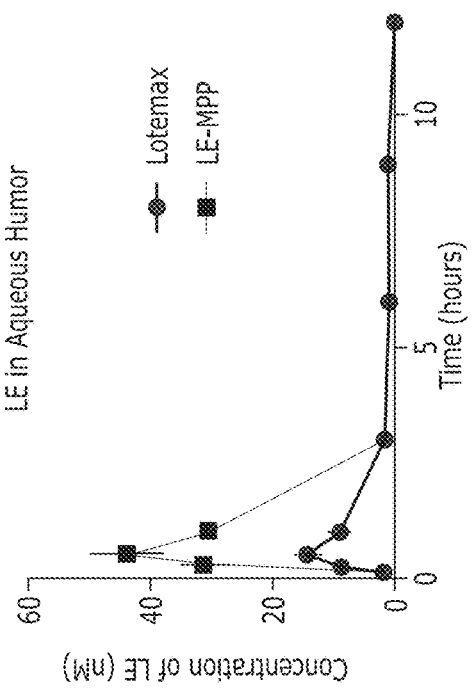
FIGS. 26A-26R are plots showing pharmacokinetics of LE and its two main metabolites, PJ-91 and PJ-90, in ocular tissues (e.g., conjunctiva, cornea, aqueous humor, iris and ciliary body (ICB), and central *retina*) and plasma in vivo. Rabbits were given one 50 μL dose of 0.5% Lotemax® or 0.4% LE MPP in each eye. Error bars show standard errors of the mean (n=6).
Figure 26I:
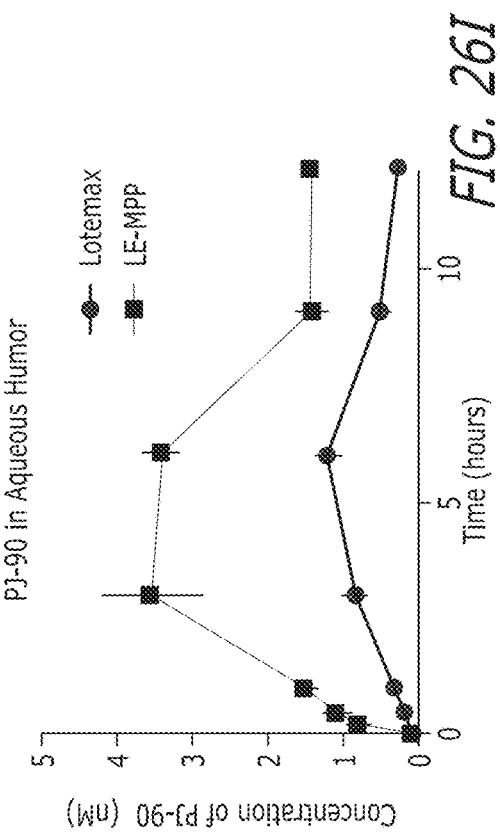
Figure 26H:
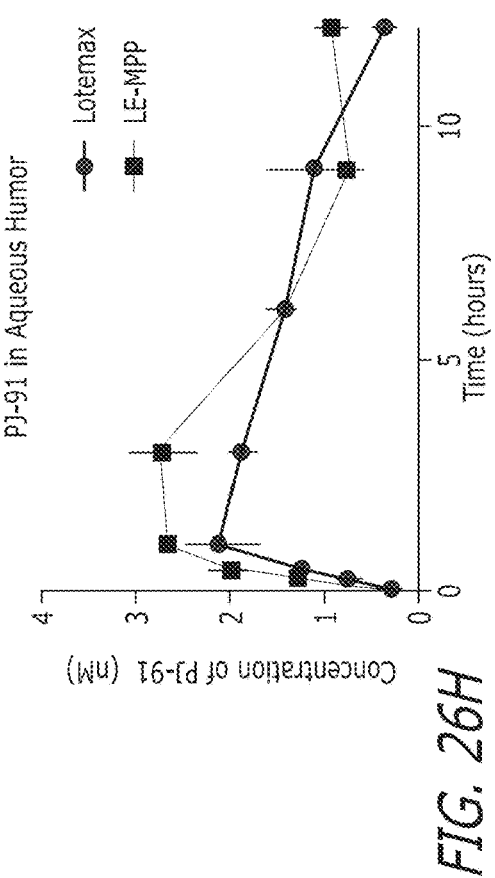

LE MPPs were compared to Lotemax®+F127, a formulation in which F127 (0.5 wt %) was added to Lotemax®. In vivo, a single topical instillation of LE MPPs to New Zealand white rabbits produced significantly higher exposure of LE in cornea, compared to an equivalent dose of Lotemax® or Lotemax®+F127 (FIG. 24). LE MPPs result in a 4.4- and 2.3-fold enhancement of AUC of LE concentration in cornea over Lotemax® and Lotemax®+F127, respectively. While Lotemax®+F127 does result a 2-fold increase of AUC of LE concentration in cornea as compared to Lotemax® alone, these results demonstrate that the MPP's capability to enhance the exposure, in the eye, of a drug that is formulated with the MPP is not solely due to the presence of Pluronic® F127 in the formulation.

than the LE MPP dose (FIGS. 26A-26R). Pharmacokinetic parameters are listed in Table 16. These results demonstrate the dose of LE can be lowered by 20% with the LE MPP formulation and still achieve enhanced exposure over Lotemax®.

TABLE 16

Pharmacokinetic parameters of Loteprednol Etabonate (LE) in ocular tissues in vivo.
Rabbits were given one 50 μL dose of 0.5% Lotemax ® or 0.4% LE MPP in each eye.

|  |  | Plasma | Aqueous Humor | Conjunctiva | Cornea | Iris Ciliary Body (ICB) | Retina (center-punch) |
|---|---|---|---|---|---|---|---|
| Lotemax ® | $T_{max}$ (h) | 0.25 | 0.50 | 0.083 | 0.083 | 0.50 | 0.50 |
|  | $C_{max}$ (nM) | 0.704 | 14.0 | 2430 | 1330 | 105 | 4.47 |
|  | $t_{1/2\ elimination}$ (h) | 1.88 | 2.31 | 4.26 | 3.75 | 3.04 | 9.18 |
|  | $AUC_{0\text{-}last}$ (nM · h) | 1.62 | 30.0 | 3450 | 2420 | 194 | 14.8 |
|  | $AUC_{0\text{-}inf}$ (nM · h) | 1.69 | 30.5 | 4070 | 2710 | 200 | 22.4 |
| LE MPP | $T_{max}$ (h) | 0.50 | 0.50 | 0.083 | 0.083 | 0.25 | 0.50 |
|  | $C_{max}$ (nM) | 2.55 | 43.7 | 6280 | 4850 | 293 | 14.5 |
|  | $t_{1/2\ elimination}$ (h) | 1.71 | 1.57 | 1.92 | 1.89 | 1.49 | 1.55 |
|  | $AUC_{0\text{-}last}$ (nM · h) | 4.55 | 66.0 | 3450 | 3570 | 442 | 31.5 |
|  | $AUC_{0\text{-}inf}$ (nM · h) | 4.71 | 66.4 | 3490 | 3610 | 445 | 31.9 |

Example 17

This non-limiting example shows that a formulation including LE MPP enhances exposure of LE in the anterior chamber of the eye compared to Lotemax®.

Figure 25:
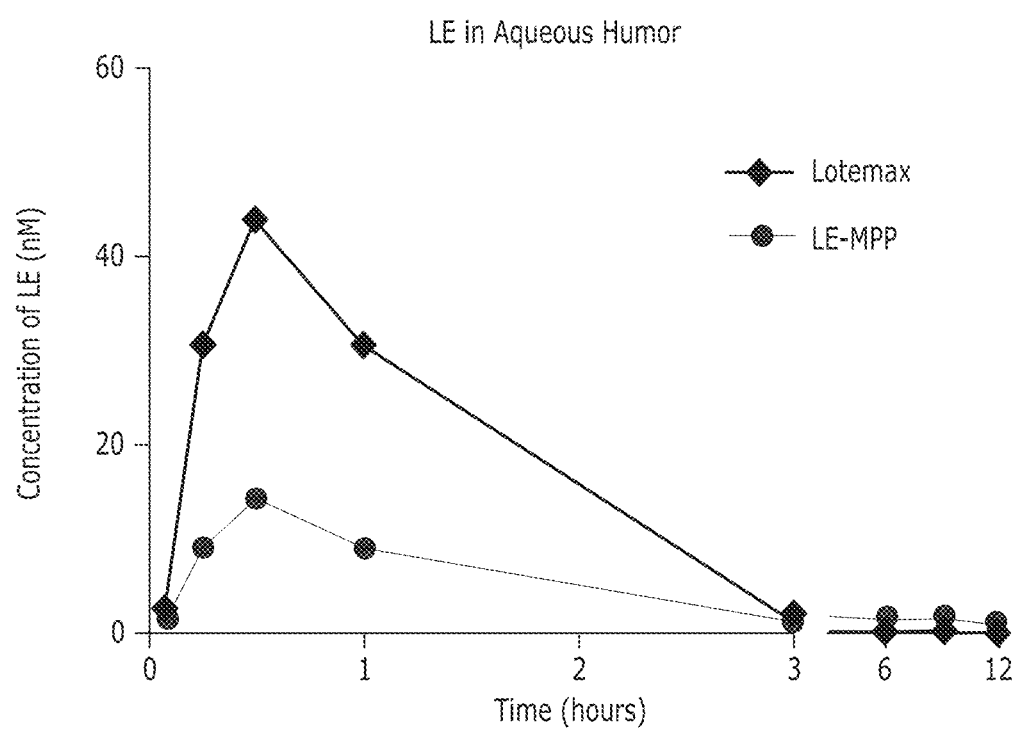
FIG. 25 is a plot showing the pharmacokinetics of LE in ocular tissues in vivo. Rabbits were given one 50 μL dose of 0.5% Lotemax® or 0.4% LE MPPs in each eye. Error bars show standard errors of the mean (n=6).

In order to demonstrate that the enhanced exposure of LE from LE MPPs translates not only to the surface of the eye, but penetrates within the ocular globe, levels of LE in the aqueous humor obtained from LE MPPs and Lotemax® formulations were compared. In vivo, a single topical instillation of LE MPPs to New Zealand white rabbits produced significantly higher LE levels in the aqueous humor compared to a dose of Lotemax® despite the fact that the Lotemax® dose is 20% larger (FIG. 25). LE MPPs (containing 0.4% LE) result in an $AUC_{0\text{-}3hr}$ enhancement of 3 fold over Lotemax® (containing 0.5% LE). These results demonstrate the enhanced exposure achievable with the MPP technology is not limited to the surface of the eye but extends into the anterior chamber. In addition, the dose of LE can be lowered by 20% with the LE MPP formulation and can still achieve enhanced exposure compared to Lotemax®.

Example 18

This non-limiting example demonstrates that a formulation including LE MPP that contains 20% less LE showed improved exposure in rabbit eye and plasma compared to Lotemax®.

In order to demonstrate the enhanced exposure from LE MPP can be sustained at lower doses than currently marketed formulations, such as Lotemax®, LE MPP was given at a dose 20% lower than Lotemax®. Levels of LE and two of its main metabolites, PJ-91 and PJ-90, from LE MPP and Lotemax® were determined. In vivo, a single topical instillation of LE MPP containing 0.4 wt % LE to New Zealand white rabbits produced significantly higher levels of LE in all tissues/fluids tested (e.g., conjunctiva, cornea, aqueous humor, iris and ciliary body (ICB), central retina, and plasma) compared to a dose of Lotemax® containing 0.5 wt % LE, despite the fact that the Lotemax® dose is 20% larger Example 19

This non-limiting example demonstrates the fluticasone release profile of fluticasone-loaded MPPs containing a PEGylated copolymer and a non-PEGylated core-forming polymer.

Fluticasone-loaded MPPs were prepared according to methods similar to the ones described herein (e.g., methods described in Example 21) by co-precipitating fluticasone with PLA7A (Surmodics 100DLA7A, MW=108 KDa) as the main polymer and a PEGylated copolymer (e.g., 100DL9K-PEG2K or 8515PLGA54K-PEG2K) as the secondary polymer. The ratios of the polymeric components tested were 10/90, 20/80, and 30/70 (with PLA7A being the main component in all cases). Various PEGylated copolymers were tested in order to explore the impact of the block composition (i.e., MW of the PEG block vs. MW of the hydrophobic block) on properties of resulting particles. In particular, the ability of resulting particles to penetrate mucus, control drug release, and maintain colloidal stability throughout the formulation process was assessed.

Figure 27:
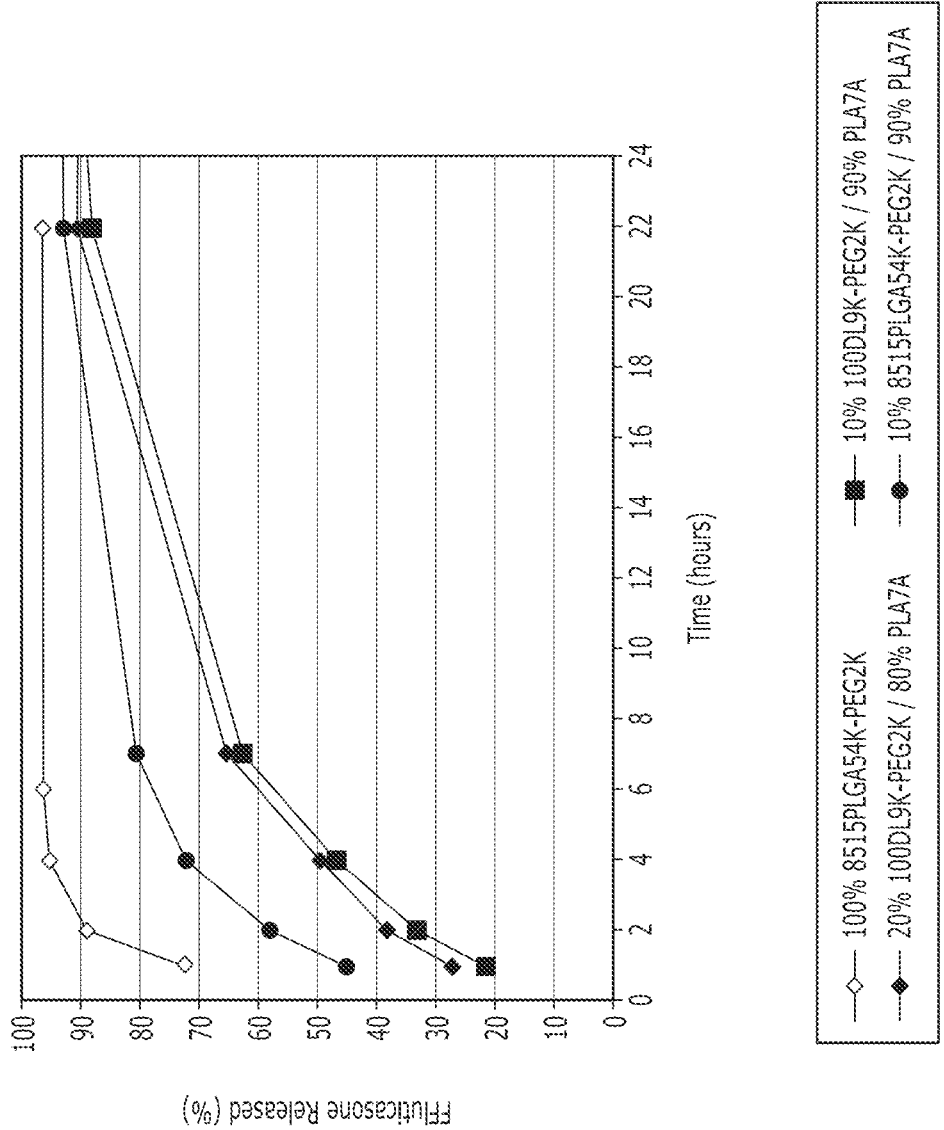
FIG. 27 is a plot showing in vitro release profiles for various PEGylated MPPs loaded with fluticasone. Release conditions: 37° C., PBS with 0.5% Tween 80.

It was found that, while many compositions led to satisfactory drug release and mucus-penetration, good colloidal stability could not be achieved with most of them (see FIG. 27). Colloidal stability is especially important since the current formulation process involves isolation and purification of the MPPs by centrifugation and resuspension. The poor colloidal stability of many compositions was manifested, in part, by the inability to resuspend product obtained after the centrifugation step. The compositions that resulted in MPPs with good colloidal stability as well as good control over drug release (e.g., a continuous release over 24 hours in vitro as in this Example) appear to have a relatively high surface coverage of PEG on the particle (e.g., at least about 0.18 PEG chains per $nm^2$) at a relatively low overall PEG content in the particle (e.g., less than about 3 wt % of the total polymer content). In other words, combinations of PLA7A with PEG-copolymers with a relatively short hydrophobic block (e.g., 100DL9K-PEG2K) result in MPPs that are more colloidally stable than similar combinations of PEG-copolymers with a relatively long hydrophobic block (e.g., 8515PLGA54K-PEG2K) (see FIG. 27).

Example 20

This non-limiting example demonstrates that MPPs comprising sorafenib avoided entrapment in human cervicovaginal mucus and were able to diffuse through mucus.

Figure 28A:
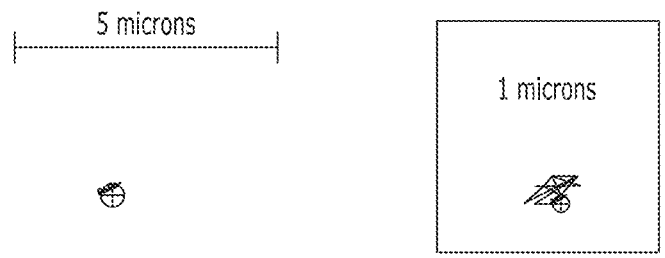
FIGS. 28A-28B show representative 15-second trajectories of conventional nanoparticles (FIG. 28A) and MPPs described herein (FIG. 28B) in human cervicovaginal mucus. The MPPs avoided entrapment and were able to diffuse through mucus.
Figure 28B:
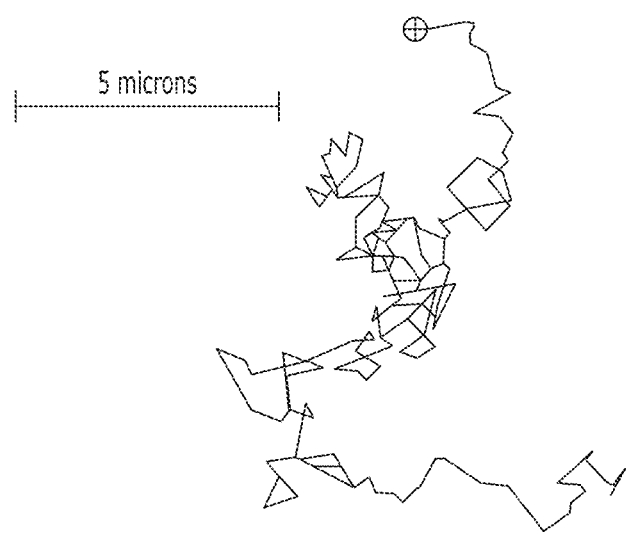

MPPs comprising sorafenib may be prepared according to methods described herein (e.g., methods described in Examples 21 and 29). Mobility of conventional nanoparticles and the MPPs described herein in human cervicovaginal mucus was characterized by bulk transport and/or microscopy as described in Examples 2 and 10, respectively. The results are shown in FIGS. 28A-28B. The conventional nanoparticles were trapped in human cervicovaginal mucus, whereas the MPPs described herein avoided entrapment and were able to diffuse through mucus.

Example 21

This non-limiting example demonstrates that topical delivery of sorafenib, (a small molecule receptor tyrosine kinase (RTK) inhibitor) formulated as MPP greatly enhances sorafenib levels in the *retina* and choroid of the eye. This example also shows that sorafenib levels in anterior segment tissues of the eye depend on the MPP release rate and can be reduced without significantly affecting sorafenib levels at the back of the eye.

Sorafenib-loaded MPPs with relatively fast drug release (MPP1) were prepared by a milling procedure: an aqueous dispersion containing drug and Pluronic F127 (F127) was stirred with zirconium oxide beads, as grinding medium, until particle size was reduced below 300 nm as measured by dynamic light scattering. This method employs excipients approved by the FDA for use in ophthalmic products and produced a stable aqueous nanosuspension of MPPs.

Sorafenib-loaded MPPs with relatively slow drug release kinetics (MPP2) were prepared by encapsulating sorafenib into a biodegradable polymeric nanoparticle decorated with a coating described herein. For example, a solution containing sorafenib free base (LC Labs), PLA (Polylactide, 100DL7A, Surmodics), and PLA-PEG (poly(ethylene glycol)-co-polylactide, 100DL-mPEG2K, Surmodics) in tetrahydrofuran was added at a controlled rate to an excess of aqueous solution of Pluronic® F127 with stirring. The produced particles were stirred at room temperature to let the volatiles evaporate and to crystallize out sorafenib that was unencapsulated. The crystals of unencapsulated sorafenib were removed by filtration through a suitable sized glass fiber filter. The nanoparticles were isolated from the filtrate by centrifugation and washed once with aqueous Pluronic® F127. The final product of nanoparticles was resuspended in Pluronic® F127.

Sorafenib concentrations in the MPP formulations were confirmed by HPLC. The size of the MPPs was measured by dynamic light scattering, using a Zetasizer Nano ZS90 (Malvern Instruments). In vitro drug release was evaluated at 37° C. in 50 mM phosphate buffer (pH 7.4) in the presence of 0.5% Tween 80 to ensure sink conditions, such as experimental conditions that are well-below saturation solubility.

The pharmacokinetics of sorafenib following a single topical administration of the MPPs or a non-MPP comparator was evaluated in New Zealand white rabbits (NZW) at a contract research organization. An aqueous suspension of sorafenib was used as the non-MPP comparator. Each animal received a 50 μL topical instillation containing 5 mg/mL sorafenib in both eyes (n=6). Ocular tissues, including cornea and an 8 mm punch of choroid and of *retina* from the back of the eye, were harvested at various time points. The punch was used to target the area at the back of the eye where the human *macula* would be as this is the target for AMD therapy. Sorafenib levels were determined by LC/MS.

MPP1 and MPP2 formulated as described above formed stable nanosuspensions with a Z-average diameter of 187 nm (PDI=0.172) and 222 nm (PDI=0.058), respectively. Since MPP1 was essentially a suspension of the pure drug sorafenib, the drug release was driven largely by drug dissolution, which is relatively rapid. In the case of MPP2, the drug sorafenib was encapsulated in PLA polymers, and the drug loading was 20%. The polymeric composition of MPP2, including the molecular weight of PLA, the ratio of PLA to PLA-PEG, and the composition of PLA-PEG, was systematically varied in order to achieve a release rate well-differentiated from MPP1. The MPP2 formulation demonstrated continuous drug release over about 24 hrs in vitro.

Figure 29A:
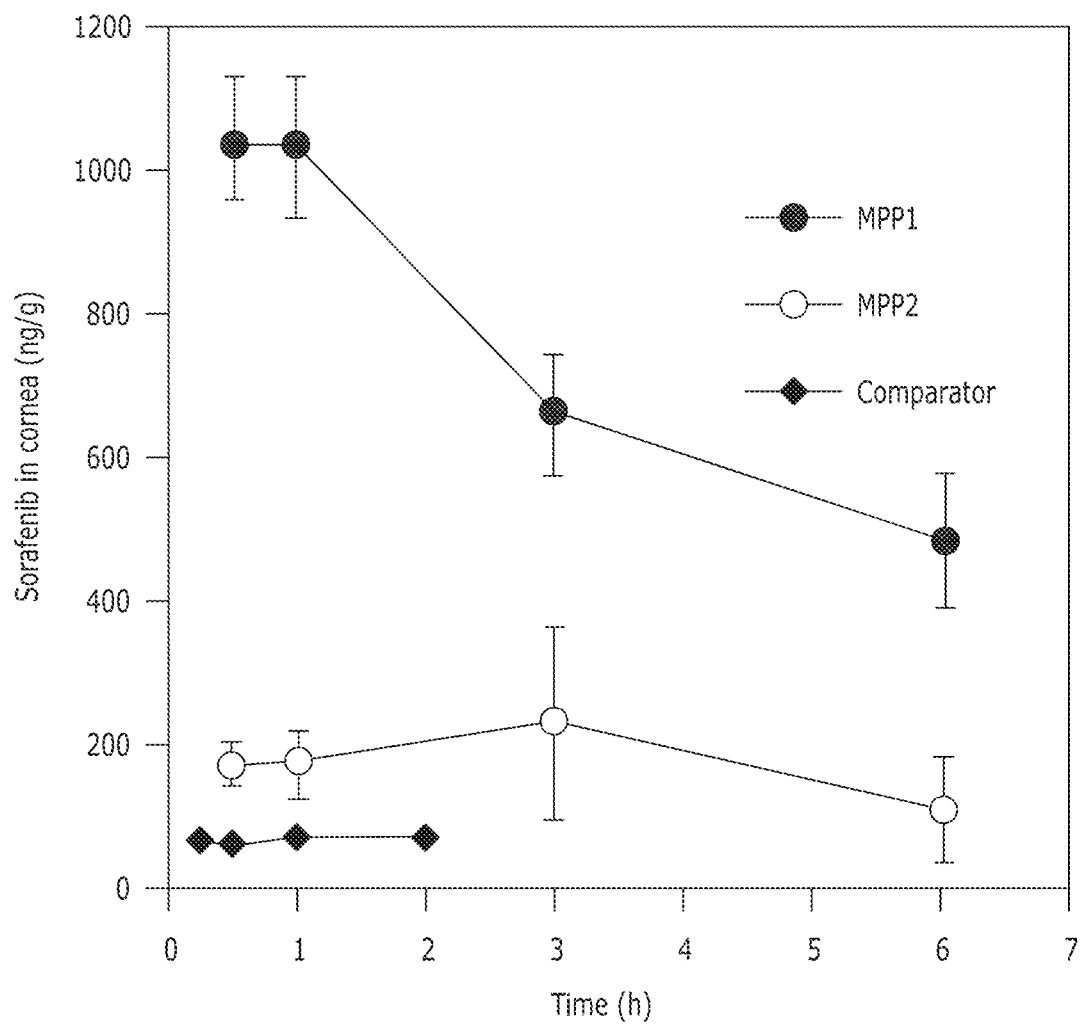
FIGS. 29A-29B are plots showing sorafenib levels in cornea (FIG. 29A) and *retina* (FIG. 29B) of New Zealand white rabbits following a single topical instillation of MPPs of sorafenib (e.g., MPP1 and MPP2) and a non-MPP comparator (e.g., an aqueous suspension of sorafenib). Error bars show standard errors of the mean (n=6).
Figure 29B:
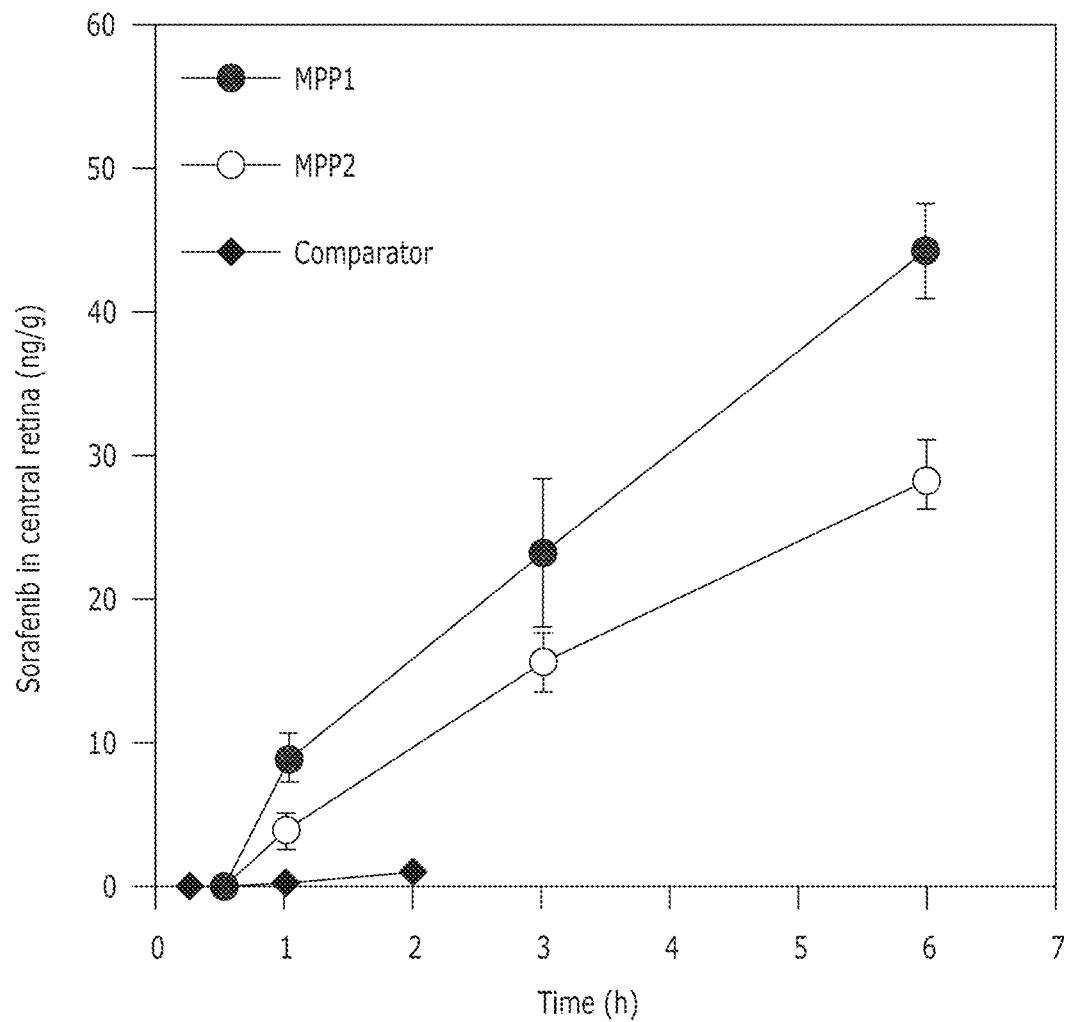

In the cornea, a single dose of the fast-releasing MPP1 formulation produced sorafenib levels up to 18-fold higher than those from the comparator and sustained an at least 7-fold enhancement over the comparator for at least 6 hours. In contrast, the slow-releasing MPP2 formulation produced only an approximately 3-fold enhancement over the comparator steadily sustained over the course of 6 hours. However, in posterior segment tissues (e.g., *retina* and choroid), both MPP1 and MPP2 produced similarly high sorafenib levels, well-outperforming the comparator (FIGS. 29A-29B). In fact, the levels of sorafenib in the *retina* produced by the MPP formulations approached or exceeded reported cellular $IC_{50}$ values against VEGFR-2 (37 ng/g) and PDGFR-β (14 ng/g) for sorafenib, a relatively low potency, first-generation RTK inhibitor. Furthermore, both MPP formulations were well tolerated as assessed by Draize scoring.

These results not only demonstrate a proof-of-concept that the MPPs described herein, and compositions thereof, can greatly enhance delivery of a pharmaceutical agent to the back of the eye via topical administration but also suggest that topical delivery of a small molecule RTK inhibitor formulated as MPPs may have a potential in the treatment of a broad range of ocular diseases, such as AMD.

Example 22

This non-limiting example demonstrates that a formulation including LE MPPs improved the exposure of LE in the aqueous humor of the rabbit eye compared to Lotemax® gel.

In order to demonstrate that enhanced exposure of LE from LE MPPs can be sustained at lower doses compared not only to marketed suspension formulations, but also to marketed gel formulations, levels of LE were determined when LE MPPs (dosed at 0.4% LE) and Lotemax® gel (dosed at 0.5% LE) were used. Gel and ointment formulations are popularly used in an attempt to increase exposure in the eye by delivering LE in a viscous matrix. Gel and ointment formulations often blur vision and are less comfortable and harder to install than a liquid eye drop.

To generate LE MPPs, a milling procedure was employed according to the methods described herein. For example, an aqueous dispersion containing LE and Pluronic® F127 (F127) was milled with a grinding medium until the particle size was reduced to below about 300 nm as measured by dynamic light scattering. Mucus mobility was characterized in human cervicovaginal mucus based on the previously described characterization methods.

Figure 30:
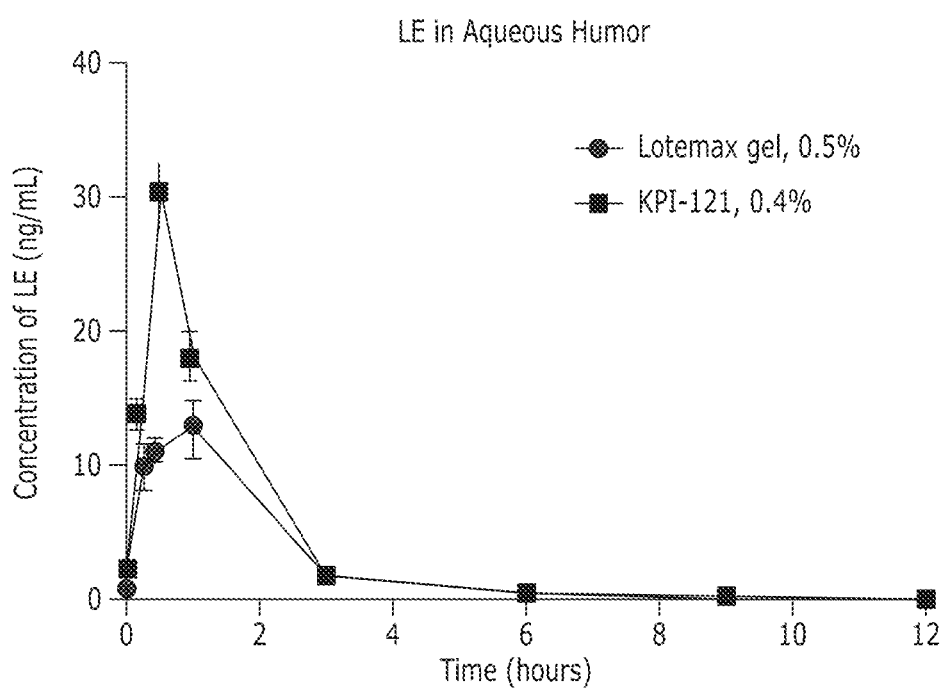
FIG. 30 is a plot showing the pharmacokinetics (PK) of LE in aqueous humor in vivo. The rabbits were given one 35 μL dose of 0.5% Lotemax® gel or 0.4% LE MPPs in each eye. Error bars show standard errors of the mean (n=6).

In vivo, a single topical instillation of LE MPPs (KPI-121) to New Zealand white rabbits produced higher LE levels in aqueous humor compared to a dose of Lotemax® gel despite the fact that the Lotemax® gel dose was 20% higher and in a viscous matrix (FIG. 30). The $AUC_{0-3}$ of the LE MPPs was 1.5 times higher than that of Lotemax® gel. The $C_{max}$ of the LE MPPs was 2.4 times higher than that of Lotemax® gel. These results indicate that the MPPs described herein outperform the viscous matrix used in Lotemax® gel and that the dose of LE may be lowered by 20% with the LE MPP formulation and may still achieve similar or enhanced exposure compared to Lotemax® gel.

Example 23

This non-limiting example demonstrates that LE MPPs show dose-dependent exposure in the aqueous humor of New Zealand white rabbits.

Figure 31A:
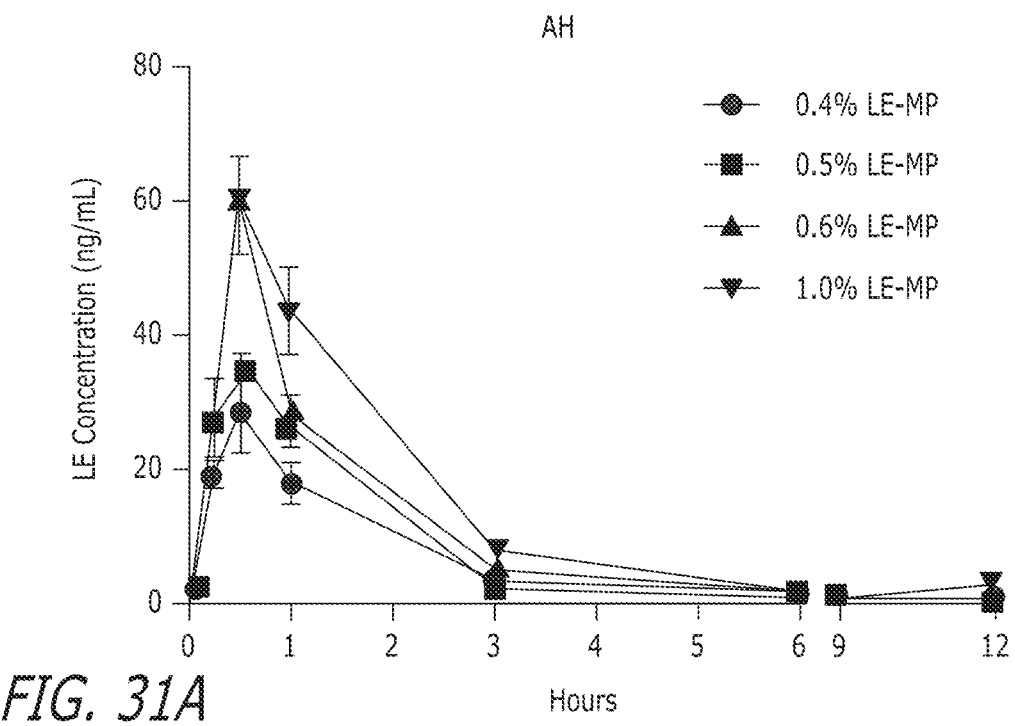
FIG. 31A is a plot showing the pharmacokinetics of LE in the aqueous humor of New Zealand white rabbits in vivo. The rabbits were given one 50 μL dose of different percentages of LE MPPs in each eye. Error bars show standard errors of the mean (n=6).
Figure 31B:
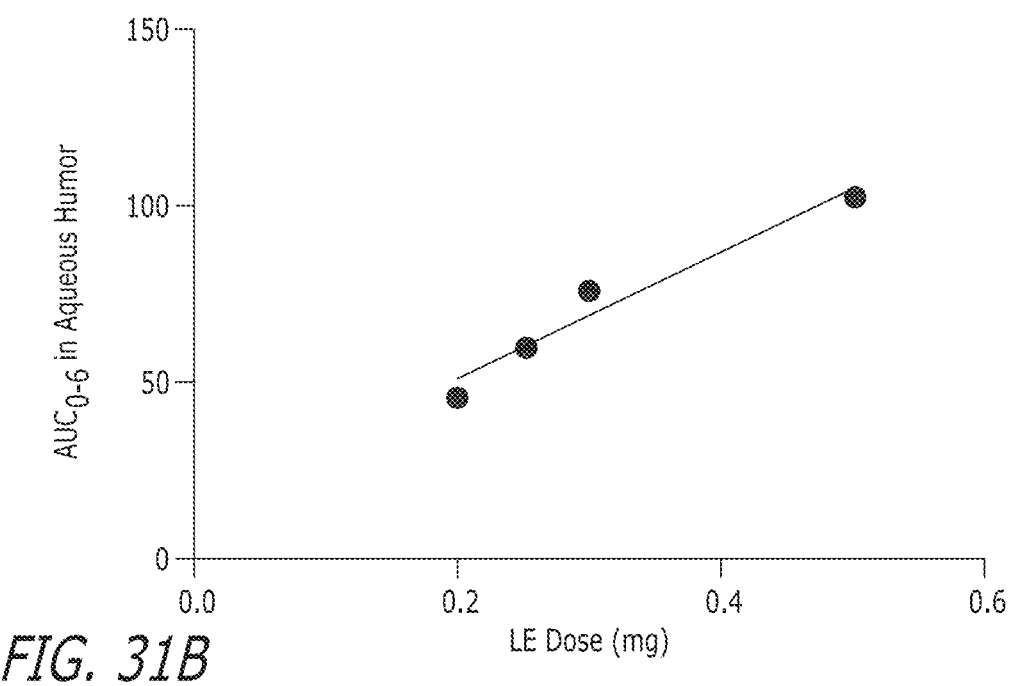
FIG. 31B is a plot showing the $AUC_{0-6}$ of LE in the aqueous humor of the NZW rabbits in vivo. The rabbits were given one 50 μL dose of different percentages of LE MPPs in each eye.

In order to demonstrate that the exposure of LE from an LE MPP formulation is dose dependent, a dose ranging study was performed. To generate LE MPPs, a milling process according to the methods described herein was employed. For example, an aqueous dispersion containing drug and Pluronic® F127 (F127) was milled with a grinding medium until the particle size was reduced to below about 300 nm as measured by dynamic light scattering. Mucus mobility was characterized in human cervicovaginal mucus based on the previously described characterization methods. Dilutions were performed to give LE MPP suspensions that included 0.4%, 0.5%, 0.6%, or 1% LE. In vivo, a single topical instillation of LE MPPs to New Zealand white rabbits produced LE levels in the aqueous humor of the rabbits which were dependent on the dose given (FIGS. 31A-31B). These results demonstrate the LE MPPs exhibit dose-dependent pharmacokinetics (PK).

Example 24

This non-limiting example demonstrates that LE MPPs may be stably formulated in the presence of one or more ionic components, such as sodium chloride.

In order to demonstrate that LE MPPs may be formulated with ionic components, such as ionic salts, and can remain physically stable in such a formulation, sodium chloride, a tonicity agent with a well-known safety profiles in humans, was introduced into the LE MPPs. It is commonly known in the art that ionic components should not be added to particle suspensions as the ionic components tend to destabilize the particle suspensions. Surprisingly, this is not the case with LE MPPs.

It is known that, to achieve a formulation of an osmolarity of about 300 mOsm/kg, the concentration of sodium chloride in the formulation is typically about 0.9%. A combination of 1.2% glycerin and 0.45% sodium chloride generally also yields an isotonic solution and was tested to compare different levels of sodium chloride.

Figure 32:
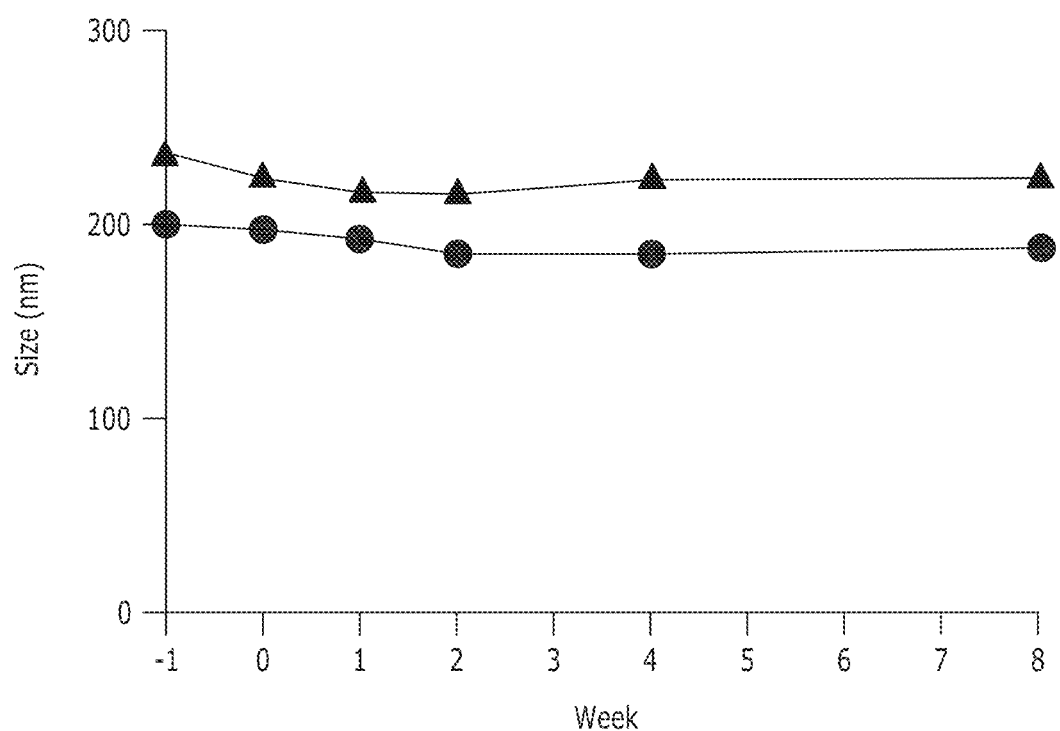
FIG. 32 is a plot showing the stability of LE MPPs in the presence of ionic components, such as sodium chloride. Triangles: 0.45% sodium chloride. Squares: 0.9% sodium chloride. LE MPPs were monitored by dynamic light scattering (DLS). Sizes at Week −1 represent particle sizes of the LE MPPs immediately after milling and before the LE MPPs were diluted to the final concentration on Week 0.

To generate nanoparticles, a milling process according to the methods described herein was employed. For example, an aqueous dispersion containing LE and Pluronic® F127 (F127) was milled with a grinding medium until the particle size was reduced to below about 300 nm as measured by dynamic light scattering. The physical stability of the resulted isotonic formulations was tested by monitoring the size of the particles in the formulations using dynamic light scattering (DLS). It was discovered that the particles in the formulations containing two different concentrations of sodium chloride were very stable in size as shown in FIG. 32. In FIG. 32, the data depicted with the triangular markers had a higher percentage of NaCl in the formulation than the data depicted with the circular markers. These results demonstrate that LE MPPs can be formulated into stable compositions in the present of ionic components, such as sodium chloride.

Example 25

This non-limiting example demonstrates that particles containing Pluronic® F127 and diclofenac or ketorolac may be mucus penetrating.

In order to demonstrate that particles comprising a core containing an NSAID and comprising a surface-altering agent (e.g., Pluronic® F127) may be mucus penetrating, two NSAIDs, i.e., diclofenac and ketorolac, were studied.

Figure 41:
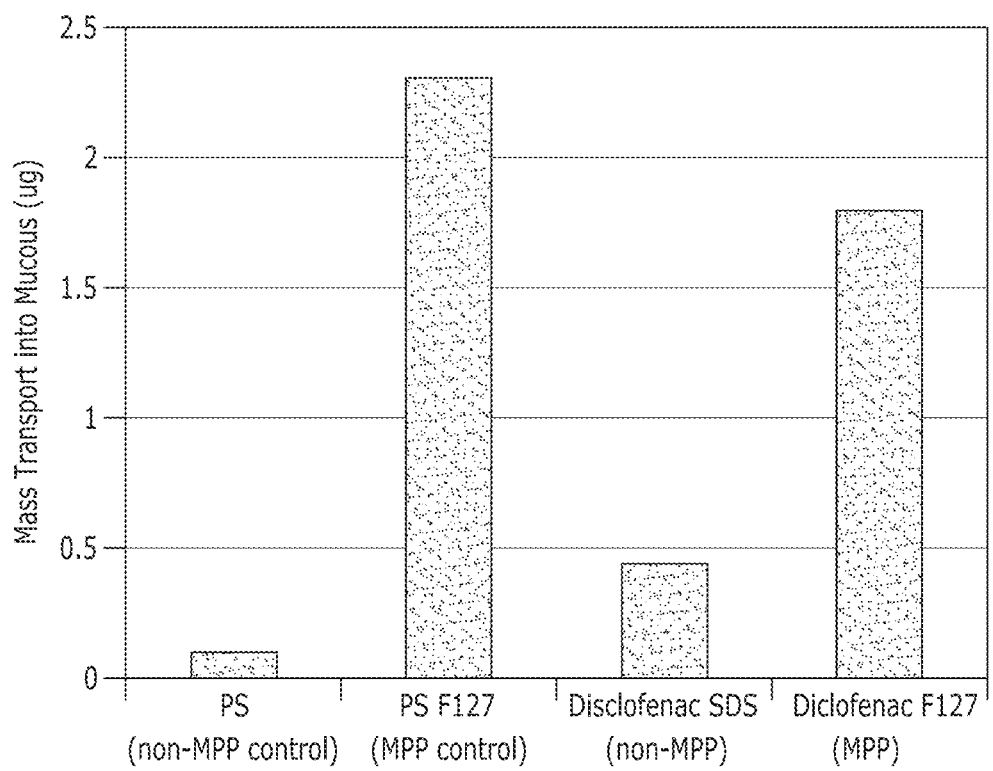
FIG. 41 is a bar graph showing the bulk transport of particles containing diclofenac into human cervicovaginal mucus. Polystyrene particles containing no surface-altering agents (PS) were used as a negative, non-MPP control. Particles containing polystyrene in the core and Pluronic® F127 as the surface-altering agents (PS F127) were used as a positive, MPP control. Diclofenac F127 stands for particles containing diclofenac in the core and Pluronic® F127 as the surface-altering agents. Diclofenac SDS stands for particles containing diclofenac in the core and sodium dodecyl sulfate (SDS) as the surface-altering agents.

To form particles containing diclofenac or ketorolac, a milling procedure was employed according to methods described herein. In one set of experiments, an aqueous dispersion containing Pluronic® F127 and one of ketorolac free acid and diclofenac free acid was milled with a grinding medium until the particle size was reduced to below about 300 nm as measured by dynamic light scattering. To generate similarly sized non-MPP comparators, a similar milling procedure was employed except that SDS was used as the surface-altering agent instead of Pluronic® F127. The mucus mobility of the produced particles was characterized in human cervicovaginal mucus based on the previously described microscopy methods. In the case of diclofenac, the mucus mobility was additionally characterized by the previously described bulk transport method. The results are shown in FIG. 41. The data demonstrate that the particles containing Pluronic® F127 and one of ketorolac and diclofenac were mucus penetrating, whereas the particles containing SDS and one of ketorolac and diclofenac were not mucus penetrating.

Example 26

This non-limiting example demonstrates a method of forming MPPs including bromfenac calcium, and compositions and/or formulations thereof.

Figure 34:
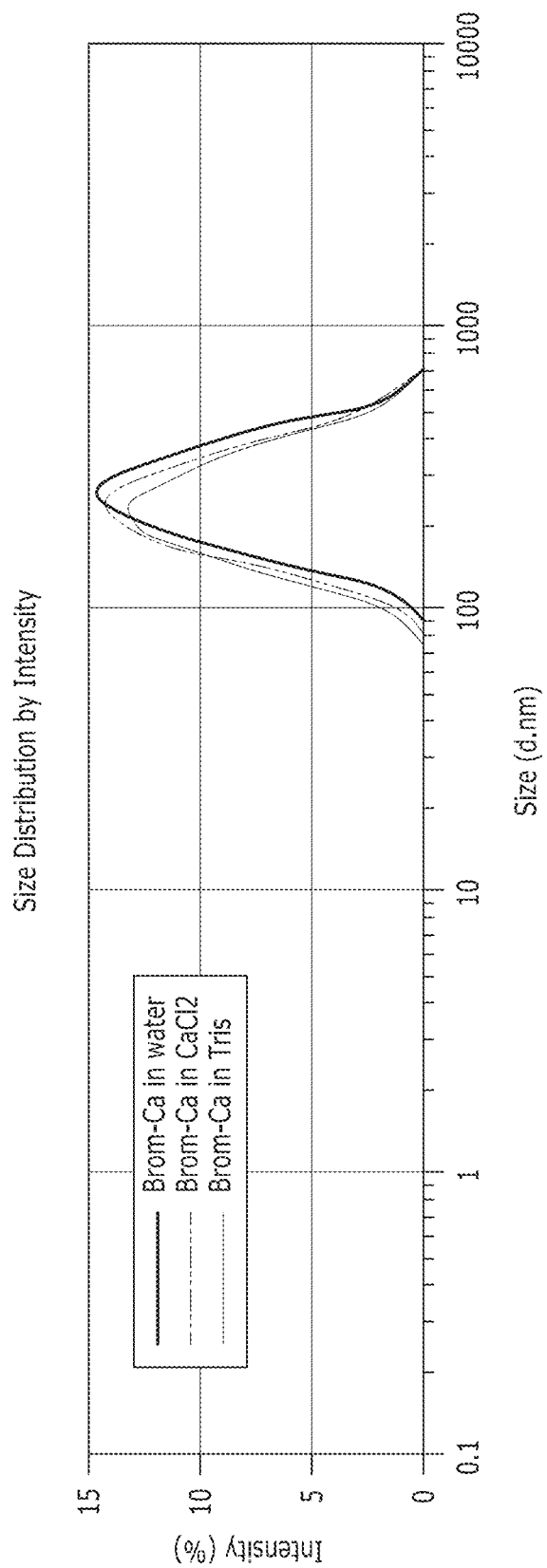
FIG. 34 is a plot showing an exemplary particle size distribution of bromfenac calcium MPPs in formulations containing the MPPs. Bromfenac calcium was milled in water, 125 mM of $CaCl_2$, or 50 mM of Tris buffer. The particle sizes were measured by dynamic light scattering. All three formulations had a Z-average diameter of about 200 nm and a polydispersity index <0.2.
Figure 35A:
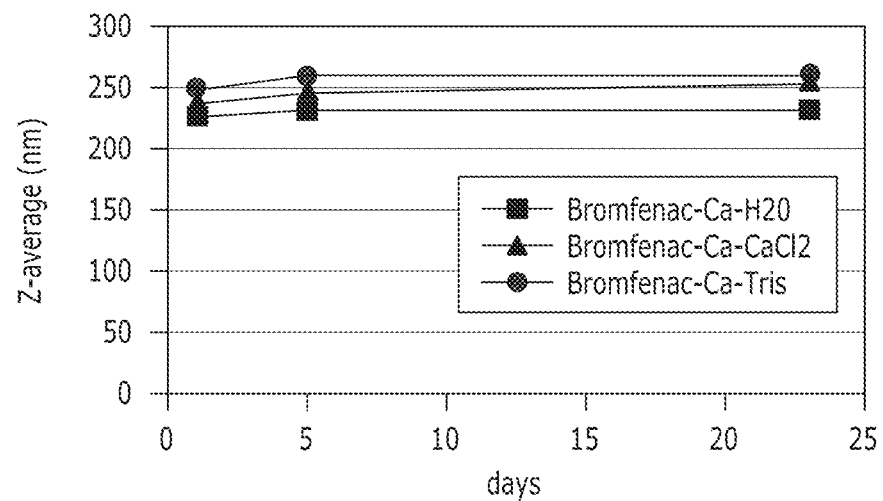
FIGS. 35A-35D are plots showing that MPPs including bromfenac calcium are stable over extended period of time when stored at room temperature.
Figure 35B:
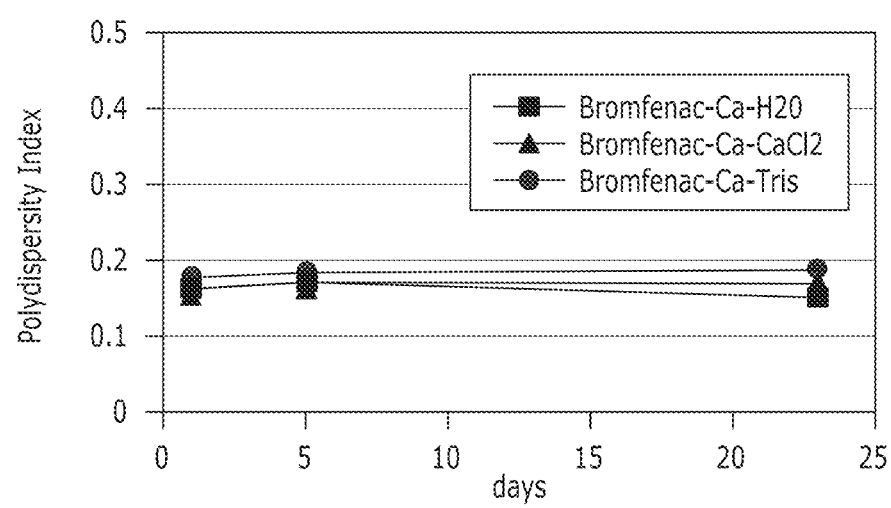
Figure 35C:
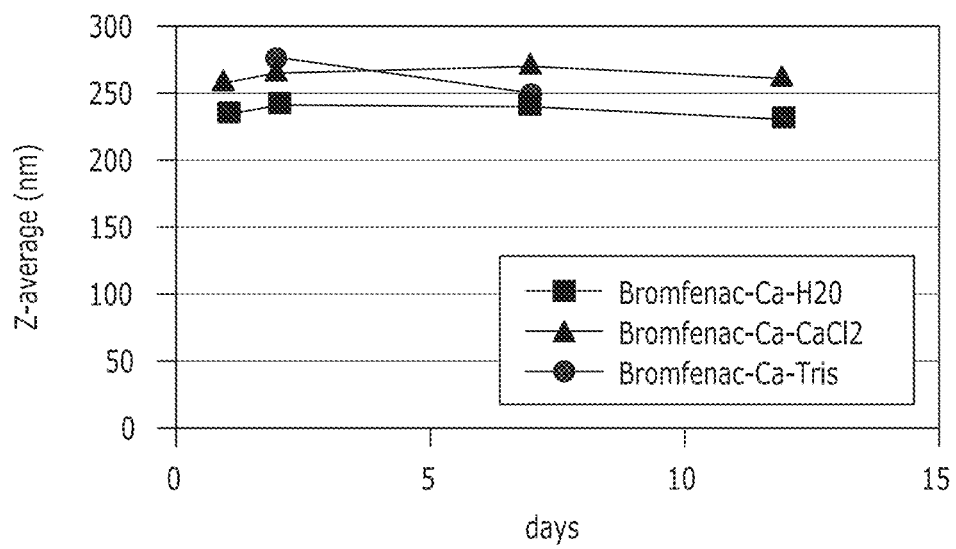
Figure 35D:
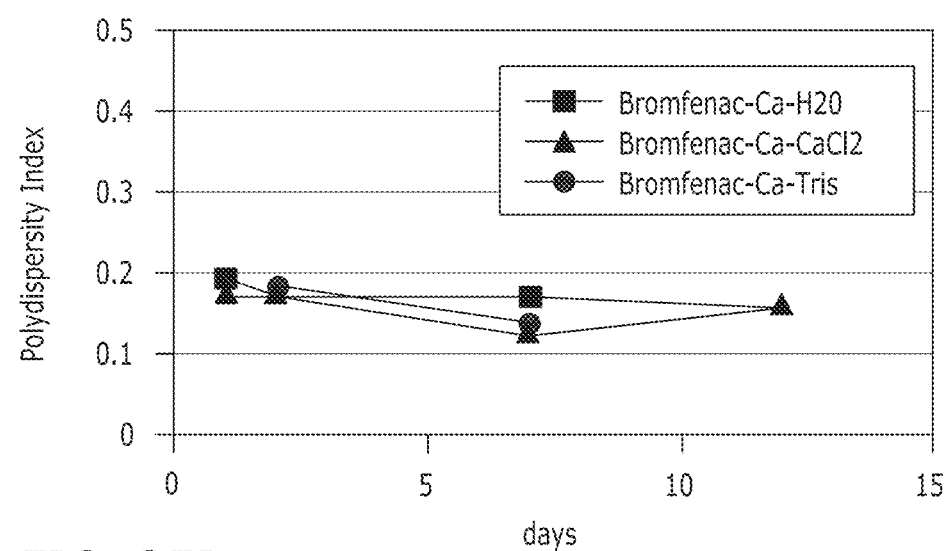

MPPs including bromfenac calcium as the core and Pluronic® F127 (F127) as a muco-inert surface-altering agent, and compositions and/or formulations including these MPPs, were prepared using a method similar to the methods described in Example 2. In one set of experiments, bromfenac calcium was nanomilled in an aqueous dispersion containing bromfenac calcium and Pluronic® F127 using zirconium oxide beads as grinding medium, until the particle size was reduced below 300 nm as measured by dynamic light scattering. The resulted nanomilled suspension can be diluted to a lower concentration if desired. In some experiments, bromfenac calcium was milled in water, 125 mM of $CaCl_2$, or 50 mM of Tris buffer to give three formulations. The particle size of the obtained MPPs in the three formulations was measured by dynamic light scattering, and the results are shown in FIG. 34. All three formulations had a Z-average diameter of about 200 nm and a polydispersity index <0.2. These data demonstrate that the bromfenac calcium MPPs are small and uniform in size and thus are suitable for ocular applications.

Example 27

This non-limiting example demonstrates that MPPs including bromfenac calcium, and compositions and/or formulations thereof, are stable when stored at room temperature.

MPPs including bromfenac calcium, and compositions and/or formulations thereof, may be prepared according to methods in Example 26. The MPPs, compositions, and/or formulations were stored at room temperature for days, and the particle Z-average size and polydispersity index of the MPPs were determined by dynamic light scattering. The results are shown in FIGS. 35A-35D. These data demonstrate that the bromfenac calcium MPPs maintained good particle size stability over extended period of time when stored at room temperature.

Enhanced mucus mobility of bromfenac calcium MPPs in human cervicovaginal mucus was confirmed by fluorescent microscopy and high resolution dark field microscopy (data not shown).

Example 28

This non-limiting example demonstrates that excipients in compositions and/or formulations containing bromfenac calcium MPPs may improve the chemical stability of bromfenac calcium MPPs.

To improve the chemical stability of bromfenac calcium in MPPs, different excipient compositions were explored for the milling step and the final formulation that either (1) lower the solubility of bromfenac or (2) maintain a pH range at which bromfenac is most stable. Table 20 shows the pH and solubility of bromfenac calcium MPPs in two buffers (125 mM $CaCl_2$ and 50 mM Tris) and, for comparison, in unbuffered water. The chemical stability of bromfenac calcium MPPs in 125 mM $CaCl_2$, which reduced the drug solubility, and in 50 mM Tris, which maintained the pH of the solution at about 8, was markedly enhanced compared to that in in water.

TABLE 20 pH, solubility, and chemical stability of bromfenac calcium MPP suspensions containing 0.09% w/v bromfenac in the presence of various excipient compositions at room temperature.*
Formulation: bromfenac calcium suspension (0.09% w/v bromfenac)

| Vehicle | | | | |
|---|---|---|---|---|
| Buffer | Concentration of Pluronic ®F127 (% w/v) | pH | Solubility (mg/mL) | % peak area* |
| None (water) | 0.5 | 6.87 | 0.21 | 0.13 (day 7) |
|  | 0.09 | 6.75 | 0.20 | 0.09 (day 23) |
| 125 mM $CaCl_2$ | 0.5 | 6.48 | 0.03 | 0 (day 7) |
|  | 0.09 | 6.60 | 0.07 | 0 (day 23) |
| 50 mM Tris buffer | 0.5 | 8.03 | 0.25 | 0 (day 7) |
|  | 0.09 | 7.98 | 0.27 | 0 (day 23) |

*The chemical stability of bromfenaccalcium was determined as % chromatographic peak area for the lactam degradant of bromfenac.

Example 29

This non-limiting example demonstrates that MPPs containing sorafenib or linifanib enhanced the exposure of sorafenib or linifanib at the back of the eye of rabbits.

In order to demonstrate that enhanced mucus penetration is useful not only at the front of the eye, but can lead to enhanced exposure at the back of the eye as well, sorafenib and linifanib, two receptor tyrosine kinase inhibitors, were formulated as MPPs. Small molecule RTK inhibitors that act on vascular endothelial growth factor receptor (VEGFR) have potential as therapy for age-related macular degeneration (AMD). If topical delivery of an RTK inhibitor could provide sufficient levels of the RTK inhibitor at the back of the eye then repeated intravitreal injections, used by current therapies, could be avoided. Delivery of an RTK inhibitor to the back of the eye would also be beneficial in a number of other diseases which affect posterior segment tissues.

To generate MPPs containing an RTK inhibitor (e.g., sorafenib and linifanib), a milling procedure similar to that used for Loteprednol Etabonate was employed: an aqueous dispersion containing the RTK inhibitor and F127 or sodium dodecyl sulfate (SDS) was milled with a grinding medium until the particle size was reduced to below about 300 nm as measured by dynamic light scattering. Mucus mobility was characterized in human cervicovaginal mucus based on the previously described characterization methods. Sorafenib and linifanib were processed into MPPs when milled with F127 and into non-MPPs when milled with SDS.

Figure 36A:
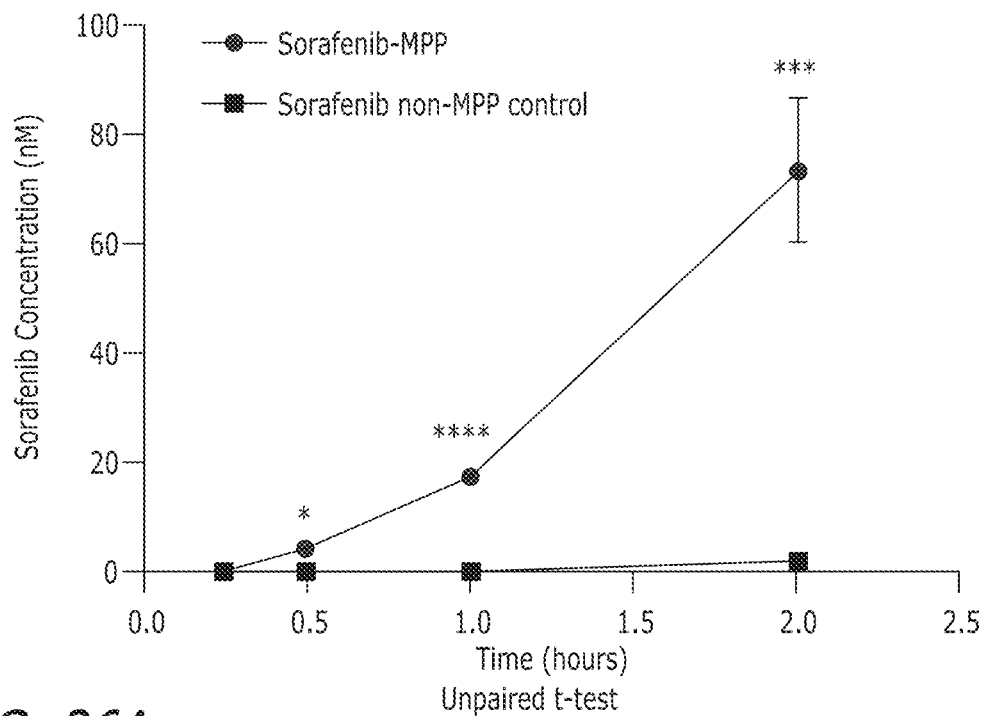
FIGS. 36A-36B are plots showing the pharmacokinetics of sorafenib and linifanib in center-punch *retina* of New Zealand white rabbits in vivo.

In vivo, a single 50 µL topical instillation of 0.5% sorafenib-MPP to New Zealand White rabbits produced sorafenib levels in the *retina* of the rabbit which were 45 times higher than sorafenib levels from the non-MPP control at 2 hours and 96 fold above cellular $IC_{50}$ (FIG. 36A). A central punch of 8 mm in diameter was taken from the *retina* where the human *macula* would be in order to measure sorafenib levels at the back of the eye where AMD therapies would be targeted. The sorafenib-MPP outperforms the sorafenib non-MPP by a statistically significant amount.

Figure 36B:
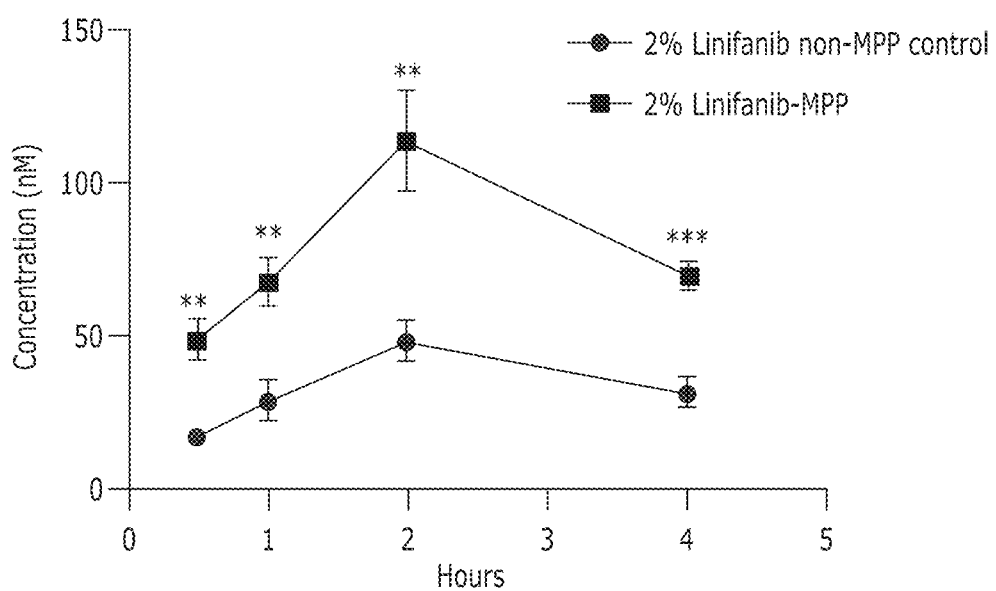

In vivo, a single 50 µL topical instillation of 2% linifanib-MPP to New Zealand White rabbits produced linifanib levels in the center punch *retina* which were approximately 2 fold higher than linifanib levels from the non-MPP control over the full 4 hours examined and 777 fold above cellular $IC_{50}$ at 4 hours (FIG. 36B). Again the difference between MPP and non-MPP was statistically significant.

These results demonstrate that enhanced mucus penetration can enable higher drug exposure at the back of the eye. The application of this technology can be used to improve drug exposure in any tissue of the eye, whether at the ocular surface or the back of the eye.

Example 30

This non-limiting example demonstrates that MPPs containing MGCD-265 or pazopanib generated therapeutically relevant levels of MGCD-265 or pazopanib at the back of the eye of rabbits.

In order to demonstrate the wide applicability of the MPP technology to the delivery of small molecule RTK inhibitors in therapeutically relevant (e.g., therapeutically effective) levels to the back of the eye, two additional compounds were studied: MGCD-265 and pazopanib.

To generate the MPPs, a milling procedure similar to that used for loteprednol etabonate was employed: an aqueous dispersion containing MGCD-265 or pazopanib and F127 was milled with a grinding medium until the particle size was reduced to below about 300 nm as measured by dynamic light scattering. Mucus mobility was characterized in human cervicovaginal mucus based on the previously described characterization methods. Both MGCD-265 and pazopanib were processed into MPPs when milled with F127.

Figure 37A:
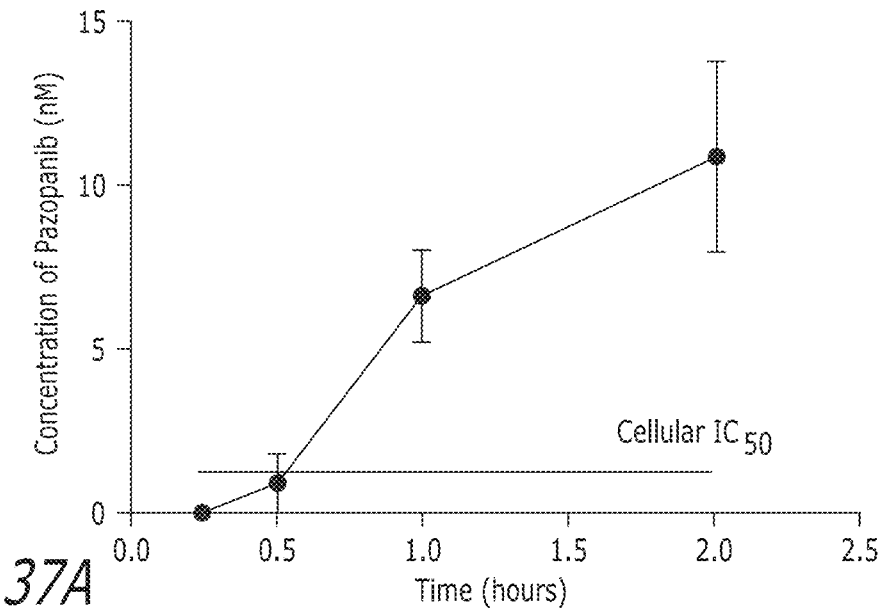
FIGS. 37A-37B are plots showing the pharmacokinetics of pazopanib and MGCD-265 in center-punch *retina* of New Zealand white rabbits in vivo.

In vivo, a single 50 µL topical instillation of 0.5% pazopanib-MPP to New Zealand White rabbits produced pazopanib levels in the center punch *retina* which were 9 fold higher than the cellular $IC_{50}$ at 4 hours (FIG. 37A).

Figure 37B:
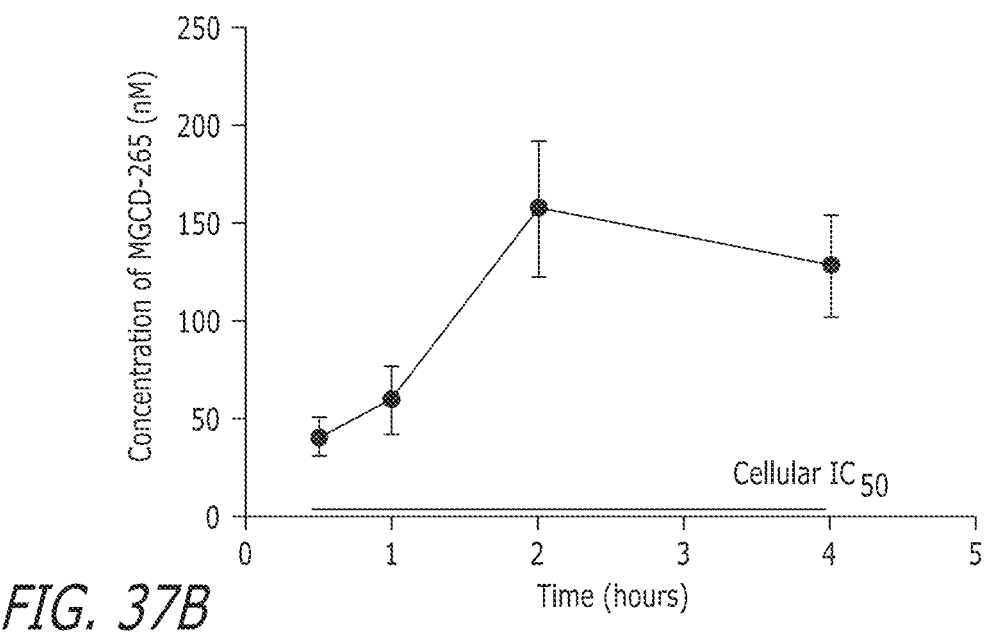

In vivo, a single 50 µL topical instillation of 2% MGCD-265-MPP to New Zealand White rabbits produced MGCD- 265 levels in the *retina* which were 37 fold higher than the cellular $IC_{50}$ at 30 minutes and 116 fold higher than the cellular $IC_{50}$ at 4 hours (FIG. 37B).

These results, along with Example 29, demonstrate that a variety of RTK inhibitors can be formulated as MPPs and the levels of the RTK inhibitors achieved at the back of the eye with topical administration are relevant to the active concentrations (cellular $IC_{50}$) of the RTK inhibitors.

Example 31

This non-limiting example demonstrates that a single topical administration of cediranib-MPPs produced therapeutically relevant drug levels at the back of the eye of rabbits for 24 hours.

In order to demonstrate the potential for MPPs containing a drug to sustain therapeutically relevant drug levels at the back of the eye of rabbits over a 24 hour period, cediranib, an RTK inhibitor, was formulated as MPPs. If topical delivery of a drug could provide therapeutically relevant levels of the drug at the back of the eye, repeated intravitreal injections, which are used in current AMD therapies, could be avoided. Ideally, this topical therapy would sustain drug levels at the back of the eye to provide less frequent dosing.

To generate the MPPs, a milling procedure similar to that used for Loteprednol Etabonate was employed: an aqueous dispersion containing cediranib and Pluronic® F127 was milled with a grinding medium until the particle size was reduced to below about 300 nm as measured by dynamic light scattering. Mucus mobility was characterized in human cervicovaginal mucus based on the previously described characterization methods. Cediranib was processed into MPPs when milled with F127.

Figure 38A:
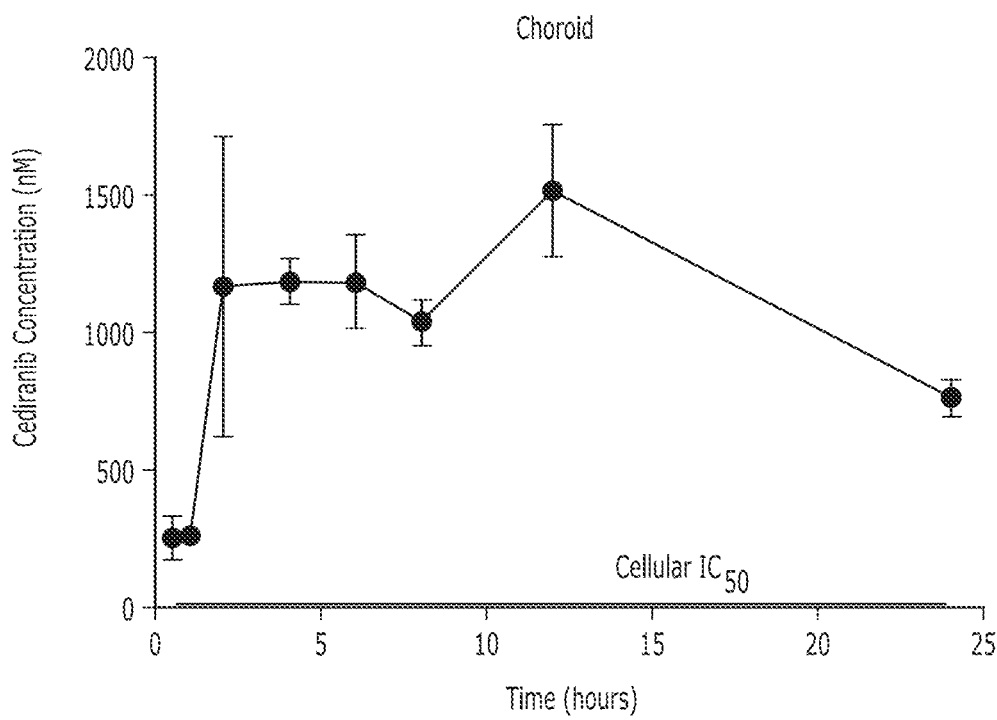
FIGS. 38A-38B are plots showing the pharmacokinetics of cediranib in ocular tissues of HY79b pigmented rabbits in vivo.
Figure 38B:
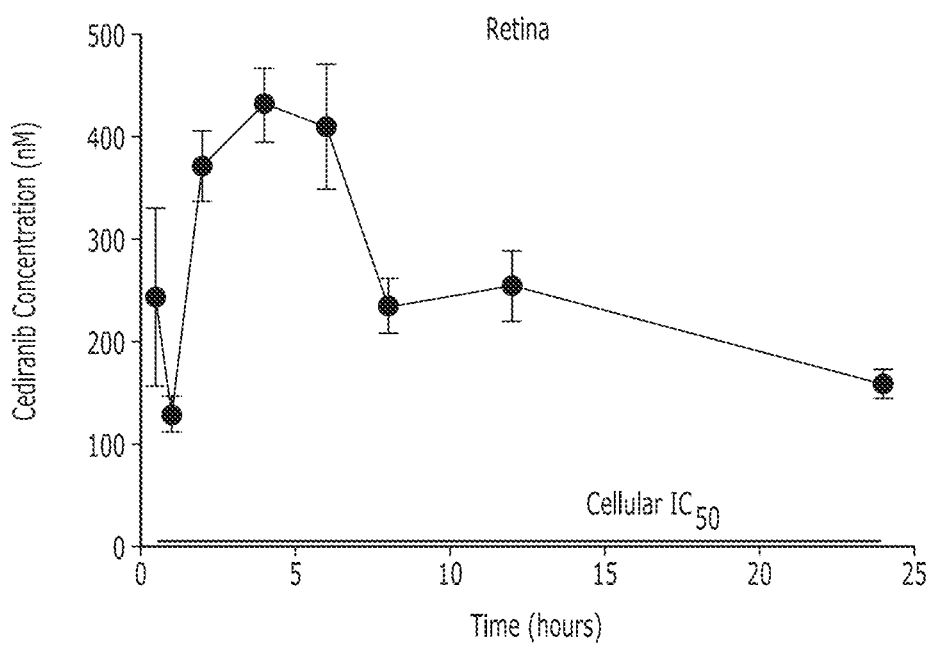

In vivo, a single 50 μL topical instillation of 2% cediranib-MPP to HY79b pigmented rabbits produced cediranib levels in the choroid of the rabbit which were 4,800 fold over cellular $IC_{50}$ at 24 hours (FIG. 38A) and cediranib levels in the *retina* of the rabbit which were 1,000 fold over cellular $IC_{50}$ at 24 hours (FIG. 38B). These results demonstrate the exposure achievable at the back of the eye with the MPP technology can be in therapeutically relevant ranges and that relevant drug exposure can be maintained over a long period of time (e.g., at least 24 hours).

Example 32

This non-limiting example demonstrates that a single topical administration of axitinib-MPP produced therapeutically relevant axitinib levels at the back of the eye of Dutch belted rabbits for 24 hours.

In order to demonstrate the potential for MPPs to sustain therapeutically relevant drug levels at the back of the eye of rabbits over a 24 hour period, axitinib, an RTK inhibitor, was formulated as MPPs. If topical delivery of a drug could provide therapeutically relevant levels of the drug at the back of the eye, repeated intravitreal injections, which are used by current AMD therapies, could be avoided. Ideally, this topical therapy would sustain drug levels at the back of the eye to provide less frequent dosing.

To generate nanoparticles, a milling procedure similar to that used for loteprednol etabonate was employed: an aqueous dispersion containing axitinib and F127 was milled with a grinding medium until the particle size was reduced to below about 300 nm as measured by dynamic light scattering. Mucus mobility was characterized in human cervico- vaginal mucus based on the previously described characterization methods. Axitinib was processed into MPPs when milled with F127.

Figure 39A:
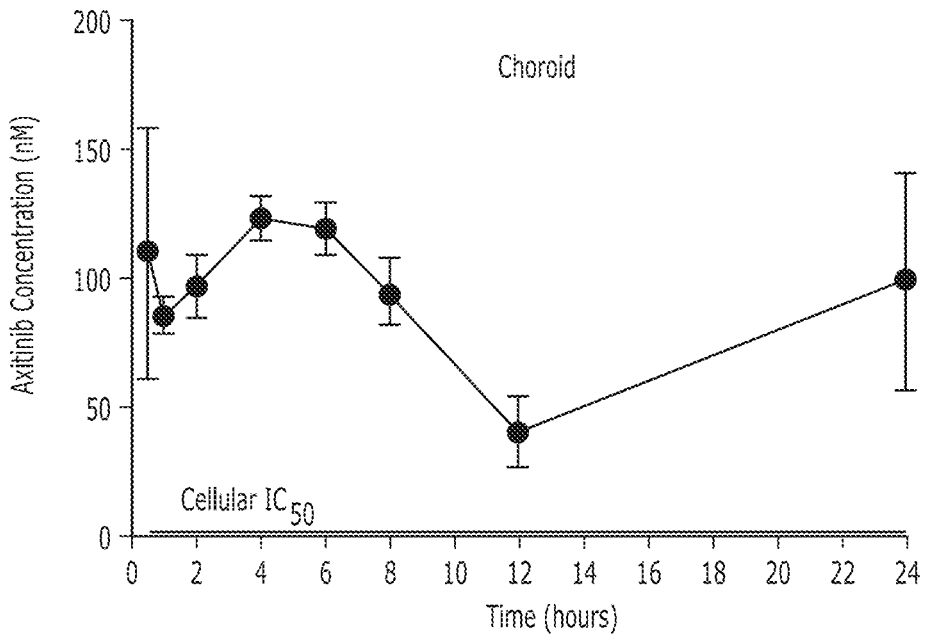
FIGS. 39A-39B are plots showing the pharmacokinetics of axitinib in ocular tissues of Dutch belted rabbits in vivo.
Figure 39B:
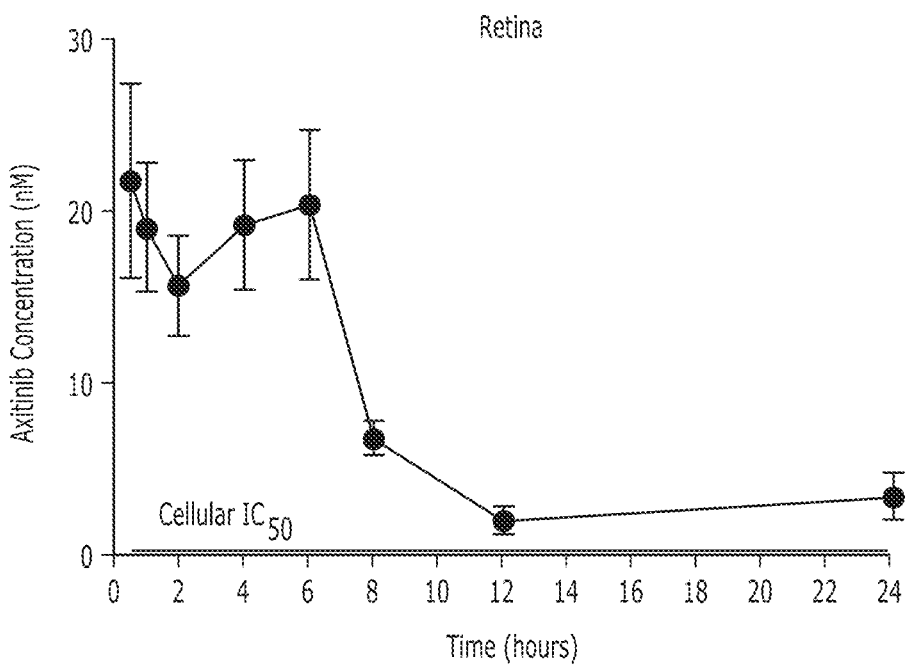

In vivo, a single 50 μL topical instillation of 2% axitinib-MPP to Dutch belted rabbits produced therapeutically relevant drug levels in the choroid of the rabbit 1,100 fold over cellular $IC_{50}$ at 24 hours (FIG. 39A) and levels in the *retina* of the rabbit which were 37 fold over cellular $IC_{50}$ at 24 hours (FIG. 39B). These results demonstrate the exposure achievable at the back of the eye with the MPP technology can be in therapeutically relevant ranges and that relevant drug exposure can be maintained over a long period of time (e.g., at least 24 hours).

Example 33

This non-limiting example demonstrates that axitinib-MPP reduced vascular leakage in a rabbit VEGF (vascular endothelial growth factor receptor)-challenge model.

Figure 40A:
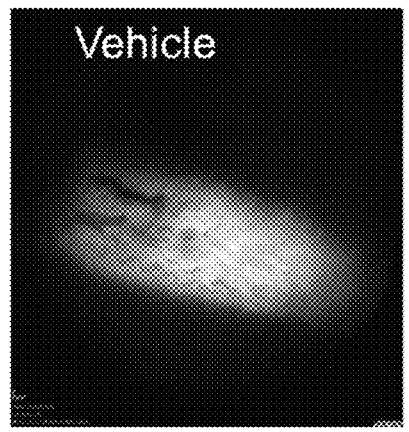
FIGS. 40A-40C are images showing the efficacy of axitinib-MPP in a rabbit VEGF (vascular endothelial growth factor receptor)-challenge model. Dutch belted rabbits were dosed with 50 μL of 5% axitinib-MPP every 4 hours on days 1-6. On day 3, the rabbits received an intravitreal injection of VEGF. On day 6, the rabbits were accessed for leakage via fluorescein angiography. Rabbits in the vehicle (negative control) group received vehicle every 4 hours on days 1-6. Rabbits in the Avastin® (positive control) group received one intravitreal injection of Avastin® on day 1.
Figure 40B:
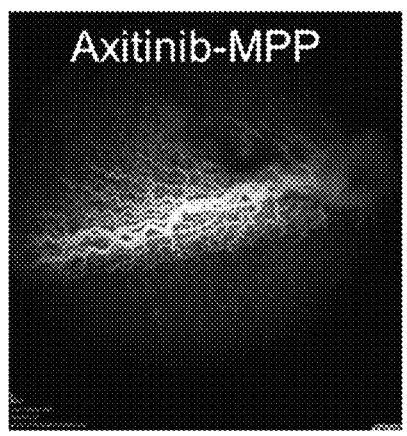
Figure 40C:
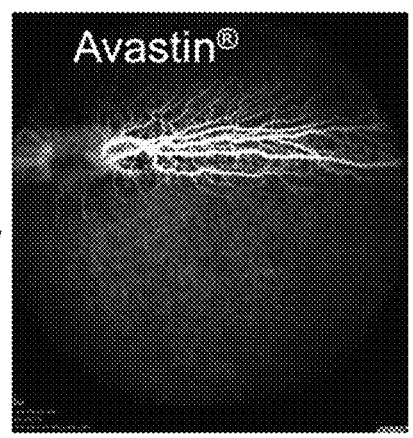

In order to demonstrate the therapeutic potential of the MPP technology in the treatment of an eye disease of the back of the eye, axitinib-MPPs were studied in an acute VEGF-challenge model. In this model, Dutch belted rabbits were given an intravitreal injection of VEGF to stimulate vascular growth. Fluorescein angiography was used to determine the degree to which the rabbits developed abnormal vascular and leakage. Representative images from fluorescein angiography after treatment with vehicle, axitinib-MPP, or Avastin® are shown in FIGS. 40A-40C. Rabbits which were dosed with vehicle showed a large amount of vessel growth, tortuosity, and leakage. Rabbits treated with Avastin®, commonly used off-label to treat AMD in humans and with a different mechanism of action than axitinib, showed no change in retinal vasculature. Rabbits treated with axitinib-MPP showed some vessel growth but significantly less leakage than the vehicle group. These results demonstrate the exposure achievable at the back of the eye using the MPP technology is sufficient to significantly reduce vascular leakage in an acute challenge model and has potential as an effective therapy in AMD and other back-of-the-eye diseases.

Example 34

This non-limiting example demonstrates that LE MPPs containing Pluronic® F127, Tween 80®, or PVA as the surface-altering agent showed improved exposure of LE in rabbits compared to Lotemax®.

In order to demonstrate that the LE MPPs' ability to enhance the exposure of LE is not limited to the inclusion of F127 as the surface-altering agent in the LE MPPs, two additional surface-altering agents were studied: Tween 80® and polyvinyl alcohol (PVA). Tween 80® is an FDA approved surface-altering agent which consists of PEGylated sorbitan forming a head group and an alkyl tail. Tween 80® is different from a range of other surface-altering agents (e.g., F127 and PVA) in that, among other things, it is oligomeric and thus significantly lower in molecular weight. PVA is an FDA approved polymer produced by, e.g., partially hydrolyzing polyvinyl acetate, creating a random copolymer of polyvinyl acetate and polyvinyl alcohol. PVA is different from a range of other surface-altering agents (e.g., F127 and Tween 80®) in that, among other things, it contains no PEG. In Examples 4-6, it is shown that some PVAs enable mucus penetration while other PVAs do not. This differentiated mucus penetration behavior may be controlled by the molecular weight and degree of hydrolysis of PVA. Based on the results from these Examples, a PVA that has a molecular weight of about 2 kDa and is about 75% hydrolyzed was selected for the study of mucus penetration properties of LE MPPs.

To form the LE MPPs, a milling procedure was employed as described herein. In one set of experiments, an aqueous dispersion containing LE and one surface-altering agent selected from F127, Tween 80®, and PVA (2 kDa, 75% hydrolyzed) was milled with a grinding medium until the particle size was reduced to below about 300 nm as measured by dynamic light scattering. Mucus mobility was characterized in human cervicovaginal mucus based on the previously described characterization methods. All three LE MPPs (i.e., LE-F127, LE-Tween80, and LE-PVA) showed mucus penetrating properties (FIG. 42).

Figure 42:
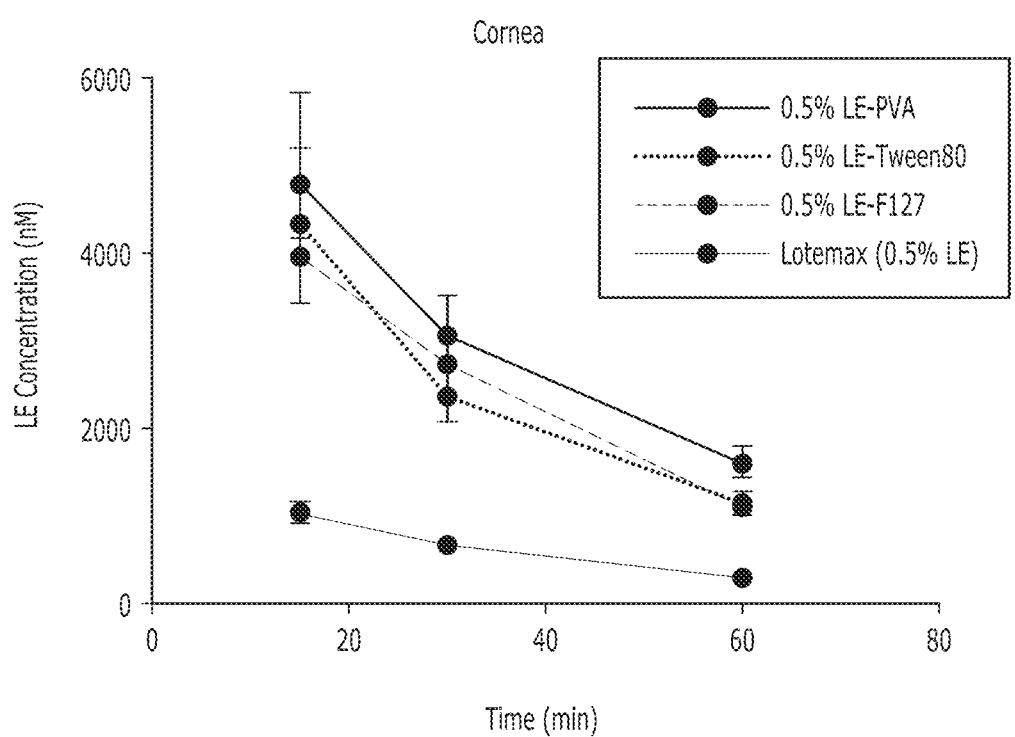
FIG. 42 is a plot showing the pharmacokinetics of Loteprednol Etabonate (LE) in the cornea of New Zealand white rabbits in vivo. Rabbits were given one 50 μL dose of each one of the three LE-MPPs (i.e., LE-F127, LE-Tween80, and LE-PVA) or Lotemax® in each eye. The PVA had a molecular weight of about 2 kDa and was about 75% hydrolyzed. The dose of LE was 0.5% in all instances. Error bars show standard errors of the mean (n=6).

In vivo, a single topical instillation of each one of the three LE MPPs to New Zealand white rabbits produced LE levels in the cornea of the rabbit which were significantly higher than the LE levels from a similarly administered dose of Lotemax® (FIG. 42). These results demonstrate that the MPPs, compositions, and/or formulations containing a drug enhance exposure of the drug based on the mucus penetrating properties of the particles.

Other Embodiments

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A topical pharmaceutical composition comprising:
   (A) a plurality of coated nanoparticles, each coated nanoparticle comprising:
      (i) a core particle comprising a corticosteroid, wherein the corticosteroid constitutes at least 80 wt % of the core particle by weight, and
      (ii) a mucus penetration-enhancing coating surrounding the core particle, the mucus penetration-enhancing coating comprising
         a) a triblock copolymer comprising a hydrophilic block-hydrophobic block-hydrophilic block configuration, wherein the hydrophobic block has a molecular weight of at least about 2 kDa, and the hydrophilic blocks constitute at least about 15 wt % of the triblock copolymer, or b) a polysorbate, wherein the mucus penetration-enhancing coating is present on the outer surface of the core particle at a density of at least 0.01 molecules/nm$^2$; and (B) one or more ophthalmically acceptable carriers, additives, and/or diluents;

wherein the mucus penetration-enhancing coating is present in the pharmaceutical composition in an amount of between about 0.001% and about 5% by weight.

2. The topical pharmaceutical composition of claim 1, wherein the mucus-penetration-enhancing coating is non-covalently adsorbed to the core particle.

3. The topical pharmaceutical composition of claim 1, wherein the corticosteroid is present in the pharmaceutical composition in an amount between about 0.01% and about 5% by weight in total.

4. The topical pharmaceutical composition of claim 1, wherein the topical pharmaceutical composition is a topical suspension.

5. The topical pharmaceutical composition of claim 1, wherein the plurality of coated particles have an average smallest cross-sectional dimension of less than about 1 micron.

6. The topical pharmaceutical composition of claim 1, wherein the mucus penetration-enhancing coating is present on the surfaces of the coated particles at a density of at least about 0.1 molecules per nanometer squared.

7. The topical pharmaceutical composition of claim 1, wherein the mucus penetration-enhancing coating comprises a triblock copolymer comprising a hydrophilic block-hydrophobic block-hydrophilic block configuration, wherein the hydrophobic block has a molecular weight of at least about 2 kDa, and the hydrophilic blocks constitute at least about 15 wt % of the triblock copolymer, wherein the hydrophobic block associates with the surface of the core particle, and wherein the hydrophilic block is present at the surface of the coated particle and renders the coated particle hydrophilic.

8. The topical pharmaceutical composition of claim 7, wherein the hydrophilic blocks of the triblock copolymer constitute at least about 30 wt % of the triblock polymer and less than or equal to about 80 wt % of the triblock copolymer.

9. The topical pharmaceutical composition of claim 7, wherein the hydrophobic block portion of the triblock copolymer has a molecular weight of at least about 3 kDa and less than or equal to about 8 kDa.

10. The topical pharmaceutical composition of claim 7, wherein the triblock copolymer is poly(ethylene oxide)-poly(propylene oxide)-poly(ethylene oxide) or poly(ethylene glycol)-poly(propylene oxide)-poly(ethylene glycol).

11. The topical pharmaceutical composition of claim 1, wherein the mucus penetration-enhancing coating has a molecular weight of at least about 4 kDa.

12. The topical pharmaceutical composition of claim 1, wherein the polydispersity index of the mucus-penetrating pharmaceutical composition is less than or equal to about 0.5.

13. A method of treating an ocular condition in a subject, the method comprising:

administering the topical pharmaceutical composition of claim 1 to an eye of a subject;

wherein the ocular condition is selected from inflammation, macular degeneration, macular edema, uveitis, dry eye, blepharitis, and cystoid macular edema.

* * * * *